(12) United States Patent
Anderson et al.

(10) Patent No.: US 10,550,159 B2
(45) Date of Patent: Feb. 4, 2020

(54) NEISSERIA MENINGITIDIS COMPOSITION AND METHODS THEREOF

(71) Applicant: PFIZER INC., New York, NY (US)

(72) Inventors: Annaliesa Sybil Anderson, Upper Saddle River, NJ (US); Susan Kay Hoiseth, Tampa, FL (US); Kathrin Ute Jansen, New York, NY (US); Justin Keith Moran, West Nyack, NY (US); Mark E. Ruppen, Garnerville, NY (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/208,347

(22) Filed: Dec. 3, 2018

(65) Prior Publication Data

US 2019/0127426 A1 May 2, 2019

Related U.S. Application Data

(63) Continuation of application No. 15/630,147, filed on Jun. 22, 2017, now Pat. No. 10,196,429, which is a continuation of application No. 15/237,005, filed on Aug. 15, 2016, now Pat. No. 9,724,402, which is a continuation of application No. 14/604,620, filed on Jan. 23, 2015, now Pat. No. 9,561,269, which is a continuation of application No. 13/787,594, filed on Mar. 6, 2013, now Pat. No. 8,986,710.

(60) Provisional application No. 61/609,257, filed on Mar. 9, 2012.

(51) Int. Cl.
*A61K 39/095* (2006.01)
*C07K 14/22* (2006.01)

(52) U.S. Cl.
CPC ............ *C07K 14/22* (2013.01); *A61K 39/095* (2013.01)

(58) Field of Classification Search
CPC ........ A61K 39/095; A61K 2039/55577; A61K 2039/6018; A61K 2039/55505; A61K 39/00; A61K 39/39; A61K 2039/505; A61K 2039/55511; A61K 2039/53; A61K 2039/54; A61K 2039/545; A61K 2039/55555; A61K 2039/55572; A61K 2039/58; A61K 2039/6037; A61K 2039/6068; A61K 2039/6087; A61K 2039/70; A61K 31/194; A61K 31/4172; A61K 38/164; A61K 39/0016; A61K 39/092; A61K 39/12; A61K 39/13; A61K 39/295; A61K 47/543; A61K 47/646; A61K 2039/5252; C07K 14/22; C07K 16/1217; C07K 14/3156; C07K 2319/00; C07K 2319/55
See application file for complete search history.

(56) References Cited

U.S. PATENT DOCUMENTS

| | | |
|---|---|---|
| 4,376,110 A | 3/1983 | David et al. |
| 4,554,101 A | 11/1985 | Hopp |
| 4,650,764 A | 3/1987 | Temin et al. |
| 4,666,829 A | 5/1987 | Glenner et al. |
| 4,708,871 A | 11/1987 | Geysen |
| 4,797,368 A | 1/1989 | Carter et al. |
| 4,861,719 A | 8/1989 | Miller |
| 4,912,094 A | 3/1990 | Myers et al. |
| 4,925,792 A | 5/1990 | Rappuoli |
| 4,980,289 A | 12/1990 | Temin et al. |
| 5,057,540 A | 10/1991 | Kensil et al. |
| 5,078,996 A | 1/1992 | Conlon, III et al. |
| 5,124,263 A | 6/1992 | Temin et al. |
| 5,139,941 A | 8/1992 | Muzyczka et al. |
| 5,254,339 A | 10/1993 | Morein |
| 5,399,346 A | 3/1995 | Anderson et al. |
| 5,459,127 A | 10/1995 | Felgner et al. |
| 5,514,581 A | 5/1996 | Ferrari et al. |
| 5,550,213 A | 8/1996 | Anderson et al. |
| 5,565,204 A | 10/1996 | Kuo et al. |
| 5,580,859 A | 12/1996 | Felgner et al. |
| 5,583,038 A | 12/1996 | Stover |
| 5,589,466 A | 12/1996 | Felgner et al. |
| 5,597,572 A | 1/1997 | Huergo et al. |
| 5,614,382 A | 3/1997 | Metcalf |
| 5,668,004 A | 9/1997 | O'Donnell |
| 5,723,127 A | 3/1998 | Scott et al. |
| 5,739,118 A | 4/1998 | Carrano et al. |
| 5,955,580 A | 9/1999 | Green et al. |
| 6,113,918 A | 9/2000 | Johnson et al. |
| 6,130,085 A | 10/2000 | Hamers et al. |

(Continued)

FOREIGN PATENT DOCUMENTS

| | | |
|---|---|---|
| CA | 2012311 C | 9/1990 |
| EP | 0125023 B1 | 11/1984 |

(Continued)

OTHER PUBLICATIONS

Rodriguez, A.P., et al., "The Epidemiological Impact of Antimeningococcal B Vaccination in Cuba", Mem Inst Oswaldo Cruz, Jul.-Aug. 1999, 94 (4): 433-440 (1999).

(Continued)

*Primary Examiner* — Padmavathi Baskar
(74) *Attorney, Agent, or Firm* — Anna C. Chau

(57) ABSTRACT

In one aspect, the invention relates to a non-lipidated and non-pyruvylated *Neisseria meningitidis* serogroup B polypeptide and methods of use thereof. In another aspect, the invention relates to an immunogenic composition including an isolated non-lipidated, non-pyruvylated ORF2086 polypeptide from *Neisseria meningitidis* serogroup B, and at least one conjugated capsular saccharide from a meningococcal serogroup, and methods of use thereof.

15 Claims, 24 Drawing Sheets

Specification includes a Sequence Listing.

(56) References Cited

U.S. PATENT DOCUMENTS

| | | |
|---|---|---|
| 6,149,919 A | 11/2000 | Domenighini et al. |
| 6,165,995 A | 12/2000 | Hilgers |
| 6,207,646 B1 | 3/2001 | Krieg et al. |
| 6,245,892 B1 | 6/2001 | Oaks et al. |
| 6,270,775 B1 | 8/2001 | Cleary |
| 6,281,337 B1 | 8/2001 | Cannon-Carlson et al. |
| 6,299,884 B1 | 10/2001 | Van Nest et al. |
| 6,355,253 B1 | 3/2002 | Zlotnick |
| 6,355,255 B1 | 3/2002 | Cleary et al. |
| 6,610,310 B2 | 8/2003 | Hilgers |
| 6,951,653 B2 | 10/2005 | Cleary et al. |
| 7,115,730 B1 | 10/2006 | Pizza et al. |
| 7,118,757 B1 | 10/2006 | Seid et al. |
| 7,285,281 B2 | 10/2007 | Green et al. |
| 7,291,588 B2 | 11/2007 | Pizza et al. |
| 7,332,174 B2 | 2/2008 | Green et al. |
| 7,361,355 B2 | 4/2008 | Green et al. |
| 7,384,640 B1 | 6/2008 | Holmes et al. |
| 7,576,176 B1 | 8/2009 | Fraser et al. |
| 7,608,278 B2 | 10/2009 | Hoiseth et al. |
| 7,785,608 B2 | 8/2010 | Zlotnick et al. |
| 7,803,387 B2 | 9/2010 | Arico et al. |
| 7,820,789 B2 | 10/2010 | Kirkham et al. |
| 8,039,007 B2 | 10/2011 | Rappuoli et al. |
| 8,101,194 B2 | 1/2012 | Zlotnick et al. |
| 8,273,360 B2 | 9/2012 | Pizza et al. |
| 8,398,988 B2 | 3/2013 | Contori et al. |
| 8,563,006 B2 | 10/2013 | Zlotnick et al. |
| 8,563,007 B1 | 10/2013 | Zlotnick et al. |
| 8,574,597 B2 | 11/2013 | Zlotnick |
| 8,632,995 B2 | 1/2014 | Sun et al. |
| 8,834,888 B2 | 9/2014 | Contorni |
| 8,986,710 B2 | 3/2015 | Anderson et al. |
| 9,107,873 B2 | 8/2015 | Zlotnick et al. |
| 9,132,182 B2 | 9/2015 | Zlotnick et al. |
| 9,168,293 B2 | 10/2015 | Zlotnick et al. |
| 9,249,196 B2 | 2/2016 | Fraser et al. |
| 9,249,198 B2 | 2/2016 | Fraser et al. |
| 9,266,929 B2 | 2/2016 | Fraser et al. |
| 9,267,163 B2 | 2/2016 | Arico et al. |
| 9,556,240 B2 | 1/2017 | Khandke et al. |
| 9,561,269 B2 | 2/2017 | Zlotnick et al. |
| 9,623,101 B2 | 4/2017 | Zlotnick et al. |
| 9,724,402 B2 | 8/2017 | Anderson et al. |
| 9,757,443 B2 | 9/2017 | Anderson et al. |
| 9,757,444 B2 | 9/2017 | Zlotnick et al. |
| 9,802,987 B2 | 10/2017 | Dilts et al. |
| 9,822,150 B2 | 11/2017 | Anderson et al. |
| 2004/0110670 A1 | 6/2004 | Arico et al. |
| 2004/0167068 A1 | 8/2004 | Zlotnick et al. |
| 2004/0249125 A1 | 12/2004 | Pizza et al. |
| 2006/0251670 A1 | 11/2006 | Comanducci et al. |
| 2006/0257413 A1 | 11/2006 | Zlotnick et al. |
| 2007/0020622 A1 | 1/2007 | Lee et al. |
| 2007/0049532 A1 | 3/2007 | Feige et al. |
| 2007/0082007 A1 | 4/2007 | Zlotnick et al. |
| 2007/0148729 A1 | 6/2007 | Farley et al. |
| 2007/0253964 A1 | 11/2007 | Zlotnick et al. |
| 2009/0035328 A1 | 2/2009 | Granoff |
| 2009/0202593 A1 | 8/2009 | Zlotnick et al. |
| 2011/0076299 A1 | 3/2011 | Zlotnick et al. |
| 2011/0189187 A1 | 8/2011 | Zlotnick |
| 2011/0312510 A1 | 12/2011 | Mak et al. |
| 2012/0034261 A1 | 2/2012 | Zlotnick et al. |
| 2012/0070457 A1 | 3/2012 | Daugherty et al. |
| 2012/0093852 A1 | 4/2012 | Anderson et al. |
| 2012/0107339 A1 | 5/2012 | Granoff et al. |
| 2012/0301496 A1 | 11/2012 | Zlotnick et al. |
| 2012/0308595 A1 | 12/2012 | Zlotnick et al. |
| 2013/0171194 A1 | 7/2013 | Khandke et al. |
| 2013/0243807 A1 | 9/2013 | Anderson et al. |
| 2014/0113329 A1 | 4/2014 | Sun et al. |
| 2015/0071959 A1 | 3/2015 | Anderson et al. |
| 2015/0216960 A1 | 8/2015 | Zlotnick et al. |
| 2015/0335724 A1 | 11/2015 | Zlotnick et al. |
| 2016/0017006 A1 | 1/2016 | Dilts et al. |
| 2016/0030543 A1 | 2/2016 | Zlotnick et al. |

FOREIGN PATENT DOCUMENTS

| | | |
|---|---|---|
| EP | 0171496 B1 | 2/1986 |
| EP | 0173494 A2 | 3/1986 |
| EP | 0184187 A2 | 6/1986 |
| EP | 0185573 B1 | 6/1986 |
| EP | 0467714 A1 | 7/1991 |
| EP | 0178220 B1 | 1/1992 |
| EP | 0488528 B1 | 11/1995 |
| EP | 0453242 B1 | 8/1996 |
| EP | 1296713 B1 | 9/2003 |
| EP | 1326634 B1 | 4/2006 |
| EP | 2351767 A2 | 8/2011 |
| GB | 0121591.2 | 11/1918 |
| JP | 1144977 A | 6/1989 |
| WO | 1986/01533 A1 | 3/1986 |
| WO | 1987/01130 A1 | 2/1987 |
| WO | 1987/002671 A1 | 5/1987 |
| WO | 1989/07150 A1 | 8/1989 |
| WO | 1990/02806 A1 | 3/1990 |
| WO | 1990/10458 A1 | 9/1990 |
| WO | 1991/18088 A1 | 11/1991 |
| WO | 1992/05263 A1 | 4/1992 |
| WO | 1992/19265 A1 | 11/1992 |
| WO | 1993/09239 A1 | 5/1993 |
| WO | 1994/12649 A2 | 6/1994 |
| WO | 1994/21807 A2 | 9/1994 |
| WO | 1994/26914 A1 | 11/1994 |
| WO | 1994/28152 A1 | 12/1994 |
| WO | 1994/28938 A1 | 12/1994 |
| WO | 1995/02697 A1 | 1/1995 |
| WO | 1995/07358 A1 | 3/1995 |
| WO | 1995/18863 A1 | 7/1995 |
| WO | 1995/21931 A1 | 8/1995 |
| WO | 1995/22617 A1 | 8/1995 |
| WO | 1995/26411 A2 | 10/1995 |
| WO | 1995/28494 A1 | 10/1995 |
| WO | 1996/10038 A1 | 4/1996 |
| WO | 1996/14086 A1 | 5/1996 |
| WO | 1996/17823 A1 | 6/1996 |
| WO | 1996/22378 A1 | 7/1996 |
| WO | 1996/25508 A1 | 8/1996 |
| WO | 1996/29412 A1 | 9/1996 |
| WO | 1996/39036 A1 | 12/1996 |
| WO | 1996/40718 A1 | 12/1996 |
| WO | 1997/19182 A1 | 5/1997 |
| WO | 1998/08543 A1 | 3/1998 |
| WO | 1998/08874 A1 | 3/1998 |
| WO | 1998/17805 A2 | 4/1998 |
| WO | 1999/01157 A1 | 1/1999 |
| WO | 1999/01158 A1 | 1/1999 |
| WO | 1999/01175 A1 | 1/1999 |
| WO | 1999/10372 A1 | 3/1999 |
| WO | 1999/24578 A2 | 5/1999 |
| WO | 1999/27944 A1 | 6/1999 |
| WO | 1999/36544 A2 | 7/1999 |
| WO | 1999/40200 A1 | 8/1999 |
| WO | 1999/48525 A1 | 9/1999 |
| WO | 1999/55730 A2 | 11/1999 |
| WO | 1999/55872 A1 | 11/1999 |
| WO | 1999/57280 A1 | 11/1999 |
| WO | 1999/61053 A1 | 12/1999 |
| WO | 2000/18434 A1 | 4/2000 |
| WO | 2000/22430 A2 | 4/2000 |
| WO | 2000/42192 A1 | 7/2000 |
| WO | 2000/43518 A1 | 7/2000 |
| WO | 2000/44890 A1 | 8/2000 |
| WO | 2000/45841 A2 | 8/2000 |
| WO | 2000/50075 A2 | 8/2000 |
| WO | 2000/57906 A1 | 10/2000 |
| WO | 2000/66741 A2 | 11/2000 |
| WO | 2000/66791 A2 | 11/2000 |
| WO | 2000/71574 A2 | 11/2000 |
| WO | 2000/71725 A2 | 11/2000 |
| WO | 2001/04316 A2 | 1/2001 |

(56) References Cited

FOREIGN PATENT DOCUMENTS

| | | |
|---|---|---|
| WO | 2001/31019 A2 | 5/2001 |
| WO | 2001/37863 A2 | 5/2001 |
| WO | 2001/38350 A2 | 5/2001 |
| WO | 2001/41800 A2 | 6/2001 |
| WO | 2001/52885 A1 | 7/2001 |
| WO | 2001/64920 A2 | 9/2001 |
| WO | 2001/64922 A2 | 9/2001 |
| WO | 2002/058737 A2 | 8/2002 |
| WO | 2002/079243 A2 | 10/2002 |
| WO | 2002/079246 A2 | 10/2002 |
| WO | 2002/083710 A2 | 10/2002 |
| WO | 2002/083711 A2 | 10/2002 |
| WO | 2002/098368 A2 | 12/2002 |
| WO | 2002/098369 A2 | 12/2002 |
| WO | 2003/007985 A2 | 1/2003 |
| WO | 2003/009869 A1 | 2/2003 |
| WO | 2003/020756 A2 | 3/2003 |
| WO | 2003/047619 A2 | 6/2003 |
| WO | 2003/063766 A2 | 8/2003 |
| WO | 2003/080678 A1 | 10/2003 |
| WO | 2003/094834 A2 | 11/2003 |
| WO | 2003/094960 A2 | 11/2003 |
| WO | 2004/019977 A2 | 3/2004 |
| WO | 2004/019992 A1 | 3/2004 |
| WO | 2004/032958 A1 | 4/2004 |
| WO | 2004/046177 A2 | 6/2004 |
| WO | 2004/048404 A2 | 6/2004 |
| WO | 2004/065603 A2 | 8/2004 |
| WO | 2004/067030 A2 | 8/2004 |
| WO | 2004/067033 A1 | 8/2004 |
| WO | 2004/083251 A2 | 9/2004 |
| WO | 2004/094596 A2 | 11/2004 |
| WO | 2005/000345 A2 | 1/2005 |
| WO | 2005/004908 A1 | 1/2005 |
| WO | 2005/020964 A1 | 3/2005 |
| WO | 2005/032583 A2 | 4/2005 |
| WO | 2005/033148 A1 | 4/2005 |
| WO | 2005/065708 A2 | 7/2005 |
| WO | 2005/090985 A1 | 9/2005 |
| WO | 2005/090986 A2 | 9/2005 |
| WO | 2005/102384 A2 | 11/2005 |
| WO | 2005/103230 A2 | 11/2005 |
| WO | 2005/105140 A2 | 11/2005 |
| WO | 2005/105141 A2 | 11/2005 |
| WO | 2005/108580 A1 | 11/2005 |
| WO | 2005/113607 A2 | 12/2005 |
| WO | 2006/000920 A2 | 1/2006 |
| WO | 2006/011060 A2 | 2/2006 |
| WO | 2006/024954 A2 | 3/2006 |
| WO | 2006/027685 A2 | 3/2006 |
| WO | 2006/046143 A2 | 5/2006 |
| WO | 2006/067632 A2 | 6/2006 |
| WO | 2006/075170 A1 | 7/2006 |
| WO | 2006/081259 A2 | 8/2006 |
| WO | 2006/096701 A2 | 9/2006 |
| WO | 2006/120576 A2 | 11/2006 |
| WO | 2007/000314 A2 | 1/2007 |
| WO | 2007/000341 A2 | 1/2007 |
| WO | 2007/000342 A2 | 1/2007 |
| WO | 2007/000343 A2 | 1/2007 |
| WO | 2007/026249 A2 | 3/2007 |
| WO | 2007/028408 A1 | 3/2007 |
| WO | 2007/060548 A2 | 5/2007 |
| WO | 2007/071786 A2 | 6/2007 |
| WO | 2007/127665 A2 | 8/2007 |
| WO | 2007/111940 A2 | 10/2007 |
| WO | 2007/127668 A2 | 11/2007 |
| WO | 2007/144316 A2 | 12/2007 |
| WO | 2007/144317 A2 | 12/2007 |
| WO | 2008/001222 A2 | 1/2008 |
| WO | 2008/001224 A2 | 1/2008 |
| WO | 2008/013943 A2 | 1/2008 |
| WO | 2008/079372 A2 | 7/2008 |
| WO | 2008/084411 A2 | 7/2008 |
| WO | 2008/149238 A2 | 12/2008 |
| WO | 2009/010877 A2 | 1/2009 |
| WO | 2009/016515 A2 | 2/2009 |
| WO | 2009/050586 A1 | 4/2009 |
| WO | 2009/104097 A1 | 8/2009 |
| WO | 2009/109550 A1 | 9/2009 |
| WO | 2009/114485 A2 | 9/2009 |
| WO | 2009/143168 A2 | 11/2009 |
| WO | 2009/158142 A1 | 12/2009 |
| WO | 2010/027872 A1 | 3/2010 |
| WO | 2010/028096 A2 | 3/2010 |
| WO | 2010/028859 A1 | 3/2010 |
| WO | 2010/067202 A2 | 6/2010 |
| WO | 2010/070453 A2 | 6/2010 |
| WO | 2010/077422 A2 | 7/2010 |
| WO | 2010/109323 A1 | 9/2010 |
| WO | 2010/109324 A1 | 9/2010 |
| WO | 2010/127172 A2 | 11/2010 |
| WO | 2011/024072 A2 | 3/2011 |
| WO | 2011/039631 A2 | 4/2011 |
| WO | 2011/042516 A2 | 4/2011 |
| WO | 2011/051893 A1 | 5/2011 |
| WO | 2011/080595 A2 | 7/2011 |
| WO | 2011/110531 A2 | 9/2011 |
| WO | 2011/110634 A1 | 9/2011 |
| WO | 2011/110635 A1 | 9/2011 |
| WO | 2011/126863 A1 | 10/2011 |
| WO | 2011/161653 A1 | 12/2011 |
| WO | 2012/020326 A1 | 2/2012 |
| WO | 2012/025873 A2 | 3/2012 |
| WO | 2012/031271 A1 | 3/2012 |
| WO | 2012/032169 A1 | 3/2012 |
| WO | 2012/032489 A1 | 3/2012 |
| WO | 2012/032498 A2 | 3/2012 |
| WO | 2012/035519 A1 | 3/2012 |
| WO | 2012/117377 A1 | 9/2012 |
| WO | 2012/134975 A1 | 10/2012 |
| WO | 2013/132452 A2 | 9/2013 |
| WO | 2014/136064 A2 | 9/2014 |
| WO | 2015/033251 A2 | 3/2015 |
| WO | 2016/132294 A1 | 8/2016 |

OTHER PUBLICATIONS

Romero et al, "Current Status of Meningococcal Group B Vaccine Candidates: Capsular or Noncapsular?" Clinical Microbiology Reviews 7(4):559-575 (1994).

Rose et al, "Pyruvic Acid is Attached Through Its Central Carbon Atom to the Amino Terminus of the Recombinant DNA-derived DNA-binding Protein Ner of Bacteriophage Mu", The Journal of Biological Chemistry 267 (27):19101-19106 (1992).

Rosenqvist et al, "Human Antibody Responses to Meningococcal Outer Membrane Antigens after Three Doses of the Norwegian Group B Meningococcal Vaccine", Infection and Immunity 63(12):4642-4652 (1995).

Rosenqvist, E., et al., "Effect of Aluminium Hydroxide and Meningococcal Serogroup C Capsular Polysaccharide on the Immunogenicity and Reactogenicity of a Group B Neisseria Meningitides Outer Membrane Vesicle Vaccine", Dev Biol Stand, 1998, 92: 323-333.

Rosenstein et al, "Meningococcal Vaccines", Infectious Disease Clinics of North America 15(1):155-169 (2001).

Ross, et al., "Identification of Vaccine Candidate Antigens from a Genomic Analysis of Porphyromonas gingivalis", Vaccine 19:4135-4142 (2001).

Sahagan et al, "A Genetically Engineered Murine/Human Chimeric Antibody Retains Specificity for Human Tumor-Associated Antigen", The Journal of Immunology 137(3):1066-1074 (1986).

Salzberg et al, "Microbial gene identification using interpolated Markov models", Nucleic Acids Research 26 (2):544-548 (1998).

Sambrook et al, Molecular Cloning: A Laboratory Manual, Third Edition, Cold Spring Harbor Laboratory Press, Cold Spring Harbor, New York (2001).

Sambrook et al, "Analysis and Cloning of Eukaryotic Genomic DNA", Molecular Cloning: A Laboratory Manual, Second Edition, Cold Spring Harbor Laboratory Press, Cold Spring Harbor, New York, Chapter 9, pp. 9.1-9.62 (1989).

(56) References Cited

OTHER PUBLICATIONS

Sambrook et al, "Synthetic Oligonucleotide Probes", Molecular Cloning: A Laboratory Manual, Second Edition, Cold Spring Harbor Laboratory Press, Cold Spring Harbor, New York, Chapter 11, pp. 11.1-11.61 (1989).
Samulski et al, "A Recombinant Plasmid from Which an Infectious Adeno-Associated Virus Genome Can Be Excised In Vitro and Its Use to Study Viral Replication", Journal of Virology 61(10):3096-3101 (1987).
Samulski et al, "Helper-Free Stocks of Recombinant Adeno-Associated Viruses: Normal Integration Does Not Require Viral Gene Expression", Journal of Virology 63(9):3822-3828 (1989).
Sanger Centre FTP files [online] URL: ftp://ftp.sanger.ac.uk/pub/pathogens/nm/, dated Jul. 23, 2008.
Sanger Centre's "Projects" website as of Dec. 10, 1997 as retrievable via http://web.archive.org, accessed Mar. 15, 2010.
Sankaran et al, "Modification of Bacterial Lipoproteins", Methods in Enzymology 250:683-697 (1995).
Sankaran, K., et al., ""Lipid Modification of Bacterial Prolipoprotein"", The Journal of Biological Chemistry, 269 (31):19701-19706 (1994).
Sastalla et al, "Codon-Optimized Fluorescent Proteins Designed for Expression in Low-GC Gram-Positive Bacteria", Applied and Environmental Microbiology, 75(7):2099-2110 (2009).
Saukkonen et al, "Protective efficacy of monoclonal antibodies to class 1 and class 3 outer membrane proteins of Neisseria meningitidis B:15:P1.16 in infant rat infection model: new prospects for vaccine development", Microbial Pathogenesis 3:261-267 (1987).
Sedegah et al, "Improving Protective Immunity Induced by DNA-Based Immunization: Priming with Antigen and GM-CSf-Encoding Plasmid DNA and Boosting witih Antigen-Expressing Recombinant Poxvirus", The Journal of Immunology 164:5905-5912 (2000).
Sedegah et al, "Protection against malaria by immunization with plasmid DNA encoding circumsporozoite protein", Proc. Natl. Acad. Sci. 91:9866-9870 (1994).
Seib et al, "Characterization of Diverse Subvariants of the Meningococcal Factor H (fH) Binding Protein for Their Ability to Bind fH, to Mediate Serum Resistance, and to Induce Bactericidal Antibodies", Infection and Immunity 79 (2):970-981 (2011).
Sepelyak et al, "Adsorption of Pepsin by Aluminum Hydroxide I: Adsorption Mechanism", Journal of Pharmaceutical Sciences 73(11):1514-1517 (1984).
Sequence Analysis in Molecular Biology. Treasure Trove or Trivial Pursuit, Gunnar von Heijne, Academic Press (1987).
Sequence Analysis Primer, Gribskov and Devereux, eds., M Stockton Press, New York 1991.
Sequence for "Putative Lipoprotein [Neisseria Meningitidis Z2491]", NCBI Reference Sequence:YP_002342062.1, dated May 6, 2009, accessed Aug. 4, 2009.
Serruto et al, "Genome-based approaches to develop vaccines against bacterial pathogens", Vaccine 27:3245-3250 (2009).
Sierra, G.V.G., et al.,"Vaccine Against Group B Neisseria Meningitidis: Protection Trial and Mass Vaccination Results in Cuba" NIPH Annals, 14 (2): 195-210 (1991).
Smith et al., "Nucleotide sequence determination and genetic analysis of the bacteroides plasmid, pBI143," Plasmid 34(3):211-222 (1995).
Snape et al, "Immunogenicity of Two Investigational Serogroup B Meningococcal Vaccines in the First Year of Life", The Pediatric Infectious Disease Journal 29(11):e71-e79 (2010).
Snapper et al, "Bacterial Lipoproteins May Substitute for Cytokines in the Humoral Immune Response to T Cell-Independent Type II Antigens", The Journal of Immunology 155:5582-5589 (1995).
Snapper et al, "IL-3 and Granulocyte-Macrophage Colony-Stimulating Factor Strongly Induce lg secretion by Sort-Purified Murine B Cells Activated Through the Membrane lg, but Not the CD40, Signaling Pathway", The Journal of Immunology 154:5842-5850 (1995).
Sonnenberg et al, "Definition of *Mycobacterium* tuberculosis Culture Filtrate Proteins by Two-Dimensional Polyacrylamide Gel Electrophoresis, N-Terminal Amino Acid Sequencing, and Electrospray Mass Spectrometry", Infection and Immunity 65(11):4515-4524 (1997).
Sonnhammer et al, "Pfam: A Comprehensive Database of Protein Domain Families Based on Seed Alignments", Proteins: Structure, Function, and Genetics 28:405-420 (1997).
Stedman's Medical Dictionary, Illustrated, 24th Edition, Williams & Wilkins, Baltimore, Maryland, p. 707 (1982).
Stevens, "Streptococcal Toxic-Shock Syndrome: Spectrum of Disease, Pathogenesis, and New Concepts in Treatment", Emerging Infectious Diseases 1(3):69-78 (1995).
Stockbauer et al, "A natural variant of the cysteine protease virulence factor of group A *Streptococcus* with an arginine-glycine-aspartic acid (RGD) motif preferentially binds human integrins alphavbeta3 and alphaIIbbeta3", Proc. Natl. Acad. Sci. 96:242-247 (1999).
Stratford-Perricaudet et al, "Widespread Long-term Gene Transfer to Mouse Skeletal Muscles and Heart", J. Clin. Invest. 90:626-630 (1992).
Strauss, "Using DNA Fragments as Probes", Current Protocols in Molecular Biology, Supp. 24, 6.3.1-6.3.6 (1993).
Suhrbier, "Multi-epitope DNA vaccines", Immunology and Cell Biology, 75(4):402-408 (1997).
Sun et al, "Chimeric antibody with human constant regions and mouse variable regions directed against carcinoma-associated antigen 17-1A", Proc. Natl. Acad. Sci. 84:214-218 (1987).
Supplementary Declaration by Dr. Julian Parkhill submitted in Opposition Proceedings against Novartis EP1645631 on May 10, 2010.
Supplementary Submission in Opposition Proceedings against Novartis EP 1 645 631 submitted May 25, 2010.
Sutcliff et al, "Lipoproteins of Gram-Positive Bacteria", Journal of Bacteriology 177(5):1123-1128 (1995).
Sworn Statement from Dr. Giovanna Campanella submitted in Opposition Proceedings against Novartis EP1409013 on Nov. 10, 2011.
Sworn Statement from Dr. Rino Rappuoli submitted in Opposition Proceedings against Novartis EP1645631 on Oct. 14, 2011.
Tappero et al, "Immunogenicity of 2 Serogroup B Outer-Membrane Protein Meningococcal Vaccines", JAMA 281 (16):1520-1527 (1999).
Tarkka et al, "Antibody production to a meningococcal outer membrane protein cloned into live *Salmonella* typhimurium aroA vaccine strain", Micrb. Pathogen 6:327-335 (1989).
Telford et al., "Chapter 1: Genomics and Proteomics in Vaccine Design", New Bacterial Vaccines, Kleweur Academic/Plenum Publishers, USA, pp. 1-11 (2003).
Molinari et al, "The Fibronectin-Binding Protein of *Streptococcus pyogenes*, Sfbl, Is Involved in the Internalization of Group A Streptococci by Epithelial Cells", Infection and Immunity 65(4):1357-1363 (1997).
Morbidity and Mortality Weekly Report (MMWR), Recommendations and Reports, Case Definitions for Infectious Conditions Under Public Health Surveillance, May 2, 1997, vol. 46, No. RR-10.
Moreno et al, "Immunity and Protection of Mice Against Neisseria meningitidis Group B by Vaccination, Using Polysaccharide Complexed with Outer Membrane Proteins: A Comparison with Purified B Polysaccharide", Infection and Immunity 47(2):527-533 (1985).
Morley et al, "Vaccine prevention of meningococcal disease, coming soon?", Vaccine 20:666-687 (2002).
Morrison et al, "Chimeric human antibody molecules: Mouse antigen-binding domains with human constant region Domains", Proc. Natl. Acad. Sci. 81:6851-6855 (1984).
Mountzouros et al, "Detection of Complement-Mediated Antibody-Dependent Bactericidal Activity in a Fluorescence-Based Serum Bactericidal Assay for Group B Neisseria meningitidis", Journal of Clinical Microbiology 38 (8):2878-2884 (2000).
Moxon, "Applications of molecular microbiology to vaccinology," Lancet 350(9086):1240-1244 (1997).
Munkley et al., "Blocking of Bactericidal Killing of Neisseria meningitidis by Antibodies Directed Against Class 4 Outer Membrane Protein", Microbial Pathogenesis 11:447-452 (1991).

(56) References Cited

OTHER PUBLICATIONS

Murphy et al, "Sequence Diversity of the Factor H Binding Protein Vaccine Candidate in Epidemiologically Relevant Strains of Serogroup B Neisseria meningitidis" The Journal of Infectious Diseases 200:379-389 (2009).
Murphy, E., "HM807466: Neisseria meningitidis strain M08452 factor H binding protein variant B153 (fhbp) gene, partial cds.", URL:http://getentry.ddbj.nig.ac.jp/getentry/na/HM807466/?filetype=html, Jul. 21, 2010.
Nakai et al, "Expert System for Predicting Protein Localization Sites in Gram-Negative Bacteria", Proteins: Structure, Function, and Genetics 11:95-110 (1991).
Naldini et al, "Lentiviruses as gene transfer agents for delivery to non-dividing cells", Current Opinion in Biotechnology 9:457-463 (1998).
Nassif, "A Furtive Pathogen Revealed", Science 287:1767-1768 (2000).
Navarre et al, "Surface Proteins of Gram-Positive Bacteria and Mechanisms of Their Targeting to the Cell Wall Envelope", Microbiology and Molecular Biology Reviews 63(1):174-229 (1999).
NCBI GenBank No: AAF42204.1, Tettelin, H. et al., "Hypothetical protein [Neisseria meningitidis]", Feb. 25, 2000, accessed Jul. 12, 2012.
NCBI GenBank : ACI46791, "Factor H binding protein variant A04_001, partial [Neisseria meningitidis]". Aug. 4, 2009.
NCBI GenBank No: EF108319.1, O'Leary, M. M. et al., Neisseria meningitidis strain NM452 FHBP/GNA1870 variant (GNA1870) gene, complete cds, Nov. 8, 2006, accessed Sep. 5, 2012.
NCBI GenBank: ACI46789.1; "Factor H binding protein variant A62_001, partial [Neisseria meningitidis]", Aug. 4, 2009.
NCBI GenBank: ACB38141.1, factor H-binding protein [Neisseria meningitidis] (Jun. 4, 2010).
NCBI GenBank: AY330365.1; "Neisseria meningitidis strain CDC1492 factor H binding protein variant A22_001 (fhbp) gene, partial cds"; Mar. 12, 2009; accessed Jun. 3, 2014.
NCBI GenBank: AY330400.1; "Neisseria meningitidis strain M982 factor H binding variant B09_001 (fhbp) gene, partial cds"; Mar. 12, 2009; accessed Jun. 3, 2014.
NCBI GenBank: AY330401.1; "Neisseria meningitidis strain 880049 factor H binding protein variant B03_001 (fhbp) gene, partial cds"; Mar. 12, 2009; accessed Jun. 3, 2014.
NCBI GenBank: FJ184103.1; "Neisseria meningitidis factor H binding protein variant A12_001 (fhbp) gene, partial cds"; Aug. 4, 2009; accessed Jun. 3, 2014.
NCBI GenBank: FJ184126.1; "Neisseria meningitidis factor H binding protein variant B02_001 (fhbp) gene, partial cds"; Aug. 4, 2009; accessed Jun. 3, 2014.
NCBI GenBank: FJ184157.1; "Neisseria meningitidis factor H binding protein variant B44_001 (fhbp) gene, partial cds"; Aug. 4, 2009; accessed Jun. 3, 2014.
NCBI GenBank: FJ184233.1, "Neisseria meningitidis factor H binding protein variant B09_004 (fhbp) gene, partial cds" (Aug. 4, 2009).
Neisseria gonorrhoeae FA 1090 chromosome Entire clone gono strain FA1090, complete sequence. GenBank Accession gono AE004969, 2153894 bp, Sep. 26, 2000.
Nielsen et al, "Identification of prokaryotic and eukaryotic signal peptides and prediction of their cleavage sites", Protein Engineering 10(1):1-6 (1997).
Nimenrix product monograph, gsk.com/media/673251/nimenrix.pdf, accessed Feb. 19, 2015, date of revision Jan. 9, 2015.
Nimenrix product monograph, http://webprod5.hc-sc.gc.ca/dpd-bdpp/item-iteme.do?pm-mp=00033642, accessed Mar. 2016. Date of revision Nov. 9, 2015.
Nizet et al, "Genetic Locus for Streptolysin S Production by Group A *Streptococcus*", Infection and Immunity 68 (7):4245-4254 (2000).
Nordstrand et al, "Allele Substitution of the Streptokinase Gene Reduces the Nephritogenic Capacity of Group A Streptococcal Strain NZ131", Infection and Immunity 68(3):1019-1025 (2000).
Notice of Opposition against Novartis EP 1 645 631 submitted Jul. 23, 2008.
Novartis submits Bexsero®, a multi-component meningococcal B vaccine, for regulatory review in Europe, Novartis Media Release (Dec. 23, 2010).
Okuda et al, Lipoprotein sortingin bacteria, Annu. Rev. Microbiol., 65:239-259 (2011).
Olmsted et al, "High-Resolution Visualization by Field Emission Scanning Electron Microscopy of Enterococcus faecalis Surface Proteins Encoded by the Pheromone-Inducible Conjugative Plasmid pCF10", Journal of Bacteriology 175(19):6229-6237 (1993).
Opponent's Further Submission in Preparation of Oral Proceedings in Opposition against Novartis EP 1 645 631 submitted Nov. 3, 2011.
Opposition documents (part 1 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 2 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 3 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 4 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 5 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 6 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 7 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 8 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 9 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 10 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 11 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition papers EP2343308 May 2-9, 2016; 274 pages; accessed https://register.epo.org/application?number=EP10183020&lng=en&tab=doclist on May 16, 2016.
Opposition papers EP2343308 Apr. 6-13, 2016; 30 pages; accessed https://register.epo.org/application?number=EP10183020&lng=en&tab=doclist on May 16, 2016.
Fischetti et al, "Conservation of a hexapeptide sequence in the anchor region of surface proteins from Gram-positive cocci", Molecular Microbiology 4(9):1603-1605 (1990).
Fleischmann et al, "Whole-Genome Random Sequencing and Assembly of Haemophilus influenzae Rd", Science 269:496-501 (1995).
Fletcher et al, "Vaccine Potential of the Neisseria meningitidis 2086 Lipoprotein", Infection and Immunity 72 (4):2088-2100 (2004).

(56) References Cited

OTHER PUBLICATIONS

Fogg et al,"Constitutive Expression of Fibronectin Binding in *Streptococcus pyogenes* as a Result of Anaerobic Activation of rofA", Journal of Bacteriology 179(19):6172-6180 (1997).

Fontana et al, "A genomic approach to identify vaccine candidates against gonococcus", Abstract from the 13th International Pathogenic Neisseria Conference, Oslo Norway, Sep. 1-6, 2002, p. 248 (http://neisseria.org/ipnc/history.shtml).

Foster et al, "Surface protein adhesins of *Staphylococcus aureus*", Trends in Microbiology 6(12):484-488 (1998).

Frankel et al, "Characterization of diphtheria fusion proteins targeted to the human interleukin-3 receptor", Protein Engineering 13(8):579-591 (2000).

Fraser et al, "Genomic sequence of a Lyme disease spirochaete, Borrelia burgdorferi", Nature 390:580-591 (1997).

Fredriksen et al, "Production, Characterization and Control of MenB-Vaccine <<Folkehelsa>>: An Outer Membrane Vesicle Vaccine Against Group B Meningococcal Disease", NIPH Annals 14(2):67-80 (1991).

Fukasawa et al, "Neisseria meningitidis serogroup C polysaccharide and serogroup B outer membrane vesicle conjugate as a bivalent meningococcus vaccine candidate", Vaccine 17:2951-2958 (1999).

Gentz et al, "Bioassay for trans-activation using purified human immunodeficiency virus tat-encoded protein: Trans-activation requires mRNA synthesis", Proc. Natl. Acad. Sci. 86:821-824 (1989).

Geysen et al, "A Priori Delineation of a Peptide Which Mimics a Discontinuous Antigenic Determinant", Molecular Immunology, 23(7):709-715 (1986).

Geysen et al, "Use of peptide synthesis to probe viral antigens for epitopes to a resolution of a single amino acid", Proc. Natl. Acad. Sci. USA, 81(13):3998-4002 (1984).

Gil, J., et al., Proteomic Study via a Non-Gel Based Approach of Meningococcal Outer Membrane Vesicle Vaccine Obtained from Strain CU385 Human Vaccines, 5 (5): 347-356 (2009).

Giuliani et al, "The Region Comprising Amino Acids 100 to 255 of Neisseria meningitidis Lipoprotein GNA 1870 Elicits Bactericidal Antibodies", Infection and Immunity 73(2):1151-1160 (2005).

Giuliani et al, "A universal vaccine for serogroup B meningococcus" Proc Natl Acad Sci 103(29):10834-10839 (2006).

*GlaxoSmithKline UK Ltd v Wyeth Holdings LLC* [2016] EWHC 1045 (Ch) (May 12, 2016); Case No. HP-2015-000002; 66 pages; accessed http://www.bailii.org/ew/cases/EWHC/Ch/2016/1045.html on Jul. 11, 2016.

Gold et al., "Chapter 78. Translational Initiation", *Escherichia coli* and *Salmonella typhimurium*: Cellular and Molecular Biology, Ed. Neidhardt FC, vol. 2, pp. 1302-1307 (1987).

Goldschneider et al, "Human Immunity to the Meningococcus I. The Role of Humoral Antibodies", Journal of Experimental Medicine 129(6):1307-1326 (1969).

Goldschneider et al, "Human Immunity to the Meningococcus II. Development of Natural Immunity", Journal of Experimental Medicine 129(6):1327-1348 (1969).

Gomez et al, "The Bacillus subtilis lipoprotein LpIA causes cell lysis when expressed in *Escherichia coli*", Microbiology 140:1839-1845 (1994).

Gotschlich et al, "Human Immunity to the Meningococcus. IV. Immunogenicity of Group A and Group C Meningococcal Polysaccharides in Human Volunteers", Journal of Experimental Medicine 129(6):1367-1384 (1969).

Gotschlich et al, "Human Immunity to the Meningococcus. V. The Effect of Immunization with Meningococcal Group C Polysaccharide on the Carrier State", Journal of Experimental Medicine 129(6):1385-1395 (1969).

Graham et al, "Characteristics of a Human Cell Line Transformed by DNA from Human Adenovirus Type 5", J. Gen. Virology 36:59-72 (1977).

Graham, "Covalently closed circles of human adenovirus DNA are infectious", The EMBO Journal 3(12):2917-2922 (1984).

Grandi, "Reverse Vaccinology: A Critical Analysis", Encyclopedia of Genetics, Genomics, Proteomics and Bioinformatics, pp. 1320-1330 (2005).

Green et al, "The e (P4) Outer Membrane Protein of Haemophilus influenzae: Biologic Activity of Anti-e Serum and Cloning and Sequencing of the Structural Gene", Infection and Immunity 59(9):3191-3198 (1991).

Greenspan et al, "Defining epitopes: It's not as easy as it seems", Nature Biotechnology 17:936-937 (1999).

Griffin et al, "Computer Analysis of Sequence Data", Methods in Molecular Biology, vol. 24, Part 1, Chapter 1, Humana Press, New Jersey (1994).

Gupta, "Aluminum compounds as vaccine adjuvants", Advanced Drug Delivery Reviews 32(3):155-172 (1998).

Guzman et al, "Tight Regulation, Modulation, and High-Level Expression by Vectors Containing the Arabinose PBAD Promoter", Journal of Bacteriology 177(14):4121-4130 (1995).

Hacker et al, "Pathogenicity islands of virulent bacteria: structure, function and impact on microbial evolution", Molecular Microbiology 23(6):1089-1097 (1997).

Hanski et al, "Expression of protein F, the fibronectin-binding protein of *Streptococcus pyogenes* JRS4, in heterologous streptococcal and enterococcal strains promotes their adherence to respiratory epithelial cells", Infection and Immunity 60(12):5119-5125 (1992).

Hanski et al, "Protein F, a fibronectin-binding protein, is an adhesin of the group A *Streptococcus Streptococcus pyogenes*", Proc. Natl. Acad. Sci. 89:6172-6176 (1992).

Hansson et al, "Expression of Truncated and Full-Length Forms of the Lyme Disease Borrelia Outer Surface Protein A in *Escherichia coli*", Protein Expression and Purification 6:15-24 (1995).

Harris et al, "Preclinical evidence for the potential of a bivalent fHBP vaccine to prevent Neisseria meningitidis serogroup C disease", Human Vaccines 7(Supplement):68-74 (2011).

Havrix prescribing information, https://www.gsksource.com/pharma/content/dam/GlaxoSmithKline/US/en/Prescribing_Information/Havrix/pdf/HAVRIX.pdf, revised Jul. 2014, accessed Feb. 18, 2015.

Hayashi et al, "Lipoproteins in Bacteria", Journal of Bioenergetics and Biomembranes 22(3):451-471 (1990).

Hedari, et al., Meningococcal Serogroups A, C, W-135, and Y Tetanus Toxoid Conjugate Vaccine: A New Conjugate Vaccine Against Invasive Meningococcal Disease., Infect Drug Resist.;7:85-99 (2014).

Hem et al, "Chapter 9: Structure and Properties of Aluminum-Containing Adjuvants", Vaccine Design: The Subunit and Adjuvant Approach, Plenum Press, New York, pp. 249-276 (1995).

Hernandez-Sanchez et al, "lambda bar minigene-mediated inhibition of protein synthesis involves accumulation of peptidyl-tRNA and starvation for tRNA", The EMBO Journal 17(13):3758-3765 (1998).

Hornyik et al, "Cerebrospinal Fluid Shunt Infection by Neisseria sicca", Pediatr Neurosurg 21:189-191 (1994).

Houghten, "General Method for the rapid solid-phase synthesis of large numbers of peptides: Specificity of antigen-antibody interaction at the level of individual amino acids", Proceedings of the National Academy of Sciences of USA 82:5131-5135 (1985).

Huang et al, "The streptokinase gene of group A streptococci: cloning, expression in *Escherichia coli*, and sequence analysis", Molecular Microbiology 3(2):197-205 (1989).

Hung, "The Neisseria meningitidis Macrophage Infectivity Potentiator Protein Induces Cross-Strain Serum Bactericidal Activity and Is a Potential Serogroup B Vaccine Candidate", Infection and Immunity, 79(9):3784-3791 (2011).

Hynes et al, "Analysis of a Second Bacteriophage Hyaluronidase Gene from *Streptococcus pyogenes*: Evidence for a Third Hyaluronidase Involved in Extracellular Enzymatic Activity", Infection and Immunity 63(8):3015-3020 (1995).

Hynes et al, "The extracellular hyaluronidase gene (hylA) of *Streptococcus pyogenes*", FEMS Microbiology Letters 184:109-112 (2000).

Interlocutory Decision of the Opposition Division in Opposition against Novartis EP 1 645 631 dated May 21, 2012.

(56) References Cited

OTHER PUBLICATIONS

Isberg et al, "Binding and internalization of microorganisms by integrin receptors", Trends in Microbiology 2(1):10-14 (994).
Jackson et al, U.S. Appl. No. 60/098,685, filed Sep. 1, 1998.
Opposition notice EP2343308_(Nov. 13, 2015); 21 pages; accessed https://register.epo.org/application?number=EP10183020&lng=en&tab=doclist on Apr. 21, 2016.
Oudega et al, "A lipoprotein signal peptide plus a cysteine residue at the amino-terminal end of the periplasmic proteins beta-lactamase is sufficient for its lipid modification, processing and membrane localization in *Escherichia coli*", FEMS Microbiology Letters 108:353-360 (1993).
Oudega et al, "*Escherichia coli* SecB, SecA, and SecY Proteins Are Required for Expression and Membrane Insertion of the Bacteriocin Release Protein, a Small Lipoprotein", Journal of Bacteriology 175(5):1543-1547 (1993).
Pajon et al, "Frequency of factor H-binding protein modular groups and susceptibility to cross-reactive bactericidal activity in invasive meningococcal isolates", Vaccine 28:2122-2129 (2010).
Pannekoek et al, "Construction of recombinant neisserial Hsp60 proteins and mapping of antigenic domains", Molecular Microbiology 15(2):277-285 (1995).
Paoletti et al, "Potency of clinical group B streptococcal conjugate vaccines", Vaccine, 19(15-16):2118-2126 (2001).
Park et al, "DIVCLUS: an automatic method in the GEANFAMMER package that finds homologous domains in single- and multi-domain proteins", Bioinformatics 14(2):144-150 (1998).
Parkhill et al, "Complete DNA sequence of a serogroup A strain of Neisseria meningitidis Z2491", Nature 404:502-506 (2000).
Parkhill, "Campylobacter jejuni genome sequence at the Sanger Centre", (May 8, 1998), available at: http://www.bio.net/bionet/mm/bionews/1997-May/00442.html.
Patel, M., "Outbreaks of Serogroup B Meningococcal Disease on University Campuses—2013", Medical Officer, Meningitis and Vaccine Preventable Diseases Branch, http://www.cdc.gov/vaccines/acip/meetings/downloads/slides-2014-02/04-Mening-Patel.pdf, 16 Pages, Apr. 3, 2014.
Patentees' Further Submission Under Rule 116 EPC in Opposition against Novartis EP 1 645 631 submitted Oct. 14, 2011.
Patentees' Response to Opposition against Novartis EP 1 645 631 submitted May 8, 2009.
Patentees' Submissions Under Rule 116 EPC in Opposition against Novartis EP 1 645 631 submitted Sep. 13, 2011.
PCT Annex to Form PCT/ISA/206 Communication Relating to the Results of the Partial International Search, PCT/US2007/026238.
PCT International Search Report for PCT/IB2011/053934 dated Jan. 20, 2012.
PCT International Search Report for PCT/US02/32369 dated Nov. 14, 2003.
PCT International Search Report for PCT/US2007/026238 dated Feb. 23, 2009.
Perrett et al, "Towards an improved serogroup B Neisseria meningitidis vaccine", Expert Opin. Biol. Ther. 5 (12):1611-1625 (2005).
Pettersson et al., "Vaccine potential of the Neisseria meningitidis Lactoferrin-binding Proteins LbpA and LbpB", Vaccine, 24(17):3545-3557 (2006).
Pettersson, et al., "The meningococcal lactoferrin receptor", IPNC Abstract (1998).
Phase II clinical results for Novartis vaccine, Novartis Media Release (Oct. 9, 2008).
Phillips, "The challenge of gene therapy and DNA delivery", Journal of Pharmacy and Pharmacology 53:1169-1174 (2001).
Pierschbacher et al, "Influence of Stereochemistry of the Sequence Arg-Gly-Asp-Xaa on Binding Specificity in cell Adhesion", The Journal of Biological Chemistry 262(36):17294-17298 (1987).
Pillai et al, "Outer membrane protein (OMP) based vaccine for Neisseria meningitidis serogroup B", Vaccine 23:2206-2209 (2005).
Pizza et al, "Factor H-binding protein, a unique meningococcal vaccine antigen", Vaccine 26(Supp8):I46-I48 (2008).
Pizza et al, "Identification of Vaccine Candidates Against Serogroup B Meningococcus by Whole-Genome Sequencing", Science 287:1816-1820 (2000).
Pizza, Preparation of Meningococcal Antigens (2005), available at: http://cordis.europa.eu/search/index.cfm?fuseaction=result.document&RS_LANG=EN&RS_RCN=7461241&q=.
Podbielski et al, "The Group A Streptococcal virR49 Gene Controls Expression of Four Structural vir Regulon Genes", Infection and Immunity 63(1):9-20 (1995).
Pollitt et al, "Effect of Amino Acid Substitutions at the Signal Peptide Cleavage Site of the *Escherichia coil* Major Outer Membrane Lipoprotein", The Journal of Biological Chemistry 261(4):1835-1837 (1986).
Poolman et al, "Colony variants of Neisseria meningitidis strain 2996 (B-2b:P1.2): influence of class-5 outer membrane proteins and lipopolysaccharides", J Med Microbiol 19(2):203-209 (1985).
Poolman, "Bacterial Outer Membrane Protein Vaccines: The Meningococcal Example", Advances in Experimental Medicine & Biology 397:73-77 (1996).
Poolman, "Development of a meningococcal vaccine," Infectious Agents and Disease 4(1):13-28 (1995).
Preliminary Opinion of the Opposition Division in Opposition against Novartis EP 1 645 631 dated Jun. 24, 2011.
Proft et al, "Identification and Characterization of Novel Superantigens from *Streptococcus pyogenes*", J. Exp. Med. 189(1):89-101 (1999).
Progress through the Sanger Institute FTP Server, submitted in Opposition Proceedings against Novartis EP1645631 on May 8, 2009.
Prome et al, "Characterization of new amino-terminal blocking groups in the normal human adult hemoglobin HbA1b", Eur. Mass Spectrom. 1(2):195-201 (1995).
Prome et al, "Structure of the Human Adult Hemoglobin Minor Fraction A1b bu Electrospray and Secondary Ion Mass Spectrometry. Pyruvic Acid as Amino-Terminal Blocking Group", The Journal of Biological Chemistry 266 (20):13050-13054 (1991).
Prosecution history of U.S. Appl. No. 13/455,326, dated Apr. 26, 2013, (Third-party submission under 37 CFR 1.290).
PSORT analysis of 200 of the sequences disclosed in PCT/US99/09346, submitted in Opposition Proceedings against Novartis EP1645631 on May 25, 2010 Part 1.
PSORT analysis of 200 of the sequences disclosed in PCT/US99/09346, submitted in Opposition Proceedings against Novartis EP1645631 on May 25, 2010 Part 2.
PSORT analysis of Seq ID Nos. 4 and 6, and of 'Contig295' 300mer, submitted in Opposition Proceedings against Novartis EP1645631 on May 8, 2009.
PSORT prediction result for Seq ID No. 2, submitted in Opposition Proceedings against Novartis EP1645631 on May 25, 2010.
Pugsley, "The Complete General Secretory Pathway in Gram-Negative Bacteria", Microbiological Reviews 57 (1):50-108 (1993).
Quinn et al, "Immunological Relationship between the Class I Epitope of Streptococcal M Protein and Myosin", Infection and Immunity 66(9):4418-4424 (1998).
Random House Dictionary, Random House, New York, p. 546 (1984).
Reda et al, "Phylogenetic Distribution of Streptococcal Superantigen SSA Allelic Variants Provides Evidence for Horizontal Transfer of ssa within *Streptococcus pyogenes*", Infection and Immunity 64(4):1161-1165 (1996).
Registration document for VA-MENGOC-BC® Vaccine Together with Translation Into English and Translation Certificate.
Resinger, et al., "Safety, Tolerability, and Immunogenicity of Gardasil Given Concomitantly with Menactra and Adacel" Pediatrics; 125 (6):1142-1151 (2010).
Richmond, et al, On Behalf of the 2001 Study Investigators, "Safety, immunogenicity, and tolerability of meningococcal serogroup B bivalent recombinant lipoprotein 2086 vaccine in healthy adolescents: a ranomised, single-blind, placebo-controlled, phase 2 trial", www.thelancet.com/infection, 13 pages, Published online May 7, 2012.
Rinaudo et al, "Vaccinology in the genome era", The Journal of Clinical Investigation, 119(9):2515-2525 (2009).

(56) References Cited

OTHER PUBLICATIONS

Jiang et al, "Broad vaccine coverage predicted for a bivalent recombinant factor H binding protein based vaccine to prevent serogroup B meningococcal disease", Vaccine 28:6086-6093 (2010).
Johnson et al., "Analysis of the Human Ig Isotype Response to Lactoferrin Binding Protein A from Neisseria meningitidis", FEMS Immunology and Medical Microbiology 25(4):349-354 (1999).
Jones et al, "The Importance of the Location of Antibody Binding on the M6 Protein for Opsonization and Phagocytosis of Group A M6 Streptococci", J. Exp. Med. 167:1114-1123 (1988).
JVCI-CMR website showing Z2491 Sanger sequence (http://cmr.jvci.org/tigr-scripts/CMR/shared/Genomes.cgi and inks) printed on Jul. 1, 2010.
Kafri et al, "A Packaging Cell Line for Lentivirus Vectors", Journal of Virology 73(1):576-584 (1999).
Kaplitt et al, "Expression of a Functional Foreign Gene in Adult Mammalian Brain following in Vivo Transfer via a Herpes Simplex Virus Type 1 Defective Viral Vector", Molecular and Cellular Neurosciences 2:320-330 (1991).
Kihlberg et al, "Protein H, an Antiphagocytic Surface Protein in *Streptococcus pyogenes*", Infection and Immunity 67 (4):1708-1714 (1999).
Klein et al, "Distinctive properties of signal sequences from bacterial lipoproteins", Protein Engineering 2(1):15-20 (1988).
Koeberling at el, "Bactericidal Antibody Responses Elicited by a Meningococcal Outer Membrane Vesicle Vaccine with Overexpressed Factor H-binding Protein and Genetically Attenuated Endotoxin", The Journal of Infectious Diseases 198:262-270 (2008).
Koebnik, "Proposal for a peptidoglycan-associating alpha-helical motif in the C-terminal regions of some bacterial cell-surface proteins", Molecular Microbiology 16(6):1269-1270 (1995).
Kohler et al, "Continuous cultures of fused cells secreting antibody of predefined specificity", Nature 256:495-497 (1975).
Kuipers et al, "Improved site-directed mutagenesis method using PCR", Nucleic Acids Research 19(16):4558 (1991).
Kuo et al, "Efficient Gene Transfer into Primary Murine Lymphocytes Obviating the Need for Drug Selection", Blood 82(3):845-852 (1993).
Kyte et al, "A Simple Method for Displaying the Hydropathic Character of a Protein", J. Mol. Biol. 157:105-132 (1982).
Landt et al, "A general method for rapid site-directed mutagenesis using the polymerase chain reaction", Gene 96:125-128 (1990).
Lasalle et al, "An Adenovirus Vector for Gene Transfer into Neurons and Glia in the Brain", Science 259:988-990 (1993).
Lebkowski et al, "Adeno-Associated Virus: a Vector System for Efficient Introduction and Integration of DNA into a Variety of Mammalian Cell Types", Molecular and Cellular Biology 8(10):3988-3996 (1988).
Levrero et al, "Defective and nondefective adenovirus vectors for expressing foreign genes in vitro and in vivo", Gene 101:195-202 (1991).
Liu et al, "Chimeric mouse-human IgG1 antibody that can mediate lysis o f cancer cells", Proc. Natl. Acad. Sci. 84:3439-3443 (1987).
Liu et al, "High-throughput imaging of bacterial colonies grown on filter plates with application to serum bactericidal assays", Journal of Immunological Methods 292(1-2):187-193 (2004).
Loessner et al, "Evidence for a Holin-Like Protein Gene Fully Embedded Out of Frame in the Endolysin Gene of *Staphylococcus aureus* Bacteriophage 187", Journal of Bacteriology 181(15):4452-4460 (1999).
Lukashin et al, "GeneMark.hmm: new solutions for gene finding", Nucleic Acids Research 26(4):1107-1115 (1998).
Lukomski et al, "Extracellular Cysteine Protease Produced by *Streptococcus pyogenes* Participates in the Pathogenesis of Invasive Skin Infection and Dissemination in Mice", Infection and Immunity 67(4):1779-1788 (1999).
Lunn et al, "Effects of Prolipoprotein Signal Peptide Mutations on Secretion of Hybrid Prolipo-beta-lactamase in *Escherichia coli*", The Journal of Biological Chemistry 262(17):8318-8324 (1987).

Machy et al, "Gene transfer from targeted liposomes to specific lymphoid cells by electroporation", Proc. Natl. Acad. Sci. 85:8027-8031 (1988).
Madore, "Characterization of immune response as an indicator of Haemophilus influenzae type b vaccine efficacy", The Pediatric Infectious Disease Journal 17(9):Supplement:S207-S210 (1998).
Mann, et al, "Construction of a Retrovirus Packaging Mutant and Its Use to Produce Helper-Free Defective Retrovirus", Cell 33:153-159 (1983).
Markowitz et al, "A Safe Packaging Line for Gene Transfer: Separating Viral Genes on Two Different Plasmids", Journal of Virology 62(4):1120-1124 (1988).
Marshall, H.S., et al., "A phase 2 open-label safety and immunogenicity study of a meningococcal B bivalent LP2086 vaccine in healthy adults", Vaccine, 31(12):1569-1575 (2013).
Martin et al, "Highly Conserved Neisseria meningitidis Surface Protein Confers Protection against Experimental Infection", J. Exp. Med. 185(7):1173-1183 (1997).
Mascioni et al, "Structural Basis for the Immunogenic Properties of the Meningococcal Vaccine Candidate LP2086", Journal of Biological Chemistry 284(13):8738-8746 (2009).
Masignani et al, "Vaccination against Neisseria meningitidis Using Three Variants of the Lipoprotein GNA1870", J. Exp. Med. 197(6):789-799 (2003).
Matsuka et al, "Fibrinogen Cleavage by the *Streptococcus pyogenes* Extracellular Cysteine Protease and Generation of Antibodies That Inhibit Enzyme Proteolytic Activity", Infection and Immunity 67(9):4326-4333 (1999).
Mazmanian et al, "*Staphylococcus aureus* Sortase, an Enzyme that Anchors Surface Proteins to the Cell Wall", Science 285:760-763 (1999).
McAtee et al, "Characterization of a Helicobacter pylori vaccine candidate by proteome techniques", Journal of Chromatography B, Biomedical Sciences and Applications 714:325-333 (1998).
McAtee et al, "Identification of Potential Diagnostic and Vaccine Candidates of Helicobacter pylori by "Proteome" Technologies", Helicobacter 3(3):163-169 (1998).
McAtee et al, "Identification of Potential Diagnostic and Vaccine Candidates of Helicobacter pylori by Two-Dimensional Gel Electrophoresis, Sequence Analysis, and Serum Profiling", Clinical and Diagnostic Laboratory Immunology 5(4):537-542 (1998).
McCormick, "Human Gene Therapy: The First Round", BioTechnology 3(8):689-693 (1985).
McGuiness et al, "Class 1 outer membrane protein of Neisseria meningitidis: epitope analysis of the antigenic diversity between strains, implications for subtype definition and molecular epidemiology", Molecular Microbiology 7 (4):505-514 (1993).
McNeil et al, "Detection of LP2086 on the cell surface of Neisseria meningitidis and its accessibility in the presence of serogroup B capsular polysaccharide", Vaccine 27:3417-3421 (2009).
Mejlhede et al, "Ribosomal—1 Frameshifting during Decoding of Bacillus subtilis cdd Occurs at the Sequence CGA AAG", Journal of Bacteriology 181(9):2930-2937 (1999).
Menactra prescribing information, http://www.fda.gov/downloads/BiologicsBloodVaccines/Vaccines/ApprovedProducts/UCM131170.pdf, revised Aug. 26, 2014, accessed Feb. 14, 2015.
Menactra, Australian Public Assessment Report for Groups A, C, Y and W-135 Meningococcal Polysaccharide Diphtheria Toxoid Conjugate Vaccine, https://www.tga.gov.au/file/1277/download , Aug. 31, 2011, accessed Feb. 13, 2015 (part 1 and 2).
Mencevax, New Zealand data sheet, http://www.medsafe.govt.nz/profs/datasheet/m/Mencevaxacwyinj.pdf, date of preparation Mar. 25, 2014, accessed Feb. 14, 2015.
Menveo Package insert, http://www.fda.gov/downloads/BiologicsBloodVaccines/Vaccines/ApprovedProducts/UCM201349.pdf, accessed Feb. 19, 2015, revised Aug. 2013.
Milagres et al., "Specificity of Bactericidal Antibody Response to Serogroup B Miningococcal Strains in Brazilian Children after Immunization with an Outer Membrane Vaccine", Infection and Immunity 66(10):4755-4761 (1998).
Miller et al, "Improved Retroviral Vectors for Gene Transfer and Expression", BioTechniques 7(9):980-990 (1992).

(56) References Cited

OTHER PUBLICATIONS

Minutes of Oral Proceedings in Opposition against Novartis EP 1 645 631 dated Mar. 5, 2012.
Mir et al, "Long-term, high level in vivo gene expression after electric pulse-mediated gene transfer into skeletal muscle", Academie des sciences 321:893-899 (1998).
Moe, et al., "Sequential Immunization with Vesicles Prepared from Heterologous Neisseria meningitidis Strains Elicits Broadly Protective Serum Antibodies to Group B Strains", Infection and Immunity, Nov. 2002, 70:11, 6021-6031.
ASSAF-CASALS and DBAIBO, Meningococcal Quadrivalent Tetanus Toxoid Conjugate Vaccine (MenACWY-TT, Nimenrix): A review of Its Immunogenicity, Safety, Co-Adminstration, and Antibody Persistence, Human Vaccines and Immunotherapeutics, 12(7):1825-1837 (2016).
Baker, "Prevention of Meningococcal Infection in the United States" Current Recommendations and Future Considerations, Journal of Adolescent Health, 59(2): S29-S37 (2016).
Biagini, et al., "Expression of Factor H Binding Protein in Meningococcal Strains Can Vary at Least 15-Fold and is Genetically Determined", Preceedings of the National Academy of Sciences, 113:1: (2016).
Gandhi, et al., Characteristics of a New Meningococcal Serogroup B Vaccine, Bivalent rLP2086 (MenB-FHbp: Trumenba) (2016).
Lee, L., et al, "Clinical Review STN: 125549 Application Type Biologics License Application STN# 125549 CBER Received Date Division/Office DVRPA/OVRR Priority Review Yes Reviewer Name", XP055265361, Retrieved from the Internet: URL:http://www.fda.gov/downloads/BiologicsBloodVaccines/Vaccines/ApprovedProducts/UCM424626, Jun. 16, 2014.
McNeil, L., "Role of Factor H Binding Protein in Neisseria Meningitidis Virulence and Its Potential as a Vaccine Candidate to Broadly Protect Against Meningococcal Disease" Microbiology and Molecular Biology Reviews, 77(2): 234-252 (2013).
Polakowski, L., "Pharmacovigilance Plan Review—Trumenba", XP055266007, Retrieved form the Internet: URL: http://www/fda.gov/downloads/BiologicsBlood/Vaccines/Vaccines/ApprovedProducts/UCM424630: pp. 1-28, Nov. 23, 2014.
Saez-Llorens, et al., "Immunogenicity and Safety of Investigational Vaccine Formulations Against Meningococcal Serogroups A, B, C, W, and Y in Healthy Adolescents" Human Vaccines and Immunotherapeutics, 11(6):1507-1517 (2015).
Computational Molecular Biology: Sources and Methods for Sequence Analysis, Lesk A.M. et., Oxford University Press, New York, 1988.
Courtney et al, "Cloning, Sequencing, and Expression of a Fibronectin/Fibrinogen-Binding Protein from Group A Streptococci", Infection and Immunity 62(9):3937-3946 (1994).
Cserzo et al, "Prediction of transmembrane alpha-helices in prokaryotic membrane proteins: the dense alignment surface method", Protein Engineering 10(6):673-676 (1997).
Cunningham et al, "Immunological Crossreactivity Between the Class I Epitope of Streptococcal M Protein and Myosin", Adv Exp Med Biol 418:887-892 (1997).
Curiel et al, "High-Efficiency Gene Transfer Mediated by Adenovirus Coupled to DNA-Polylysine Complexes", Human Gene Therapy 3:147-154 (1992).
Curriculum Vitae of Professor Paul M. Dunman, Ph.D., submitted in Opposition Proceedings against Novartis EP 1 645631 on Sep. 14, 2011.
Curriculum Vitae of Lakshmi Khandke, Ph.D., submitted in Opposition Proceedings against Novartis EP1409013 on Nov. 18, 2011.
Dale et al, "Hyaluronate Capsule and Surface M Protein in Resistance to Opsonization of Group A Streptococci", Infection and Immunity 64(5):1495-1501 (1996).
Dale et al, "Passive Protection of Mice Against Group A Streptococcal Pharyngeal Infection by Lipoteichoic Acid", The Journal of Infectious Diseases 169:319-323 (1994).
Dale et al, "Recombinant, octavalent group A streptococcal M protein vaccine", Vaccine 14(10):944-948 (1996).

Database EMBL [Online] EBI, Kohara, Y., "Caenorhabditis elegans cDNA clone yk26f2: 5' end, single read," Database accession No. D35881 (Aug. 13, 1994).
Database Geneseq 'Online', "N. gonorrhoeae amino acid sequence Seq ID 1586", XP002320505, Mar. 7, 2003.
Database Geneseq 'Online', "Neisseria meningitidis ORF 741 protein sequence Seq ID No. 2536", XP002320506, Mar. 21, 2000.
Database Geneseq Online, "N. meningitidis NL096 fHBP protein fragment Seq ID 76", XP002703350, Database accession No. AXQ90374, Nov. 26, 2009.
Database Geneseq Online, "Neisseria meningitides ORF2086 protein-encoding gene SedID61" AAY75530, Jan. 29, 2004.
Database Geneseq Online, "Neisseria meningitidis ORF2086 protein-encoding gene SedID61" AAZ54292-NT, Jan. 29, 2004.
Database Geneseq Online, "Neisseria meningitidis modified fHBP fusion protein SEQ:140", XP002703351, Database accession No. AZG10689, Apr. 28, 2011.
Database Geneseq Online, "Neisseria meningitidis modified fHBP NL096 Seq:76", XP002703352,Database accession No. AZG10625, Apr. 28, 2011.
Database UniPro 'Online', "Hypothetical Protein NMB1870", XP002308111, Oct. 1, 2000.
Database UniProt 'Online', "Putative lipoprotein N meningitidis (Serotype A)", XP002320503, Oct. 1, 2000.
"Database Uniprot [Online] Jul. 4, 2004, "SubName: Full=Factor H binding protein variant A05_001";Flags: Fragment", retrieved from EBI; Uniprot database accession No. Q6VS29; Database entry from Oct. 28, 2014, entry version 29, sequence version 1See strains Neisseria meningitidis M98-250732 & M98250771.
"Database Uniprot [Online] Jul. 5, 2004, "Factor H binding protein variant A22_001"; Flags: Fragment",retrieved from EBI; Uniprot database accession No. Q6VS35; Database entry from Oct. 28, 2014, entryversion 28, sequence version 2 updated on Sep. 23, 2008See strains Neisseria meningitidis: CDC-1034 and L4-891.
Database UniProt Online, "Subname: Full=Factor H binding protein variant A62_001; Subname: Full=Factor H binding protein variant A62_002; Flags: Fragment", XP002703353, Database accession No. C0JF81, May 5, 2009.
Datasheet for MENCEVAX™, International Data Sheet version 2.1 (May 15, 2000).
Datasheet for MENOMUNE™, product information as of Feb. 2001.
Datasheet for MeNZB® vaccine product prepared Jun. 23, 2009.
De et al, "Purification and characterization of *Streptococcus pneumoniae* palmitoylated pneumococcal surface adhesin A expressed in *Escherichia coli*", Vaccine 18:1811-1821 (2000).
Declaration by Dr. Julian Parkhill, submitted in Opposition Proceedings against Novartis EP1645631 on Jul. 23, 2008.
Declaration by Professor Paul Dunman, submitted in Opposition Proceedings against Novartis EP1645631 on Sep. 14, 2011.
Declaration of Dr. Ellen Murphy, submitted in Opposition Proceedings against Novartis EP 1 645 631 on Sep. 14, 2011.
Declaration of Emilio A. Emini, Ph.D., submitted in Opposition Proceedings against Novartis EP1645631 on Nov. 3, 2011.
Declaration of Lakshmi Khandke, Ph.D., submitted in Opposition Proceedings against Novartis EP1409013 on Dec. 21, 2011.
Definition of "epitope" from Henderson's Dictionary of Biological Terms, 11th edition, Eleanor Lawrence ed., pp. 37, 184 and cover pages (1997).
Delgado et al., "Lipoprotein NMB0928 from Neisseria meningitidis Serogroup B as a Novel Vaccine Candidate", Vaccine 25:8420-8431 (2007).
Dempsey et al., "The physical map of the chromosome of a serogroup A strain of Neisseria meningitidis shows complex rearrangements relative to the chromosomes of the two mapped strains of the closely related species N. gonorrhoeae," Journal of Bacteriology 177(22):6390-6400 (1995).
Devereux et al, "A comprehensive set of sequence analysis programs for the VAX", Nucleic Acids Research 12 (1):387-395 (1984).
Duby et al, "Using Synthetic Oligonucleotides as Probes", Current Protocols in Molecular Biology, Supp. 2, 6.4.1-6.4.10 (1993).

(56) References Cited

OTHER PUBLICATIONS

Eddy, "Hidden Markov models", Current Opinion in Structural Biology 6:361-365 (1996).
Ellen et al, "M Protein-Associated Adherence of *Streptococcus pyogenes* to Epithelial Surfaces: Prerequisite for Virulence", Infection and Immunity 5(5):826-830 (1972).
Ellis, "New Technologies for Making Vaccines", Vaccines, Plotkin et al. editors, W.B. Saunders Company, Philadelphia, Chapter 29, pp. 568-575 (1988).
Eng et al, "An Approach to Correlate Tandem Mass Spectral Data of Peptides with Amino Acid Sequences in a Protein Database", J Am Soc Mass Spectrom 5:976-989 (1994).
EP Application No. 070751615 Response to Communication submitted Oct. 28, 2009.
Erdile et al, "Role of Attached Lipid in Immunogenicity of Borrelia burgdorferi OspA", Infection and Immunity 61 (1):81-90 (1993).
Farley et al., "Characterization, cloning and expression of different subfamilies of the ORF2086 gene from Neisseria meningitidis", Abstracts of the Thirteenth International Pathogenic Neisseria Conference, (Ed) Caugant et al., Oslo, Norway, p. 124, Sep. 1-6, 2002.
Farley, J., et al. poster entitled "Characterization, Cloning and Expression of Different Subfamlies of the ORF 2086 gene Neisseria Meningitidis", presented at the Thirteenth International Pathogenic Neisseria Conference (the 'IPNC Dslo 2002'), hosted at the Norwegian Institute of Public Health, Oslo, Norway between Sep. 1, 2002 and Sep. 6, 2002, as evidenced by photographs and transcript thereof.
Feavers et al, "Meningococcal protein antigens and vaccines", Vaccine 275:B42-B50 (2009).
Felgner et al, "Cationic liposome-mediated transfection", Nature 337:387-388 (1989).
Felgner et al, "Lipofection: a highly efficient, lipid-mediated DNA-transfection procedure", Proc. Natl. Acad. Sci. 84:7413-7417 (1987).
Final Written Submission in Preparation of Oral Proceedings in Opposition against Novartis EP 1 645 631 submitted Sep. 14, 2011.
Findlow et al, "Multicenter, Open-Label, Randomized Phase II Controlled Trial of an Investigational Recombinant Meningococcal Serogroup B Vaccine With and Without Outer Membrane Vesicles, Administered in Infance", Clinical Infectious Diseases 51(10):1127-1137 (2010).
Tettelin et al, "Complete Genome Sequence of Neisseria meningitidis Serogroup B Strain MC58", Science 287:1809-1815 (2000).
Tondella et al, "Distribution of Neisseria meningitidis Serogroup B Serosubtypes and Serotypes Circulating in the United States", Journal of Clinical Microbiology 38(9):3323-3328 (2000).
Ton-That et al, "Purification and characterization of sortase, the transpeptidase that cleaves surface proteins of *Staphylococcus aureus* at the LPXTG motif", Proc Natl Acad Sci 96(22):12424-12429 (1999).
Uli, et al., "Outer Membrane Vesicles of VA-MENGOC-BC Vaccine Against Serogroup B of Neisseria Meningitidis: Analysis of Protein Components by Two-Dimensional Gel Electrophoresis and Mass Spectrometry", Proteomics, 2006, 6, 3389-3399.
Ulmer et al, "Heterologous Protection Against Influenza by Injection of DNA Encoding a Viral Protein", Science 259:1745-1748 (1993).
University of Oklahoma-Neisseria gonorrhoeae webpage to retrieve genome [online] URL: http://dna1.chem.ou.edu/gono.html, Apr. 5, 2004, accessed Aug. 3, 2012.
U.S. Pat. No. 8,398,988 B2 Prosecution History (Feb. 23, 2012-Feb. 27, 2013).
Van Der Ende, A., et al., "Deletion of porA by Recombination between Clusters of Repetitive Extragenic Palindromic Sequences in Neisseria meningitidis", Infection and Immunity, 67(6):2928-2934 (1999).
Van Der Ende, A., et al., "Multiple Mechanisms of Phase Variation of PorA in Neisseria meningitidis", Infection and Immunity 68(12):6685-6690 (2000).
Van Der Ley et al., "Construction of Neisseria meningitidis Strains Carrying Multiple Chromosomal the porA gene for Use in the production of a Multivalent Outer Membrane Vesicle Vaccine", Vaccine 13(4):401-407 (1995).
Wahl et al, "Improved Radioimaging and Tumor Localization with Monoclonal F(ab')2", J Nucl Med 24:316-325 (1983).
Webster's II New Riverside University Dictionary, The Riverside Publishing Company, p. 933 (1984).
Weldingh et al, "Two-Dimensional Electrophoresis for Analysis of *Mycobacterium* tuberculosis Culture Filtrate and Purification and Characterization of Six Novel Proteins", Infection and Immunity 66(8):3492-3500 (1998).
Welsch et al, Factor H and Neisserial pathogenesis', Vaccine 26(Supp8):I40-I45 (2008).
Welsch et al, "Protective Activity of Monoclonal Antibodies to Genome-Derived Neisserial Antigen 1870, a Neisseria meningitidis Candidate Vaccine", The Journal of Immunology 172:5606-5615 (2004).
Wiertz et al, "T-Cell Responses to Outer Membrane Proteins of Neisseria meningitidis: Comparative Study of the Opa, Opc, and Por A Proteins", Infection and Immunity 64(1) 298-304 (1996).
Williams et al, "Introduction of foreign genes into tissues of living mice by DNA-coated microprojectiles", Proc. Natl. Acad. Sci. 88:2726-2730 (1991).
Wilson et al, "Hepatocyte-directed Gene Transfer in Vivo Leads to Transient Improvement of Hypercholesterolemia in Low Density Lipoprotein Receptor-deficient Rabbits", The Journal of Biological Chemistry 267(2):963-967 (1992).
Witze et al, Mapping Protein Post-Translational Modifcations with Mass Spectrometry, Nat Methods, Oct.; 4(10): 798-806 (2007).
Wolf et al, "Conditions Affecting Direct Gene Transfer into Rodent Muscle In Vivo", Biotechniques, 11(4):474-485 (1991).
Wolff et al, "Direct Gene Transfer into Mouse Muscle in Vivo", Science 247:1465-1468 (1990).
Woods et al., "Resistance to Meningococcemia Apparently Conferred by Anti-H.8 Monoclonal Antibody Is Due to Contaminating Endotoxin and Not to Specific Immunoprotection", Infection and Immunity 55(8):1927-1928 (1987).
Wu et al, "Receptor-mediated Gene Delivery and Expression in Vivo", The Journal of Biological Chemistry 263 (29):14621-14624 (1988).
Wu et al, "Receptor-mediated in Vitro Gene Transformation by a Soluble DNA Carrier System", The Journal of Biological Chemistry 262(10):4429-4432 (1987).
Wyeth Neisseria Meningitidis Serogroup B Vaccine, Vaccine and Related Biological Products Advisory Committee Pre-Meeting Background Document, URL:http://www.fda.gov/downloads/AdvisoryCommittees/CommitteesMeetingMaterials/BloodVaccinesandOtherBiologics/VaccinesandRelatedBiologicalProductsAdvisoryCommittee/UCM249479.pdf, Mar. 4, 2011.
Yakushi et al, "A new ABC transporter mediating the detachment of lipid-modified proteins from membranes", Nature Cell Biology 2:212-218 (2000).
Yakushi et al, "Lethality of the Covalent Linkage between Mislocalized Major Outer Membrane Lipoprotein and the Peptidoglycan of *Escherichia coli*", Journal of Bacteriology 179(9):2857-2862 (1997).
York, "Pfizer's Investigational Vaccine, rLP2086, for Invasive Meningococcal Serogroup B Disease", Sabin Vaccine Institute, http://www.sabin.org/sites/sabin.org/files/Laura%20J%20York.pdf, accessed Aug. 1, 2014.
Yutsudo et al, "The Gene Encoding a New Mitogenic Factor in a *Streptococcus pyogenes* Strain Is Distributed Only in Group A Streptococci", Infection and Immunity 62(9):4000-4004 (1994).
Zagursky et al, "Bioinformatics: Use in Bacterial Vaccine Delivery", BioTechniques 31(3):636-659 (2001).
Zavascki et al, "First Case Report of Neisseria lactamica Causing Cavitary Lung Disease in an Adult Organ Transplant Recipient", Journal of Clinical Microbiology 44(7):2666-2668 (2006).
Zhu et al, "Evaluation of Recombinant Lipidated P2086 Protein as a Vaccine Candidate for Group B Neisseria meningitidis in a Murine Nasal Challenge Model", Infection and Immunity 73(10):6838-6845 (2005).

(56) References Cited

OTHER PUBLICATIONS

Zollinger, "New and Improved Vaccines Against Meningococcal Disease", New Generation Vaccines, 2nd Ed., Myron M. Levine, et al. eds., Marcel Dekker, Inc., New York, NY pp. 469-488 (1997).
Zufferey et al, "Self-Inactivating Lentivirus Vector for Safe and Efficient In Vivo Gene Delivery", Journal of Virology 72(12):9873-9880 (1998).
Deasy et al, Challenges for Development of Meningococcal Vaccines in Infants and Children, Expert Review of Vaccines 10(3): 335-343 (2011).
Aasel et al., "Most antibodies to PorB and Rmp do not bind to viable meningococci, but bind strongly to ethanol-killed bacteria", Abstract from the 11th International Pathogenic Neisseria Conference (Nice France, Nov. 1-6, 1998), pp. 37-38 (http://neisseria.org/ipnc/history.shtml).
Abdillahi et al, "Whole-cell ELISA for typing Neisseria meningitidis with monoclonal antibodies", FEMS Microbiology Letters 48:367-371 (1987).
Abdillahi et al, "Neisseria meningitidis group B serosubtyping using monoclonal antibodies in whole-cell Elisa", Microbial Pathogenesis 4:27-32 (1988).
Achtman et al, "Epidemic Spread and Anitgenic Variability of Neisseria Meningitidis", Trends in Microbiology 3 (5):186-192 (1995).
Adacel Prescribing information, http://www.fda.gov/downloads/biologicsbloodvaccines/vaccines/approvedproducts/ucm142764.pdf, "Revised: [XX/201X]", accessed Feb. 14, 2015.
Alm et al, "Genomic-sequence comparison of two unrelated isolates of the human gastric pathogen Helicobacter pylori", Nature 397:176-180 (1999).
Altschul et al, "Basic Local Alignment Search Tool", J. Mol. Biol. 215:403-410 (1990).
Altschul et al, "Protein database searches for multiple alignments", Proc. Natl. Acad. Sci. 87:5509-5513 (1990).
Altschul et al, "Gapped BLAST and PSI-BLAST: a new generation of protein database search programs", Nucleic Acids Research 25(17): 3389-3402 (1997).
Ambrosch et al, "Immunogenicity and side-effects of a new tetravalent meningococcal polysaccharide vaccine", Bulletin of the World Health Organization 61(2):317-323 (1983).
Andersen, et al, "Immune Responses to Meningococcal Outer Membrane Vesicles After Intranasal Immunisation", Twelfth International Pathogenic Neisseria Conference, Nov. 12-17, 2000, Galveston, Texas (Abstract #057).
Anderson, "Techniques for the preservation of three-dimensional structure in preparing specimens for the electron microscope", Transactions of the New York Academy of Sciences, 13:130-134 (1951).
Anderson et al; "Potential Impact of the Bivalent rLP2086 Vaccine on Neisseria meningitidis Invasive Disease and Carriage Isolates in Two Adolescent Populations"; poster presented at the 30th Annual Meeting of the European Society for Paediatric Infectious Diseases; May 8-12, 2012; Thessaloniki, Greece; http://epostersonline.s3.amazonaws.com/espid2012/espid2012.02400cf.NORMAL.pdf, May 12, 2012.
Anderson, "Elicitation of Functional Antibodies by a Group B Neisseria meningitidis Bivalent rLP2086 Vaccine in Non-Human Primates", NHP IPNC Poster Presentation 2008.
Ausubel et al, Current Protocols in Molecular Biology, Sections 2.10, 6.3 & 6.4 (1995).
Bambini et al, "Distribution and genetic variability of three vaccine components in a panel of strains representative of the diversity of serogroup B meningococcus", Vaccine 27:2794-2803 (2009).
Bantam Medical Dictionary, Third Edition, pp. 302-303 (2000).
Barbour et al, "New tricks of tick-borne pathogen", Nature 390:553 & 555 (1997).
Bateman et al, "The Pfam Protein Families Database", Nucleic Acids Research 28(1):263-266 (2000).
Beard et al, "Transcription Mapping of Mouse Adenovirus Type 1 Early Region 3", Virology 175:81-90 (1990).
Beernink et al, "Prevalence of Factor H-Binding Protein Variants and NadA among Meningococcal Group B Isolates from the United States: Implications for the Development of a Multicomponent Group B Vaccine", The Journal of Infectious Diseases 195:1472-1479 (2007).
Beernink, P.T., et al., "The modular architecture of meningococcal factor H-binding protein", Microbiology, 155:2873-2883 (2009).
Bender et al, "Evidence that the Packaging Signal of Moloney Murine Leukemia Virus Extends into the gag Region", Journal of Virology 61(5):1639-1646 (1987).
Benson, "Tandem repeats finder: a program to analyze DNA sequences", Nucleic Acids Research 27(2):573-580 (1999).
Bergmann et al, "An endogenously synthesized decamer peptide efficiently primes cytotoxic T cells specific for the HIV-1 envelope glycoprotein", Eur. J. Immunol., 23(11):2777-2781 (1993).
Bergmann et al, "Flanking Residues Alter Antigenicity and Immunogenicity of Multi-Unit CTL Epitopes", The Journal of Immunology, 157:3242-3249 (1996).
Bernfield et al., "Identification of a novel vaccine candidate for group B Neisseria meningitidis", Abstracts of the Thirteenth International Pathogenic Neisseria Conference, (Ed) Caugant et al. Oslo, Norway, p. 116, Sep. 1-6, 2002.
Bernstein et al, "Gene Transfer with Retrovirus Vectors", Genet. Eng. 7:235-261 (1985).
Better et al, Escherichia coli Secretion of an Active Chimeric Antibody Fragment, Science 240:1041-1043 (1988).
Beuvery et al, "Preparation and Immunochemical Characterization of Meningococcal Group C Polysaccharide-Tetanus Toxoid Conjugates as a New Generation of Vaccines", Infection and Immunity 40(1):39-45 (1983).
Beuvery et al, "Preparation and Physicochemical and Immunological Characterization of Polysaccharide-Outer Membrane Protein Complexes of Neisseria meningitidis", Infection and Immunity 40(1):369-380 (1983).
Biocomputing: Informatics and Genome Projects, Smith D.W., ed., Academic Press, New York (1994).
Bjune, et al., "Effect of Outer Membrane Vesicle Vaccine Against Group B Meningococcal Disease in Norway", The Lancet, 338(8775):1093-1096 (1991).
Borrow et al, "Meningococcal surrogates of protection-serum bactericidal antibody activity", Vaccine 23:2222-2227 (2005).
Boslego et al, "Chapter 17: Gonorrhea Vaccines", Vaccines and Immunotherapy, SJ Cryz Jr. ed., Pergamon Press, pp. 211-223 (1991).
Boulianne et al, "Production of functional chimaeric mouse/human antibody", Nature 312:643-646 (1984).
Brown, "Hybridization Analysis of DNA Blots", Current Protocols in Molecular Biology, Supp. 21, 2.10.1-2.10.16 (1993).
Budroni, S. et al., "Neisseria Meningitidis is Structured in Clades Associated with Restriction Modification Systems that Modulate Homologous Recombination", PNAS, Mar. 15, 2011,108 (11): 4494-4499 and supporting information pp. 1-17 (2011).
Cabilly et al, "Generation of antibody activity from immunoglobulin polypeptide chains produced in Escherichia coli", Proc. Natl. Acad. Sci. 81:3273-3277 (1984).
Callahan, P.M., et al., "The Importance of Surface Charge in the Optimization of Antigen-Adjuvant Interactions", Pharmaceutical Research, 8(7):851-858 (1991).
Cannon, "Conserved Lipoproteins of Pathogenic Neisseria Species Bearing the H.8 Epitope: Lipid-Modified Azurin and H.8 Outer Membrane Protein", Clinical Microbiology Reviews 2(Suppl):S1-S4 (1989).
Cantini et al, "Solution Structure of the Immunodominant Domain of Protective Antigen GNA1870 of Neisseria meningitidis", The Journal of Biological Chemistry 281(11):7220-7227 (2006).
Carillo et al, "The Multiple Sequence Alignment Problem in Biology", SIAM J. Appl. Math. 48(5):1073-1082 (1988).
Chao et al, "Endocarditis due to Neisseria sicca: Report of One Case", Acta Paed Sin 38(3):229-231 (1997).
Chen et al, "Cloning and Expression of the Streptococcal C5a Peptidase Gene in Escherichia coli: Linkage to the Type 12 M Protein Gene", Infection and Immunity 57(6):1740-1745 (1989).

(56) References Cited

OTHER PUBLICATIONS

Chen et al., "Determination of the Optimal Aligned Spacing Between the Shine—Dalgarno Sequence and the Translation Initiation Codon of *Escherichia coli* mRNAs", Nucleic Acids Research 22(23):4953-4957 (1994).

Cheetham, et al., "An HPLC Method for the Determination of Acetyl and Pyruvyl Groups in Polysaccharides, Carbohydrade Polymers", School of Chemistry, The University of New South Wales, 5 (6): 399-406 (1985).

Chmouryguina et al, "Conservation of the C5a Peptidase Genes in Group A and B Streptococci", Infection and Immunity 64(7):2387-2390 (1996).

Cockerill et al, "Molecular, Serological, and Clinical Features of 16 Consecutive Cases of Invasive Streptococcal Disease", Clinical Infectious Diseases 26:1448-1458 (1998).

Coleman et al, "Virus Attenuation by Genome-Scale Changes in Codon Pair Bias", Science, 320:1784-1787 (2008).

FIG. 1A

P2086 Non-lipidated Variant Nucleic Acid Sequences

>A04 Variant Nucleic Acid Sequence (SEQ ID NO: 1)
TGCAGCAGCGGCGAGGCGGAAGCGGAGGCGGGGTGTCGCCGCCGACATCGGCCGGGCTTGCCGGATGCACTAACTGCGCCGCCGACC
ATAAAGACAAAGGTTTGAAATCCCTGACATTGGAAGACTCCATTCCCAAAACGGAACACTGACCCTGTCGGCACAAGGTGC
GGAAAAACTTTCAAAGCCGGCGACAAAGACAACAGCCTCAACACTGGCAAGCGGCGAATTCAAATATACAAACGACACTCCG
TTCGTGCAAAAATCGAAGTGGACGGACAAAATCAACCATCACACCCGACAAAATCAACCGCTCCTTCCTTGTCAG
CCGTCGTTGCCCTACAGATTGAAGAAAAATCAACCGCCTTCAACTGCCGGCGAAAATCGATAACCAAGCATTCAGCTCCGAC
CGGTTTGGGCGGAGAACATACCGCCTTCAACTGCCGCCGGCGTATCACGGCAAATCGAACACCTGACACGCTACGG
GATGCGCGGGAAAACTGTCGAGCTTGCCGCCGAACTCAAAGCAGATGAAAAATCACACGCCGTCATTTTGGGCGACACGCTACGG
AGCAGAATGTCGAGCTTGCCGCCGAACTCAAAGCAGATGAAAAATCACACGCCGTCATTTTGGGCGACACGCTACGG
CAGCGAGAAAAAGGCCACTTACCACCTCGCCCCTTTTTCGCGCGAATCGCGGCTCGGCAACCGTGAAGATA
GGGGAAAAGGTTCACGAAATCGGCATCGCCGGCAAACAGTAG >A05 Variant Nucleic Acid Sequence (SEQ ID NO: 2)
TGCAGCAGCGGCGAAGCGGAAGCGGAGGCGGTGTCGCCGCCGACATCGGCCGATGCACTAACTGCGCCGC
TCGACATAAAGACAAAGGTTTGAAATCCCTGACATTGGAAGACTCCATTTCCCAAAACGGAACACTGACCCTGTCGCACA
AGTGCGCGGAAAACTTTCAAAGCCGGCGACAAAGACAACAGTCTCAATAACGACAAACCATTGAAGAACGACAAATCAGCCGC
TTCGACTTTGTGCAAAAATCGAAGTGGACGGCAAGCGGCGAATTTCAAATATACAAATACAAACAGGACC
ACTCCGCCGTCGTTGCCCTACAGATTGAAAAAATCAACAACCCCGACAGCCTGATAAACCAACGCTCCTTCCT
TGTCAGCGGTTTGGGCGGGAAAACTGACCGCCTATACCGCCGAACTGACCAAGTATCACGGCAAAGCATTCAGC
TCCGACGGATGCGAGCAGAAATGTCGAGCTTGCCTCCCGCAAAGCAGATGAAAATCAACAGGACACACACGCGCAAAA
CACCCGAGCGACGAATGCGGCTACCACACTGCCTCTTTTCGGCGACCTGCAGCCCAAGAAATCGGCTCGGCAACCGTG
CTACGGCAGCGAAGAAAAAGGCCACTTACCACCTCGCTCTTTTCGGCGACCTGCAGCCCAAGAAATCGGCTCGGCAACCGTG
AAGATAAGGGAAAAGGTTCACGAAATCGGCATCGCCGGCAAACAGTAG

FIG. 1B

>A12 Variant Nucleic Acid Sequence (SEQ ID NO: 3)
TGCAGCAGCGGAGGGGCGGGGTGTCGCCGACATCGGCGGGGGCTTGCCGATGCACTAACCGCACCGCTCGACCATAAAG
ACAAAAGTTTGCAGTCTTTGACGCTGGATCAGTCCGTCAAATTGAAGAACGACAAGGTCAGCCGCTTCGACTTTATCCGTCAAATC
AACTTATGGAAACGGCGACAACCATCACGCTGGCAAGCGGCGAATTTCAAATATACAAAGAACCACTCCGCGTCGTTGCCCTAC
GAAGTGGACGGACAAACCATCAACAACCCCGACAAAATCGACAGCCTGATAAACCAACGCTCCTTCCTTGTCAGCGGTTTGGGCGGAGA
AGATTGAAAAAAATCAACAACAGGCCTGACGGCAAAGCCGAGTATCACGGCAAAGCATTCAGCTCCGAACCCGAACGGCAGG
ACATACCGCCTTCAACTCCATTGATTTTACCAAAGCAGAATGAAAAACAGGGTTACGGCAGAATCGAACACCTGAAAACGCCCGAGC
CTGCACTACTCCGCCGAACTGCCCTTTCGGCGACCGCCAAGAAATCGCGCGCCAAGAAATCGCCCGGCTCGGCAACCCGTGAAGATAAGGAAAAAGGTTCAC
TTGCCCTCCGGCCGAACTCCATTGATTTTACCAAAGCAGAATGAAAAACAGGGGTTACGGCAGAATCGAACACCTGAAAACGCCCGAGC
CACTTACCACCTCCGCCCTTTCGGCGACCGCCAAGAAATCGCGCGCCAACCCGTGAAGATAAGGAAAAAGGTTCAC
GAAATCGGCATCGCCGGGCAAACAGTAG >A12-2 Variant Nucleic Acid Sequence (SEQ ID NO: 4)
TGCAGCAGCGGAGGGGCGGGGTGTCGCCGACATTGGTGCCGATGCACTAACCGCACCGCTCGACCATAAAG
ACAAAAGTTTGCAGTCTTTGACGCTGGATCAGTCCGTCAAATTGAAGAACGACAAGGTCAGCCGCTTCGACTTTATCCGTCAAATC
AACTTATGAAACGGCGACAACCATCAACAACCCGACAGCCTCAATACGCTGGCAAGCGGCGAATTTCAAATATACAAAGAACCACTCCGCGTCGTTGCCCTAC
GAAGTGGACGGACAAACCATCAACAACCCCGACAAAATCGACAGCCTGATAAACCAACGCTCCTTCCTTGTCAGCGGTTTGGGGAGA
AGATTGAAAAAATCAACAACAGGCCTGACGCCTGACGCCTGACGGCAAAGCCGAGTATCACGGCAAAGCATTCAGCTCCGACTCCGAAAACGCCCGAACGGCAGG
ACATACCGCCTTCAACCAACTGCCCTTGATTTTACCAAAAAACAGGGTTACGGCAAATCAAAAACAGGGGTTACGGCAGAATGAAAAACACACGCGCAGAATGTCGAGC
CTGCACTACTCCATTGATTTTTACCAAAGCAGATGAAAACACACGGGCAGATGAAAAGG
TTGCCTCCGGCCGAACTCGACTCGCCCTCATTTTGGGGCGACACGCGTACGCCGGCGAGATAAGGAAAAAGG
CACTTACCACCTCCGCCCTTTCGGCGACCGCAAGAAATCGCCCAAGAAATCGCGGCCAACCCGTGAAGATAAGGAAAAAGGTTCAC
GAAATCGGCATCGCCGGGCAAACAGTAG

FIG. 1C

>A22 Variant Nucleic Acid Sequence (SEQ ID NO: 5)
TGCAGCAGGGAGGGCGGGCCGGTGTCCGCTGGATCAGTCCGTCAGGGCAAATTGAAGAACGACAAGGTCAGCCGCTTGACTTTATCCGTCAAATC
ACAAAAGTTTGCAGTCTTTGACGCGCCGGTGTCGCCCGACATCGGCGGCGGGGCTTGCCGATGCACTAACCGCACCGCTCGACCATAAAG
AACTTATGGAAACGGCGACAGCCTCATTACCTTGGAGAGCGGGAGAGTTCCAAATTGAAGAACGACAAGGTCAGCCGCTTGACTTTATCCGTCAAATC
GAAGTGGACGGGCAGCAGCTCATTACCTTGGAGAGCGGGAGAGTTCCAAATTGAAGAACGACAAGGTCAGCCGCTTGACTTTATCCGTCAAATC
AGATTGAAAAAATCAACAACCCCGACAAAATCGACAGCCTGATAAACCAACGCTCCTTCCTTGTCAGCGGTTTGGGTGGAGA
ACATACCGCCCTTCAACTGCCGACGTATCACGGGACACGGCCAAAATCGAACACCTTGAAAACACCCGAGCAAAATGTCGAGC
CTGACCTATACCGCCGAACTCATAGATTTCGCCGCCAAACAGGACACGGCCAAAATCGAACACCTTGAAAACACCCGAGCGAAAAGG
TTGCCTCCGCGAACTCATAGATTTCGCCGCCTTTTCGGCGACCGCGCCCAAGAAAATCGCCGGCCAACCGTCGGCAACCGTGAAGATAAGGGAAAAGGTTCAC
CACTTACCACCTCGCCCCTTTTCGGCGACCGCGCCCAAGAAAATCGCCGGCTCGGCAACCGTCGGCAACCGTGAAGATAAGGGAAAAGGTTCAC
GAAATCGGCCATCGCCGGCAAACAGTAG >B02 Variant Nucleic Acid Sequence (SEQ ID NO: 6)
TGCAGCGGGAGGCGCGGCGAAGCGGAGGGCGGTGTCGCCGGGCTTGCCGATGCACTAACCGCAC
CGCTCGACCATAAAGGACAAAGAAGTTTGAAATCCCGACATTGGAAGACTCCAAAACGAACACTGACCCTGTCGC
ACAAGTGCGGAAAGAACTTTCAAAGCCGGACAACAGTCCAACACAGCAAACTGAAGAACGACAAATCAGC
CGCTTCGACTTTATCCGTCAAATCGAAGTGGACGGGCAGCTCATTACCTTGGAGAGCGGAGAGTTCCAAGTGTACAAACAAA
GCCATTCCGCCCTTAACCGCGAACAGTGGGCGAACAGCTACAAGACTCCGGAAGCATTCCGGAAGATGGTTGCGAAACGCCAGTT
CAGAATCGGCGACATAGTGGGCGAACATACATCTTTTGACAAGCTTCCCAAGACGTCATGGCGACATATCGGGACGGCG
TTCGGTTCAGACGTTGACCTGGCCGAACAAACTGACCTACACCATAGATTTCGCCGGCGATATCAAGCCGCAAAATCGAACATT
TGAAATCGCCCTGAACTGTTGACCTGGCCGAAGCAGTTACCTCTCTAGGCATCTTTGGGCAAGCCCAAGGAAGTTGCCGGCAGCGCG
CGTCCTTTACAACCAAGCCGATCAAGGCAGTTACCTCTCTAGGCATCTTTGGGCAAGCCCAAGGAAGTTGCCGGCAGCGCG
GAAGTGGAAACCGGCAAAACGGCAATAACGGCAATATCGCCATATCGCCATATCGGTCTTGCCGCAAGCAATAA

FIG. 1D

>B03 Variant Nucleic Acid Sequence (SEQ ID NO: 7)
TGCAGCAGGCGGAGGCGGCGGTGTCGCCGGATCAGTCGCTGGATGCACTAACCGCTCGACCATAAAG
ACAAAAGTTTGCAGTCTCTTTGACGCGGACAGCCTTAATACGGGCAAATTGAAGAACGAGAAAACTGAAGCTGGCGCACAAGGTGCGGAAAA
AACTTATGGAAACGGCGACAGCCTTAATACGGGACAAGTTCAGCGGTTTCGACTTTATCCGTCAAATC
GAAGTGGACGGGCAGCGGGAAGCTCATTACCTTGGAGAGCGGAGAGTTCCAAGTGTACAAACAAAGCCATTCCGCCTTAACCGCCCTTC
AGACCGAGCAAGAACAAGATCCAGAGACTTCCGGAGAAGATGGTTGCGAAAACGCCGGTTCAAAATCGGCGACATAGCGGGCGA
ACATACATCTTTTGACAAGCTTCCCAAAGACGTTCATGGGACACGGCCAAACAGGACACCATGCCGTTCATCAGCGGTTCGCCGGACGATGCCCGGCGCG
AAACTGACCTATATCAGATTTGCTGCCAAATCGAACATTGAAATCGCCCTTTACAATCAAGACGAGAA
AGCTTGCCACCGCCTATATCAGCCGATGAAAAAAACACCATGCCCGTCATCAGCGGTTGCCGCAGCCCAAGGAAGTTGCCCGGCAAGTGGAAACCGCAAACGGCATA
AGGCAGTTACTCCCCTCGGTATCTTTGGCGCCAAGCAATAA
CACCATATCGGTCTTGCCGCCAAGCAATAA >B09 Variant Nucleic Acid Sequence (SEQ ID NO: 8)
TGCAGCGGGAGGGGCGGTGTCGCCGACATCGTTGCCGATGCACTAACCGCACCGCTCGACCATAAAG
ACAAAGGTTTGCAGTCTCTTTAACGCTGGATCAGTCGCTGGATCAGTCGCCGTCAGGAGAAAACTGAAGCTGGCGCACAAGGTGCGGAAAA
AACTTATGAAACGGCGACAGCCTTAATACGGGCGACAAGTTCAGCGGTTTCGACTTTATCCGTCAAATC
GAAGTGGACGGGAAGCTCATTACCTTGGAGAGCGGAGAGTTCCAAGTGTACAAACAAAGCCATTCCGCCTTAACCGCCCTTC
AGACCGAGCAAGTACAAGACTCGGAGGATTCCGGAGAAGTTGCGAAACGCCAGTTGCGACATATCGGGACGATGCCCGGCGA
ACATACATCTTTTGACAAGCTTCCCAAACGCCAGTTGCGACATATCGGCGACATGCGGACAGTCGACGTTCGGTTCAGACGCATGCTGGCGGA
AAACTGACCTATATAGATTTCGCCGCCAAGCATTGAAAACGCCAAAATCGGCGACATATCGGCGACAGTCGCAATGTCG
AGCTTTGCCACCCGCCTATATCAAGCCGGACGATGAAAAACGCCGGTTCCGTCCTTTACAACCAAGACGAGAA
AGCCAGTTACTCCCGTATCTTTGGCGCCAAGCAGTAA
CACCATATCGGTCTTGCCGCCAAGCAGTAA

FIG. 1E

>B22 Variant Nucleic Acid Sequence (SEQ ID NO: 9)
TGCAGCAGGGAGGGCGGCGGTGTCGACATCGGCCGATGCACTAACCGCTCGACCATAAAG
ACAAAAGTTTGCAGTCTTTGACGCTGGATCAGTCCGTCAGGAAAAACGAGAAACTGAAGCTGCGGCACAAGGTGCGGAAAA
AACTTATGGAAACGGCGACAGCCTCAATACGGGCAAATTGAAGAACGACAAGGTCAGCCGCTTCGACTTTATCCGTCAAATC
GAAGTGGACGGGCAAGCTACAAGATTCGGAGCTCATTACCTTGGAGAGTGTACAAACAAAGCCATTCCGCCTTAACCGCCCTTC
AGACCGAGCAAGTACAAGATTCGGAGCATTCAGGAAGATGGTTGCGAAAACGCCAGTTCAGATTCGGCGATATAGCGGGTGA
ACATACATCTTTTGACAAGCTTCCCAGGCGGGACATATCGCCAAGCAGGACAACGGCAAATCGAACATTTGAAATCGCCAGAACTCAATGTTG
AAACTGACCTACACCATAGATTTCGCCGCCAAGCAGGACATAGCGCAAATCGAACATTTGAAATCGCCTTTACAACCGAGAA
ACCTGGCCCTCCGATATCAAGCCATCTTAGGCATCTTTGCCGCAGCCCAAGAGTTGCCGGCAGCGCAGAAGTGGAAACCGCAAACGGCATA
AGGCAGTTACTCTCTAGGCATCTTTGCCGCCAAGCAGTAA
CGCCATATCGGTCTTGGCCTTGCCGCCAAGCAGTAA >B24 Variant Nucleic Acid Sequence (SEQ ID NO: 10)
TGCAGCGGAGGGCGGCGGTGTTGTCGCCGCCGATCATCGGTCCGATGCACTAACCGCACCGCTCGACCATAAAG
ACAAAAGGTTTGCAGTCTTTGACGCTGGATCAGTCCGTCAGGAAAAACGAGAAACTGAAGCTGGCGACAAGGTGCGGAAAA
AACTTATGAAACGGTGACAGCCTCAATACGGGCAAATTGAAGAACGACAAGGTCAGCCGTTTCGACTTTATCCGCCAAATC
GAAGTGGACGGGCAAGCTACAAGATTCGGAGCATTCGGAGAGTGGAGCTCATTACCTTGGAGAGTACAAACAAAGCCATTCCGCCTTAACCGCCTTTC
AGACCGAGCAAATACAAGATTCGGAGAGTTCCAAGATGGTTGCGAAATCGCCAGTTCAGATTCGGCGACATAGCGGGCGA
ACATACATCTTTTGACACCATAGATTTCGCCGCCAAGCAGGACACATATGCCGACATATCCGGCGATGCCGGGCGA
AAACTGACCTACACCATAGATTTCGCCGCCAAGCAGGACATCAAGCCGGAAATGGAAATCGAACATTTGAAATCGCCAAGAACTCAATGTCG
ACCTGGCCGCCGATATCAAGCCGGATGGAAAACGCCATGCCGTCATCAGCGGTTCCGTCCTTTACAACCAAGCCGAGAA
AGGCAGTTACTCCCTCGGTATCTTTTGCGCCGAAGTGGAAAACCCGTAAACGGCATA
CGCCATATCGGCCCTTGCCGCCAAGCAATAA

FIG. 1F

>B44 Variant Nucleic Acid Sequence (SEQ ID NO: 11)
TGCAGCAGCGGGAGGCGGCGGAAGCGGAGGCGGGGCGGTGTCGCCGACATCGGCGCGGGCTTGCCGATGCACTAACCGCAC
CGCTCGACCATAAAGACAAAGGTTTGAAATCCCTGACATTGGAAGACTCCATTTCCCAAAACGAACACTGACCCTGTCGGC
ACAAGGTGCGGAAAGAACTTTCAAAGCCGGCGACAAACAGTCTCAACACAGGCAAACTGAAGAACGACAAAATCAGC
CGCTTCGACTTTTATCCGTCAAATCGAAGTCGGACCAGGCAGCTCATTACCTTGGAGAGCGGAGAGTTCCAAGTGTACAAACAAA
GCCATTCCGCCTTAACCGCCCCTTCAGACGAAGTACCGAGCAAGTACAAGACTCGGAGCATTCCGGAAGATGTTGCGAAACGCCAGTT
CAGAGAATCGGCGACATAGTGGGCGAACATACATCTTTTGGCAAGCTTCCAAAGACGTCATGGCCAAGCAGGACACGGCAAATCGGGGACGGCG
TTCGGTTTCAGACGATGCCGCCGGGAACTACACCATAGAGATTTCGCCGCAAGATTTCGCCGCAAATCGAACATT
TGAAATCGCCAGAACTCAATGTTGACCTGCCGCCGATATCAAGCCGATGAAAACACCATGCCGTCATCAGCGGTTC
CGTCCTTTACAACCAAGCCGAGAAAGGCAGTTACTCTCTAGGCATCTTTGCGGCAAGCCCAGGAAGCCCAAGCCCAAGCCCAGCCGG
GAAGTGGAAACCGCAAACGGCCATATCGGTCTTGCCGCCAAGCAATAA

FIG. 2A

P2086 Non-lipidated Variant Amino Acid Sequences

>A04 Variant Amino Acid Sequence (SEQ ID NO: 12)
CSSGGGGVAADIGTGLADALTAPLDHKDKGLKSLTLEDSIPQNGTLTLSAQGAEKTFKAGDKDNSLNTGKLKNDKISRFD
FVQKIEVDGQTITLASGEFQIYKQDHSAVVALQIEKINNPDKIDSLINQRSFLVSGLGGEHTAFNQLPGDKAEYHGKAFS
DAGGKLTYTIDFAAKQGHGKIEHLKTPEQNVELAAAELKADEKSHAVILGDTRYGSEEKGTYHLALFGDRAQEIAGSATVKI
GEKVHEIGIAGKQ >A05 Variant Amino Acid Sequence (SEQ ID NO: 13)
CSSGSGSGGGGVAADIGTGLADALTAPLDHKDKGLKSLTLEDSISQNGTLTLTLSAQGAEKTFKVGDKDNSLNTGKLKNDKISR
FDFVQKIEVDGQTITLASGEFQIYKQDHSAVVALQIEKINNPDKIDSLINQRSFLVSGLGGEHTAFNQLPSGKAEYHGKAFS
SDDAGGKLTYTIDFAAKQGHGKIEHLKTPEQNVELASAELKADEKSHAVILGDTRYGSEEKGTYHLALFGDRAQEIAGSATV
KIREKVHEIGIAGKQ >A12 Variant Amino Acid Sequence (SEQ ID NO: 14)
CSSGGGGVAADIGAGLADALTAPLDHKDKSLQSLTLDQSVRKNEKLKLAAQGAEKTYGNGDSLNTGKLKNDKVSREDFIRQI
EVDGQTITLASGEFQIYKQNHSAVVALQIEKINNPDKIDSLINQRSFLVSGLGGEHTAFNQLPDGKAEYHGKAFSSDDPNGR
LHYSIDFTKKQGYGRIEHLKTPEQNVELASAELKADEKSHAVILGDTRYGGEEKGTYHLALFGDRAQEIAGSATVKIREKVH
EIGIAGKQ >A22 Variant Amino Acid Sequence (SEQ ID NO: 15)
CSSGGGGVAADIGAGLADALTAPLDHKDKSLQSLTLDQSVRKNEKLKLAAQGAEKTYGNGDSLNTGKLKNDKVSREDFIRQI
EVDGQLITLESGEFQIYKQDHSAVVALQIEKINNPDKIDSLINQRSFLVSGLGGEHTAFNQLPSGKAEYHGKAFSSDDAGGK
LTYTIDFAAKQGHGKIEHLKTPEQNVELASAELKADEKSHAVILGDTRYGGEEKGTYHLALFGDRAQEIAGSATVKIREKVH
EIGIAGKQ

FIG. 2B

>B02 Variant Amino Acid Sequence (SEQ ID NO: 16)
CSSGGGSGGGVAADIGAGLADALTAPLDHKDKGLKSLTLEDSISQNGTLTLSAQGAERTFKAGDKDNSLNTGKLKNDKIS
RFDFIRQIEVDGQLITLESGEFQVKQSHSALTALQTEQVQDSEHSGKMVAKRQFRIGDIVGEHTSFDKLPKDVMATYRGTA
FGSDDAGGKLTYTIDFAAKQGHGKIEHLKSPELNVDLAAADIKPDEKHHAVISGSVLYNQAEKGSYSLGIFGGQAQEVAGSA
EVETANGIRHIGLAAKQ >B03 Variant Amino Acid Sequence (SEQ ID NO: 17)
CSSGGGVAADIGAGLADALTAPLDHKDKSLQSLTLDQSVRKNEKLKLAAQGAEKTYGNGDSLNTGKLKNDKVSRFDFIRQI
EVDGQLITLESGEFQVYKQSHSALTALQTEQEQDPEHSGKMVAKRRFKIGDIAGEHTSFDKLPKDIAGEHTSFDKLPKGGSATYRGTAFGSDDAGG
KLTYTIDFAAKQGHGKIEHLKSPELNVELATAYIKPDEKHHAVISGSVLYNQDEKGSYSLGIFGGQAEVAGSAEVETANGI
HHIGLAAKQ >B09 Variant Amino Acid Sequence (SEQ ID NO: 18)
CSSGGGVAADIGAGLADALTAPLDHKDKGLQSLTLDQSVRKNEKLKLAAQGAEKTYGNGDSLNTGKLKNDKVSRFDFIRQI
EVDGKLITLESGEFQVYKQSHSALTALQTEQVQDSEDSGKMVAKRQFRIGDIAGEHTSFDKLPKGGSATYRGTAFGSDDAGG
KLTYTIDFAAKQGHGKIEHLKSPELNVELATAYIKPDEKRHAVISGSVLYNQDEKGSYSLGIFGGQAEVAGSAEVETANGI
HHIGLAAKQ >B22 Variant Amino Acid Sequence (SEQ ID NO: 19)
CSSGGGVAADIGAVLADALTAPLDHKDKSLQSLTLDQSVRKNEKLKLAAQGAEKTYGNGDSLNTGKLKNDKVSRFDFIRQI
EVDGQLITLESGEFQVYKQSHSALTALQTEQVQDSEHSGKMVAKRQFRIGDIAGEHTSFDKLPEGGRATYRGTAFGSDDASG
KLTYTIDFAAKQGHGKIEHLKSPELNVDLAASDIKPDKKRHAVISGSVLYNQAEKGSYSLGIFGGQAEVAGSAEVETANGI
RHIGLAAKQ

FIG. 2C

>B24 Variant Amino Acid Sequence (SEQ ID NO: 20)
CSSGGGGVAADIGAGLADALTAPLDHKDKGLQSLTLDQSVRKNEKLKLAAQGAEKTYGNGDSLNTGKLKNDKVSRFDFIRQI
EVDGQLITLESGEFQVYKQSHSALTAFQTEQIQDSEHSGKMVAKRQFRIGDIAGEHTSFDKLPEGGRATYRGTAFGSDDAGG
KLTYTIDFAAKQGNGKIEHLKSPELNVDLAAADIKPDGKRHAVISGSVLYNQAEKGSYSLGIFGGKAQEVAGSAEVKTVNGI
RHIGLAAKQ >B44 Variant Amino Acid Sequence (SEQ ID NO: 21)
CSSGGGGSGGGGVAADIGAGLADALTAPLDHKDKGLKSLTLEDSISQNGTLTLSAQGAERTFKAGDKDNSLNTGKLKNDKIS
RFDFIRQIEVDGQLITLESGEFQVYKQSHSALTALQTEQVQDSEHSGKMVAKRQFRIGDIVGEHTSFGKLPKDVMATYRGTA
FGSDDAGGKLTYTIDFAAKQGHGKIEHLKSPELNVDLAAADIKPDEKHHAVISGSVLYNQAEKGSYSLGIFGGQAQEVAGSA
EVETANGIRHIGLAAKQ

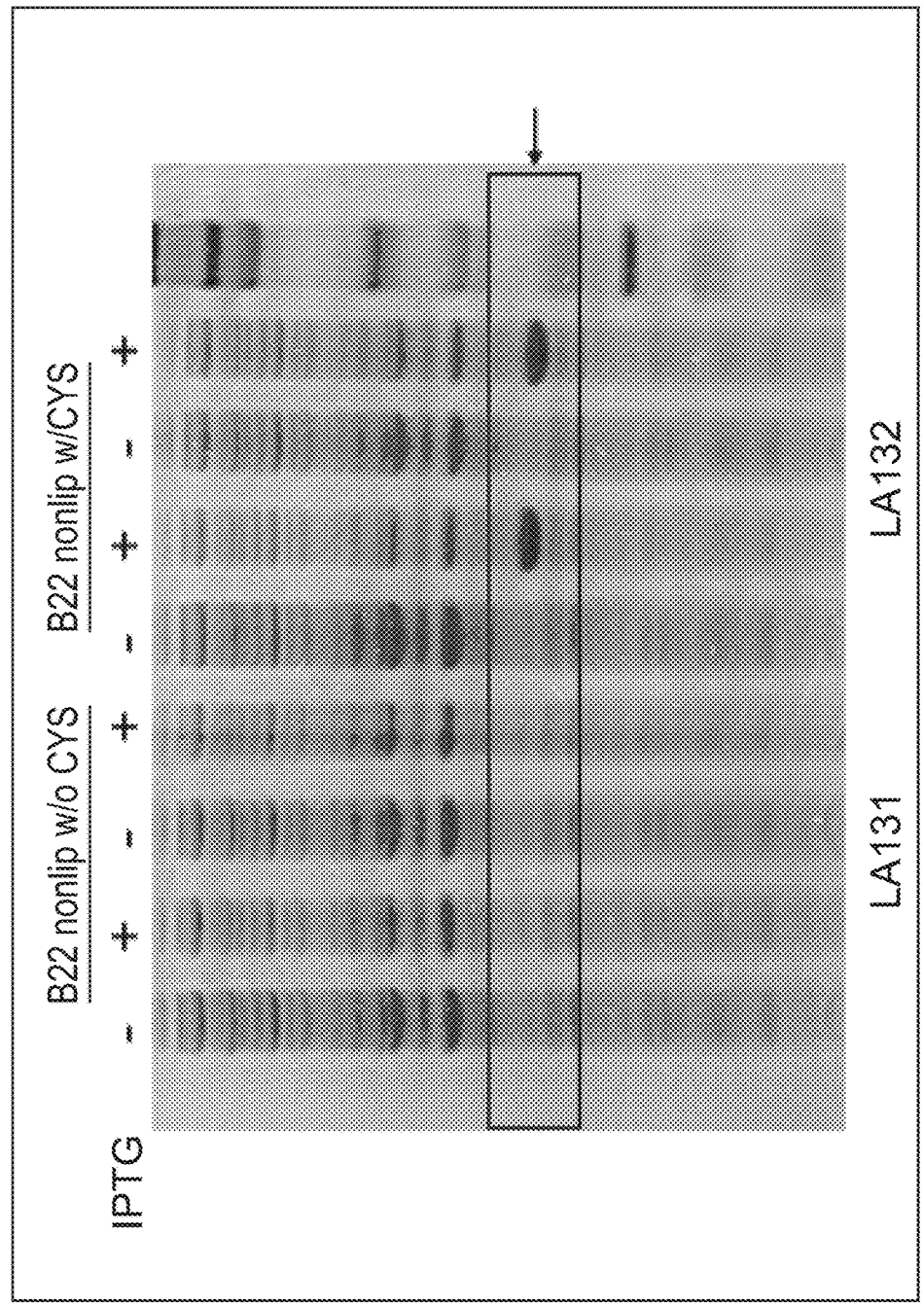

FIG. 5

Effect of Gly/Ser Stalk Length on Non-lipidated ORF2086 Variant Expression

| Protein Variant | Coomassie Expression w/o N-term Cys | Extra Gly/Ser? |
|---|---|---|
| B01<br>CSSGGGGSGSGGGGVTADIGTGLADADALTAP | Yes | Yes (+5) |
| B44<br>CSSGGGGSGSGGGGVAADIGAGLADADALTAP | Yes | Yes (+5) |
| A05<br>CSSGGGSGSGGGGVAADIGTGLADADALTAP | Yes | Yes (+4) |
| A22<br>CSSGGGGGVAADIGAGLADADALTAP | No* | No |
| B22<br>CSSGGGGGVAADIGAVLADADALTAP | No* | No |
| A19<br>CSSGGGGGVAADIGAGLADADALTAP | No* | No |

*Yes if add back N-term Cys

FIG. 7

Codon Optimization Increases Expression of Non-lipidated B22 and A22 Variants

N-terminal B09 Gly codon changes applied to B22 and A22

FIG. 8A

>SEQ ID NO: 43

AGCTCTGGAGGTGGAGGAAGCGGGGAGTTGCAGCAGACATTGGAGCAGGATTAGCAGATGCACTGACGGCACCGT
TGGATCATAAGACAAAGGCTTGAAATCGCTTACCTTACACAAATGGCACCCTTACCTTGTCCGCGCA
AGGCGCTGAACGTACTTTTAAAGCCGGGTGACAAAGATAATAGCTTAAATACAGGTAAACTCAAAAATGATAAAATCTCGCGT
TTTGATTTCATTCGTCAAATCGAAGTAGATGGCCAACTTATTACATTAGAAAGCGGTGAATTCCAAGTATATAAACAATCCC
ATTCAGCACTTACAGCATTGTCGGTGAACATACAAGCTTCGGAAAATTACCAAAAGATGTGATGGCGACCTATCGCGGTACGGCATTT
CATCGGTGACATTGTCGGTGAACATACAAGCTTCGGAAAATTACCAAAAGATGTGATGGCGACCTATCGCGGTACGGCATTT
GGATCAGATGATGCAGGCGGTAAATTAACTTTGACTTTGCAGCAAAACATTGACTTTGCAGCAAATTGAACATTTAA
AATCTCCCGAACTTAACGTAGATCTCGCAGCAGATATTAAACCAGATGAAAAACACCACGCAGTCATTTCAGGTTCAGT
TTTATACAATCAGGCAGAAAAAGGTTCGTACTTCGTCACATTGGGTTAGCGGCGAAACAATAA
GTAGAAACGGCAAATGGCATTTCGTCACATTGGGTTAGCGGCGAAACAATAA

>SEQ ID NO: 44

SSGGGGSGGGGVAADIGAGLADALTAPLDHKDKGLKSLTLEDSISQNGTLTLSAQGAERTFKAGDKDNSLNTGKLKNDKISR
FDFIRQIEVDGQLITLESGEFQVYKQSHSALTALQTEQVQDSEHSGKMVAKRQFRIGDIVGEHTSFGKLPKDVMATYRGTAF
GSDDAGGKLTYTIDFAAKQGHGKIEHLKSPELNVDLAAADIKPDEKHHAVISGSVLYNQAEKGSYSLGIFGGQAQEVAGSAE
VETANGIRHIGLAAKQ.

FIG. 8B

> SEQ ID NO: 51
AGCAGGGAGGCGGCGAAGCGGAGGCGGCGGTGTCGCCGCCGACATCGGCCGATGCACTAACCGCACCGC
TCGACCATAAAGACAAAGGTTTGAAATCCCTGACATTGGAAGACTTCCAAACGGAACACTGACCCTGTCGGCACA
AGGTGCGGAAAGAACTTTCAAAGCCGGCGACAAAGACAACAGTCTCAACACAGGCAAACTGAAGAACGACAAATCAGCCGC
TTCGACTTTATCCGTCAAATCGAAGTGGAACCGGCAGCCAAGTACAAGACTCGGAGAGCGGAGAGTTCCAAGTGTACAAACAAAGCC
ATTCCGCCCTTAACCGCCCTTCAGAACGGAACATAGTCCCAGAGCAAGTACAAGACTCCGGAGCATTCCGGAAGATGGTTGCGAAACGCCAGTTCAG
AATCGGGACACATAGTGGGCGCGGAAAAACTGACCTGACCTACACCATAGATTTCGCCGCCAAGCTTCCCAAAGACGTCATGGCAGGGACACGGGAACGTCGGGACGGCGTTC
GGTTCAGACGATGCCGGCGGAAAACTGACCTGTGACCTACACCATAGATTTCGCCGCCAAGACCGGATGCATCTTTGGGCATCTTCTAGGCAGTTACTCTCTAGGCAGTTGCCCGCCAAGAAGTTGCCCGGCAGCGCGGAA
AATCGCCAGAACTCAATGTTGACCTGTGACCTACACCATAGATTTCGCCGCCAAGACCGGATGCATCTTTGGGCATCTTCTAGGCAGTTACTCTCTAGGCAGTTGCCCGCCAAGAAGTTGCCCGGCAGCGCGGAA
CCTTTACAACCAAGCGAGAAGGCAGTTACTCTCTAGGCAGTTGCCCGCCAAGAATCGGAAAGCCATATCGGTCTTTGCCGCCAAGCAATAA
GTGGAAAACCGCAAACGCCATATCGGTCTTTGCCGCCAAGCAATAA

> SEQ ID NO: 45
AGCTCTGGAGTGGAGGAAGCGGGGCGGTGGAGTTGCAGCAGACATTGGAGCAGGATTAGCAGATGCACTGACGGCACCGT
TGGATCATAAAGACAAAGGCTTGCAGTCGCTTACCTTAGATCAGTCAGTCGTGTCAGTACAGTCAGGAAAAATGAGAAACTTAAGTTGGCGGCA
AGGCGCTGAAAAAACTTATGGAAACGGTGACAAGCTTAAATCAAAAATGATAAAGTCTCGCGTTTTGATTTC
ATTCGTCAAATCGAAGTAGAATGGCAAGCTTATTACATTAGAAAGCGGTGAATTCCAAGTATATAAACATCCATTCAGCAC
TTACAGCATTGCAACAGGTCGAACAGTTCCGCAAGAAGATTCCGCAAAATGTAGCTAAACGTCAATTCCGCATCGGTGA
CATTGCGGGTGAACATACAAGCTTGCGACAAATTACCAAAAAGGCGGCCAGTTCATCGCGACCTATCGCGCAAATTGAACATTTAAAATCTCCG
GATGCAGCGGTAAATTAACTTATACAAATTGACTTTGCAGCAAGATGAAAAAACGCCAGTCATTCAGGTTCATTTCAGTTTTTATACAA
AACTTAACGTAGAGCTCGCAACCGCATATATTTAGGTTATATTTCTTTTTGGCAGGCTCAAGAAGTTGCAGTAGCGCAGAAGTAGAAACG
TCAGGACGAAAAGGTTCGTACTCTCTTTAGGTATTTTTGGCGAAACAATAA
GCAAATGGCATTCACCACATTGGGTTAGCGTTAGCGGGAAACAATAA

FIG. 8C

>SEQ ID NO: 50
SSGGGGSGGGGVAADIGAGLADALTAPLDHKDKGLQSLTLDQSVRKNEKLKLAAQGAEKTYGNGDSLNTGKLKNDKVSRFD
FIRQIEVDGKLITLESGEFQVYKQSHSALTALQTEQVQDSEDSGKMVAKRQFRIGDIAGEHTSEDKLPKGGSATYRGTAFG
SDDAGGKLTYTIDFAAKQGHGKIEHLKSPELNVELATAYIKPDEKRHAVISGSVLYNQDEKGSYSLGIFGGQAQEVAGSAE
VETANGIHHIGLAAKQ

> SEQ ID NO: 46
AGCTCTGGAGGTGGAGGAGTTGCAGCAGGATTAGCAGACACATTGACGGCACCGTTGGATCATAAAGAC
AAAGGCTTGCAGTCGCTTACCTTAGATCAGTCTGTCAGGAAACTCAAGTTGGCGCAAGGCGCTGAAAAA
ACTTATGGAAACGGGTGCAAGCTTATTACATTAGAAAGCGGTGAATTCCAAGTATATAAACAATCCCATTCAGCACTTACAGCATTG
GAAGTAGATGGCAAGCAGTTCCAAGACTCAGAAGATTCCCAGAAGCGGTCAAATGGTGCGACCTATCGCCATCGGTGACATTGCGGGT
CAAACCGAACAGGTCCAAGACTCAGAAGATTCCCAGAAGCGGTCAAATGGTGCGACCTATCGCCATCGGTGACATTGCGGGT
GAACATACAAGCTTCGACAAATTACCAAAAGGCGGCAGTGCAGAACAAGGACATGGCAAAATGAACATTTAAAATCTCCCGAACTTAAC
GGTAAATTAACTTATACAATTGACTTTGCAGCAAACCAGATGAAAAACGCCAGTCATTTCAGTTCAGTTTTATACAATCAGGAC
GTAGAGCTCGCAACCGCATATATTAAGGTATTTTTGGCGGGCAAGCTCAAGAAGTTGCAGGTAGCCAGAAGTAGAAACGGCAAAT
GAAAAAGGTTCGTACTCTTTAGGTATTTTTGGCGGGCAAGCTCAAGAAGTTGCAGGTAGCCAGAAGTAGAAACGGCAAAT
GGCATTCACCACATTGGGTTAGCGGCGAAACAATAA

FIG. 8D

>SEQ ID NO: 47
AGCAGCGGGGCGGTGGAGTTGCAGCAGACATTGGAGCAGGATTAGCAGATGCACTGACGGCACCGTTGGATCATAAAGACA
AAGGCTTTGCAGTCGCTTACCCTTAGATCAGTCTGTGTAAACTCAGGAAAAATGAGAAACTTAAGTTGGCGGCGCACCGTTGGATCATAAAGACA
TTATGGAAAACGGTGACAGCTTAAATACAGGTAAACTCAAAAATGATAAAGTCTCGCGTTTTGATTTCATTCGTCAAATCGAA
GTAGATGGCAAGCTTATTACATTAGAAAGCGGTGAATTCCAAGTATATAAACAATCCCATTCAGCACTTACAGCATTGCAAA
CCGAACAGTCCAAGACTCAGAAGATTCCGGCAAAATGGTAGCTAAACGTCAATTCGCGGTACGCCATCGCGGTGACATTGCGGGTGAACA
TACAAGCTTCGACAAATTACCAAAAGGCGCAAAACAAGGACATGCCAAAATTAAAATCCCGAACTTAACGTAGAGC
TTAACTTATACAAATTGACTTTGCAGCAAATGAAAAAACGCCAGTCATTTCAGTTTTATACAATCAGACGAAAAAGG
TCGCAACCGCATATATTAAACCAGATAAGCTCAGATTGCAGGTAGCGCAGAAGTAGAAACGGCAATGGCATTCAC
TTCGTACTCTTTTAGGTATTTTTGGCGGCGAAACAATAA
CACATTGGGTTAGCGGCGAAACAATAA

>SEQ ID NO: 48
AGCAGCGGAGGGGCGGTGTCGCCGCCGACATCGGTGCGGGCTTGCCGATGCACTAACCGCACCGCTCGACCATAAAGACA
AAGGTTTGCAGTCTCTTTAACACTGGATCAGTCCGTCAGGGAAAAACGAGAAACTGAAGCTGGCGCAAGGTGCGGAAAAAAC
TTATGGAAAACGGGACACAGCCCTTAATACGGCAAATTGAAGAACGACAAGGTCAGCCGCTTCGACTTTATCCGTCAAATCGAA
GTGGACGGGAAGCTCATTACCGGAGACTCGGAGAGTTCCAAGTGTACAAAACAAGCCATTCCGCCTTAACCGCCCCTTCAGA
CCGAGCAAGTACAAGACTCGGAGGATTCCCAAGGTTGCGAAGATGGTTGCGACATATCGGCAGTTCAGAATCGGCGACATAGCGGGCGAACA
TACATCTTTTGACACTATAGATTTCGCCGAACAGCGGCAAGCAGGACACGGCAAAATCGAACATTTGAAATCGCCCAGATGCTGGCGGAAAA
CTGACCTACTATAGATTTCGCCGGATGAAAAACGCCATGCCGGTTCCGTCCTTTACAACCAAGACGAGAAAGG
TTGCCACCGGGTATCTTCAAGCCGGCAAGCCCAAGCCCAAGTTGCCAGCGCAAGCGGAAGTGAAACGGCATACAC
CAGTTACTCCCCGGTATCTTTTGCCGCCAAGCAGTAA
CATATCGGTCTTGCCGCCAAGCAGTAA

FIG. 8E

>SEQ ID NO: 49
SSGGGGVAADIGAGLADALTAPLDHKDKGLQSLTLDQSVRKNEKLKLAAQGAEKTYGNGDSLNTGKLKNDKVSRFDFIRQIE
VDGKLITLESGEFQVYKQSHSALTALQTEQVQDSEDSGKMVAKRQFRIGDIAGEHTSFDKLPKGGSATYRGTAFGSD
DAGGKLTYTIDFAAKQGHGKIEHLKSPELNVELATAYIKPDEKRHAVISGSVLYNQDEKGSYSLGIFGGQAQEVAGSAEVET
ANGIHHIGLAAKQ

>SEQ ID NO: 54
AGCAGCGGAAGCGGAGGCGGCGAGGCGGCGGTGTCGCCGCCGATGCACTAACTGCGCCGCTCG
ACCATAAAGACAAAGGTTTGAAATCCCTGACATTGGAAGACTCCATTCCCAAAACGAACACTGACCCTGTCGGCACAAGG
TGCGGAAAAAACTTTCAAAGTCGGCGACAAGTCTCAATACAGCAGACAAATTGAAGACGAACATATACAACAGCCGCTTC
GACTTTGTGCAAAAATCGAAGTGGACAGATTGAAAAATCAACAAACCCGCAAGCTGCAACAAATCGACAGCCTGATAAACCAAGCTCCTTCCTTGT
CCGCCGTCGTTGCCCTACAGATTGAAAAATCAACAAACCCGCAAGCTGCAACAAATCGACAGCCTGATAAACCAAGCTCCTTCCTTGT
CAGCGGTTTGGGCGGGAAAACTGCGAGCTTGCCTCCGCTATACCGACCTATAGAACTTCACGGCAAAGCATTCAGCTCC
GACGATGCCGGCAGAATGTCGAGCTTGCCTCCGCTATACCGACCTATAGAACTTCACGGCAAAGCATTCAGCTCC
CCGAGCAGCAGAATAAAAGGCACTTACCACCTCGCTCTTTTTCGGCGACAGATGAAAAATCACACGCCGTCATTTTGCCGACACGCGCTA
CGGCAGCAGAATAAAAGGCACTTACCACCTCGCTCTTTTTCGGCGACAGATGAAAAATCACACGCCGTCATTTTGCCGACACGCGCTA
ATAAGGGAAAAAGGTTCACGAAATCGGCATCGCCGCAAACAGTAG

>SEQ ID NO: 55
SSGSGSGGGGVAADIGTGLADALTAPLDHKDKGLKSLTLEDSISQNGTLTLSAQGAEKTFKVGDKDNSLNTGKLKNDKISRF
DFVQKIEVDGQTITLASGEFQIYKQDHSAVVALQIEKINNPDKIDSLINQRSFLVSGLGGEHTAFNQLPSGKAEYHGKAFSS
DDAGGKLTYTIDFAAKQGHGKIEHLKTPEQNVELASAELKADEKSHAVILGDTRYGSEEKGTYHLALFGDRAQEIAGSATVK
IREKVHEIGIAGKQ.

FIG. 8F

> SEQ ID NO: 57
SSGGGSGGGVTADIGTGLADADALTAPLDHKDKGLKSLTLEDSISQNGTLTLSAQGAEKTYGNGDSLNTGKLKNDKVSRFDF
IRQIEVDGQLITLESGEFQVYKQSHSALTALQTEQEQDPEHSEKMVAKRRFRIGDIAGEHTSFDKLPKDVMATYRGTAFGSD
DAGGKLTYTIDFAAKQGHGKIEHLKSPELNVDLAVAYIKPDEKHHAVISGSVLYNQDEKGSYSLGIFGEKAQEVAGSAEVET
ANGIHHIGLAAKQ

> GenBank AY330406 (SEQ ID NO: 58)
CSSGGGSGGGVTADIGTGLADADALTAPLDHKDKGLKSLTLEDSISQNGTLTLSAQGAEKTYGNGDSLNTGKLKNDKVSRFD
FIRQIEVDGQLITLESGEFQVYKQSHSALTALQTEQEQDPEHSEKMVAKRRFRIGDIAGEHTSFDKLPKDVMATYRGTAFGS
DDAGGKLTYTIDFAAKQGHGKIEHLKSPELNVDLAVAYIKPDEKHHAVISGSVLYNQDEKGSYSLGIFGEKAQEVAGSAEVE
TANGIHHIGLAAKQ >GenBank FJ184191 (SEQ ID NO: 59)
CSSGGGGVAADIGAGLADADALTAPLDHKDKGLQSLLILDQSVRKNEKLKLAAQGAEKTYGNGDSLNTGKLKNDKVSRFDFIRQI
EVDGQLITLESGEFQVYKQSHSALTALQTEQVQDSEHSGKMVAKRQFRIGDIAGEHTSFDKLPEGGRATYRGTAFSSDDAGG
KLIYTIDFAAKQGHGKIEHLKSPELNVDLAAADIKPDEKHHAVISGSVLYNQAEKGSYSLGIFGGKAQEVAGSAEVKTVNGI
RHIGLAAKQ > GenBank AY330385 (SEQ ID NO: 60)
CSSGGGGVAADIGAGLADADALTAPLDHKDKSLQSLTLDQSVRKNEKLKLAAQGAEKTYGNGDSLNTGKLKNDKVSRFDFIRQI
EVDGQLITLESGEFQVYKQSHSALTALQTEQVQDSEHSGKMVAKRQFRIGDIAGEHTSFDKLPEGGRATYRGTAFGSDDASG
KLTYTIDFAAKQGHGKIEHLKSPELNVDLAASDIKPDEKKRHAVISGSVLYNQAEKGSYSLGIFGGQAQEVAGSAEVETANGI
RHIGLAAKQ

FIG. 8G

> SEQ ID NO: 61

GGCAGCAGCGGAGGCGGCGGTGTCGCCGCCGACATCGGCGCGGTGCTTGCCGATGCACTAACCGCACCGCTCGACCATAAAG
ACAAAAGTTTGCAGTCTTTGACGCGCTGGATCAGTCCGTCAGGAGAAAACGAGAAACTGAAGCTGGCGCACAAGGTGCGAAAA
AACTTATGGAAACGGCGACAGCCCTCAATTACGGGCAAATTGAAGACGACAAGGTCAGCCGCTTCGACTTTATCCGTCAAATC
GAAGTGGACGGGCAGCTCATTACCTTGGAGAGCGGAGAGTTCCAAGTGTACAAACAAAGCCATTCCGCCTTAACCGCCCTTC
AGACCGAGGAGCAAGTACAAGATTCAGGAGGAAGATGGTTGCGAAAACGCCAGTTCAGGCATTCGGTTCAGACGATGCCAGTGGA
ACATACATCTTTTGACAAGCTTCCCGAAGGCGGACACATATCGCGGGACAGGCAGCAAATATCGAAAACATTTGAAATCGCGGAACATTTGAAATCGCCAGAACTCAATGTTG
AAACTGACCTACACCATAGATTTCGCCGATAAAAAACGCCATGCCGTCGTCAGCGGTTCCGTCCTTTACAACCAAGCCGAGAA
ACCTGGCCGCCTCCGATATCAAGCCGGATATCAAGCCGGATAAAAAACGCCATGCCGTCGTCATCAGCGGTTCCGTCCTTTACAACCAAGCCGAGAA
AGGCAGTTACTCTCTAGGCATCTTTGGCGGGCAAGCCCAGGAAGTTGCCGGGCCAGAAGTGGGAAACCGCAAACGGCATA
CGCCATATCGGTCTTGCCGCCAAGCAGTAA

> SEQ ID NO: 62

GSSGGGGVAADIGAVLADALTAPLDHKDKSLQSLTLDQSVRKNEKLKLAAQGAEKTYGNGDSLNTGKLKNDKVSRFDFIRQI
EVDGQLITLESGEFQVYKQSHSALTALQTEQVQDSEHSGKMVARRQFRIGDIAGEHTSFDKLPEGGRATYRGTAFGSDDASG
KLTYTIDFAAKQGHGKIEHLKSPELNVDLAASDIKPDKKRHAVISGSVLYNQAEKGSYSLGIFGGQAEVAGSAEVETANGI
RHIGLAAKQ

FIG. 8H

> SEQ ID NO: 63
GGCAGCAGCGGAGGCGGCGGCGGTGTCGCCGCCGACATCGGCGCGGGCTTGCCGATGCACTAACCGCTCGACCATAAAG
ACAAAAGTTTGCAGTCTTTGACGCTGGATCAGTCCGTCAGGCCTCAATTACGCGGCAAATTGAAGAACGACAAGGTCACACTTTATCCGTCAAATC
AACTTATGGAAACGGCGACAGCCCTCAATTACCTTTCGACTTTATCCGTCAAATC
GAAGTGGACGGGCAGCTCATTACCTTGGAGAGCGGAGAGTTCCAAATATACAACCAACGCTCCTTCCTTGTCAGCGGTTTGGGTGGAGA
AGATTGAAAAAATCAACAACCAACTGCCCCAGCCTGATAAACCGAGTATCACGGCAAAGCCCAGCATTCAGCTCCGACATTGCTGGCGGAAAA
ACATACCGCCTTCAACCAATCGATAGATTTCGCCGCCAAACTGCCCCAGCGGCAAACAGGACACGGCAAATCGAACACTTGAAAACACCGAGCAAAATGTCGAGC
CTGACCTATACCAATAGATTTCGCCGCCAAACTGCCCCAGCGGCAAACAGGACACGGCAAATCGAACACTTGAAAACACCGAGCAAAATGTCGAGC
TTGCCTCCGCCGAACTCAAAGCAGATGAAAAATCACACGCCGTCATTTTGGGCGACACGCCGCTACGCGGCGAAGAAAAAGG
CACTTACCACCTCGCCCTTTTCGGCGACCAGATAAGCCCAAGAAATCGCCGGCTCGGCAACCGTCGGCAACCGTCGAAGATAAGGGAAAAGGTTCAC
GAAATCGGCATCGCCGGCAAACAGTAA

> SEQ ID NO: 64
GSSGGGGVAADIGAGLADALTAPLDHKDKSLQSLTLDQSVRKNEKLKLAAQGAEKTYGNGDSLNTGKLKNDKVSRFDFIRQI
EVDGQLITLESGEFQIYKQDHSAVVALQIEKINNPDKIDSLINQRSFLVSGLGGEHTAFNQLPSGKAEYHGKAFSSDDAGK
LTYTIDFAAKQGHGKIEHLKTPEQNVELASAELKADEKSHAVILGDTRYGGEEKGTVHLALFGDRAQEIAGSATVKIREKVH
EIGIAGKQ

FIG. 9A

|  | | 1 | | | | | | 60 |
|---|---|---|---|---|---|---|---|---|
| A05 | (1) | CSSGSGSG | GGGVAADIGT | GLADALTAPL | DHKDKGLKSL | TLEDSTSQNG | TLTITSAQGA | EKT |
| A12 | (1) | CSSG---- | GGGVAADIGA | GLADALTAPL | DHKDKSLQSL | TLEDQSVRKN | EKLAAQGA | EKT |
| A22 | (1) | CSSG---- | GGGVAADIGA | GLADALTAPL | DHKDKSLQSL | TLDQSVRKN | EKLKIAAQGA | EKT |
| A62 | (1) | CSSG---- | GGGVAADIGA | GLADALTAPL | DHKDKGLQSL | TLDQSVRKN | EKLKIAAQGA | EKT |
| B09 | (1) | CSSG---- | GGGVAADIGA | GLADALTAPL | DHKDKGLQSL | TLDQSVRKN | EKLKIAAQGA | EKT |
| B24 | (1) | CSSG---- | GGGVAADIGA | GLADALTAPL | DHKDKGLQSL | TLDQSVRKN | EKLKIAAQGA | EKT |
| Consensus | (1) | CSSG | GGGVAADIGA | GLADALTAPL | DHKDKGLQSL | TLDQSVRKN | EKLKLAAQGA | EKT |

|  | | 61 | | | | | | 120 |
|---|---|---|---|---|---|---|---|---|
| A05 | (61) | FKVGDKDNS | LNTGKLKNDR | ISRFDFVQKI | EVDGQTITTL | ASGEFQIYKQ | DHSAVVALQI | EK |
| A12 | (57) | YGNGD---- | SLNTGKLKND | VSRFDEIRQI | EVDGQTITTL | ASGEFQIYKQ | NHSAVVALQI | EK |
| A22 | (57) | YGNGD---- | SLNTGKLKND | VSRFDEIRQI | EVDGQLITLE | SGEFQVYKQ | SHSAVVALQI | EK |
| A62 | (57) | YGNGD---- | SLNTGKLKND | VSRFDEIRQI | EVDGKLITLE | SGEFQVYKQ | SHSAITALQI | EQ |
| B09 | (57) | YGNGD---- | SLNTGKLKND | VSRFDEIRQI | EVDGKLITLE | SGEFQVYKQ | SHSAITALQI | EQ |
| B24 | (57) | YGNGD---- | SLNTGKLKND | VSRFDEIRQI | EVDGQLITLE | SGEFQVYKQ | SHSAITAFQI | EQ |
| Consensus | (61) | YGNGD | SLNTGKLKND | VSRFDEIRQI | EVDGQLITLE | SGEFQIYKQ | SHSALVALQT | EQ |

FIG. 9B

```
              121                                                           180
A05       (121) HNNPEKIDSLINQRSFLVSGLGGEHTAFNQLPSG-KAEYHGKAFSDDAGGKLTYTIDFA
A12       (114) HNNPEKIDSLINQRSFLVSGLGGEHTAFNQLPDG-KAEYHGKAFSDDPNGRLHYSIDFT
A22       (114) HNNPEKIDSLINQRSFLVSGLGGEHTAFNQLPSG-KAEYHGKAFSDDPNGRLHYSIDFA
A62       (114) VQDSEDSGMVAKRQFRIGDIAGEHTSFDKLPKGGSAIYRGTAFGSDDAGGKLTYTIDFA
B09       (114) VQDSEDSGMVAKRQFRIGDIAGEHTSFDKLPKGGSAIYRGTAFGSDDAGGKLTYTIDFA
B24       (114) HQDSEHSGMVAKRQFRIGDIAGEHTSFDKLPEGGRAIYRGTAFGSDDAGGKLTYTIDFA
Consensus (121) INNSDKSGSLINQRSFRISGIAGEHTAFNQLP GGKATYRGTAFSSDDAGGKLTYTIDFA 181                                                           240
A05       (180) AKQGHGKIEHLKTPEQNVELASAELKADEKSHAVILGDTRYGGEEKGTYHLALFGDRAQE
A12       (173) KIQGYGKIERIEHLKTPEQNVELASAELKADEKSHAVILGDTRYGGEEKGTYHLALFGDRAQE
A22       (173) AKQGHGKIEHLKTPEQNVELASAELKADEKSHAVILGDTRYGGEEKGTYHLALFGDRAQE
A62       (174) AKQGHGKIEHLKSPELNVELATAYIKPDEKRHAVISGSVLYNQDEKGSYSLGIFGGQAQE
B09       (174) AKQGHGKIEHLKSPELNVDIAAADIKPDGKRHAVISGSVLYNQAEKGSYSLGIFGGKAQE
B24       (174) AKQGNGKIEHLKSPELNVDIAAADIKPDGKRHAVISGSVLYNQAEKGSYSLGIFGGKAQE
Consensus (181) AKQGHGKIEHLKTPEQNVELASAELKADEKSHAVILGDTRYGGEEKGTYHLALFGDRAQE 241                              262
A05       (240) IAGSATVKIREKVHEIGIAGKQ                (SEQ ID NO: 13)
A12       (233) IAGSATVKIREKVHEIGIAGKQ                (SEQ ID NO: 14)
A22       (233) IAGSATVKIREKVHEIGIAGKQ                (SEQ ID NO: 15)
A62       (234) IAGSATVKIREKVHEIGIAGKQ                (SEQ ID NO: 70)
B09       (234) VAGSAEVETANGTHHIGIAAKQ                (SEQ ID NO: 18)
B24       (234) VAGSAEVKTVNGIRHIGIAAKQ                (SEQ ID NO: 20)
Consensus (241) IAGSATVKIREKVHEIGIAGKQ                (SEQ ID NO: 78)
```

NEISSERIA MENINGITIDIS COMPOSITION AND METHODS THEREOF

CROSS REFERENCE TO RELATED APPLICATIONS

The present application is a continuation of and claims priority to U.S. patent application Ser. No. 15/630,147 (now allowed), filed on Jun. 22, 2017, which is a continuation of U.S. patent application Ser. No. 15/237,005 (now U.S. Pat. No. 9,724,402), filed on Aug. 15, 2016, which is a continuation of and claims priority to U.S. patent application Ser. No. 14/604,620 (now U.S. Pat. No. 9,561,269), filed on Jan. 23, 2015, which is a continuation of and claims priority to U.S. patent application Ser. No. 13/787,594 (now U.S. Pat. No. 8,986,710), filed on Mar. 6, 2013, which claims priority to U.S. Provisional Patent Application Ser. No. 61/609,257 filed Mar. 9, 2012. Each of the aforementioned applications is herein incorporated by reference in their entireties.

FIELD OF THE INVENTION

The present invention relates to Neisseria meningitidis compositions and methods thereof.

BACKGROUND OF THE INVENTION

Neisseria meningitids is a Gram-negative encapsulated bacterium that can cause sepsis, meningitis and death. N. meningitidis can be classified into about 13 serogroups (including serogroups A, B, C, E29, H, I, K, L, W-135, X, Y and Z) based on chemically and antigenically distinctive polysaccharide capsules. Five of the serogroups (A, B, C, Y, and W135) are responsible for the majority of disease.

Meningococcal meningitis is a devastating disease that can kill children and young adults within hours despite the availability of antibiotics. There is a need for improved immunogenic compositions against meningococcal serogroups A, B, C, Y, and W135 and/or X.

SUMMARY OF THE INVENTION

To meet these and other needs, the present invention relates to Neisseria meningitidis compositions and methods thereof.

In one aspect, the invention relates to an isolated polypeptide including an amino acid sequence that is at least 95% identical to SEQ ID NO: 71, wherein the first twenty amino acid residues of the sequence does not contain a cysteine.

In one embodiment, the isolated polypeptide includes the amino acid sequence at positions 1-184 of SEQ ID NO: 71.

In one embodiment, the isolated polypeptide includes the amino acid sequence at positions 158-185 of SEQ ID NO: 71. In another embodiment, the isolated polypeptide includes the amino acid sequence at positions 159-186 of SEQ ID NO: 71.

In one embodiment, the isolated polypeptide includes at least 6 contiguous amino acids from the amino acid sequence at positions 185-254 of SEQ ID NO: 71.

In one embodiment, the isolated polypeptide is non-pyruvylated.

In one embodiment, the isolated polypeptide is non-lipidated.

In one embodiment, the isolated polypeptide is immunogenic.

In one embodiment, the isolated polypeptide includes the amino acid sequence consisting of the sequence set forth in SEQ ID NO: 71.

In one aspect, the invention relates to an isolated polypeptide including an amino acid sequence that is at least 95% identical to SEQ ID NO: 76, wherein the first twenty amino acid residues of the sequence does not contain a cysteine.

In one embodiment, the isolated polypeptide includes the amino acid sequence SEQ ID NO: 76.

In one embodiment, the isolated polypeptide includes the amino acid sequence SEQ ID NO: 76, wherein the cysteine at position 1 is deleted. In another embodiment, the isolated polypeptide includes the amino acid sequence SEQ ID NO: 76, wherein the cysteine at position 1 is substituted with an amino acid that is not a Cys residue. In one embodiment, the isolated polypeptide includes the amino acid sequence SEQ ID NO: 77.

In one embodiment, the isolated polypeptide is non-pyruvylated. In one embodiment, the isolated polypeptide is non-lipidated. In one embodiment, the isolated polypeptide is immunogenic.

In another aspect, the invention relates to an immunogenic composition including the polypeptide as in any of the embodiments aforementioned. In another aspect, the invention relates to an immunogenic composition including the polypeptide as in any of the embodiments described herein.

In one aspect, the invention relates to an isolated nucleic acid sequence encoding an isolated polypeptide consisting of the amino acid sequence set forth in SEQ ID NO: 71.

In one embodiment, the isolated nucleic acid sequence includes SEQ ID NO: 72.

In one aspect, the invention relates to an immunogenic composition including an isolated non-lipidated, non-pyruvylated ORF2086 polypeptide from Neisseria meningitidis serogroup B, and at least one conjugate selected from: a) a conjugate of a capsular saccharide of Neisseria meningitidis serogroup A; b) a conjugate of a capsular saccharide of Neisseria meningitidis serogroup C; c) a conjugate of a capsular saccharide of Neisseria meningitidis serogroup W135, and d) a conjugate of a capsular saccharide of Neisseria meningitidis serogroup Y.

In one embodiment, the immunogenic composition includes at least two conjugates selected from: a) a conjugate of a capsular saccharide of Neisseria meningitidis serogroup A; b) a conjugate of a capsular saccharide of Neisseria meningitidis serogroup C; c) a conjugate of a capsular saccharide of Neisseria meningitidis serogroup W135, and d) a conjugate of a capsular saccharide of Neisseria meningitidis serogroup Y.

In one embodiment, the immunogenic composition includes at least three conjugates selected from: a) a conjugate of a capsular saccharide of Neisseria meningitidis serogroup A; b) a conjugate of a capsular saccharide of Neisseria meningitidis serogroup C; c) a conjugate of a capsular saccharide of Neisseria meningitidis serogroup W135, and d) a conjugate of a capsular saccharide of Neisseria meningitidis serogroup Y.

In one embodiment, the immunogenic composition includes a conjugate of a capsular saccharide of Neisseria meningitidis serogroup A; a conjugate of a capsular saccharide of Neisseria meningitidis serogroup C; a conjugate of a capsular saccharide of Neisseria meningitidis serogroup W135, and a conjugate of a capsular saccharide of Neisseria meningitidis serogroup Y.

In one embodiment, the polypeptide is a subfamily A polypeptide.

In one embodiment, the polypeptide is a subfamily B polypeptide.

In one embodiment, the polypeptide is a non-pyruvylated non-lipidated A05.

In one embodiment, the polypeptide is a non-pyruvylated non-lipidated A12.

In one embodiment, the polypeptide is a non-pyruvylated non-lipidated A22.

In one embodiment, the polypeptide is a non-pyruvylated non-lipidated B01.

In one embodiment, the polypeptide is a non-pyruvylated non-lipidated B09.

In one embodiment, the polypeptide is a non-pyruvylated non-lipidated B44.

In one embodiment, the polypeptide is a non-pyruvylated non-lipidated B22.

In one embodiment, the polypeptide is a non-pyruvylated non-lipidated B24.

In one embodiment, the polypeptide is a non-pyruvylated non-lipidated A62.

In one embodiment, the polypeptide includes the amino acid sequence selected from the group consisting of SEQ ID NO: 44, SEQ ID NO: 49, SEQ ID NO: 55, SEQ ID NO: 66, SEQ ID NO: 68, SEQ ID NO: 71, and SEQ ID NO: 75. In one embodiment, the polypeptide includes the amino acid sequence SEQ ID NO: 77.

In one aspect, the invention relates to a method of inducing an immune response against *Neisseria meningitidis* in a mammal. The method includes administering to the mammal an effective amount of an immunogenic composition including an isolated non-lipidated, non-pyruvylated ORF2086 polypeptide from *Neisseria meningitidis* serogroup B, and at least one conjugate selected from: a) a conjugate of a capsular saccharide of *Neisseria meningitidis* serogroup A; b) a conjugate of a capsular saccharide of *Neisseria meningitidis* serogroup C; c) a conjugate of a capsular saccharide of *Neisseria meningitidis* serogroup W135; and d) a conjugate of a capsular saccharide of *Neisseria meningitidis* serogroup Y.

In one aspect, the invention relates to a method of eliciting a bactericidal antibody against *Neisseria meningitidis* serogroup C in a mammal. The method includes administering to the mammal an effective amount of an immunogenic composition including an isolated non-lipidated, non-pyruvylated ORF2086 polypeptide from *Neisseria meningitidis* serogroup B.

In one embodiment, the polypeptide consists of the amino acid sequence set forth in SEQ ID NO: 71 or the amino acid sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21, wherein the cysteine at position 1 is deleted. In another embodiment, the polypeptide includes the amino acid sequence set forth in SEQ ID NO: 76. In yet another embodiment, the cysteine at position 1 of the polypeptide is deleted. In a further embodiment, the polypeptide includes the amino acid sequence set forth in SEQ ID NO: 77.

In one embodiment, the immunogenic composition further includes at least one conjugate selected from: a) a conjugate of a capsular saccharide of *Neisseria meningitidis* serogroup A; b) a conjugate of a capsular saccharide of *Neisseria meningitidis* serogroup C; c) a conjugate of a capsular saccharide of *Neisseria meningitidis* serogroup W135, and d) a conjugate of a capsular saccharide of *Neisseria meningitidis* serogroup Y.

In one aspect, the invention relates to a method of eliciting a bactericidal antibody against *Neisseria meningitidis* serogroup Y in a mammal. The method includes administering to the mammal an effective amount of an immunogenic composition including an isolated non-lipidated, non-pyruvylated ORF2086 polypeptide from *Neisseria meningitidis* serogroup B.

In one embodiment, the polypeptide consists of the amino acid sequence set forth in SEQ ID NO: 71 or the amino acid sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21, wherein the cysteine at position 1 is deleted. In another embodiment, the polypeptide includes the amino acid sequence set forth in SEQ ID NO: 76. In yet another embodiment, the cysteine at position 1 of the polypeptide is deleted. In a further embodiment, the polypeptide includes the amino acid sequence set forth in SEQ ID NO: 77.

In one embodiment, the immunogenic composition further includes at least one conjugate selected from: a) a conjugate of a capsular saccharide of *Neisseria meningitidis* serogroup A; b) a conjugate of a capsular saccharide of *Neisseria meningitidis* serogroup C; c) a conjugate of a capsular saccharide of *Neisseria meningitidis* serogroup W135, and d) a conjugate of a capsular saccharide of *Neisseria meningitidis* serogroup Y.

In another aspect, the invention relates to a method of eliciting a bactericidal antibody against *Neisseria meningitidis* in a mammal, including administering to the mammal an effective amount of an immunogenic composition including an isolated non-lipidated, non-pyruvylated ORF2086 polypeptide from *Neisseria meningitidis* serogroup B, and at least one conjugate selected from: a) a conjugate of a capsular saccharide of *Neisseria meningitidis* serogroup A; b) a conjugate of a capsular saccharide of *Neisseria meningitidis* serogroup C; c) a conjugate of a capsular saccharide of *Neisseria meningitidis* serogroup W135, and d) a conjugate of a capsular saccharide of *Neisseria meningitidis* serogroup Y.

BRIEF DESCRIPTION OF THE DRAWINGS

FIG. 1A-F: P2086 Variant Nucleic Acid Sequences.

FIG. 2A-C: P2086 Variant Amino Acid Sequences. The Gly/Ser stalk in the N-terminal tail of each variant is underlined.

FIG. 4: Removal of N-terminal Cys Results in Loss of Expression in *E. coli*.

FIG. 5: Effect of Gly/Ser Stalk Length on Non-lipidated ORF2086 Variant Expression. The sequence associated with the protein variant labeled B01 is set forth in SEQ ID NO: 35. The sequence associated with the protein variant labeled B44 is set forth in SEQ ID NO: 36. The sequence associated with the protein variant labeled A05 is set forth in SEQ ID NO: 37. The sequence associated with the protein variant labeled A22 is set forth in SEQ ID NO: 38. The sequence associated with the protein variant labeled B22 is set forth in SEQ ID NO: 39. The sequence associated with the protein variant labeled A19 is set forth in SEQ ID NO: 40.

FIG. 7: Codon Optimization Increases Expression of Non-lipidated B22 and A22 Variants. The left panel demonstrates expression of the N-terminal Cys-deleted B22 variant before (lanes 1 and 3) and after (lanes 2 and 4) IPTG induction. The right panel demonstrates expression of the N-terminal Cys-deleted A22 variant before (lane 7) and after (lane 8) IPTG induction. Lanes 5 and 6 are molecular weight standards.

FIG. 8A-H: P2086 Variant Nucleic and Amino Acid Sequences

FIG. 9A-9B: Sequence alignment of selected wild-type subfamily A and B fHBP variants discussed in Examples 15-19. Note that the N-terminus of A62 is 100% identical to B09 and its C-terminus is 100% identical to A22. The sequences shown are A05 (SEQ ID NO: 13); A12 (SEQ ID NO: 14); A22 (SEQ ID NO: 15); A62 (SEQ ID NO: 70); B09 (SEQ ID NO: 18); B24 (SEQ ID NO: 20); and Consensus (SEQ ID NO: 78).

SEQUENCE IDENTIFIERS

SEQ ID NO: 1 sets forth a DNA sequence for the *N. meningitidis*, serogroup B, 2086 variant A04 gene, which includes a codon encoding an N-terminal Cys.

SEQ ID NO: 2 sets forth a DNA sequence for the *N. meningitidis*, serogroup B, 2086 variant A05 gene, which includes a codon encoding an N-terminal Cys.

SEQ ID NO: 3 sets forth a DNA sequence for the *N. meningitidis*, serogroup B, 2086 variant A12 gene, which includes a codon encoding an N-terminal Cys.

SEQ ID NO: 4 sets forth a DNA sequence for the *N. meningitidis*, serogroup B, 2086 variant A12-2 gene, which includes a codon encoding an N-terminal Cys.

SEQ ID NO: 5 sets forth a DNA sequence for the *N. meningitidis*, serogroup B, 2086 variant A22 gene, which includes a codon encoding an N-terminal Cys.

SEQ ID NO: 6 sets forth a DNA sequence for the *N. meningitidis*, serogroup B, 2086 variant B02 gene, which includes a codon encoding an N-terminal Cys.

SEQ ID NO: 7 sets forth a DNA sequence for the *N. meningitidis*, serogroup B, 2086 variant B03 gene, which includes a codon encoding an N-terminal Cys.

SEQ ID NO: 8 sets forth a DNA sequence for the *N. meningitidis*, serogroup B, 2086 variant B09 gene, which includes a codon encoding an N-terminal Cys.

SEQ ID NO: 9 sets forth a DNA sequence for the *N. meningitidis*, serogroup B, 2086 variant B22 gene, which includes a codon encoding an N-terminal Cys.

SEQ ID NO: 10 sets forth a DNA sequence for the *N. meningitidis*, serogroup B, 2086 variant B24 gene, which includes a codon encoding an N-terminal Cys.

SEQ ID NO: 11 sets forth a DNA sequence for the *N. meningitidis*, serogroup B, 2086 variant B44 gene, which includes a codon encoding an N-terminal Cys.

SEQ ID NO: 12 sets forth the amino acid sequence for the *N. meningitidis*, serogroup B, 2086 variant A04, which includes an N-terminal Cys at amino acid position 1.

SEQ ID NO: 13 sets forth the amino acid sequence for the *N. meningitidis*, serogroup B, 2086 variant A05, which includes an N-terminal Cys at amino acid position 1.

SEQ ID NO: 14 sets forth the amino acid sequence for the *N. meningitidis*, serogroup B, 2086 variant A12, which includes an N-terminal Cys at amino acid position 1.

SEQ ID NO: 15 sets forth the amino acid sequence for the *N. meningitidis*, serogroup B, 2086 variant A22, which includes an N-terminal Cys at amino acid position 1.

SEQ ID NO: 16 sets forth the amino acid sequence for the *N. meningitidis*, serogroup B, 2086 variant B02, which includes an N-terminal Cys at amino acid position 1.

SEQ ID NO: 17 sets forth the amino acid sequence for the *N. meningitidis*, serogroup B, 2086 variant B03, which includes an N-terminal Cys at amino acid position 1.

SEQ ID NO: 18 sets forth the amino acid sequence for the *N. meningitidis*, serogroup B, 2086 variant B09, which includes an N-terminal Cys at amino acid position 1.

SEQ ID NO: 19 sets forth the amino acid sequence for the *N. meningitidis*, serogroup B, 2086 variant B22, which includes an N-terminal Cys at amino acid position 1.

SEQ ID NO: 20 sets forth the amino acid sequence for the *N. meningitidis*, serogroup B, 2086 variant B24, which includes an N-terminal Cys at amino acid position 1.

SEQ ID NO: 21 sets forth the amino acid sequence for the *N. meningitidis*, serogroup B, 2086 variant B44, which includes an N-terminal Cys at amino acid position 1.

SEQ ID NO: 22 sets forth a DNA sequence for a forward primer, shown in Example 2. SEQ ID NO: 23 sets forth a DNA sequence for a reverse primer, shown in Example 2.

SEQ ID NO: 24 sets forth a DNA sequence for a forward primer, shown in Example 2, Table 1.

SEQ ID NO: 25 sets forth a DNA sequence for a reverse primer, shown in Example 2, Table 1.

SEQ ID NO: 26 sets forth a DNA sequence for a forward primer, shown in Example 2, Table 1.

SEQ ID NO: 27 sets forth a DNA sequence for a reverse primer, shown in Example 2, Table 1.

SEQ ID NO: 28 sets forth a DNA sequence for a Gly/Ser stalk, shown in Example 4.

SEQ ID NO: 29 sets forth the amino acid sequence for a Gly/Ser stalk, shown in Example 4, which is encoded by, for example SEQ ID NO: 28.

SEQ ID NO: 30 sets forth a DNA sequence for a Gly/Ser stalk, shown in Example 4.

SEQ ID NO: 31 sets forth the amino acid sequence a Gly/Ser stalk, shown in Example 4, which is encoded by, for example SEQ ID NO: 30.

SEQ ID NO: 32 sets forth a DNA sequence for a Gly/Ser stalk, shown in Example 4.

SEQ ID NO: 33 sets forth the amino acid sequence for a Gly/Ser stalk, which is encoded by, for example, SEQ ID NO: 32 and SEQ ID NO: 34.

SEQ ID NO: 34 sets forth a DNA sequence for a Gly/Ser stalk, shown in Example 4.

SEQ ID NO: 35 sets forth the amino acid sequence for the N-terminus of *N. meningitidis*, serogroup B, 2086 variant B01, shown in FIG. 5.

SEQ ID NO: 36 sets forth the amino acid sequence for the N-terminus of *N. meningitidis*, serogroup B, 2086 variant B44, shown in FIG. 5.

SEQ ID NO: 37 sets forth the amino acid sequence for the N-terminus of *N. meningitidis*, serogroup B, 2086 variant A05, shown in FIG. 5.

SEQ ID NO: 38 sets forth the amino acid sequence for the N-terminus of *N. meningitidis*, serogroup B, 2086 variant A22, shown in FIG. 5.

SEQ ID NO: 39 sets forth the amino acid sequence for the N-terminus of *N. meningitidis*, serogroup B, 2086 variant B22, shown in FIG. 5.

SEQ ID NO: 40 sets forth the amino acid sequence for the N-terminus of *N. meningitidis*, serogroup B, 2086 variant A19, shown in FIG. 5.

Figure 6:
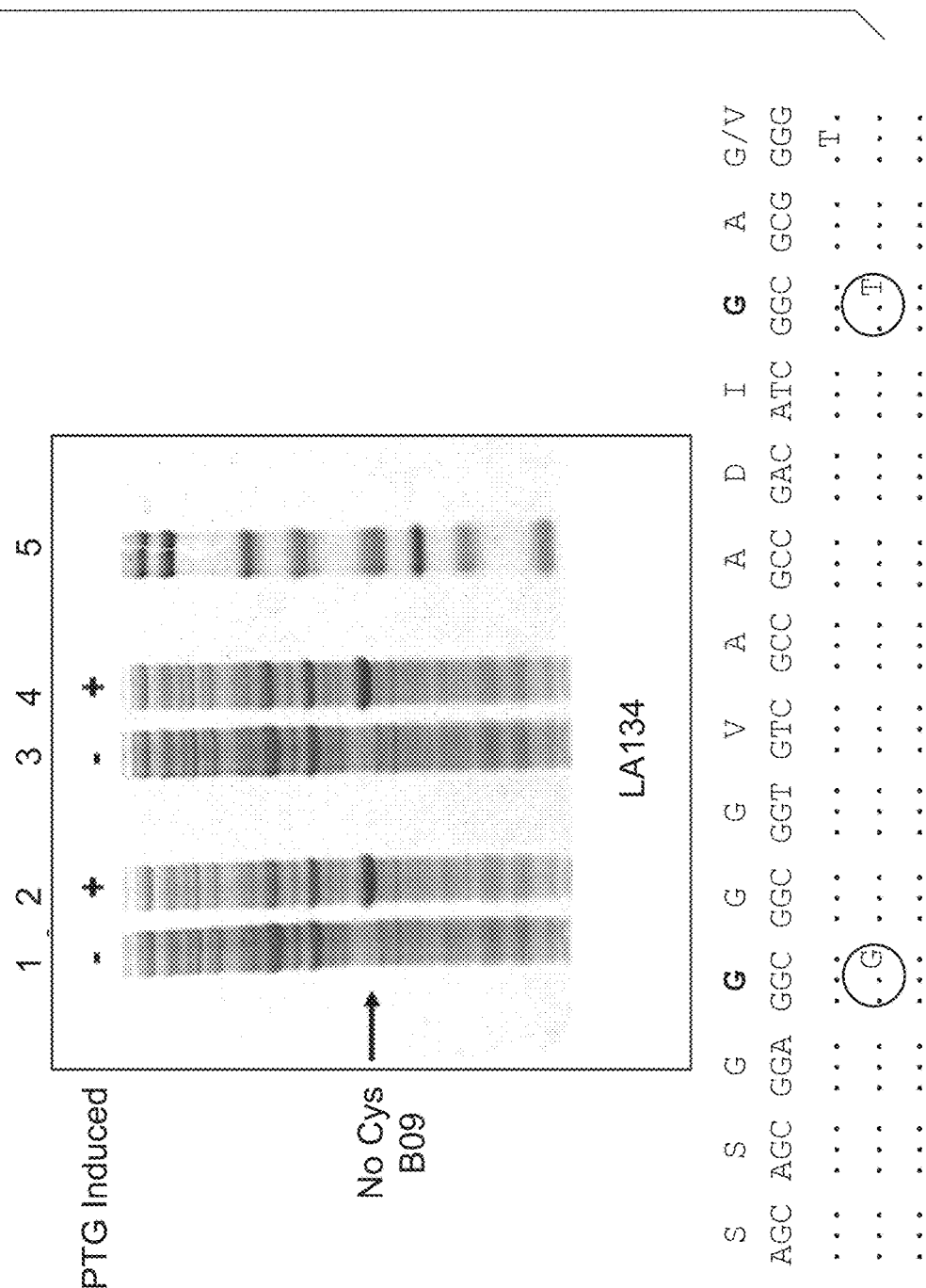
FIG. 6: High Levels of Non-lipidated B09 Expression Despite A Short Gly/Ser Stalk. The left two lanes demonstrated expression of the N-terminal Cys-deleted B09 variant before and after induction. The third and fourth lanes demonstrate expression of the N-terminal Cys positive B09 variant before and after induction. The right most lane is a molecular weight standard. The amino acid sequence shown under the image is set forth in SEQ ID NO: 41. The nucleotide sequence representative of the N-terminal Cys-deleted A22 variant, referred to as "A22_001" in the figure, is set forth in SEQ ID NO: 42, which is shown under SEQ ID NO: 41 in the figure. The nucleotide sequence representative of the N-terminal Cys-deleted B22 variant, referred to as "B22_001" in the figure, is set forth in SEQ ID NO: 52. The nucleotide sequence representative of the N-terminal Cys-deleted B09 variant, referred to as "B09_004" in the figure, is set forth in SEQ ID NO: 53.

SEQ ID NO: 41 sets forth the amino acid sequence for the N-terminus of a *N. meningitidis*, serogroup B, 2086 variant, shown in FIG. 6.

SEQ ID NO: 42 sets forth a DNA sequence for the N-terminus of *N. meningitidis*, serogroup B, 2086 variant A22, shown in FIG. 6.

SEQ ID NO: 43 sets forth a codon-optimized DNA sequence for the *N. meningitidis*, serogroup B, 2086 variant B44 gene, wherein the codon encoding an N-terminal cysteine is deleted, as compared to SEQ ID NO: 11. Plasmid pDK087 includes SEQ ID NO: 43.

SEQ ID NO: 44 sets forth the amino acid sequence for a non-lipidated *N. meningitidis*, serogroup B, 2086 variant B44. SEQ ID NO: 44 is identical to SEQ ID NO: 21 wherein the N-terminal cysteine at position 1 of SEQ ID NO: 21 is deleted. SEQ ID 44 is encoded by, for example, SEQ ID NO: 43.

SEQ ID NO: 45 sets forth a codon-optimized DNA sequence for the *N. meningitidis*, serogroup B, 2086 variant B09 gene, wherein the codon encoding an N-terminal cysteine is deleted, and wherein the sequence includes codons encoding an additional Gly/Ser region, as compared to SEQ ID NO: 8. Plasmid pEB063 includes SEQ ID NO: 45.

SEQ ID NO: 46 sets forth a codon-optimized DNA sequence for the *N. meningitidis*, serogroup B, 2086 variant B09 gene, wherein the codon encoding an N-terminal cysteine is deleted, as compared to SEQ ID NO: 8. Plasmid pEB064 includes SEQ ID NO: 46.

SEQ ID NO: 47 sets forth a codon-optimized DNA sequence for the *N. meningitidis*, serogroup B, 2086 variant B09 gene, wherein the codon encoding an N-terminal cysteine is deleted, as compared to SEQ ID NO: 8. Plasmid pEB 065 includes SEQ ID NO: 47.

SEQ ID NO: 48 sets forth a DNA sequence for the *N. meningitidis*, serogroup B, 2086 variant B09 gene, wherein the codon encoding an N-terminal cysteine is deleted, as compared to SEQ ID NO: 8. Plasmid pLA134 includes SEQ ID NO: 48.

SEQ ID NO: 49 sets forth the amino acid sequence for a non-lipidated *N. meningitidis*, serogroup B, 2086 variant B09. SEQ ID NO: 49 is identical to SEQ ID NO: 18 wherein the N-terminal cysteine at position 1 of SEQ ID NO: 18 is deleted. SEQ ID 49 is encoded by, for example, a DNA sequence selected from the group consisting of SEQ ID NO: 46, SEQ ID NO: 47, and SEQ ID NO: 48.

SEQ ID NO: 50 sets forth the amino acid sequence for the *N. meningitidis*, serogroup B, 2086 variant B09, wherein the codon encoding an N-terminal cysteine is deleted and wherein the sequence includes codons encoding an additional Gly/Ser region, as compared to SEQ ID NO: 18. SEQ ID NO: 50 is encoded by, for example, SEQ ID NO: 45.

SEQ ID NO: 51 sets forth a DNA sequence for the *N. meningitidis*, serogroup B, 2086 variant B44 gene, wherein the codon encoding an N-terminal cysteine is deleted, as compared to SEQ ID NO: 11. Plasmid pLN056 includes SEQ ID NO: 51.

SEQ ID NO: 52 sets forth a DNA sequence for the N-terminus of *N. meningitidis*, serogroup B, 2086 variant B22, shown in FIG. 6.

SEQ ID NO: 53 sets forth a DNA sequence for the N-terminus of *N. meningitidis*, serogroup B, 2086 variant B09, shown in FIG. 6.

SEQ ID NO: 54 sets forth a DNA sequence for a *N. meningitidis*, serogroup B, 2086 variant A05 gene, wherein the codon encoding an N-terminal cysteine is deleted, as compared to SEQ ID NO: 2.

SEQ ID NO: 55 sets forth the amino acid sequence for a non-lipidated *N. meningitidis*, serogroup B, 2086 variant A05. SEQ ID NO: 55 is identical to SEQ ID NO: 13 wherein the N-terminal cysteine at position 1 of SEQ ID NO: 13 is deleted. SEQ ID NO: 55 is encoded by, for example, SEQ ID NO: 54.

SEQ ID NO: 56 sets forth the amino acid sequence of a serine-glycine repeat sequence, shown in Example 7.

SEQ ID NO: 57 sets forth the amino acid sequence for a non-lipidated *N. meningitidis*, serogroup B, 2086 variant B01. SEQ ID NO: 57 is identical to SEQ ID NO: 58 wherein the N-terminal cysteine at position 1 of SEQ ID NO: 58 is deleted.

SEQ ID NO: 58 sets forth the amino acid sequence for the *N. meningitidis*, serogroup B, 2086 variant B01, which includes an N-terminal Cys at amino acid position 1.

SEQ ID NO: 59 sets forth the amino acid sequence for the *N. meningitidis*, serogroup B, 2086 variant B15, which includes an N-terminal Cys at amino acid position 1.

SEQ ID NO: 60 sets forth the amino acid sequence for the *N. meningitidis*, serogroup B, 2086 variant B16, which includes an N-terminal Cys at amino acid position 1.

SEQ ID NO: 61 sets forth a DNA sequence for the *N. meningitidis*, serogroup B, 2086 variant B22, in which the codon for the N-terminal Cys at amino acid position 1 of SEQ ID NO: 19 is replaced with a codon for a Glycine.

SEQ ID NO: 62 sets forth the amino acid sequence for the *N. meningitidis*, serogroup B, 2086 variant B22, in which the N-terminal Cys at amino acid position 1 of SEQ ID NO: 19 is replaced with a Glycine.

SEQ ID NO: 63 sets forth a DNA sequence for the *N. meningitidis*, serogroup B, 2086 variant A22, in which the codon for the N-terminal Cys at amino acid position 1 of SEQ ID NO: 15 is replaced with a codon for a Glycine.

SEQ ID NO: 64 sets forth the amino acid sequence for the *N. meningitidis*, serogroup B, 2086 variant A22, in which the N-terminal Cys at amino acid position 1 of SEQ ID NO: 15 is replaced with a Glycine.

SEQ ID NO: 65 sets forth a codon-optimized DNA sequence (pEB042) encoding a non-lipidated, non-pyruvylated A05 polypeptide.

SEQ ID NO: 66 sets forth the amino acid sequence for a non-lipidated *N. meningitidis*, serogroup B, 2086 variant A12. SEQ ID NO: 66 is identical to SEQ ID NO: 14 wherein the N-terminal cysteine at position 1 of SEQ ID NO: 14 is deleted. SEQ ID NO: 66 is encoded by, for example, SEQ ID NO: 67.

SEQ ID NO: 67 sets forth a codon-optimized DNA sequence for a non-lipidated, non-pyruvylated A12 polypeptide.

SEQ ID NO: 68 sets forth the amino acid sequence for a non-lipidated *N. meningitidis*, serogroup B, 2086 variant A22. SEQ ID NO: 68 is identical to SEQ ID NO: 15 wherein the N-terminal cysteine at position 1 of SEQ ID NO: 15 is deleted. SEQ ID NO: 68 is encoded by, for example, SEQ ID NO: 69.

SEQ ID NO: 69 sets forth a codon-optimized DNA sequence for a non-lipidated, non-pyruvylated A22 polypeptide.

SEQ ID NO: 70 sets forth the amino acid sequence for the *N. meningitidis* serogroup B, 2086 variant A62, which includes an N-terminal Cys at amino acid position 1.

SEQ ID NO: 71 sets forth the amino acid sequence for a non-lipidated *N. meningitidis*, serogroup B, 2086 variant A62. SEQ ID NO: 71 is identical to SEQ ID NO: 70 wherein the N-terminal cysteine at position 1 of SEQ ID NO: 70 is deleted.

SEQ ID NO: 72 sets forth a codon-optimized DNA sequence for SEQ ID NO: 71.

SEQ ID NO: 73 sets forth a codon-optimized DNA sequence (pDK086) for a *N. meningitidis*, serogroup B, 2086 variant A05 gene, wherein the codon encoding an N-terminal cysteine is deleted, as compared to SEQ ID NO: 2.

SEQ ID NO: 74 sets forth the amino acid sequence for the *N. meningitidis*, serogroup B, 2086 variant A29, which includes an N-terminal Cys at amino acid position 1.

SEQ ID NO: 75 sets forth the amino acid sequence for a non-lipidated *N. meningitidis*, serogroup B, 2086 variant B22. SEQ ID NO: 75 is identical to SEQ ID NO: 19 wherein the N-terminal cysteine at position 1 of SEQ ID NO: 19 is deleted.

SEQ ID NO: 76 sets forth the amino acid sequence for a *N. meningitidis*, serogroup B, 2086 variant A05.

SEQ ID NO: 77 sets forth the amino acid sequence for a non-lipidated *N. meningitidis*, serogroup B, 2086 variant A05. SEQ ID NO: 77 is identical to SEQ ID NO: 19 wherein the N-terminal cysteine at position 1 of SEQ ID NO: 76 is not present.

SEQ ID NO: 78 sets forth the amino acid sequence for a consensus sequence shown in FIG. 9A-9B.

SEQ ID NO: 79 is identical to SEQ ID NO: 78 except that the Cys at position 1 of SEQ ID NO: 78 is not present.

SEQ ID NO: 80 sets forth the amino acid sequence for the *N. meningitidis*, serogroup B, 2086 variant B24. SEQ ID NO: 80 is identical to SEQ ID NO: 20 wherein the N-terminal cysteine at position 1 of SEQ ID NO: 20 is deleted.

SEQ ID NO: 81 sets forth the amino acid sequence for the *N. meningitidis*, serogroup B, 2086 variant B24. SEQ ID NO: 81 is identical to SEQ ID NO: 20 wherein the residues at positions 1-3 of SEQ ID NO: 20 are deleted.

DETAILED DESCRIPTION OF THE INVENTION

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Definitions

The term "antigen" generally refers to a biological molecule, usually a protein, peptide, polysaccharide, lipid or conjugate which contains at least one epitope to which a cognate antibody can selectively bind; or in some instances to an immunogenic substance that can stimulate the production of antibodies or T-cell responses, or both, in an animal, including compositions that are injected or absorbed into an animal. The immune response may be generated to the whole molecule, or to one or more various portions of the molecule (e.g., an epitope or hapten). The term may be used to refer to an individual molecule or to a homogeneous or heterogeneous population of antigenic molecules. An antigen is recognized by antibodies, T-cell receptors or other elements of specific humoral and/or cellular immunity. The term "antigen" includes all related antigenic epitopes. Epitopes of a given antigen can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes may be identified by determining spatial conformation of amino acids such as by, e.g., x-ray crystallography and 2-dimensional nuclear magnetic resonance. See, e.g., Epitope Mapping Protocols, supra. Furthermore, for purposes of the present invention, an "antigen" may also be used to refer to a protein that includes modifications, such as deletions, additions and substitutions (generally conservative in nature, but they may be non-conservative), to the native sequence, so long as the protein maintains the ability to elicit an immunological response. These modifications may be deliberate, as through site-directed mutagenesis, or through particular synthetic procedures, or through a genetic engineering approach, or may be accidental, such as through mutations of hosts, which produce the antigens. Furthermore, the antigen can be derived, obtained, or isolated from a microbe, e.g. a bacterium, or can be a whole organism. Similarly, an oligonucleotide or polynucleotide, which expresses an antigen, such as in nucleic acid immunization applications, is also included in the definition. Synthetic antigens are also included, for example, polyepitopes, flanking epitopes, and other recombinant or synthetically derived antigens (Bergmann et al. (1993) *Eur. J. Immunol.* 23:2777 2781; Bergmann et al. (1996) *J. Immunol.* 157:3242 3249; Suhrbier, A. (1997) *Immunol. and Cell Biol.* 75:402 408; Gardner et al. (1998) 12th World AIDS Conference, Geneva, Switzerland, Jun. 28-Jul. 3, 1998).

The term "conservative" amino acid substitutions may be made on the basis of similarity in polarity, charge, solubility hydrophobicity, hydrophilicity, and/or the amphipathic nature of the residues involved. For example, non-polar (hydrophobic) amino acids include alanine, leucine, isoleucine, valine, proline, tryptophan, and methionine; polar/neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. In some embodiments, the conservative amino acid changes alter the primary sequence of the ORF2086 polypeptides, but do not alter the function of the molecule. When generating these mutants, the hydropathic index of amino acids can be considered. The importance of the hydropathic amino acid index in conferring interactive biologic function on a polypeptide is generally understood in the art (Kyte & Doolittle, 1982, J. Mol. Biol., 157(1):105-32). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid residue determines the secondary and tertiary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within +/−2 is preferred, those within +/−1 are particularly preferred, and those within +/−0.5 are even more particularly preferred.

Conservative amino acids substitutions or insertions can also be made on the basis of hydrophilicity. As described in U.S. Pat. No. 4,554,101, which is hereby incorporated by reference the greatest local average hydrophilicity of a polypeptide, as governed by the hydrophilicity of its adjacent amino acids, correlates with its immunogenicity and antigenicity, i.e., with a biological property of the polypeptide. U.S. Pat. No. 4,554,101 reciates that the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred; those within ±1 are particularly preferred; and those within ±0.5 are even more particularly preferred. Exemplary substitutions which take various of the foregoing characteristics into consideration are well known to those of skill in the art and include, without limitation: arginine and lysine; glutamate and aspartate; serine and threonine; glutamine and asparagine; and valine, leucine and isoleucine.

The term "effective immunogenic amount" as used herein refers to an amount of a polypeptide or composition comprising a polypeptide which is effective in eliciting an immune response in a vertebrate host. For example, an effective immunogenic amount of a rLP2086 protein of this invention is an amount that is effective in eliciting an immune response in a vertebrate host. The particular "effective immunogenic dosage or amount" will depend upon the age, weight and medical condition of the host, as well as on the method of administration. Suitable doses are readily determined by persons skilled in the art.

The term "Gly/Ser stalk" as used herein refers to the series of Gly and Ser residues immediately downstream of the N-terminal Cys residue of a protein encoded by ORF2086. There can be between 5 and 12 Gly and Ser residues in the Gly/Ser stalk. Accordingly, the Gly/Ser stalk consists of amino acids 2 to between 7 and 13 of the protein encoded by ORF2086. Preferably, the Gly/Ser stalk consists of amino acids 2 and up to between 7 and 13 of the protein encoded by ORF2086. The Gly/Ser stalks of the P2086 variants of the present invention are represented by the underlined sequences in FIG. 2 (SEQ ID NO: 12-21). As shown herein, the length of the Gly/Ser stalk can affect the stability or expression level of a non-lipidated P2086 variant. In an exemplary embodiment, effects from affecting the length of the Gly/Ser stalk are compared to those from the corresponding wild-type variant.

The term "immunogenic" refers to the ability of an antigen or a vaccine to elicit an immune response, either humoral or cell-mediated, or both.

An "immunogenic amount", or an "immunologically effective amount" or "dose", each of which is used interchangeably herein, generally refers to the amount of antigen or immunogenic composition sufficient to elicit an immune response, either a cellular (T cell) or humoral (B cell or antibody) response, or both, as measured by standard assays known to one skilled in the art.

The term "immunogenic composition" relates to any pharmaceutical composition containing an antigen, e.g. a microorganism, or a component thereof, which composition can be used to elicit an immune response in a subject. The immunogenic compositions of the present invention can be used to treat a human susceptible to *N. meningidis* infection, by means of administering the immunogenic compositions via a systemic transdermal or mucosal route. These administrations can include injection via the intramuscular (i.m.), intraperitoneal (i.p.), intradermal (i.d.) or subcutaneous routes; application by a patch or other transdermal delivery device; or via mucosal administration to the oral/alimentary, respiratory or genitourinary tracts. In one embodiment, the immunogenic composition may be used in the manufacture of a vaccine or in the elicitation of a polyclonal or monoclonal antibodies that could be used to passively protect or treat a subject.

Optimal amounts of components for a particular immunogenic composition can be ascertained by standard studies involving observation of appropriate immune responses in subjects. Following an initial vaccination, subjects can receive one or several booster immunizations adequately spaced.

The term "isolated" means that the material is removed from its original environment (e.g., the natural environment if it is naturally occurring or from it's host organism if it is a recombinant entity, or taken from one environment to a different environment). For example, an "isolated" protein or peptide is substantially free of cellular material or other contaminating proteins from the cell or tissue source from which the protein is derived, or substantially free of chemical precursors or other chemicals when chemically synthesized, or otherwise present in a mixture as part of a chemical reaction. In the present invention, the proteins may be isolated from the bacterial cell or from cellular debris, so that they are provided in a form useful in the manufacture of an immunogenic composition. The term "isolated" or "isolating" may include purifying, or purification, including for example, the methods of purification of the proteins, as described herein. The language "substantially free of cellular material" includes preparations of a polypeptide or protein in which the polypeptide or protein is separated from cellular components of the cells from which it is isolated or recombinantly produced. Thus, a protein or peptide that is substantially free of cellular material includes preparations of the capsule polysaccharide, protein or peptide having less than about 30%, 20%, 10%, 5%, 2.5%, or 1%, (by dry weight) of contaminating protein or polysaccharide or other cellular material. When the polypeptide/protein is recombinantly produced, it is also preferably substantially free of culture medium, i.e., culture medium represents less than about 20%, 10%, or 5% of the volume of the protein preparation. When polypeptide or protein is produced by chemical synthesis, it is preferably substantially free of chemical precursors or other chemicals, i.e., it is separated from chemical precursors or other chemicals which are involved in the synthesis of the protein or polysaccharide. Accordingly, such preparations of the polypeptide or protein have less than about 30%, 20%, 10%, 5% (by dry weight) of chemical precursors or compounds other than polypeptide/protein or polysaccharide fragment of interest.

Figure 3:
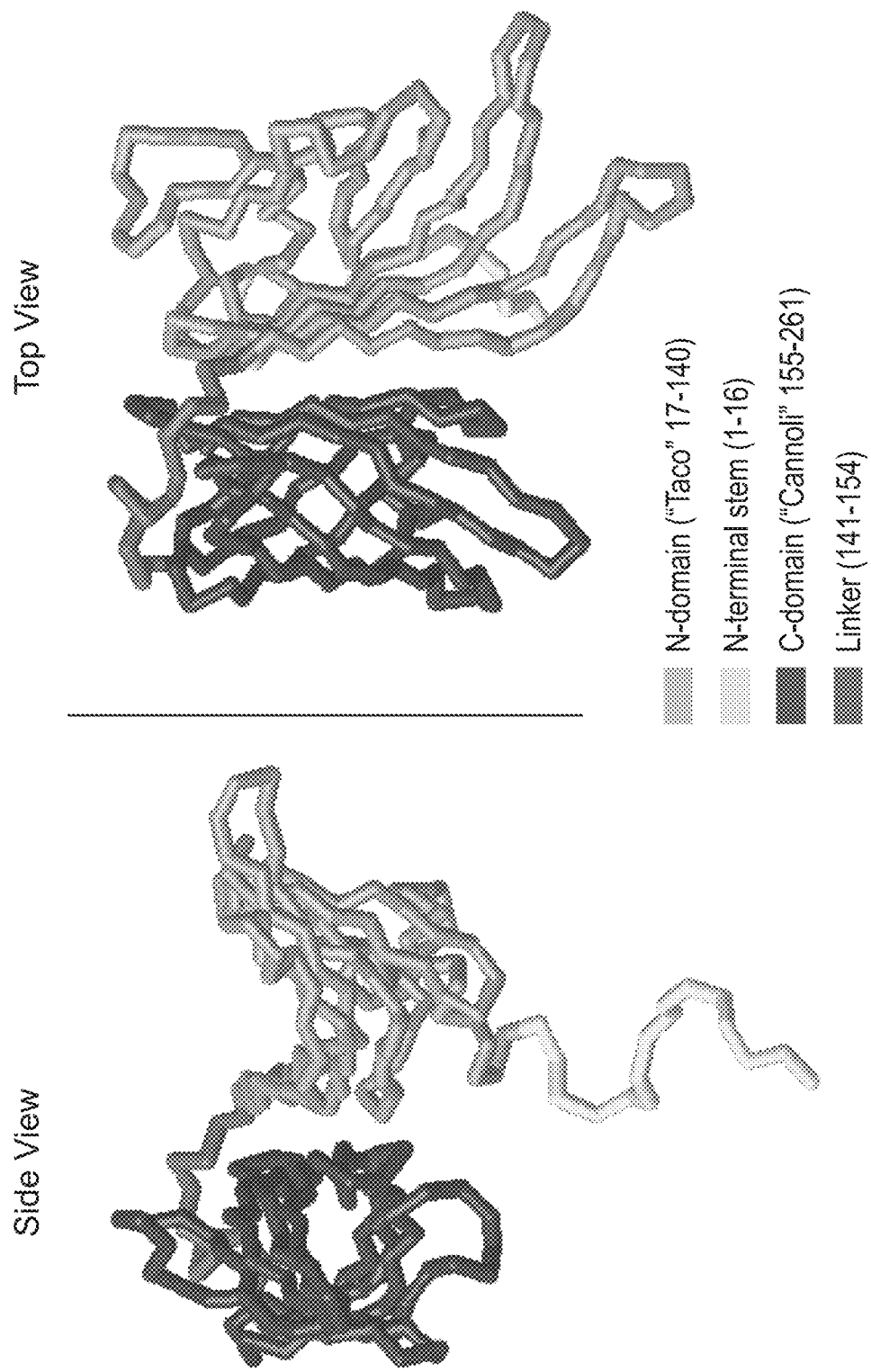
FIG. 3: Structure of the ORF2086 Protein

The term "N-terminal tail" as used herein refers to the N-terminal portion of a protein encoded by ORF2086, which attaches the protein to the cell membrane. An N-terminal tail is shown at the bottom of the side view structure in FIG. 3. An N-terminal tail typically comprises the N-terminal 16 amino acids of the protein encoded by ORF2086. In some embodiments, the N-terminal tail is amino acids 1-16 of any one of SEQ ID NOs: 12-21. The term "ORF2086" as used herein refers to Open Reading Frame 2086 from a *Neisseria* species bacteria. *Neisseria* ORF2086, the proteins encoded therefrom, fragments of those proteins, and immunogenic compositions comprising those proteins are known in the art and are described, e.g., in WO2003/063766, and in U.S. Patent Application Publication Nos. US 20060257413 and US 20090202593, each of which is hereby incorporated by reference in its entirety.

The term "P2086" generally refers to the protein encoded by ORF2086. The "P" before "2086" is an abbreviation for "protein." The P2086 proteins of the invention may be lipidated or non-lipidated. "LP2086" and "P2086" typically refer to lipidated and non-lipidated forms of a 2086 protein, respectively. The P2086 protein of the invention may be recombinant. "rLP2086" and "rP2086" typically refer to lipidated and non-lipidated forms of a recombinant 2086 protein, respectively. "2086" is also known as factor H-binding protein (fHBP) due to its ability to bind to factor H.

The term "pharmaceutically acceptable diluent, excipient, and/or carrier" as used herein is intended to include any and all solvents, dispersion media, coatings, antibacterial and antifungal agents, isotonic and absorption delaying agents, and the like, compatible with administration to humans or other vertebrate hosts. Typically, a pharmaceutically acceptable diluent, excipient, and/or carrier is a diluent, excipient, and/or carrier approved by a regulatory agency of a Federal, a state government, or other regulatory agency, or listed in the U.S. Pharmacopeia or other generally recognized pharmacopeia for use in animals, including humans as well as non-human mammals. The term diluent, excipient, and/or "carrier" refers to a diluent, adjuvant, excipient, or vehicle with which the pharmaceutical composition is administered. Such pharmaceutical diluent, excipient, and/or carriers can be sterile liquids, such as water and oils, including those of petroleum, animal, vegetable or synthetic origin. Water, saline solutions and aqueous dextrose and glycerol solutions can be employed as liquid diluents, excipients, and/or carriers, particularly for injectable solutions. Suitable pharmaceutical diluents and/or excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting, bulking, emulsifying agents, or pH buffering agents. These compositions can take the form of solutions, suspensions, emulsion, sustained release formulations and the like. Examples of suitable pharmaceutical diluent, excipient, and/or carriers are described in "Remington's Pharmaceutical Sciences" by E. W. Martin. The formulation should suit the mode of administration. The appropriate diluent, excipient, and/or carrier will be evident to those skilled in the art and will depend in large part upon the route of administration.

A "protective" immune response refers to the ability of an immunogenic composition to elicit an immune response, either humoral or cell mediated, which serves to protect the subject from an infection. The protection provided need not be absolute, i.e., the infection need not be totally prevented or eradicated, if there is a statistically significant improvement compared with a control population of subjects, e.g. infected animals not administered the vaccine or immunogenic composition. Protection may be limited to mitigating the severity or rapidity of onset of symptoms of the infection. In general, a "protective immune response" would include the induction of an increase in antibody levels specific for a particular antigen in at least 50% of subjects, including some level of measurable functional antibody responses to each antigen. In particular situations, a "protective immune response" could include the induction of a two fold increase in antibody levels or a four fold increase in antibody levels specific for a particular antigen in at least 50% of subjects, including some level of measurable functional antibody responses to each antigen. In certain embodiments, opsonising antibodies correlate with a protective immune response. Thus, protective immune response may be assayed by measuring the percent decrease in the bacterial count in a serum bactericidal activity (SBA) assay or an opsonophagocytosis assay, for instance those described below. Such assays are also known in the art. For meningococcal vaccines, for example, the SBA assay is an established surrogate for protection. In some embodiments, there is a decrease in bacterial count of at least 10%, 25%, 50%, 65%, 75%, 80%, 85%, 90%, 95% or more, as compared to the bacterial count in the absence of the immunogenic composition.

The terms "protein", "polypeptide" and "peptide" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature, but which may be non-conservative), to a native sequence, preferably such that the protein maintains the ability to elicit an immunological response within an animal to which the protein is administered. Also included are post-expression modifications, e.g. glycosylation, acetylation, lipidation, phosphorylation and the like.

Active variants and fragments of the disclosed polynucleotides and polypeptides are also described herein. "Variants" refer to substantially similar sequences. As used herein, a "variant polypeptide" refers to a polypeptide derived from the native protein by a modification of one or more amino acids at the N-terminal and/or C-terminal end of the native protein. The modification may include deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant polypeptides continue to possess the desired biological activity of the native polypeptide, that is, they are immunogenic. A variant of an polypeptide or polynucleotide sequence disclosed herein (i.e. SEQ ID NOS: 1-25 or 39) will typically have at least about 65%, 70%, 75%, 80%, 85%, 90%, 91%, 92%, 93%, 94%, 95%, 96%, 97%, 98%, 99% or more sequence identity with the reference sequence.

The term "fragment" refers to a portion of an amino acid or nucleotide sequence comprising a specified number of contiguous amino acid or nucleotide residues. In particular embodiments, a fragment of a polypeptide disclosed herein may retain the biological activity of the full-length polypeptide and hence be immunogenic. Fragments of a polynucleotide may encode protein fragments that retain the biological activity of the protein and hence be immunogenic. Alternatively, fragments of a polynucleotide that are useful as PCR primers generally do not retain biological activity. Thus, fragments of a nucleotide sequence disclosed herein may range from at least about 15, 20, 30, 40, 50, 60, 70, 80, 90, 100, 110, 120, 130, 140, 150, 175, 200, 225, 250, 300, 400, 500, 600, 700, 800, 900, 1000, 1100, 1200, 1300, 1400, or 1500 contiguous nucleotides or up to the full-length polynucleotide. Fragments of a polypeptide sequence disclosed herein may comprise at least 10, 15, 20, 25, 30, 50, 60, 70, 80, 90, 100, 110, 120, 130, 140, 150, 160, 170, 180, 190, 200, 225, 250, 275, 300, 400, 425, 450, 475, or 500 contiguous amino acids, or up to the total number of amino acids present in the full-length polypeptide.

The term "recombinant" as used herein refers to any protein, polypeptide, or cell expressing a gene of interest that is produced by genetic engineering methods. The term "recombinant" as used with respect to a protein or polypeptide, means a polypeptide produced by expression of a recombinant polynucleotide. The proteins of the present invention may be isolated from a natural source or produced by genetic engineering methods. "Recombinant," as used herein, further describes a nucleic acid molecule, which, by virtue of its origin or manipulation, is not associated with all or a portion of the polynucleotide with which it is associated in nature. The term "recombinant" as used with respect to a host cell means a host cell which includes a recombinant polynucleotide.

The term "subject" refers to a mammal, bird, fish, reptile, or any other animal. The term "subject" also includes humans. The term "subject" also includes household pets. Non-limiting examples of household pets include: dogs, cats, pigs, rabbits, rats, mice, gerbils, hamsters, guinea pigs, ferrets, birds, snakes, lizards, fish, turtles, and frogs. The term "subject" also includes livestock animals. Non-limiting examples of livestock animals include: alpaca, bison, camel, cattle, deer, pigs, horses, llamas, mules, donkeys, sheep, goats, rabbits, reindeer, yak, chickens, geese, and turkeys.

The term "mammals" as used herein refers to any mammal, such as, for example, humans, mice, rabbits, non-human primates. In a preferred embodiment, the mammal is a human.

The terms "vaccine" or "vaccine composition", which are used interchangeably, refer to pharmaceutical compositions comprising at least one immunogenic composition that induces an immune response in a subject.

General Description

The present invention also identifies previously unidentified difficulties expressing non-lipidated P2086 variants and provides methods for overcoming these difficulties and novel compositions therefrom. While plasmid constructs encoding non-lipidated P2086 variants provided strong expression of the non-lipidated variants, these variants were pyruvylated on the N-terminal Cys. Pyruvylation prevents or reduces the likelihood of manufacturing consistency or uniformity of the polypeptides. The inventors further found that deletion of the N-terminal Cys from the non-lipidated P2086 variant sequences avoided pyruvylation of non-lipidated P2086 variants. Attempts to overcome the pyruvylation by deletion of the codon for the N-terminal Cys either abrogated expression or resulted in the expression of insoluble variants. Alternatively, removal of the N-terminal Cys from the non-lipidated P2086 variants decreased expression in some variants. Surprisingly, however, the inventors discovered that at least non-pyruvylated non-lipidated A05, A12, A22, A62, B01, B09, B22, and B44 variants can be expressed despite deletion of the N-terminal Cys residue. Generally, these polypeptides could be expressed without additional modifications other than the Cys deletion, as compared to the corresponding wild-type non-lipidated sequence. See, for example, Examples 2 and 4. Furthermore, the inventors discovered that the non-pyruvylated non-lipidated variants were surprisingly immunogenic and they unexpectedly elicited bactericidal antibodies.

Accordingly, the present invention provides two methods for overcoming or reducing the likelihood of these difficulties in expressing non-lipidated variants. However, additional methods are contemplated by the present invention. The first method was to vary the length of the Gly/Ser stalk in the N-terminal tail, immediately downstream of the N-terminal Cys. The second method was codon optimization within the N-terminal tail. However, optimization of additional codons is contemplated by the present invention. These methods provide enhanced expression of soluble non-lipidated P2086 variants. For example, in one embodiment, enhanced expression of soluble non-lipidated P2086 variants is compared to expression of the corresponding wild-type non-lipidated variants.

Isolated Polypeptides

The inventors surprisingly discovered isolated non-pyruvylated, non-lipidated ORF2086 polypeptides. The inventors further discovered that the polypeptides are unexpectedly immunogenic and are capable of eliciting a bactericidal immune response.

As used herein, the term "non-pyruvylated" refers to a polypeptide having no pyruvate content. Non-lipidated ORF2086 polypeptides having a pyruvate content typically exhibited a mass shift of +70, as compared to the corresponding wild-type polypeptide. In one embodiment, the inventive polypeptide does not exhibit a mass shift of +70 as compared to the corresponding wild-type non-lipidated polypeptide when measured by mass spectrometry. See, for example, Example 10.

In another embodiment, the isolated non-pyruvylated, non-lipidated ORF2086 polypeptide includes a deletion of an N-terminal cysteine residue compared to the corresponding wild-type non-lipidated ORF2086 polypeptide. The term "N-terminal cysteine" refers to a cysteine (Cys) at the N-terminal or N-terminal tail of a polypeptide. More specifically, the "N-terminal cysteine" as used herein refers to the N-terminal cysteine at which LP2086 lipoproteins are lipidated with a tripalmitoyl lipid tail, as is known in the art. For example, when referring to any one of SEQ ID NOs:

12-21 as a reference sequence, the N-terminal cysteine is located at position 1. As another example, when referring to SEQ ID NO: 70 as a reference sequence, the N-terminal cysteine is located at position 1.

The term "wild-type non-lipidated ORF2086 polypeptide" or "wild-type non-lipidated 2086 polypeptide" or "wild-type non-lipidated polypeptide" as used herein refers to an ORF2086 polypeptide having an amino acid sequence that is identical to the amino acid sequence of the corresponding mature lipidated ORF2086 polypeptide found in nature. The only difference between the non-lipidated and lipidated molecules is that the wild-type non-lipidated ORF2086 polypeptide is not lipidated with a tripalmitoyl lipid tail at the N-terminal cysteine.

As is known in the art, the non-lipidated 2086 form is produced by a protein lacking the original leader sequence or by a leader sequence which is replaced with a portion of sequence that does not specify a site for fatty acid acylation in a host cell. See, for example, WO2003/063766, and in U.S. Patent Application Publication Nos. US 20060257413 and US 20090202593, which is incorporated herein by reference in its entirety.

Examples of a non-lipidated ORF2086 include not only a wild-type non-lipidated ORF2086 polypeptide just described but also polypeptides having an amino acid sequence according to any one of SEQ ID NOs: 12-21 wherein the N-terminal Cys is deleted and polypeptides having an amino acid sequence according to any one of SEQ ID NOs: 12-21 wherein the N-terminal Cys is substituted with an amino acid that is not a Cys residue. Another example of a non-lipidated ORF2086 polypeptide includes a polypeptide having an amino acid sequence according to SEQ ID NO: 70 wherein the N-terminal Cys is deleted and a polypeptide having an amino acid sequence according to SEQ ID NO: 70 wherein the N-terminal Cys is substituted with an amino acid that is not a Cys residue. Further examples of a non-lipidated ORF2086 polypeptide include amino acid sequences selected from SEQ ID NO: 44 (B44), SEQ ID NO: 49 (B09), SEQ ID NO: 55 (A05), SEQ ID NO: 57 (B01), SEQ ID NO: 58 (B01), SEQ ID NO: 62 (B22), SEQ ID NO: 64 (A22), and SEQ ID NO: 75 (B22). Yet further examples of a non-lipidated ORF2086 polypeptide include amino acid sequences selected from SEQ ID NO: 66 (A12), SEQ ID NO: 68 (A22), and SEQ ID NO: 71 (A62). More examples include SEQ ID NO: 80 (B24) and SEQ ID NO: 81 (B24). Additional examples of a non-lipidated ORF2086 polypeptide include the amino acid sequences set forth in SEQ ID NO: 76 and SEQ ID NO: 77. In one embodiment, the non-lipidated polypeptide includes the amino acid sequence that is at least about 60%, 65%, 70%, 75%, 80%, 85%, 86%, 87%, 88%, 89%, 90%, 91%, 92%, 93%, 94%, 95%, 96%, 97%, 98%, 99%, or 100% identical to a sequence encoding the corresponding non-lipidated polypeptide. For example, in an exemplary embodiment, the non-lipidated A62 polypeptide includes the amino acid sequence that is at least about 60%, 65%, 70%, 75%, 80%, 85%, 86%, 87%, 88%, 89%, 90%, 91%, 92%, 93%, 94%, 95%, 96%, 97%, 98%, 99%, or 100% identical to SEQ ID NO: 71.

Examples of a wild-type non-lipidated ORF2086 polypeptide include polypeptides having an amino acid sequence according to any one of SEQ ID NOs: 12-21, shown in FIG. 2, SEQ ID NO: 58, SEQ ID NO: 59, and SEQ ID NO: 60. Another example of a wild-type non-lipidated ORF2086 polypeptide includes a polypeptide having the amino acid sequence according to SEQ ID NO: 70. These exemplary wild-type non-lipidated ORF2086 polypeptides include an N-terminal Cys.

As used herein, for example, a "non-lipidated" B44 polypeptide includes a polypeptide having the amino acid sequence selected from SEQ ID NO: 21, SEQ ID NO: 21 wherein the N-terminal Cys at position 1 is deleted, and SEQ ID NO: 44. A "wild-type non-lipidated" B44 polypeptide includes a polypeptide having the amino acid sequence SEQ ID NO: 21. A "non-pyruvylated non-lipidated" B44 polypeptide includes a polypeptide having the amino acid sequence selected from SEQ ID NO: 21 wherein the N-terminal Cys at position 1 is deleted, and SEQ ID NO: 44.

As another example, as used herein, a "non-lipidated" B09 polypeptide includes a polypeptide having the amino acid sequence selected from SEQ ID NO: 18, SEQ ID NO: 18 wherein the N-terminal Cys at position 1 is deleted, SEQ ID NO: 49, and SEQ ID NO: 50. A "wild-type non-lipidated" B09 polypeptide includes a polypeptide having the amino acid sequence SEQ ID NO: 18. A "non-pyruvylated non-lipidated" B09 includes a polypeptide having the amino acid sequence selected from SEQ ID NO: 18 wherein the N-terminal Cys at position 1 is deleted, SEQ ID NO: 49, and SEQ ID NO: 50.

As yet a further example, as used herein, a "non-lipidated" A05 polypeptide includes a polypeptide having the amino acid sequence selected from SEQ ID NO: 13, SEQ ID NO: 13 wherein the N-terminal Cys at position 1 is deleted, and SEQ ID NO: 55. Another example of a "non-lipidated" A05 polypeptide includes a polypeptide having the amino acid sequence selected from SEQ ID NO: 13 wherein the N-terminal Cys at position 1 is substituted with an amino acid that is not a Cys residue. An additional example of a "non-lipidated" A05 polypeptide includes a polypeptide having the amino acid sequence set forth in SEQ ID NO: 76. Yet another example of a "non-lipidated" A05 polypeptide includes a polypeptide having the amino acid sequence set forth in SEQ ID NO: 77. A "wild-type non-lipidated" A05 includes a polypeptide having the amino acid sequence SEQ ID NO: 13. A "non-pyruvylated non-lipidated" A05 includes a polypeptide having the amino acid sequence selected from SEQ ID NO: 13 wherein the N-terminal Cys at position 1 is deleted and SEQ ID NO: 55. Further examples of a "non-pyruvylated non-lipidated" A05 includes a polypeptide having the amino acid sequence selected from SEQ ID NO: 13 wherein the N-terminal Cys at position 1 is substituted with an amino acid that is not a Cys residue; SEQ ID NO: 76 wherein the Cys at position 1 is deleted; SEQ ID NO: 76 wherein the Cys at position 1 is substituted with an amino acid that is not a Cys residue; and SEQ ID NO: 77.

As used herein, a "non-lipidated" A62 polypeptide includes a polypeptide having the amino acid sequence selected from SEQ ID NO: 70, SEQ ID NO: 70 wherein the N-terminal Cys at position 1 is deleted, and SEQ ID NO: 71. Another example of a non-lipidated A62 polypeptide includes a polypeptide having SEQ ID NO: 70 wherein the N-terminal Cys at position 1 is substituted with an amino acid that is not a Cys residue. A "wild-type non-lipidated" A62 polypeptide includes a polypeptide having the amino acid sequence SEQ ID NO: 70. A "non-pyruvylated non-lipidated" A62 includes a polypeptide having the amino acid sequence selected from SEQ ID NO: 70 wherein the N-terminal Cys at position 1 is deleted, and SEQ ID NO: 71. Another example of a non-pyruvylated non-lipidated A62 polypeptide includes a polypeptide having SEQ ID NO: 70 wherein the N-terminal Cys at position 1 is substituted with an amino acid that is not a Cys residue. Preferably, a "non-pyruvylated non-lipidated" A62 includes a polypeptide having the amino acid sequence set forth in SEQ ID NO: 71.

As used herein, a "non-lipidated" A12 polypeptide includes a polypeptide having the amino acid sequence selected from SEQ ID NO: 14, SEQ ID NO: 14 wherein the N-terminal Cys at position 1 is deleted, and SEQ ID NO: 66. A "wild-type non-lipidated" A12 polypeptide includes a polypeptide having the amino acid sequence SEQ ID NO: 14. A "non-pyruvylated non-lipidated" A12 includes a polypeptide having the amino acid sequence selected from SEQ ID NO: 14 wherein the N-terminal Cys at position 1 is deleted, and SEQ ID NO: 66.

As used herein, a "non-lipidated" A22 polypeptide includes a polypeptide having the amino acid sequence selected from SEQ ID NO: 15, SEQ ID NO: 15 wherein the N-terminal Cys at position 1 is deleted, SEQ ID NO: 64, and SEQ ID NO: 68. A "wild-type non-lipidated" A22 polypeptide includes a polypeptide having the amino acid sequence SEQ ID NO: 15. A "non-pyruvylated non-lipidated" A22 includes a polypeptide having the amino acid sequence selected from SEQ ID NO: 15 wherein the N-terminal Cys at position 1 is deleted, SEQ ID NO: 64, and SEQ ID NO: 68. Preferably, a "non-pyruvylated non-lipidated" A22 includes a polypeptide having the amino acid sequence set forth in SEQ ID NO: 68.

The term "deletion" of the N-terminal Cys as used herein includes a mutation that deletes the N-terminal Cys, as compared to a wild-type non-lipidated polypeptide sequence. For example, a "deletion" of the N-terminal Cys refers to a removal of the amino acid Cys from a reference sequence, e.g., from the corresponding wild-type sequence, thereby resulting in a decrease of an amino acid residue as compared to the reference sequence. Unless otherwise described, the terms "N-terminal Cys," "N-terminal Cys at position 1," "Cys at position 1" are interchangeable.

In another embodiment, the N-terminal Cys is substituted with an amino acid that is not a Cys residue. For example, in an exemplary embodiment, the N-terminal Cys at position 1 of SEQ ID NOs: 12-21 includes a C→G substitution at position 1. See, for example, SEQ ID NO: 62 as compared to SEQ ID NO: 19 (B22 wild-type), and SEQ ID NO: 64 as compared to SEQ ID NO: 15 (A22 wild-type). Exemplary amino acids to replace the N-terminal Cys include any non-Cys amino acid, preferably a polar uncharged amino acid such as, for example, glycine. In a preferred embodiment, the substitution is made with a non-conservative residue to Cys.

The inventors surprisingly discovered that expressing non-lipidated ORF2086 polypeptides having a deletion of an N-terminal Cys residue resulted in no detectable pyruvylation when measured by mass spectrometry, as compared to the corresponding wild-type non-lipidated ORF2086 polypeptide. Examples of non-pyruvylated non-lipidated ORF2086 polypeptides include those having an amino acid sequence selected from the group consisting of SEQ ID NO:12 (A04), SEQ ID NO:13 (A05), SEQ ID NO:14 (A12), SEQ ID NO:15 (A22), SEQ ID NO:16 (B02) SEQ ID NO:17 (B03), SEQ ID NO:18 (B09), SEQ ID NO:19 (B22), SEQ ID NO: 20 (B24), SEQ ID NO: 21 (B44), and SEQ ID NO: 70 (A62), wherein the cysteine at position 1 is deleted. Another example of a non-pyruvylated non-lipidated ORF2086 polypeptide includes a polypeptide having the amino acid sequence SEQ ID NO: 58 (B01), wherein the cysteine at position 1 is deleted. Additional examples of isolated non-pyruvylated, non-lipidated ORF2086 polypeptides include polypeptides having an amino acid sequence selected from the group consisting of SEQ ID NO: 44, SEQ ID NO: 49, SEQ ID NO: 50, SEQ ID NO: 55, SEQ ID NO: 66, SEQ ID NO: 68, SEQ ID NO: 71, and SEQ ID NO: 75. A further example of a non-pyruvylated non-lipidated ORF2086 polypeptide includes a polypeptide having the amino acid sequence SEQ ID NO: 57 (B01). Another example of an isolated non-pyruvylated non-lipidated ORF2086 polypeptide includes a polypeptide having SEQ ID NO: 77 (A05); a polypeptide having SEQ ID NO: 76 (A05) wherein the Cys at position 1 is deleted; and a polypeptide having SEQ ID NO: 76 (A05) wherein the Cys at position 1 is substituted with an amino acid that is not a Cys residue. Further examples of non-pyruvylated non-lipidated ORF2086 polypeptides include those having an amino acid sequence selected from the group consisting of SEQ ID NO:12 (A04), SEQ ID NO:13 (A05), SEQ ID NO:14 (A12), SEQ ID NO:15 (A22), SEQ ID NO: 58 (B01), SEQ ID NO:16 (B02) SEQ ID NO:17 (B03), SEQ ID NO:18 (B09), SEQ ID NO:19 (B22), SEQ ID NO: 20 (B24), SEQ ID NO: 21 (B44), and SEQ ID NO: 70 (A62) wherein the cysteine at position 1 is substituted with an amino acid that is not a Cys residue. Preferably, the non-pyruvylated non-lipidated 2086 polypeptide includes at least about 250, 255, or 260 consecutive amino acids, and at most about 270, 269, 268, 267, 266, 265, 264, 263, 260, 259, 258, 257, 256, or 255 consecutive amino acids. Any minimum value may be combined with any maximum value to define a range. More preferably, the polypeptide has at least 254 or 262 consecutive amino acids. In some embodiments, the polypeptide has at most 262 consecutive amino acids. In other embodiments, the polypeptide has at most 254 consecutive amino acids. In one embodiment, the non-pyruvylated non-lipidated polypeptide includes the amino acid sequence that is at least about 60%, 65%, 70%, 75%, 80%, 85%, 86%, 87%, 88%, 89%, 90%, 91%, 92%, 93%, 94%, 95%, 96%, 97%, 98%, 99%, or 100% identical to a sequence encoding the corresponding non-pyruvylated non-lipidated polypeptide. For example, in an exemplary embodiment, the non-pyruvylated non-lipidated A62 polypeptide includes the amino acid sequence that is at least about 60%, 65%, 70%, 75%, 80%, 85%, 86%, 87%, 88%, 89%, 90%, 91%, 92%, 93%, 94%, 95%, 96%, 97%, 98%, 99%, or 100% identical to SEQ ID NO: 71.

In one embodiment, the isolated non-pyruvylated, non-lipidated ORF2086 polypeptide is encoded by a nucleotide sequence that is operatively linked to an expression system, wherein the expression system is capable of being expressed in a bacterial cell. In an exemplary embodiment, the nucleotide sequence is linked to a regulatory sequence that controls expression of the nucleotide sequence.

Suitable expression systems, regulatory sequences, and bacterial cells are known in the art. For example, any plasmid expression vector, e.g., PET™ (Novogen, Madison Wis.) or PMAL™ (New England Biolabs, Beverly, Mass.) can be used as long as the polypeptide is able to be expressed in a bacterial cell. Preferably, the PET™ vector is used for cloning and expression of recombinant proteins in *E. coli*. In the PET™ system, the cloned gene may be expressed under the control of a phage T7 promotor. Exemplary bacterial cells include *Pseudomonas fluorescens*, and preferably, *E. coli*.

In one aspect, the invention relates to a non-pyruvylated non-lipidated ORF2086 polypeptide obtainable by the process. The polypeptide is preferably isolated. The invention further relates to compositions that include a non-pyruvylated non-lipidated ORF2086 polypeptide obtainable by a process. The composition is preferably an immunogenic composition. The process includes expressing a nucleotide sequence encoding a polypeptide having the amino acid sequence selected from the group consisting of SEQ ID NO:12, SEQ ID NO:13, SEQ ID NO:14, SEQ ID NO:15, SEQ ID NO:16 SEQ ID NO:17, SEQ ID NO:18, SEQ ID NO:19, SEQ ID NO: 20, SEQ ID NO: 21, SEQ ID NO: 58, and SEQ ID NO: 70, wherein the cysteine at position 1 is deleted. In another embodiment, the process includes expressing a nucleotide sequence encoding a polypeptide having the amino acid sequence SEQ ID NO: 76, wherein the cysteine at position 1 is deleted. In a further embodiment, the process includes expressing a nucleotide sequence encoding a polypeptide having the amino acid sequence selected from the group consisting of SEQ ID NO:12, SEQ ID NO:13, SEQ ID NO:14, SEQ ID NO:15, SEQ ID NO:16 SEQ ID NO:17, SEQ ID NO:18, SEQ ID NO:19, SEQ ID NO: 20, SEQ ID NO: 21, SEQ ID NO: 58, and SEQ ID NO: 70, wherein the cysteine at position 1 is substituted with an amino acid that is not a Cys residue. The nucleotide sequence is operatively linked to an expression system that is capable of being expressed in a bacterial cell.

In one embodiment, the process includes expressing a nucleotide sequence encoding a polypeptide having the amino acid sequence selected from the group consisting of SEQ ID NO: 44, SEQ ID NO: 49, SEQ ID NO: 50, SEQ ID NO: 55, SEQ ID NO: 66, SEQ ID NO: 68, SEQ ID NO: 71, SEQ ID NO: 57, and SEQ ID NO: 75. In another embodiment, the process includes expressing a nucleotide sequence encoding a polypeptide having the amino acid sequence SEQ ID NO: 77. In another embodiment, the nucleotide sequence is selected from the group consisting of SEQ ID NO: 43, SEQ ID NO: 51, SEQ ID NO: 46, SEQ ID NO: 47, SEQ ID NO: 48, SEQ ID NO: 45, SEQ ID NO: 54, SEQ ID NO: 65, SEQ ID NO: 67, SEQ ID NO: 69, and SEQ ID NO: 72. Preferably the bacterial cell is E. coli.

B09, B44, A05:

In one aspect, the invention relates to a composition that includes a first isolated polypeptide, which includes the amino acid sequence set forth in SEQ ID NO: 49 (B09), and a second isolated polypeptide, which includes the amino acid sequence set forth in SEQ ID NO: 44 (B44). In a preferred embodiment, the polypeptides are immunogenic. In another preferred embodiment, the composition further includes an ORF2086 subfamily A polypeptide from serogroup B N. meningitidis. Preferably, the ORF2086 subfamily A polypeptide is a non-pyruvylated non-lipidated ORF2086 subfamily A polypeptide. In an exemplary embodiment, the ORF2086 subfamily A polypeptide is A05, examples of which include, for example, SEQ ID NO: 13, wherein the N-terminal cysteine at position 1 is deleted, and SEQ ID NO: 55. In another exemplary embodiment, the composition includes a non-pyruvylated non-lipidated A05 polypeptide having the amino acid sequence SEQ ID NO: 76 wherein the Cys at position 1 is deleted; SEQ ID NO: 76 wherein the Cys at position 1 is substituted with an amino acid that is not a Cys residue; and SEQ ID NO: 77.

Polypeptide Domains

In another aspect, the invention relates to a method for producing an isolated polypeptide. The method includes expressing in a bacterial cell a polypeptide, which includes a sequence having greater than 90% identity to SEQ ID NO:21, said sequence includes at least one domain selected from the group consisting of amino acids 13-18 of SEQ ID NO: 21, amino acids 21-34 of SEQ ID NO: 21, and amino acids 70-80 of SEQ ID NO: 21, or a combination thereof, wherein the polypeptide lacks an N-terminal cysteine. The method further includes purifying the polypeptide. The polypeptide produced therein includes a non-pyruvylated non-lipidated ORF2086 polypeptide. Preferably, the polypeptide is immunogenic. In a preferred embodiment, the bacterial cell is E. coli.

Examples of polypeptides that include at least one domain selected from the group consisting of amino acids 13-18 of SEQ ID NO: 21, amino acids 21-34 of SEQ ID NO: 21, and amino acids 70-80 of SEQ ID NO: 21, or a combination thereof, include SEQ ID NO: 12 (A04), SEQ ID NO: 13 (A05), SEQ ID NO: 14 (A12), SEQ ID NO: 15 (A22), SEQ ID NO: 16 (B02), SEQ ID NO: 17 (B03), SEQ ID NO: 18 (B09), SEQ ID NO: 19 (B22), SEQ ID NO: 20 (B24), and SEQ ID NO: 21 (B44). Preferably the cysteine at position 1 of these polypeptides is deleted. In another embodiment, the cysteine at position 1 is substituted with an amino acid that is not a Cys residue. Further exemplary polypeptides include SEQ ID NO: 44, SEQ ID NO: 49, SEQ ID NO: 50, SEQ ID NO: 55, SEQ ID NO: 62, and SEQ ID NO: 64. Another exemplary polypeptide includes SEQ ID NO: 70 and SEQ ID NO: 71. A further exemplary polypeptide includes SEQ ID NO: 76. Yet another exemplary polypeptide includes SEQ ID NO: 77. Additional examples include SEQ ID NO: 80 (B24) and SEQ ID NO: 81 (B24).

In one exemplary embodiment, the isolated polypeptide sequence further includes at least one domain selected from the group consisting of amino acids 96-116 of SEQ ID NO: 21, amino acids 158-170 of SEQ ID NO: 21, amino acids 172-185 of SEQ ID NO: 21, amino acids 187-199 of SEQ ID NO: 21, amino acids 213-224 of SEQ ID NO: 21, amino acids 226-237 of SEQ ID NO: 21, amino acids 239-248 of SEQ ID NO: 21, or a combination thereof. Examples of polypeptides that include at least one domain selected from the group consisting of amino acids 13-18 of SEQ ID NO: 21, amino acids 21-34 of SEQ ID NO: 21, and amino acids 70-80 of SEQ ID NO: 21, or a combination thereof, and further including at least one domain selected from the group consisting of amino acids 96-116 of SEQ ID NO: 21, amino acids 158-170 of SEQ ID NO: 21, amino acids 172-185 of SEQ ID NO: 21, amino acids 187-199 of SEQ ID NO: 21, amino acids 213-224 of SEQ ID NO: 21, amino acids 226-237 of SEQ ID NO: 21, amino acids 239-248 of SEQ ID NO: 21, or a combination thereof, include SEQ ID NO: 16 (B02), SEQ ID NO: 17 (B03), SEQ ID NO: 18 (B09), SEQ ID NO: 19 (B22), SEQ ID NO: 20 (B24), and SEQ ID NO: 21 (B44). Preferably the cysteine at position 1 of these polypeptides is deleted. Further exemplary polypeptides include a polypeptide having the amino acid sequence selected from SEQ ID NO: 44, SEQ ID NO: 49, SEQ ID NO: 50, and SEQ ID NO: 55, and SEQ ID NO: 62.

In one aspect, the invention relates to an isolated polypeptide produced by a process described herein. In one embodiment, the isolated polypeptide is a non-pyruvylated non-lipidated polypeptide. In another aspect, the invention relates to an immunogenic composition produced by a process described herein.

Nucleotide Sequences Encoding the Polypeptides

B09:

In one aspect, the invention relates to an isolated polypeptide that includes the amino acid sequence set forth in SEQ ID NO: 18 wherein the N-terminal Cys at position 1 is deleted or SEQ ID NO: 49. Exemplary nucleotide sequences that encode SEQ ID NO: 49 include sequences selected from SEQ ID NO: 46, SEQ ID NO: 47, and SEQ ID NO: 48. Preferably, the nucleotide sequence is SEQ ID NO: 46. In one aspect, the invention relates to an isolated nucleotide sequence that includes SEQ ID NO: 46. In one aspect, the invention relates to an isolated nucleotide sequence that includes SEQ ID NO: 47. In one aspect, the invention relates to an isolated nucleotide sequence that includes SEQ ID NO: 48.

In one aspect, the invention relates to a plasmid including a nucleotide sequence selected from SEQ ID NO: 46, SEQ ID NO: 47, SEQ ID NO: 48, and SEQ ID NO: 45, wherein the plasmid is capable of being expressed in a bacterial cell. Suitable expression systems, regulatory sequences, and bacterial cells are known in the art, as described above. Preferably, the bacterial cell is *E. coli*.

In another aspect, the invention relates to an isolated polypeptide that includes the amino acid sequence set forth in SEQ ID NO: 50. In an exemplary embodiment, SEQ ID NO: 50 is encoded by SEQ ID NO: 45.

B44:

In yet another aspect, the invention relates to an isolated polypeptide that includes the amino acid sequence set forth in SEQ ID NO: 21 wherein the N-terminal Cys is deleted or SEQ ID NO: 44. Exemplary nucleotide sequences that encode SEQ ID NO: 44 include sequences selected from SEQ ID NO: 43 and SEQ ID NO: 51. Preferably, the nucleotide sequence is SEQ ID NO: 43. In one aspect, the invention relates to an isolated nucleotide sequence that includes SEQ ID NO: 43.

A05:

In one aspect, the invention relates to an isolated polypeptide that includes the amino acid sequence set forth in SEQ ID NO: 13 (A05) wherein the N-terminal Cys at position 1 is deleted or SEQ ID NO: 55. Exemplary nucleotide sequences that encode SEQ ID NO: 55 include sequences selected from SEQ ID NO: 54, SEQ ID NO: 65, and SEQ ID NO: 73. Preferably, the nucleotide sequence is SEQ ID NO: 65. In one aspect, the invention relates to an isolated nucleotide sequence that includes SEQ ID NO: 54. In one aspect, the invention relates to an isolated nucleotide sequence that includes SEQ ID NO: 65. In one aspect, the invention relates to an isolated nucleotide sequence that includes SEQ ID NO: 73.

A12:

In another aspect, the invention relates to an isolated polypeptide that includes the amino acid sequence set forth in SEQ ID NO: 14 (A12) wherein the N-terminal Cys is deleted or SEQ ID NO: 66. Exemplary nucleotide sequences that encode SEQ ID NO: 66 include SEQ ID NO: 67. In one aspect, the invention relates to an isolated nucleotide sequence that includes SEQ ID NO: 67.

A22:

In yet another aspect, the invention relates to an isolated polypeptide that includes the amino acid sequence set forth in SEQ ID NO: 15 (A22) wherein the N-terminal Cys is deleted or SEQ ID NO: 68. Exemplary nucleotide sequences that encode SEQ ID NO: 68 include SEQ ID NO: 69. In one aspect, the invention relates to an isolated nucleotide sequence that includes SEQ ID NO: 69.

A62:

In one aspect, the invention relates to an isolated polypeptide having an amino acid sequence that is at least 95% identical to SEQ ID NO: 71, wherein the first 20 amino acid residues of the sequence does not contain a cysteine. Preferably, the polypeptide includes the amino acid sequence as shown at positions 1-184 of SEQ ID NO: 71. The polypeptide is preferably non-lipidated and non-pyruvylated. In another embodiment, the polypeptide is immunogenic.

In another embodiment, the isolated polypeptide includes a fragment of A62. Exemplary fragments of A62 includes any number of contiguous residues from SEQ ID NO: 70 or SEQ ID NO: 71. In one embodiment, the isolated polypeptide includes the amino acid sequence at positions 158-185 of SEQ ID NO: 71. In another embodiment, the isolated polypeptide includes the amino acid sequence at positions 159-186 of SEQ ID NO: 71. In one embodiment, the polypeptide includes at least 6 contiguous amino acids from the amino acid sequence at positions 185-254 of SEQ ID NO: 71.

In another aspect, the invention relates to an isolated nucleic acid sequence encoding an isolated polypeptide having an amino acid sequence that is at least 95% identical to SEQ ID NO: 71, wherein the first 20 amino acid residues of the sequence does not contain a cysteine. Preferably, the polypeptide consists of the amino acid sequence set forth in SEQ ID NO: 71. In one embodiment, the isolated nucleic acid sequence includes SEQ ID NO: 72.

In yet another aspect, the invention relates to an isolated polypeptide that includes the amino acid sequence set forth in SEQ ID NO: 70 (A62) wherein the N-terminal Cys is deleted or SEQ ID NO: 71. Exemplary nucleotide sequences that encode SEQ ID NO: 71 include SEQ ID NO: 72. In one aspect, the invention relates to an isolated nucleotide sequence that includes SEQ ID NO: 72.

Immunogenic Compositions

In a preferred embodiment, the compositions described herein including an isolated non-pyruvylated non-lipidated ORF2086 polypeptide are immunogenic. Immunogenic compositions that include a protein encoded by a nucleotide sequence from *Neisseria meningitidis* ORF2086 are known in the art. Exemplary immunogenic compositions include those described in WO2003/063766, and US patent application publication numbers US 20060257413 and US 20090202593, which are incorporated herein by reference in their entirety. Such immunogenic compositions described therein include a protein exhibiting bactericidal activity identified as ORF2086 protein, immunogenic portions thereof, and/or biological equivalents thereof. The ORF2086 protein refers to a protein encoded by open reading frame 2086 of *Neisseria* species.

The protein may be a recombinant protein or an isolated protein from native *Neisseria* species. For example, *Neisseria* ORF2086 proteins may be isolated from bacterial strains, such as those of *Neisseria* species, including strains of *Neisseria meningitidis* (serogroups A, B, C, D, W-135, X, Y, Z, and 29E), *Neisseria gonorrhoeae*, and *Neisseria lactamica*, as well as immunogenic portions and/or biological equivalents of said proteins.

The ORF2086 proteins include 2086 Subfamily A proteins and Subfamily B proteins, immunogenic portions thereof, and/or biological equivalents thereof. 2086 subfamily A proteins and 2086 subfamily B proteins are known in the art, see, for example Fletcher et al., 2004 cited above and Murphy et al., *J Infect Dis.* 2009 Aug. 1; 200(3):379-89. See also WO2003/063766 and U.S. Patent Application Publication Nos. US 20060257413 and US 20090202593, each of which is hereby incorporated by reference in its entirety, which discloses SEQ ID NOs: 260 to 278 therein as representing amino acid sequences associated with proteins of 2086 Subfamily A. In addition, disclosed in WO2003/063766 are SEQ ID NOS: 279 to 299 therein as representing amino acid sequences associated with proteins of 2086 Subfamily B. WO2003/063766 is incorporated herein by reference in its entirety. The ORF2086 proteins or equivalents thereof, etc. may be lipidated or non lipidated. Preferably, the *Neisseria* ORF2086 protein is non lipidated. Alternatively, the immunogenic compositions may be combinations of lipidated and non lipidated ORF2086 proteins.

In (an) one embodiment, the immunogenic composition includes an isolated protein having at least 95% amino acid sequence identity to a protein encoded by a nucleotide sequence from *Neisseria* ORF2086. In another embodiment, the immunogenic composition includes an isolated protein having at least about 60%, 65%, 70%, 75%, 80%, 85%, 86%, 87%, 88%, 89%, 90%, 91%, 92%, 93%, 94%, 95%, 96%, 97%, 98%, 99%, or 100% identical amino acid sequence identity to a protein encoded by a nucleotide sequence from *Neisseria* ORF2086.

In one embodiment, the immunogenic composition includes an isolated protein having at least 95% amino acid sequence identity to a Subfamily A protein encoded by a nucleotide sequence from *Neisseria* ORF2086. Preferably, the immunogenic composition includes an isolated Subfamily A protein encoded by a nucleotide sequence from *Neisseria* ORF2086. In some embodiments, the ORF2086 Subfamily A polypeptide is an A05, an A04, an A12, an A62, or an A22 variant. In some embodiments, the ORF2086 Subfamily A polypeptide is an A05, an A12, or an A22 variant.

Combination of Subfamily a Polypeptides:

In one embodiment, the composition includes any combination of ORF2086 Subfamily A polypeptides. Exemplary combinations of ORF2086 Subfamily A polypeptides include, for example, A05 and A12; A05 and A22; A05 and A62; A12 and A62; A12 and A22; A22 and A62; A05, A12, and A22; A05, A12, and A62; A12, A22, and A62; and A05, A22, and A62. Preferably, the ORF2086 Subfamily A polypeptide is non-lipidated and non-pyruvylated.

In another embodiment, the immunogenic composition includes an isolated protein having at least 95% amino acid sequence identity to a Subfamily B protein encoded by a nucleotide sequence from *Neisseria* ORF2086. Preferably, the immunogenic composition includes an isolated Subfamily B protein encoded by a nucleotide sequence from *Neisseria* ORF2086. In some embodiments, the ORF2086 Subfamily B protein is a B44, a B02, a B03, a B22, a B24 or a B09 variant. In some embodiments, the ORF2086 Subfamily B protein is a B44, a B22, or a B09 variant.

Combination of Subfamily B Polypeptides:

In one embodiment, the composition includes any combination of ORF2086 Subfamily B polypeptides. Exemplary combinations of ORF2086 Subfamily B polypeptides include, for example, B09 and B22; B22 and B44; B44 and B09; B01 and B09; B01 and B22; B01 and B44; and B09, B22, and B44; B09 and B24; B22 and B24; B24 and B44; B01 and B24; B02 and B24; B02 and B01, B02 and B09; B02 and B44; B01, B09, and B24; B01, B24, and B44.

In a preferred embodiment, the immunogenic composition includes an isolated non-pyruvylated non-lipidated polypeptide having at least 95% amino acid sequence identity to a Subfamily B protein encoded by a nucleotide sequence from *Neisseria* ORF2086. For example, in some embodiments, the ORF2086 Subfamily B protein is sequences selected from a B44 having an amino acid sequence as shown in SEQ ID NO: 21; a B02 having an amino acid sequence as shown in SEQ ID NO: 16; a B03 having an amino acid sequence as shown in SEQ ID NO: 17; a B22 having an amino acid sequence as shown in SEQ ID NO:19; a B24 having an amino acid sequence as shown in SEQ ID NO: 20; a B01 having an amino acid sequence as shown in SEQ ID NO:58; or a B09 variant having an amino acid sequence as shown in SEQ ID NO:18, wherein the N-terminal Cys is deleted, or a combination thereof.

More preferably, the immunogenic composition includes a non-pyruvylated non-lipidated B09 polypeptide, a non-pyruvylated non-lipidated B44 polypeptide, or combinations thereof. In one embodiment, the composition includes a non-pyruvylated non-lipidated B09 variant having the amino acid sequence as shown in SEQ ID NO:18, wherein the N-terminal Cys is deleted, a non-pyruvylated non-lipidated B44 having the amino acid sequence as shown in SEQ ID NO: 21, wherein the N-terminal Cys is deleted, or a combination thereof. In another embodiment, the immunogenic composition includes a non-pyruvylated non-lipidated B09 having SEQ ID NO: 49, a non-pyruvylated non-lipidated B44 having SEQ ID NO: 44, or a combination thereof.

In one aspect, the invention relates to an immunogenic composition that includes an ORF2086 subfamily B polypeptide from serogroup B *N. meningitidis*, wherein the polypeptide is a non-pyruvylated non-lipidated B44. The B44 may include the amino acid sequence as shown in SEQ ID NO: 21, wherein the N-terminal Cys is deleted or SEQ ID NO: 44. In one embodiment, the composition further includes a second ORF2086 subfamily B polypeptide from serogroup B *N. meningitidis*, wherein the second polypeptide is a non-pyruvylated non-lipidated B09. The B09 may include the amino acid sequence as shown in SEQ ID NO: 18, wherein the N-terminal Cys is deleted, or SEQ ID NO: 49. In one embodiment, the immunogenic composition is a vaccine.

In another embodiment, the composition includes no more than 3 ORF2086 subfamily B polypeptides. In a further embodiment, the composition includes no more than 2 ORF2086 subfamily B polypeptides.

In a further embodiment, the composition includes at most 1, 2, or 3 species of an ORF2086 subfamily B variant. In a further embodiment, the composition includes at most 1, 2, or 3 species of an ORF2086 subfamily A variant.

Compositions Including a Subfamily B Polypeptide and a Subfamily A Polypeptide:

In one embodiment, the composition further includes one or more ORF2086 subfamily A polypeptides. In a preferred embodiment, the composition includes an A05 subfamily A polypeptide. More preferably, the A05 subfamily A polypeptide is non-lipidated and non-pyruvylated. In another preferred embodiment, the composition includes an A62 subfamily A polypeptide. More preferably, the A62 subfamily A polypeptide is non-lipidated and non-pyruvylated.

In yet another embodiment, the immunogenic composition includes an isolated protein having at least 95% amino acid sequence identity to a Subfamily A protein encoded by a nucleotide sequence from *Neisseria* ORF2086, and an isolated protein having at least 95% amino acid sequence identity to a Subfamily B protein encoded by a nucleotide sequence from *Neisseria* ORF2086.

Preferably, the immunogenic composition includes an isolated Subfamily A protein encoded by a nucleotide sequence from *Neisseria* ORF2086 and an isolated Subfamily B protein encoded by a nucleotide sequence from *Neisseria* ORF2086. More preferably, the immunogenic composition includes an isolated non-pyruvylated non-lipidated Subfamily A ORF2086 polypeptide and an isolated non-pyruvylated non-lipidated Subfamily B ORF2086 polypeptide.

Combinations:

Any combination of ORF2086 polypeptides are contemplated. In one embodiment, the composition includes at least one Subfamily A polypeptide in the absence of Subfamily B polypeptides. For example, the composition includes only Subfamily A polypeptides. In another embodiment, the composition includes at least one Subfamily B polypeptide in the absence of Subfamily A polypeptides. For example, the composition includes only Subfamily A polypeptides.

The immunogenic composition may include any Subfamily A polypeptide or combination thereof. In some embodiments, the ORF2086 Subfamily A polypeptide is an A05, an A04, an A12, or an A22 variant. In another embodiment, the ORF2086 Subfamily A polypeptide includes A62. In a preferred embodiment, the ORF2086 Subfamily A polypeptide is an A05 having an amino acid sequence as shown in SEQ ID NO: 13; an A04 having an amino acid sequence as shown in SEQ ID NO: 12; an A12 having an amino acid sequence as shown in SEQ ID NO: 14; or an A22 variant having an amino acid sequence as shown in SEQ ID NO: 15, wherein the N-terminal Cys is deleted, or any combination thereof. Yet another exemplary immunogenic composition includes a combination of isolated non-pyruvylated non-lipidated A05 and A62 Subfamily A ORF2086 polypeptides. For example, the immunogenic composition may include a polypeptide having SEQ ID NO: 55 and a polypeptide having SEQ ID NO: 71. A further exemplary immunogenic composition includes a combination of isolated non-pyruvylated non-lipidated A05 and A12 Subfamily A ORF2086 polypeptides. Another exemplary immunogenic composition includes a combination of isolated non-pyruvylated non-lipidated A12 and A62 Subfamily A ORF2086 polypeptides.

The immunogenic composition may include any Subfamily B polypeptide or combination thereof. In some embodiments, the ORF2086 Subfamily B protein is a B44, a B02, a B03, a B22, a B24 or a B09 variant. In a preferred embodiment, the ORF2086 Subfamily B protein is a B44 having the amino acid sequence as shown in SEQ ID NO: 21; a B02 having an amino acid sequence as shown in SEQ ID NO: 16; a B03 having an amino acid sequence as shown in SEQ ID NO: 17; a B22 having an amino acid sequence as shown in SEQ ID NO:19; a B24 having an amino acid sequence as shown in SEQ ID NO: 20; or a B09 variant having an amino acid sequence as shown in SEQ ID NO:18, wherein the N-terminal Cys is deleted, or a combination thereof. Yet another exemplary immunogenic composition includes a combination of isolated non-pyruvylated non-lipidated B09 and B44 Subfamily B ORF2086 polypeptides. A further exemplary immunogenic composition includes a combination of isolated non-pyruvylated non-lipidated B09 and B22 Subfamily B ORF2086 polypeptides. Another exemplary immunogenic composition includes a combination of isolated non-pyruvylated non-lipidated B22 and B44 Subfamily B ORF2086 polypeptides. An additional exemplary immunogenic composition includes a combination of isolated non-pyruvylated non-lipidated B09, B22, and B44 Subfamily B ORF2086 polypeptides.

In one embodiment, the composition includes a non-lipidated ORF2086 polypeptide in the absence of a lipidated ORF2086 polypeptide. In another embodiment, the composition includes a non-lipidated ORF2086 polypeptide and at least one lipidated ORF2086 polypeptide.

In one embodiment, the composition includes a non-pyruvylated non-lipidated ORF2086 polypeptide in the absence of a lipidated ORF2086 polypeptide. In another embodiment, the composition includes a lipidated ORF2086 polypeptide and a non-pyruvylated non-lipidated ORF2086 polypeptide. For example, the composition may include a lipidated A05 polypeptide having SEQ ID NO: 76 and a non-pyruvylated non-lipidated A05 having SEQ ID NO: 77. Another exemplary composition includes a lipidated A05 polypeptide having SEQ ID NO: 76 and a non-pyruvylated non-lipidated A62 having SEQ ID NO: 71. An additional exemplary composition includes a lipidated B01 polypeptide having SEQ ID NO: 58 and a non-pyruvylated non-lipidated A62 having SEQ ID NO: 71.

Exemplary Combinations:

One exemplary immunogenic composition includes a combination of an isolated non-lipidated A05, B09, B22, and B44 ORF2086 polypeptides. For example, the immunogenic composition may include a non-pyruvylated non-lipidated A05 (SEQ ID NO: 55) Subfamily A ORF2086 polypeptide and isolated non-pyruvylated non-lipidated B09 (SEQ ID NO: 49), B22 (SEQ ID NO: 75), and B44 (SEQ ID NO: 44) Subfamily B ORF2086 polypeptides.

Another exemplary immunogenic composition includes a combination of isolated non-pyruvylated non-lipidated A05 and A12 Subfamily A ORF2086 polypeptides and isolated non-pyruvylated non-lipidated B22 and B44 Subfamily B ORF2086 polypeptides. A further exemplary immunogenic composition includes isolated non-pyruvylated non-lipidated A05, A12, B09, and B44 polypeptides. Yet another example includes isolated non-pyruvylated non-lipidated A12, A62, B09, and B44 polypeptides. Yet a further example includes isolated non-pyruvylated non-lipidated A05, A12, A62, B09, and B44 polypeptides. Another exemplary immunogenic composition includes isolated non-pyruvylated non-lipidated A62 and B09 polypeptides. Another exemplary immunogenic composition includes isolated non-pyruvylated non-lipidated A62 and B44 polypeptides. Another exemplary immunogenic composition includes isolated non-pyruvylated non-lipidated A62, B09, and B44 polypeptides. Another exemplary immunogenic composition includes isolated non-pyruvylated non-lipidated A05, A62, and B44 polypeptides. Another exemplary immunogenic composition includes isolated non-pyruvylated non-lipidated A05, A62, B09, and B44 polypeptides.

In one embodiment, the immunogenic composition includes a 1:1 ratio of a Subfamily A protein to a Subfamily B protein. In another embodiment, the immunogenic composition includes any one of the following ratios of a Subfamily A polypeptide to a Subfamily B polypeptide: 1:1; 1:2; 1:3; 1:4; 1:5; 1:6; 1:7; 1:8; 1:9; or 1:10. In another embodiment, the immunogenic composition includes any one of the following ratios of a Subfamily B polypeptide to a Subfamily A polypeptide: 1:1; 1:2; 1:3; 1:4; 1:5; 1:6; 1:7; 1:8; 1:9; or 1:10.

Bactericidal Immune Responses

In one aspect, the isolated polypeptides and compositions described herein elicit a bactericidal immune response in a mammal against infection from any serogroup of N. meningitidis, such as a serogroup selected from serogroup A, B, C, E29, H, I, K, L, W-135, X, Y and Z. In a preferred embodiment, the isolated polypeptides and compositions described herein elicit a bactericidal immune response in a mammal against infection from serogroups A, B, C, W-135, Y and/or X.

In another aspect, the isolated polypeptides and compositions described herein elicit a bactericidal immune response in a mammal against an ORF2086 polypeptide from serogroup B *N. meningitidis*. The compositions have the ability to induce bactericidal anti-meningococcal antibodies after administration to a mammal, and in preferred embodiments can induce antibodies that are bactericidal against strains with the respective subfamilies. Further information on bactericidal responses is given below. See, for example, Examples 6, 11, 12, and 13.

In one embodiment, the compositions elicit a bactericidal immune response against a heterologous subfamily of *N. meningitidis* serogroup B. For example, a composition including a non-lipidated subfamily A polypeptide may elicit a bactericidal immune response against a subfamily A variant of *N. meningitidis* serogroup B and/or against a subfamily B variant of *N. meningitidis* serogroup B. See, for example, Examples 18-19.

In a further aspect, the isolated polypeptides and compositions described herein elicit a bactericidal immune response against at least one of serogroup A, serogroup B, serogroup C, serogroup W135, and/or serogroup Y strains of *N. meningitidis*. In a preferred embodiment, the compositions elicit a bactericidal immune response at least against serogroup B, serogroup C, and serogroup Y of *N. meningitidis*. See, for example, Example 21.

Bactericidal antibodies are an indicator of protection in humans and preclinical studies serve as a surrogate, and any new immunogenic composition candidate described herein should elicit these functional antibodies.

B09:

In one aspect, the isolated non-lipidated B09 polypeptide, and immunogenic compositions thereof, elicits bactericidal antibodies against (e.g., that can bind to) an ORF2086 polypeptide from serogroup B *N. meningitidis*, subfamily B. In an exemplary embodiment, the isolated non-pyruvylated non-lipidated B09 polypeptide having SEQ ID NO: 18 wherein the N-terminal Cys at position 1 is deleted or SEQ ID NO: 49, and immunogenic compositions thereof, elicits bactericidal antibodies against (e.g., that can bind to) an ORF2086 polypeptide from serogroup B *N. meningitidis*, subfamily A or preferably subfamily B. Preferably, the non-pyruvylated non-lipidated B09 polypeptide and immunogenic compositions thereof, elicits bactericidal antibodies against the A05 variant (SEQ ID NO: 13); B44 variant (SEQ ID NO: 21); B16 variant (SEQ ID NO: 60); B24 variant (SEQ ID NO: 20); B09 variant (SEQ ID NO: 18), or a combination thereof. In an exemplary embodiment, the non-pyruvylated non-lipidated B09 polypeptide and immunogenic compositions thereof, elicits bactericidal antibodies against B44 variant (SEQ ID NO: 21); B16 variant (SEQ ID NO: 60); B24 variant (SEQ ID NO: 20); B09 variant (SEQ ID NO: 18), or a combination thereof. See, for example, Example 11, Example 12, and Example 13.

B44:

In one aspect, the isolated non-lipidated B44 polypeptide, and immunogenic compositions thereof, elicits bactericidal antibodies against (e.g., that can bind to) an ORF2086 polypeptide from serogroup B *N. meningitidis*, subfamily B. In another exemplary embodiment, the isolated non-pyruvulated non-lipidated B44 polypeptide having SEQ ID NO: 21 wherein the N-terminal Cys at position 1 is deleted or SEQ ID NO: 44, and immunogenic compositions thereof, elicits bactericidal antibodies against (e.g., that can bind to) an ORF2086 polypeptide from serogroup B *N. meningitidis*, subfamily B. Preferably, the non-pyruvylated non-lipidated B44 polypeptide and immunogenic compositions thereof, elicits bactericidal antibodies against the B44 variant (SEQ ID NO: 21); B16 variant (SEQ ID NO: 60); B24 variant (SEQ ID NO: 20); B09 variant (SEQ ID NO: 18), or a combination thereof. See, for example, Example 11. Additionally, the non-pyruvylated non-lipidated B44 polypeptide and immunogenic compositions thereof may also elicit bactericidal antibodies that bind to the B02 variant (SEQ ID NO: 16). See, for example, Example 12 and Example 13. Moreover, the non-pyruvylated non-lipidated B44 polypeptide and immunogenic compositions thereof may also elicit bactericidal antibodies that bind to B03 variant (SEQ ID NO: 17) and B15 variant (SEQ ID NO: 59). See, for example, Example 6.

B22:

In one aspect, the isolated non-lipidated B22 polypeptide, and immunogenic compositions thereof, elicits bactericidal antibodies against (e.g., that can bind to) an ORF2086 polypeptide from serogroup B *N. meningitidis*, subfamily B. In a further exemplary embodiment, the isolated non-pyruvulated non-lipidated B22 polypeptide having SEQ ID NO: 19 wherein the N-terminal Cys at position 1 is deleted, and immunogenic compositions thereof, elicits bactericidal antibodies against (e.g., that can bind to) an ORF2086 polypeptide from serogroup B *N. meningitidis*, subfamily B. Preferably, the non-pyruvylated non-lipidated B22 polypeptide elicits bactericidal antibodies against the B44 variant (SEQ ID NO: 21); B16 variant (SEQ ID NO: 60); B24 variant (SEQ ID NO: 20); B09 variant (SEQ ID NO: 18), or a combination thereof. See, for example, Example 13.

A05:

In one aspect, the isolated non-lipidated A05 polypeptide, and immunogenic compositions thereof, elicits bactericidal antibodies against (e.g., that can bind to) an ORF2086 polypeptide from serogroup B *N. meningitidis*, subfamily A. In one embodiment, the isolated non-pyruvylated non-lipidated A05 polypeptide having SEQ ID NO: 13 wherein the N-terminal Cys is deleted or SEQ ID NO: 55, and immunogenic compositions thereof, elicits bactericidal antibodies against (e.g., that can bind to) an ORF2086 polypeptide from serogroup B *N. meningitidis*, subfamily A. In one embodiment, the isolated A05 polypeptide includes the amino acid sequence SEQ ID NO: 76, wherein the cysteine at position 1 is deleted. In another embodiment, the isolated A05 polypeptide includes the amino acid sequence SEQ ID NO: 76, wherein the cysteine at position 1 is substituted with an amino acid that is not a Cys residue. In one embodiment, the isolated A05 polypeptide includes the amino acid sequence SEQ ID NO: 77. Preferably, the non-pyruvylated non-lipidated A05 and immunogenic compositions thereof, elicits bactericidal antibodies against the A05 variant (SEQ ID NO: 13), A22 variant (SEQ ID NO: 15), A12 variant (SEQ ID NO: 14), or a combination thereof. See, for example, Example 6 and 13.

A62:

In one aspect, the isolated non-lipidated A62 polypeptide, and immunogenic compositions thereof, elicits bactericidal antibodies against (e.g., that can bind to) an ORF2086 polypeptide from serogroup B *N. meningitidis*, subfamily A. In one embodiment, the isolated A62 polypeptide includes the amino acid sequence SEQ ID NO: 70, wherein the cysteine at position 1 is substituted with an amino acid that is not a Cys residue. In another embodiment, the isolated non-pyruvylated non-lipidated A62 polypeptide having SEQ ID NO: 70 wherein the N-terminal Cys is deleted or SEQ ID NO: 71, and immunogenic compositions thereof, elicits bactericidal antibodies against (e.g., that can bind to) an ORF2086 polypeptide from serogroup B *N. meningitidis*, subfamily A and/or subfamily B. For example, the non-pyruvylated non-lipidated A62 and immunogenic compositions thereof, elicits bactericidal antibodies against the A05 variant (SEQ ID NO: 13), A12 variant (SEQ ID NO: 14), A22 variant (SEQ ID NO: 15), and A62 variant (SEQ ID NO: 70). As another example, the non-pyruvylated non-lipidated A62 and immunogenic compositions thereof, elicits bactericidal antibodies against the A29 variant, B09 variant, and B24 variant. See, for example, Examples 18-19. In another embodiment, the non-pyruvylated non-lipidated A62 and immunogenic compositions thereof, elicits bactericidal antibodies against the B16 variant.

A12:

In one embodiment, the isolated non-pyruvylated non-lipidated A12 polypeptide having SEQ ID NO: 14 wherein the N-terminal Cys is deleted or SEQ ID NO: 66, and immunogenic compositions thereof, elicits bactericidal antibodies against an ORF2086 polypeptide from serogroup B *N. meningitidis*, subfamily A and/or subfamily B. Preferably, the non-pyruvylated non-lipidated A12 and immunogenic compositions thereof, elicits bactericidal antibodies against the A05 variant (SEQ ID NO: 13), A22 variant (SEQ ID NO: 15), A12 variant (SEQ ID NO: 14), A62 variant (SEQ ID NO: 70), A29 variant, B09 variant. See, for example, Examples 18-19.

In one embodiment, the isolated non-pyruvylated non-lipidated A22 polypeptide having SEQ ID NO: 15 wherein the N-terminal Cys is deleted or SEQ ID NO: 68, and immunogenic compositions thereof, elicits bactericidal antibodies against (e.g., that can bind to) an ORF2086 polypeptide from serogroup B *N. meningitidis*, subfamily A and/or subfamily B. Preferably, the non-pyruvylated non-lipidated A22 and immunogenic compositions thereof, elicits bactericidal antibodies against the A05 variant (SEQ ID NO: 13), A22 variant (SEQ ID NO: 15), A62 variant (SEQ ID NO: 70), A29 variant. See, for example, Examples 18-19.

Method of Eliciting Bactericidal Antibodies

In one aspect, the invention relates to a method of eliciting bactericidal antibodies specific to serogroup A *N. meningitidis* in a mammal. In one aspect, the invention relates to a method of eliciting bactericidal antibodies specific to serogroup C *N. meningitidis* in a mammal. In one aspect, the invention relates to a method of eliciting bactericidal antibodies specific to serogroup W135 *N. meningitidis* in a mammal. In one aspect, the invention relates to a method of eliciting bactericidal antibodies specific to serogroup X *N. meningitidis* in a mammal. In one aspect, the invention relates to a method of eliciting bactericidal antibodies specific to serogroup Y *N. meningitidis* in a mammal. In one aspect, the invention relates to a method of eliciting bactericidal antibodies specific to serogroups A, B, C, W-135, X and/or Y *N. meningitidis* in a mammal. In one aspect, the invention relates to a method of eliciting bactericidal antibodies specific to serogroup B *N. meningitidis* in a mammal. In an exemplary embodiment, the method includes eliciting bactericidal antibodies specific to an ORF2086 subfamily B serogroup B *N. meningitidis*, an ORF2086 subfamily A serogroup B *N. meningitidis*, or a combination thereof.

The method includes administering to the mammal an effective amount of an isolated non-pyruvylated non-lipidated 2086 polypeptide or immunogenic composition thereof, as described above. See, for example, Examples 18-19, and 22.

In a preferred embodiment, the method includes eliciting bactericidal antibodies specific to an ORF2086 subfamily B serogroup B *N. meningitidis*. The isolated polypeptide or immunogenic composition includes a non-pyruvylated non-lipidated B44 polypeptide. In another preferred embodiment, the composition further includes a non-pyruvylated non-lipidated B09 polypeptide. In an exemplary embodiment, the isolated polypeptide or immunogenic composition includes SEQ ID NO: 49, SEQ ID NO: 44, or a combination thereof. In another exemplary embodiment, the isolated polypeptide or immunogenic composition includes SEQ ID NO: 18, wherein the N-terminal Cys at position 1 is deleted, SEQ ID NO: 21, wherein the N-terminal Cys at position 1 is deleted, or a combination thereof, In yet another exemplary embodiment, the isolated polypeptide or immunogenic composition includes SEQ ID NO: 19, wherein the N-terminal Cys at position 1 is deleted. In one embodiment, the immunogenic composition for eliciting bactericidal antibodies specific to an ORF2086 subfamily B serogroup B *N. meningitidis* includes at least one of a non-pyruvylated non-lipidated A05, A12, and A62 polypeptide. See, for example, Example 19.

In a preferred embodiment, the method includes eliciting bactericidal antibodies specific to an ORF2086 subfamily A serogroup B *N. meningitidis*. The isolated polypeptide or immunogenic composition includes a non-pyruvylated non-lipidated A05 polypeptide. In a preferred embodiment, the isolated polypeptide or immunogenic composition includes SEQ ID NO: 13, wherein the N-terminal Cys at position 1 is deleted. In another preferred embodiment, the composition further includes a non-pyruvylated non-lipidated B44 polypeptide. See, for example, Example 6 and 13. In an exemplary embodiment, the isolated polypeptide or immunogenic composition includes SEQ ID NO: 55, SEQ ID NO: 44, or a combination thereof. In a preferred embodiment, the isolated polypeptide or immunogenic composition includes SEQ ID NO: 13, wherein the N-terminal Cys at position 1 is deleted, SEQ ID NO: 21, wherein the N-terminal Cys at position 1 is deleted, or a combination thereof. In another exemplary embodiment, the isolated polypeptide or immunogenic composition includes SEQ ID NO: 77 (A05), SEQ ID NO: 44 (B44), or a combination thereof. In one embodiment, the immunogenic composition for eliciting bactericidal antibodies specific to an ORF2086 subfamily A serogroup B *N. meningitidis* includes at least one of a non-pyruvylated non-lipidated A05, A12, and A62 polypeptide. See, for example, Examples 18-19.

When an exemplary immunogenic composition including at least two non-pyruvylated non-lipidated ORF2086 polypeptides as described above was administered to mammals, the inventors surprisingly discovered that a synergistic bactericidal immune response may be elicited against serogroup B of *Neisseria meningitidis*, as compared to an immunogenic composition including one respective non-pyruvylated non-lipidated ORF2086 polypeptide. See, for example, Example 19. Accordingly, in one embodiment, the immunogenic composition includes at least a first non-pyruvylated non-lipidated ORF2086 polypeptide that acts synergistically with at least a second pyruvylated non-lipidated ORF2086 polypeptide to elicit an immune response against serogroup B of *Neisseria meningitidis*.

In another aspect, the invention relates to a method of eliciting bactericidal antibodies specific to serogroup C of *N. meningitidis* in a mammal. The method includes administering to the mammal an effective amount of an isolated non-pyruvylated non-lipidated 2086 polypeptide from *N. meningitidis* serogroup B or an immunogenic composition thereof, as described above. See, for example, Example 22. In one embodiment, the polypeptide includes the amino acid sequence set forth in SEQ ID NO: 71 or the amino acid sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21, wherein the cysteine at position 1 is deleted. In one embodiment, the polypeptide includes the amino acid sequence set forth in SEQ ID NO: 71 or the amino acid sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21, wherein the cysteine at position 1 is substituted with an amino acid that is not a Cys residue. In another embodiment, the immunogenic composition further includes at least one conjugate selected from: a) a conjugate of a capsular saccharide of *Neisseria meningitidis* serogroup A, b) a conjugate of a capsular saccharide of *Neisseria meningitidis* serogroup C, c) a conjugate of a capsular saccharide of *Neisseria meningitidis* serogroup W135, and d) a conjugate of a capsular saccharide of *Neisseria meningitidis* serogroup Y. An exemplary immunogenic composition includes at least an isolated non-pyruvylated non-lipidated A62 polypeptide and a) a conjugate of a capsular saccharide of *Neisseria meningitidis* serogroup A, b) a conjugate of a capsular saccharide of *Neisseria meningitidis* serogroup C, c) a conjugate of a capsular saccharide of *Neisseria meningitidis* serogroup W135, and d) a conjugate of a capsular saccharide of *Neisseria meningitidis* serogroup Y.

In a further aspect, the invention relates to a method of eliciting bactericidal antibodies specific to serogroup Y of *N. meningitidis* in a mammal. The method includes administering to the mammal an effective amount of an isolated non-pyruvylated non-lipidated 2086 polypeptide from *N. meningitidis* serogroup B or an immunogenic composition thereof, as described above. See, for example, Example 22. In one embodiment, the polypeptide includes the amino acid sequence set forth in SEQ ID NO: 71 or the amino acid sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21, wherein the cysteine at position 1 is deleted. In one embodiment, the polypeptide includes the amino acid sequence set forth in SEQ ID NO: 71 or the amino acid sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21, wherein the cysteine at position 1 is substituted with an amino acid that is not a Cys residue. In another embodiment, the immunogenic composition further includes at least one conjugate selected from: a) a conjugate of a capsular saccharide of *Neisseria meningitidis* serogroup A, b) a conjugate of a capsular saccharide of *Neisseria meningitidis* serogroup C, c) a conjugate of a capsular saccharide of *Neisseria meningitidis* serogroup W135, and d) a conjugate of a capsular saccharide of *Neisseria meningitidis* serogroup Y.

In a further aspect, the invention relates to a method of eliciting bactericidal antibodies specific to serogroup X of *N. meningitidis* in a mammal. The method includes administering to the mammal an effective amount of an isolated non-pyruvylated non-lipidated 2086 polypeptide from *N. meningitidis* serogroup B or an immunogenic composition thereof, as described above. See, for example, Example 22. In one embodiment, the polypeptide includes the amino acid sequence set forth in SEQ ID NO: 71 or the amino acid sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21, wherein the cysteine at position 1 is deleted. In one embodiment, the polypeptide includes the amino acid sequence set forth in SEQ ID NO: 71 or the amino acid sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21, wherein the cysteine at position 1 is substituted with an amino acid that is not a Cys residue. In another embodiment, the immunogenic composition further includes at least one conjugate selected from: a) a conjugate of a capsular saccharide of *Neisseria meningitidis* serogroup A, b) a conjugate of a capsular saccharide of *Neisseria meningitidis* serogroup C, c) a conjugate of a capsular saccharide of *Neisseria meningitidis* serogroup W135, and d) a conjugate of a capsular saccharide of *Neisseria meningitidis* serogroup Y.

When an exemplary immunogenic composition including four non-pyruvylated non-lipidated ORF2086 polypeptides and a conjugate of a capsular saccharide of each of *Neisseria meningitidis* serogroups A, C, W135, and Y as described above was administered to mammals, the inventors surprisingly discovered that a synergistic bactericidal immune response may be elicited at least against serogroups B, C, and Y of *Neisseria meningitidis*, as compared to an immunogenic composition including the ORF2086 polypeptides wherein conjugates of a capsular saccharide are absent, and as compared to an immunogenic composition including a conjugate of a capsular saccharide of each of *Neisseria meningitidis* serogroups A, C, W135, and Y wherein an ORF2086 polypeptide is absent. See, for example, Example 22. Accordingly, in one embodiment, the immunogenic composition includes at least one non-pyruvylated non-lipidated ORF2086 polypeptide that acts synergistically with at least one conjugate of a capsular saccharide of *Neisseria meningitidis* serogroup A, C, W135, and Y to elicit an immune response against *Neisseria meningitidis*. The immune response elicited may be against at least one of serogroups B, C, and Y of *Neisseria meningitidis*. The immunogenic composition may include a protein encoded by a nucleotide sequence from *Neisseria* ORF2086, polynucleotides, or equivalents thereof as the sole active immunogen in the immunogenic composition. Alternatively, the immunogenic composition may further include active immunogens, including other *Neisseria* sp. immunogenic polypeptides, or immunologically-active proteins of one or more other microbial pathogens (e.g. virus, prion, bacterium, or fungus, without limitation) or capsular polysaccharide. The compositions may comprise one or more desired proteins, fragments or pharmaceutical compounds as desired for a chosen indication.

Any multi-antigen or multi-valent immunogenic composition is contemplated by the present invention. For example, the immunogenic composition may include combinations of two or more ORF2086 proteins, a combination of ORF2086 protein with one or more P or A proteins, a combination of ORF2086 protein with meningococcus serogroup A, C, Y and W135 polysaccharides and/or polysaccharide conjugates, a combination of ORF2086 protein with meningococcus and pneumococcus combinations, or a combination of any of the foregoing in a form suitable for a desired administration, e.g., for mucosal delivery. Persons of skill in the art would be readily able to formulate such multi-antigen or multi-valent immunologic compositions.

In one aspect, the invention relates to an immunogenic composition including an isolated non-lipidated, non-pyruvylated ORF2086 polypeptide from *Neisseria meningitidis* serogroup B, and at least one conjugate selected from: a) a conjugate of a capsular saccharide of *Neisseria meningitidis* serogroup A, b) a conjugate of a capsular saccharide of *Neisseria meningitidis* serogroup C, c) a conjugate of a capsular saccharide of *Neisseria meningitidis* serogroup W135, and d) a conjugate of a capsular saccharide of *Neisseria meningitidis* serogroup Y.

In one embodiment, the immunogenic composition includes an isolated non-lipidated, non-pyruvylated ORF2086 polypeptide from *Neisseria meningitidis* serogroup B, and at least two of the conjugates. In another embodiment, the composition includes at least three of the conjugates. For example, the compositions may include saccharides from: serogroups A and C; serogroups A and W135, serogroups A and Y; serogroups C and W135, serogroups W135 and Y; serogroups A, C, and W135, serogroups A, C, and Y; serogroups A, W135, and Y; serogroups C and W135, and Y. Compositions including at least one serogroup C saccharide are preferred (e.g., C and Y).

In yet another embodiment, the immunogenic composition includes an isolated non-lipidated, non-pyruvylated ORF2086 polypeptide from *Neisseria meningitidis* serogroup B, and four conjugates, e.g., a conjugate of a capsular saccharide of *Neisseria meningitidis* serogroup A; a conjugate of a capsular saccharide of *Neisseria meningitidis* serogroup C; a conjugate of a capsular saccharide of *Neisseria meningitidis* serogroup W135, and a conjugate of a capsular saccharide of *Neisseria meningitidis* serogroup Y.

In a preferred embodiment, the conjugate is a conjugate of the capsular saccharide and a carrier protein. Suitable carrier proteins are known in the art. Preferably, the carrier protein is a bacterial toxin, such as a diphtheria or tetanus toxin, or toxoids or mutants thereof. Most preferably, the carrier protein is $CRM_{197}$. For example, in one embodiment, the composition includes at least one conjugate selected from (a) a conjugate of (i) the capsular saccharide of serogroup A *N. meningitidis* and (ii) $CRM_{197}$; (b) a conjugate of (i) the capsular saccharide of serogroup C *N. meningitidis* and (ii) $CRM_{197}$; (c) a conjugate of (i) the capsular saccharide of serogroup W135 *N. meningitidis* and (ii) $CRM_{197}$; and (d) a conjugate of (i) the capsular saccharide of serogroup Y *N. meningitidis* and (ii) $CRM_{197}$.

The capsular saccharides of serogroups A, C, W135, and Y are characterized and known in the art. For example, the capsular saccharide of serogroup A meningococcus is a homopolymer of ($\alpha$ 1→6)-linked N-acetyl-D-mannosamine-1-phosphate, with partial O-acetylation in the C3 and C4 positions. Acetylation at the C-3 position can be 70-95%. Conditions used to purify the saccharide can result in de-O-acetylation (e.g. under basic conditions), but it is useful to retain OAc at this C-3 position. In some embodiments, at least 50% (e.g. at least 60%, 70%, 80%, 90%, 95% or more) of the mannosamine residues in a serogroup A saccharides are 0-acetylated at the C-3 position. Acetyl groups can be replaced with blocking groups to prevent hydrolysis, and such modified saccharides are still serogroup A saccharides within the meaning of the invention.

The serogroup C capsular saccharide is a homopolymer of (a 2→9)-linked sialic acid (N-acetyl neuraminic acid). Most serogroup C strains have 0-acetyl groups at C-7 and/or C-8 of the sialic acid residues, but some clinical isolates lack these 0-acetyl groups.

The serogroup W135 saccharide is a polymer of sialic acid-galactose disaccharide units. Like the serogroup C saccharide, it has variable O-acetylation, but at sialic acid 7 and 9 positions. The structure is written as: →4)-D-Neup-NAc(7/9OAc)-$\alpha$-(2→6)-D-Gal-$\alpha$-(1→.

The serogroup Y saccharide is similar to the serogroup W135 saccharide, except that the disaccharide-repeating unit includes glucose instead of galactose. The serogroup Y structure is written as: →4)-D-NeupNAc(7/9OAc)-$\alpha$-(2→6)-D-Glc-$\alpha$-(1→. Like serogroup W135, it has variable O-acetylation at sialic acid 7 and 9 positions.

The saccharides used according to the invention may be 0-acetylated as described above, e.g., with the same O-acetylation pattern as seen in native capsular saccharides, or they may be partially or totally de-O-acetylated at one or more positions of the saccharide rings, or they may be hyper-O-acetylated relative to the native capsular saccharides.

In one embodiment, immunogenic composition includes an isolated non-lipidated, non-pyruvylated ORF2086 polypeptide from *Neisseria meningitidis* serogroup B, and at least one conjugate selected from: a) a conjugate of a capsular saccharide of *Neisseria meningitidis* serogroup A, b) a conjugate of a capsular saccharide of *Neisseria meningitidis* serogroup C, c) a conjugate of a capsular saccharide of *Neisseria meningitidis* serogroup W135, and d) a conjugate of a capsular saccharide of *Neisseria meningitidis* serogroup Y, wherein the non-lipidated, non-pyruvylated ORF2086 polypeptide includes at least one of the following: B44, B09, A05, B22, A12, A22, A62, B24, B16, B15, and B03. In one embodiment, the polypeptide includes the amino acid sequence selected from the group consisting of SEQ ID NO: 44, SEQ ID NO: 49, SEQ ID NO: 55, SEQ ID NO: 66, SEQ ID NO: 68, SEQ ID NO: 71, and SEQ ID NO: 75. In another embodiment, the polypeptide includes the amino acid sequence selected from the group consisting of SEQ ID NO: 17, SEQ ID NO: 59, SEQ ID NO: 60, and SEQ ID NO: 20, wherein the cysteine at position 1 is deleted. In another embodiment, the polypeptide includes the amino acid sequence selected from the group consisting of SEQ ID NO: 17, SEQ ID NO: 59, SEQ ID NO: 60, and SEQ ID NO: 20, wherein the cysteine at position 1 is substituted with an amino acid that is not a Cys residue.

The present invention also contemplates multi-immunization regimens wherein any composition useful against a pathogen may be combined therein or therewith the compositions of the present invention. For example, without limitation, a patient may be administered the immunogenic composition of the present invention and another immunological composition for immunizing against human papillomavirus virus (HPV), such as the HPV vaccine GARDASIL®, as part of a multi-immunization regimen. Persons of skill in the art would be readily able to select immunogenic compositions for use in conjunction with the immunogenic compositions of the present invention for the purposes of developing and implementing multi-immunization regimens.

The ORF2086 polypeptides, fragments and equivalents can be used as part of a conjugate immunogenic composition; wherein one or more proteins or polypeptides are conjugated to a carrier in order to generate a composition that has immunogenic properties against several serotypes, or serotypes of *N. meningitidis*, specifically meningococcus serogroups specifically serogroup B, and/or against several diseases. Alternatively, one of the ORF2086 polypeptides can be used as a carrier protein for other immunogenic polypeptides. Formulation of such immunogenic compositions is well known to persons skilled in this field.

Immunogenic compositions of the invention preferably include a pharmaceutically acceptable excipient, diluents, and/or carrier. Suitable pharmaceutically acceptable excipients, carriers and/or diluents include any and all conventional solvents, dispersion media, fillers, solid carriers, aqueous solutions, coatings, antibacterial and antifungal agents, isotonic and absorption delaying agents, and the like. Suitable pharmaceutically acceptable excipients, diluents, and/or carriers include, for example, one or more of water, saline, phosphate buffered saline, dextrose, glycerol, ethanol and the like, as well as combinations thereof.

Pharmaceutically acceptable excipients, diluents, and/or carriers may further include minor amounts of auxiliary substances such as wetting or emulsifying agents, preservatives or buffers, which enhance the shelf life or effectiveness of the antibody. The preparation and use of pharmaceutically acceptable excipients, diluents, and/or carriers is well known in the art. Except insofar as any conventional media or agent is incompatible with the active ingredient, use thereof in the immunogenic compositions of the present invention is contemplated.

Immunogenic compositions can be administered parenterally, e.g., by injection, either subcutaneously or intramuscularly, as well as orally or intranasally. Methods for intramuscular immunization are described by Wolff et al. *Biotechniques;* 11(4):474-85, (1991). and by Sedegah et al. *PNAS* Vol. 91, pp. 9866-9870, (1994). Other modes of administration employ oral formulations, pulmonary formulations, suppositories, and transdermal applications, for example, without limitation. Oral formulations, for example, include such normally employed excipients as, for example, pharmaceutical grades of mannitol, lactose, starch, magnesium stearate, sodium saccharine, cellulose, magnesium carbonate, and the like, without limitation. Preferably, the immunogenic composition is administered intramuscularly.

The immunogenic compositions of the present invention can further comprise one or more additional "immunomodulators", which are agents that perturb or alter the immune system, such that either up-regulation or down-regulation of humoral and/or cell-mediated immunity is observed. In one particular embodiment, up-regulation of the humoral and/or cell-mediated arms of the immune system is preferred. Examples of certain immunomodulators include, for example, an adjuvant or cytokine, or ISCOMATRIX (CSL Limited, Parkville, Australia), described in U.S. Pat. No. 5,254,339 among others.

Non-limiting examples of adjuvants that can be used in the vaccine of the present invention include the R1131 adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) Polysorbate® 80 detergent (ICI Surfactants), 2.5% (v/v) ethanol, 200 µg/ml Quil A, 100 µg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) polysorbate 80 detergent, 2.5% (v/v) ethanol, 100 µg/ml Quil A, and 50 µg/ml cholesterol.

Other "immunomodulators" that can be included in the vaccine include, e.g., one or more interleukins, interferons, or other known cytokines or chemokines. In one embodiment, the adjuvant may be a cyclodextrin derivative or a polyanionic polymer, such as those described in U.S. Pat. Nos. 6,165,995 and 6,610,310, respectively. It is to be understood that the immunomodulator and/or adjuvant to be used will depend on the subject to which the vaccine or immunogenic composition will be administered, the route of injection and the number of injections to be given.

In some embodiments, the adjuvant is saponin. In some embodiments, the saponin concentration is between 1 µg/ml and 250 µg/ml, between 5 µg/ml and 150 µg/ml, or between 10 µg/ml and 100 µg/ml. In some embodiments, the saponin concentration is about 1 µg/ml, about 5 µg/ml, about 10 µg/ml, about 20 µg/ml, about 30 µg/ml, about 40 µg/ml, about 50 µg/ml, about 60 µg/ml, about 70 µg/ml, about 80 µg/ml, about 90 µg/ml, about 100 µg/ml, about 110 µg/ml, about 120 µg/ml, about 130 µg/ml, about 140 µg/ml, about 150 µg/ml, about 160 µg/ml, about 170 µg/ml, about 180 µg/ml, about 190 µg/ml, about 200 µg/ml, about 210 µg/ml, about 220 µg/ml, about 230 µg/ml, about 240 µg/ml, or about 250 µg/ml.

In certain preferred embodiments, the proteins of this invention are used in an immunogenic composition for oral administration which includes a mucosal adjuvant and used for the treatment or prevention of *N. meningitidis* infection in a human host. The mucosal adjuvant can be a cholera toxin; however, preferably, mucosal adjuvants other than cholera toxin which may be used in accordance with the present invention include non-toxic derivatives of a cholera holotoxin, wherein the A subunit is mutagenized, chemically modified cholera toxin, or related proteins produced by modification of the cholera toxin amino acid sequence. For a specific cholera toxin which may be particularly useful in preparing immunogenic compositions of this invention, see the mutant cholera holotoxin E29H, as disclosed in Published International Application WO 00/18434, which is hereby incorporated herein by reference in its entirety. These may be added to, or conjugated with, the polypeptides of this invention. The same techniques can be applied to other molecules with mucosal adjuvant or delivery properties such as *Escherichia coli* heat labile toxin (LT).

Other compounds with mucosal adjuvant or delivery activity may be used such as bile; polycations such as DEAE-dextran and polyornithine; detergents such as sodium dodecyl benzene sulphate; lipid-conjugated materials; antibiotics such as streptomycin; vitamin A; and other compounds that alter the structural or functional integrity of mucosal surfaces. Other mucosally active compounds include derivatives of microbial structures such as MDP; acridine and cimetidine. STIMULON™ QS-21, MPL, and IL-12, as described above, may also be used.

The immunogenic compositions of this invention may be delivered in the form of ISCOMS (immune stimulating complexes), ISCOMS containing CTB, liposomes or encapsulated in compounds such as acrylates or poly(DL-lactide-co-glycoside) to form microspheres of a size suited to adsorption. The proteins of this invention may also be incorporated into oily emulsions.

An amount (i.e., dose) of immunogenic composition that is administered to the patient can be determined in accordance with standard techniques known to those of ordinary skill in the art, taking into consideration such factors as the particular antigen, the adjuvant (if present), the age, sex, weight, species, condition of the particular patient, and the route of administration.

For example, a dosage for an adolescent human patient may include at least 0.1 µg, 1 µg, 10 µg, or 50 µg of a *Neisseria* ORF2086 protein, and at most 80 µg, 100 µg, 150 µg, or 200 µg of a *Neisseria* ORF2086 protein. Any minimum value and any maximum value may be combined to define a suitable range.

Adjuvants

Immunogenic compositions as described herein also comprise, in certain embodiments, one or more adjuvants. An adjuvant is a substance that enhances the immune response when administered together with an immunogen or antigen. A number of cytokines or lymphokines have been shown to have immune modulating activity, and thus are useful as adjuvants, including, but not limited to, the interleukins 1-α, 1-β, 2, 4, 5, 6, 7, 8, 10, 12 (see, e.g., U.S. Pat. No. 5,723,127), 13, 14, 15, 16, 17 and 18 (and its mutant forms); the interferons-α, β and γ; granulocyte-macrophage colony stimulating factor (GM-CSF) (see, e.g., U.S. Pat. No. 5,078,996 and ATCC Accession Number 39900); macrophage colony stimulating factor (M-CSF), granulocyte colony stimulating factor (G-CSF), and the tumor necrosis factors α and β.

Still other adjuvants that are useful with the immunogenic compositions described herein include chemokines, including without limitation, MCP-1, MIP-1α, MIP-1β, and RANTES; adhesion molecules, such as a selectin, e.g., L-selectin, P-selectin and E-selectin; mucin-like molecules, e.g., CD34, GlyCAM-1 and MadCAM-1, a member of the integrin family such as LFA-1, VLA-1, Mac-1 and p150.95, a member of the immunoglobulin superfamily such as PECAM, ICAMs, e.g., ICAM-1, ICAM-2 and ICAM-3, CD2 and LFA-3; co-stimulatory molecules such as B7-1, B7-2, CD40 and CD40L, growth factors including vascular growth factor, nerve growth factor, fibroblast growth factor, epidermal growth factor, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; and Caspase (ICE).

Other exemplary adjuvants include, but are not limited to aluminum hydroxide; aluminum phosphate; STIMULON™ QS-21 (Aquila Biopharmaceuticals, Inc., Framingham, Mass.); MPL™ (3-O-deacylated monophosphoryl lipid A; Corixa, Hamilton, Mont.), 529 (an amino alkyl glucosamine phosphate compound, Corixa, Hamilton, Mont.), IL-12 (Genetics Institute, Cambridge, Mass.); GM-CSF (Immunex Corp., Seattle, Wash.); N-acetyl-muramyl-L-theronyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphos-phoryloxy-ethylamine) (CGP 19835A, referred to as MTP-PE); and cholera toxin. In certain preferred embodiments, the adjuvant is QS-21.

Additional exemplary adjuvants include non-toxic derivatives of cholera toxin, including its A subunit, and/or conjugates or genetically engineered fusions of the *N. meningitidis* polypeptide with cholera toxin or its B subunit ("CTB"), procholeragenoid, fungal polysaccharides, including schizophyllan, muramyl dipeptide, muramyl dipeptide ("MDP") derivatives, phorbol esters, the heat labile toxin of *E. coli*, block polymers or saponins.

Aluminum phosphate has been used as the adjuvant in a phase 1 clinical trial to a concentration 0.125 mg/dose, much lower than the limit of 0.85 mg/dose specified by the US Code of Federal Regulations [610.15(a)]. Aluminum-containing adjuvants are widely used in humans to potentiate the immune response of antigens when administered intramuscularly or subcutaneously. In some embodiments, the concentration of aluminum in the immunogenic composition is between 0.125 µg/ml and 0.5 µg/ml, between 0.20 µg/ml and 0.40 µg/ml, or between 0.20 µg/ml and 0.30 µg/ml. In some embodiments, the concentration of aluminum in the immunogenic composition is about 0.125 µg/ml, about 0.15 µg/ml, about 0.175 µg/ml, about 0.20 µg/ml, about 0.225 µg/ml, about 0.25 µg/ml, about 0.275 µg/ml, about 0.30 µg/ml, about 0.325 µg/ml, about 0.35 µg/ml, about 0.375 µg/ml, about 0.40 µg/ml, about 0.425 µg/ml, about 0.45 µg/ml, about 0.475 µg/ml, or about 0.50 µg/ml.

In a preferred embodiment, the concentration of aluminum in the immunogenic composition is between 0.125 mg/ml and 0.5 mg/ml, between 0.20 mg/ml and 0.40 mg/ml, or between 0.20 mg/ml and 0.30 mg/ml. In some embodiments, the concentration of aluminum in the immunogenic composition is about 0.125 mg/ml, about 0.15 mg/ml, about 0.175 mg/ml, about 0.20 mg/ml, about 0.225 mg/ml, about 0.25 mg/ml, about 0.275 mg/ml, about 0.30 mg/ml, about 0.325 mg/ml, about 0.35 mg/ml, about 0.375 mg/ml, about 0.40 mg/ml, about 0.425 mg/ml, about 0.45 mg/ml, about 0.475 mg/ml, or about 0.50 mg/ml.

Suitable adjuvants used to enhance an immune response further include, without limitation, MPL™ (3-O-deacylated monophosphoryl lipid A, Corixa, Hamilton, Mont.), which is described in U.S. Pat. No. 4,912,094. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918. One such AGP is 2-[(R)-3-Tetradecanoyloxytetradecanoylamino] ethyl 2-Deoxy-4-O-phosphono-3-O-[(R)-3-tetradecanoyoxytetrade-canoyl]-2-[(R)-3-tetradecanoyloxytetradecanoyl-amino]-b-D-glucopyranoside, which is also known as 529 (formerly known as RC529). This 529 adjuvant is formulated as an aqueous form (µF) or as a stable emulsion (SE).

Still other adjuvants include muramyl peptides, such as N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryl-oxy)-ethylamine (MTP-PE); oil-in-water emulsions, such as MF59 (U.S. Pat. No. 6,299,884) (containing 5% Squalene, 0.5% polysorbate 80, and 0.5% SPAN 85 (optionally containing various amounts of MTP-PE) formulated into submicron particles using a microfluidizer such as Model 110Y microfluidizer (Microfluidics, Newton, Mass.)), and SAF (containing 10% Squalene, 0.4% polysorbate 80, 5% PLURONIC-blocked polymer L121, and thr-MDP, either microfluidized into a submicron emulsion or vortexed to generate a larger particle size emulsion); incomplete Freund's adjuvant (IFA); aluminum salts (alum), such as aluminum hydroxide, aluminum phosphate, aluminum sulfate; AMPHIGEN; Avridine; L121/squalene; D-lactide-polylactide/glycoside; PLURONIC polyols; killed *Bordetella*; saponins, such as Stimulon™ QS-21 (Antigenics, Framingham, Mass.), described in U.S. Pat. No. 5,057,540, ISOMATRIX (CSL Limited, Parkville, Australia), described in U.S. Pat. No. 5,254,339, and immunostimulating complexes (ISCOMATRIX), *Mycobacterium tuberculosis*; bacterial lipopolysaccharides; synthetic polynucleotides such as oligonucleotides containing a CpG motif (e.g., U.S. Pat. No. 6,207,646); IC-31 (Intercell AG, Vienna, Austria), described in European Patent Nos. 1,296,713 and 1,326,634; a pertussis toxin (PT) or mutant thereof, a cholera toxin or mutant thereof (e.g., U.S. Pat. Nos. 7,285,281, 7,332,174, 7,361,355 and 7,384,640); or an *E. coli* heat-labile toxin (LT) or mutant thereof, particularly LT-K63, LT-R72 (e.g., U.S. Pat. Nos. 6,149,919, 7,115,730 and 7,291,588).

Methods of Producing Non-Lipidated P2086 Antigens

In one aspect, the invention relates to a method of producing a non-pyruvylated non-lipidated ORF2086 polypeptide. The method includes expressing a nucleotide sequence encoding an ORF2086 polypeptide wherein the N-terminal cysteine is deleted as compared to the corresponding wild-type sequence, and wherein the nucleotide sequence is operatively linked to an expression system that is capable of being expressed in a bacterial cell. Exemplary polypeptides produced by the method include any polypeptide described herein. For example, preferably, the polypeptide has the amino acid sequence set forth in SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 58; SEQ ID NO: 70, wherein the cysteine at position 1 is deleted, as compared to the corresponding wild-type sequence. In another preferred embodiment, the polypeptide has the amino acid sequence set forth in SEQ ID NO: 76, wherein the cysteine at position 1 is deleted. Additional exemplary polypeptides include a polypeptide having the amino acid sequences selected from SEQ ID NO: 44, SEQ ID NO: 49, SEQ ID NO: 50, SEQ ID NO: 55, SEQ ID NO: 57, SEQ ID NO: 62, SEQ ID NO: 64, SEQ ID NO: 66, SEQ ID NO: 68, SEQ ID NO: 71, and SEQ ID NO: 75. An additional exemplary polypeptide includes a polypeptide having the amino acid sequence SEQ ID NO: 77. Further examples include SEQ ID NO: 80 (B24) and SEQ ID NO: 81 (B24). The method further includes purifying the polypeptide.

In some embodiments, the invention provides a method for producing soluble non-lipidated P2086 antigens comprising the steps of cloning the ORF2086 variant nucleic acid sequence into an *E. coli* expression vector without a lipidation control sequence, transforming *E. coli* bacteria with the ORF2086 expression vector, inducing expression and isolating the expressed P2086 protein. In some embodiments, expression is induced with IPTG.

In some embodiments, the codon for the N-terminal Cys of the ORF2086 variant is deleted. Examples of such codons include TGC. In some embodiments, the codon for the N-terminal Cys of the ORF2086 variant is mutated by point mutagenesis to generate an Ala, Gly, or Val codon. In some embodiments, Ser and Gly codons are added to the N-terminal tail of the ORF2086 variant to extend the Gly/Ser stalk immediately downstream of the N-terminal Cys. In some embodiments, the total number of Gly and Ser residues within the Gly/Ser stalk is at least 7, 8, 9, 10, 11, or 12. In some embodiments, the codon for the N-terminal Cys is deleted. In some embodiments, the N-terminal 7, 8, 9, 10, 11, or 12 residues are either Gly or Ser.

In some embodiments, the codons of the N-terminal tail of the non-lipidated ORF2086 variant are optimized by point mutagenesis. In some embodiments, the N-terminal tail of the non-lipidated ORF2086 variant is optimized to match the N-terminal tail of the B09 variant. In some embodiments, the codons of the N-terminal tail of the ORF2086 variant are optimized by point mutagenesis such that the codon encoding the fifth amino acid of the ORF2086 variant is 100% identical to nucleotides 13-15 of SEQ ID NO: 8 and the codon encoding the thirteenth amino acid of the ORF2086 variant is 100% identical to nucleotides 37-39 of SEQ ID NO: 8. In some embodiments, the N-terminal tail of the non-lipidated ORF2086 variant is optimized such that the 5' 45 nucleic acids are 100% identical to nucleic acids 1-45 of SEQ ID NO: 8. In some embodiments, the N-terminal tail of the non-lipidated ORF2086 variant is optimized such that the 5' 42 nucleic acids are 100% identical to nucleic acids 4-45 of SEQ ID NO: 8. In some embodiments, the N-terminal tail of the non-lipidated ORF2086 variant is optimized such that the 5' 39 nucleic acids are 100% identical to nucleic acids 4-42 of SEQ ID NO: 8. In some embodiments, the N-terminal tail of the non-lipidated P2086 variant comprises at least one amino acid substitution compared to amino acids 1-15 of SEQ ID NO: 18. In some embodiments, the N-terminal tail of the non-lipidated P2086 variant comprises two amino acid substitutions compared to amino acids 1-15 of SEQ ID NO: 18. In some embodiments, the N-terminal tail of the non-lipidated P2086 variant comprises at least one amino acid substitution compared to amino acids 2-15 of SEQ ID NO: 18. In some embodiments, the N-terminal tail of the non-lipidated P2086 variant comprises two amino acid substitutions compared to amino acids 2-15 of SEQ ID NO: 18. In some embodiments, the amino acid substitutions are conservative amino acid substitutions.

In some embodiments, the codons of the non-lipidated variant have been optimized for increased expression. Codon optimization is known in the art. See, e.g., Sastalla et al, *Applied and Environmental Microbiology*, vol. 75(7): 2099-2110 (2009) and Coleman et al, *Science, vol.* 320: 1784 (2008). In some embodiments, codon optimization includes matching the codon utilization of an amino acid sequence with the codon frequency of the host organism chosen while including and/or excluding specific DNA sequences. In some embodiments, codon optimization further includes minimizing the corresponding secondary mRNA structure to reduce translational impediments. In some embodiments, the N-terminal tail has been codon optimized to comprise any one of SEQ ID NO: 28, 30, 32, and 34. In some embodiments, the Gly/Ser stalk has been codon optimized to comprise any one of SEQ ID NO: 28, 30, 32, and 34.

In order that this invention may be better understood, the following examples are set forth. The examples are for the purpose of illustration only and are not to be construed as limiting the scope of the invention.

Immunogenic Composition Formulations

In certain embodiments, the immunogenic compositions of the invention further comprise at least one of an adjuvant, a buffer, a cryoprotectant, a salt, a divalent cation, a non-ionic detergent, an inhibitor of free radical oxidation, a diluent or a carrier.

The immunogenic compositions of the invention may further comprise one or more preservatives in addition to a plurality of meningococcal protein antigens and capsular polysaccharide-protein conjugates. The FDA requires that biological products in multiple-dose (multi-dose) vials contain a preservative, with only a few exceptions. Vaccine products containing preservatives include vaccines containing benzethonium chloride (anthrax), 2-phenoxyethanol (DTaP, HepA, Lyme, Polio (parenteral)), phenol (Pneumo, Typhoid (parenteral), Vaccinia) and thimerosal (DTaP, DT, Td, HepB, Hib, Influenza, JE, Mening, Pneumo, Rabies). Preservatives approved for use in injectable drugs include, e.g., chlorobutanol, m-cresol, methylparaben, propylparaben, 2-phenoxyethanol, benzethonium chloride, benzalkonium chloride, benzoic acid, benzyl alcohol, phenol, thimerosal and phenylmercuric nitrate.

Formulations of the invention may further comprise one or more of a buffer, a salt, a divalent cation, a non-ionic detergent, a cryoprotectant such as a sugar, and an antioxidant such as a free radical scavenger or chelating agent, or any multiple combination thereof. The choice of any one component, e.g., a chelator, may determine whether or not another component (e.g., a scavenger) is desirable. The final composition formulated for administration should be sterile and/or pyrogen free. The skilled artisan may empirically determine which combinations of these and other components will be optimal for inclusion in the preservative containing immunogenic compositions of the invention depending on a variety of factors such as the particular storage and administration conditions required.

In certain embodiments, a formulation of the invention which is compatible with parenteral administration comprises one or more physiologically acceptable buffers selected from, but not limited to, Tris (trimethamine), phosphate, acetate, borate, citrate, glycine, histidine and succinate. In certain embodiments, the formulation is buffered to within a pH range of about 6.0 to about 9.0, preferably from about 6.4 to about 7.4.

In certain embodiments, it may be desirable to adjust the pH of the immunogenic composition or formulation of the invention. The pH of a formulation of the invention may be adjusted using standard techniques in the art. The pH of the formulation may be adjusted to be between 3.0 and 8.0. In certain embodiments, the pH of the formulation may be, or may adjusted to be, between 3.0 and 6.0, 4.0 and 6.0, or 5.0 and 8.0. In other embodiments, the pH of the formulation may be, or may adjusted to be, about 3.0, about 3.5, about 4.0, about 4.5, about 5.0, about 5.5, about 5.8, about 6.0, about 6.5, about 7.0, about 7.5, or about 8.0. In certain embodiments, the pH may be, or may adjusted to be, in a range from 4.5 to 7.5, or from 4.5 to 6.5, from 5.0 to 5.4, from 5.4 to 5.5, from 5.5 to 5.6, from 5.6 to 5.7, from 5.7 to 5.8, from 5.8 to 5.9, from 5.9 to 6.0, from 6.0 to 6.1, from 6.1 to 6.2, from 6.2 to 6.3, from 6.3 to 6.5, from 6.5 to 7.0, from 7.0 to 7.5 or from 7.5 to 8.0. In a specific embodiment, the pH of the formulation is about 5.8.

In certain embodiments, a formulation of the invention which is compatible with parenteral administration comprises one or more divalent cations, including but not limited to $MgCl_2$, $CaCl_2$ and $MnCl_2$, at a concentration ranging from about 0.1 mM to about 10 mM, with up to about 5 mM being preferred.

In certain embodiments, a formulation of the invention which is compatible with parenteral administration comprises one or more salts, including but not limited to sodium chloride, potassium chloride, sodium sulfate, and potassium sulfate, present at an ionic strength which is physiologically acceptable to the subject upon parenteral administration and included at a final concentration to produce a selected ionic strength or osmolarity in the final formulation. The final ionic strength or osmolality of the formulation will be determined by multiple components (e.g., ions from buffering compound(s) and other non-buffering salts. A preferred salt, NaCl, is present from a range of up to about 250 mM, with salt concentrations being selected to complement other components (e.g., sugars) so that the final total osmolarity of the formulation is compatible with parenteral administration (e.g., intramuscular or subcutaneous injection) and will promote long term stability of the immunogenic components of the immunogenic composition formulation over various temperature ranges. Salt-free formulations will tolerate increased ranges of the one or more selected cryoprotectants to maintain desired final osmolarity levels.

In certain embodiments, a formulation of the invention which is compatible with parenteral administration comprises one or more cryoprotectants selected from but not limited to disaccharides (e.g., lactose, maltose, sucrose or trehalose) and polyhydroxy hydrocarbons (e.g., dulcitol, glycerol, mannitol and sorbitol).

In certain embodiments, the osmolarity of the formulation is in a range of from about 200 mOs/L to about 800 mOs/L, with a preferred range of from about 250 mOs/L to about 500 mOs/L, or about 300 mOs/L-about 400 mOs/L. A salt-free formulation may contain, for example, from about 5% to about 25% sucrose, and preferably from about 7% to about 15%, or about 10% to about 12% sucrose. Alternatively, a salt-free formulation may contain, for example, from about 3% to about 12% sorbitol, and preferably from about 4% to 7%, or about 5% to about 6% sorbitol. If salt such as sodium chloride is added, then the effective range of sucrose or sorbitol is relatively decreased. These and other such osmolality and osmolarity considerations are well within the skill of the art.

In certain embodiments, a formulation of the invention which is compatible with parenteral administration comprises one or more free radical oxidation inhibitors and/or chelating agents. A variety of free radical scavengers and chelators are known in the art and apply to the formulations and methods of use described herein. Examples include but are not limited to ethanol, EDTA, a EDTA/ethanol combination, triethanolamine, mannitol, histidine, glycerol, sodium citrate, inositol hexaphosphate, tripolyphosphate, ascorbic acid/ascorbate, succinic acid/succinate, malic acid/maleate, desferal, EDDHA and DTPA, and various combinations of two or more of the above. In certain embodiments, at least one non-reducing free radical scavenger may be added at a concentration that effectively enhances long term stability of the formulation. One or more free radical oxidation inhibitors/chelators may also be added in various combinations, such as a scavenger and a divalent cation. The choice of chelator will determine whether or not the addition of a scavenger is needed.

In certain embodiments, a formulation of the invention which is compatible with parenteral administration comprises one or more non-ionic surfactants, including but not limited to polyoxyethylene sorbitan fatty acid esters, Polysorbate-80 (TWEEN 80), Polysorbate-60 (TWEEN 60), Polysorbate-40 (TWEEN 40) and Polysorbate-20 (TWEEN 20), polyoxyethylene alkyl ethers, including but not limited to BRIJ 58, BRIJ 35, as well as others such as TRITON X-100; TRITON X-114, NP40, SPAN 85 and the PLURONIC series of non-ionic surfactants (e.g., PLURONIC 121), with preferred components Polysorbate-80 at a concentration from about 0.001% to about 2% (with up to about 0.25% being preferred) or Polysorbate-40 at a concentration from about 0.001% to 1% (with up to about 0.5% being preferred).

In certain embodiments, a formulation of the invention comprises one or more additional stabilizing agents suitable for parenteral administration, e.g., a reducing agent comprising at least one thiol (—SH) group (e.g., cysteine, N-acetyl cysteine, reduced glutathione, sodium thioglycolate, thiosulfate, monothioglycerol, or mixtures thereof). Alternatively or optionally, preservative-containing immunogenic composition formulations of the invention may be further stabilized by removing oxygen from storage containers, protecting the formulation from light (e.g., by using amber glass containers).

Preservative-containing immunogenic composition formulations of the invention may comprise one or more pharmaceutically acceptable diluents, carriers or excipients, which includes any excipient that does not itself induce an immune response. Suitable excipients include but are not limited to macromolecules such as proteins, saccharides, polylactic acids, polyglycolic acids, polymeric amino acids, amino acid copolymers, sucrose (Paoletti et al, 2001, *Vaccine*, 19:2118), trehalose, lactose and lipid aggregates (such as oil droplets or liposomes). Such diluent, excipient, and/or carriers are well known to the skilled artisan. Pharmaceutically acceptable excipients are discussed, e.g., in Gennaro, 2000, Remington: The Science and Practice of Pharmacy, $20^{th}$ edition, ISBN:0683306472.

Compositions of the invention may be lyophilized or in aqueous form, i.e. solutions or suspensions. Liquid formulations may advantageously be administered directly from their packaged form and are thus ideal for injection without the need for reconstitution in aqueous medium as otherwise required for lyophilized compositions of the invention.

Direct delivery of immunogenic compositions of the present invention to a subject may be accomplished by parenteral administration (intramuscularly, intraperitoneally, intradermally, subcutaneously, intravenously, or to the interstitial space of a tissue); or by rectal, oral, vaginal, topical, transdermal, intranasal, ocular, aural, pulmonary or other mucosal administration. In a preferred embodiment, parenteral administration is by intramuscular injection, e.g., to the thigh or upper arm of the subject. Injection may be via a needle (e.g., a hypodermic needle), but needle free injection may alternatively be used. A typical intramuscular dose is 0.5 mL. Compositions of the invention may be prepared in various forms, e.g., for injection either as liquid solutions or suspensions. In certain embodiments, the composition may be prepared as a powder or spray for pulmonary administration, e.g., in an inhaler. In other embodiments, the composition may be prepared as a suppository or pessary, or for nasal, aural or ocular administration, e.g., as a spray, drops, gel or powder.

Optimal amounts of components for a particular immunogenic composition may be ascertained by standard studies involving observation of appropriate immune responses in subjects. Following an initial vaccination, subjects can receive one or several booster immunizations adequately spaced.

Packaging and Dosage Forms

Immunogenic compositions of the invention may be packaged in unit dose or multi-dose form (e.g. 2 doses, 4 doses, or more). For multi-dose forms, vials are typically but not necessarily preferred over pre-filled syringes. Suitable multi-dose formats include but are not limited to: 2 to 10 doses per container at 0.1 to 2 mL per dose. In certain embodiments, the dose is a 0.5 mL dose. See, e.g., International Patent Application WO2007/127668, which is incorporated by reference herein.

Compositions may be presented in vials or other suitable storage containers, or may be presented in pre-filled delivery devices, e.g., single or multiple component syringes, which may be supplied with or without needles. A syringe typically but need not necessarily contains a single dose of the preservative-containing immunogenic composition of the invention, although multi-dose, pre-filled syringes are also envisioned. Likewise, a vial may include a single dose but may alternatively include multiple doses.

Effective dosage volumes can be routinely established, but a typical dose of the composition for injection has a volume of 0.5 mL. In certain embodiments, the dose is formulated for administration to a human subject. In certain embodiments, the dose is formulated for administration to an adult, teen, adolescent, toddler or infant (i.e., no more than one year old) human subject and may in preferred embodiments be administered by injection.

Liquid immunogenic compositions of the invention are also suitable for reconstituting other immunogenic compositions which are presented in lyophilized form. Where an immunogenic composition is to be used for such extemporaneous reconstitution, the invention provides a kit with two or more vials, two or more ready-filled syringes, or one or more of each, with the contents of the syringe being used to reconstitute the contents of the vial prior to injection, or vice versa.

Alternatively, immunogenic compositions of the present invention may be lyophilized and reconstituted, e.g., using one of a multitude of methods for freeze drying well known in the art to form dry, regular shaped (e.g., spherical) particles, such as micropellets or microspheres, having particle characteristics such as mean diameter sizes that may be selected and controlled by varying the exact methods used to prepare them. The immunogenic compositions may further comprise an adjuvant which may optionally be prepared with or contained in separate dry, regular shaped (e.g., spherical) particles such as micropellets or microspheres. In such embodiments, the present invention further provides an immunogenic composition kit comprising a first component that includes a stabilized, dry immunogenic composition, optionally further comprising one or more preservatives of the invention, and a second component comprising a sterile, aqueous solution for reconstitution of the first component. In certain embodiments, the aqueous solution comprises one or more preservatives, and may optionally comprise at least one adjuvant (see, e.g., WO2009/109550 (incorporated herein by reference).

In yet another embodiment, a container of the multi-dose format is selected from one or more of the group consisting of, but not limited to, general laboratory glassware, flasks, beakers, graduated cylinders, fermentors, bioreactors, tubings, pipes, bags, jars, vials, vial closures (e.g., a rubber stopper, a screw on cap), ampoules, syringes, dual or multi-chamber syringes, syringe stoppers, syringe plungers, rubber closures, plastic closures, glass closures, cartridges and disposable pens and the like. The container of the present invention is not limited by material of manufacture, and includes materials such as glass, metals (e.g., steel, stainless steel, aluminum, etc.) and polymers (e.g., thermoplastics, elastomers, thermoplastic-elastomers). In a particular embodiment, the container of the format is a 5 mL Schott Type 1 glass vial with a butyl stopper. The skilled artisan will appreciate that the format set forth above is by no means an exhaustive list, but merely serve as guidance to the artisan with respect to the variety of formats available for the present invention. Additional formats contemplated for use in the present invention may be found in published catalogues from laboratory equipment vendors and manufacturers such as United States Plastic Corp. (Lima, Ohio), VWR.

EXAMPLES

Example 1: Experimental Procedures

Serum Bactericidal Assay

Cynomolgus macaques (n=5/group) were immunized intramuscularly with rLP2086 or rP2086 (A+B) proteins adsorbed to $AlPO_4$. Cynomolgus macaques are an example of non-human primates. Animals were vaccinated at weeks 0, 4 and 24, and ORF2086-specific IgG and functional antibody titers were determined at weeks 0, 4, 6 and 26. Serum ORF2086-specific IgG titers were determined against rLP2086A and B.

Functional antibody titers were examined by serum bactericidal assay (SBA) against *Neisseria meningitidis* strains expressing either LP2086 with sequences homologous or heterologous to those contained in the vaccine.

Serum bactericidal antibodies in macaques or rabbits immunized with ORF2086 vaccine were determined using SBAs with human complement. Rabbit immune sera or macaques immune sera were heat-inactivated to remove intrinsic complement activity and subsequently serially diluted 1:2 in Dulbecco's PBS with $Ca2+$ and $Mg2+$(D-PBS) in a 96-well microtiter plate to test for serum bactericidal activity against *N. meningitidis* strains. Bacteria used in the assay were grown in GC media supplemented with Kellogg's supplement (GCK) and monitored by optical density at 650 nm. Bacteria were harvested for use in the assay at a final $OD_{650}$ of 0.50-0.55, diluted in D-PBS and 1000-3000 CFU were added to the assay mixture with 20% human complement.

Human serum with no detectable bactericidal activity was used as the exogenous complement source. Complement sources were tested for suitability against each individual test strain. A complement source was used only if the number of bacteria surviving in controls without added immune sera was >75%. Ten unique complement sources were required to perform the SBAs described in this study.

After a 30 min incubation at 37° C. with 5% $CO_2$, D-PBS was added to the reaction mixture and aliquots transferred to microfilter plates filled with 50% GCK media. The microfilter plates were filtered, incubated overnight at 37° C. with 5% $CO_2$ and microcolonies were stained and quantified. The serum bactericidal titers were defined as the interpolated reciprocal serum dilution that yielded a 50% reduction in CFU compared to the CFU in control wells without immune sera. The SBA titer is defined as the reciprocal of the interpolated dilution of test serum that causes a 50% reduction in bacterial counts after a 30 min incubation at 37° C. Susceptibility to killing with ORF2086 immune sera was established if there was a 4-fold or greater rise in SBA titer for ORF2086 immune sera compared to the corresponding pre-immune sera. Sera that were negative against the assay strain at the starting dilution were assigned a titer of one half the limit of detection for the assay (i.e. 4).

Example 2: Cloning and Expression of Non-Lipidated ORF2086 Variants

The mature P2086 amino acid sequence corresponding to residues 27-286 from *N. meningitidis* strain M98250771 (A05) was originally derived from PCR amplification from genomic DNA. The forward primer, with a sequence of TGCCATATGAGCAGCGGAAGCGGAAG (SEQ ID NO: 22), annealed to the 5' sequence and contained an NdeI site for cloning. The reverse primer, with a sequence of CGGATCCCTACTGTTTGCCGGCGATGC (SEQ ID NO: 23), annealed to the 3' end of the gene and contained a termination codon TAG followed by restriction site BamHI. The 799 bp amplified fragment was first cloned into an intermediate vector PCR2.1 (Invitrogen, Carlesbac, Calif.) This plasmid was cleaved with NdeI and BamHI, and was ligated into expression vector pET9a (Novagen, Madison, Wis.) which had been cleaved with NdeI and BamHI. The resulting vector pLA100 (which includes SEQ ID NO: 54), expressed the mature Subfamily A05 P2086 from strain M98250771 without the N-terminal cysteine (see SEQ ID NO: 13 wherein the N-terminal Cys at position 1 is deleted or SEQ ID NO: 55) that would be present in the lipidated protein. BLR(DE3) *E. coli* host strain [F-ompT hsdSB(rB-mB-) gal dcm Δ(srl-recA)306::Tn10 (TetR) (DE3)] (Novagen) was used to obtain expression of fHBP.

The same cloning steps were used to prepare the B02, B03, B09, B22, B24, B44, A04, A12, and A22 N-terminal Cys-deleted variants. The N-terminal Cys-containing variants were also prepared by this same method using forward primers which also included the Cys codon (e.g. the first codon of SEQ ID NOs: 1-11). Based on the sequences provided herein, the skilled worker would be able to design forward and reverse primers for each of these variants. For example, the following primers were used to amplify the B44 non-lipidated variant followed by cloning into pET9a using NdeI and BlpI.

TABLE 1

| N-terminal Cys | Primer Sequence | SEQ ID NO |
|---|---|---|
| Included-Fwd | 5' TTTCTTcccgggAAGG AGatatacatatgTGCAGC AGCGGAGGCGGCGG 3' | 24 |
| Included-Rev | 5' TTTCTTgctcagcaTT ATTGCTTGGCGGCAAGACC GAT 3' | 25 |
| Deleted-Fwd | 5' TTTCTTcccgggAAGG AGatatacatatgAGCAGC GGAGGCGGCGG 3' | 26 |
| Deleted-Rev | 5' TTTCTTgctcagcaTT ATTGCTTGGCGGCAAGACC GAT 3' | 27 |

Results

Non-lipidated plasmid constructs were strongly expressed, but the non-lipidated protein variants were pyruvylated at the N-terminal Cys residue. See Examples 8 and 9, which describes, for example, a method for expressing the constructs. To overcome this pyruvylation, the N-terminal Cys codon was deleted. See, for example, Example 10. Deletion of the N-terminal Cys, however, abrogated expression of the A22 and B22 variants. See e.g., FIG. 4. The A05, B01, and B44 variants, however, were still expressed despite deletion of the N-terminal Cys residue. See, for example, SEQ ID NO: 13 (A05), wherein the N-terminal Cys at position 1 is deleted, SEQ ID NO: 35 (B01 N-terminus), and SEQ ID NO: 21(B44), wherein the N-terminal Cys at position 1 is deleted. See e.g., FIG. 5. In addition, expression of the non-lipidated B09 variant was not affected by deletion of the N-terminal Cys residue. See, for example, Example 4.

Example 3: Effect of Gly/Ser Stalk on Non-Lipidated Variant Expression

To determine why the A05, B01, and B44 variants were expressed in the absence of the N-terminal Cys and the A22 and B22 variants were not, the sequences of these variants were aligned. The A05, B01, and B44 variants all possess an extended series of 10 or 11 Gly and Ser residues immediately following the N-terminal Cys (i.e. Gly/Ser stalk). The A22 and B22 variants, however, only had a Gly/Ser stalk consisting of 6 Gly and Ser residues. Accordingly, the Gly/Ser stalk of the A22 and B22 variants was expanded by insertion of additional Gly and Ser residues.

Long Gly/Ser stalk variants were prepared by the methods described in Example 2 using forward primers that encode a Gly/Ser stalk with either 10 or 11 Gly and Ser residues.

The N-terminal Cys-deleted, long Gly/Ser stalk (10-11 Gly/Ser residues) A22 and B22 variants showed increased expression over the N-terminal Cys-deleted A22 and B22 short Gly/Ser stalk (6 Gly/Ser residues) variants. These expression levels, however, were still reduced compared to the A05, B01, and B44 variant expression levels.

Example 4: Codon Optimization

Expression of the non-lipidated B09 variant was not affected by deletion of the N-terminal Cys residue (see SEQ ID NO: 18, wherein the cysteine at position 1 is deleted, or SEQ ID NO: 49). See, e.g., FIG. 6. Sequence evaluation of the B09 variant demonstrated that the B09 variant has a Gly/Ser stalk consisting of 6 Gly and Ser residues, similar to the Gly/Ser stalk of the A22 and B22 variants. Indeed, the N-terminal tails of the B09 and A22 variants are identical at the amino acid level. The N-terminal tails of the B09 and A22 variants (SEQ ID NO: 53 and 42, respectively), however, vary at the nucleic acid level by 2 nucleic acids: nucleic acids 15 and 39 of SEQ ID NO: 8. See e.g., FIG. 6. The first 14 amino acids of the N-terminal tail of the B22 variant are identical to the B09 and A22 variants, and the N-terminal tail of the B22 variant only differs at the 15th amino acid. Nucleic acids 1-42 of the B22 variant are identical to nucleic acids 1-42 of the A22 variant. Nucleic acids 1-42 of the B22 variant (see SEQ ID NO: 52) are identical to nucleic acids 1-42 of B09 (see SEQ ID NO: 53) but for differences at nucleic acids 15 and 39, when optimally aligned. Accordingly, the B22 variant differs from the B09 variant at amino acids 15 and 39 of SEQ ID NO: 8. This last sentence contains a typographical error and should state that the B22 variant differs from the B09 variant at nucleic acids 15 and 39 of SEQ ID NO: 8.

To determine if the nucleic acid differences affected the expression level of the B09 variant compared to the A22 and B22 variants, the A22 and B22 variants were mutated by point mutation to incorporate nucleic acids 15 and 39 into the corresponding codons for Gly5 and Gly13. Incorporation of these silent nucleic acid mutations significantly increased expression of the A22 and B22 N-terminal Cys-deleted variants to levels similar to the N-terminal Cys-deleted B09 variant. See e.g., FIG. 7. Accordingly, codon optimization to match the B09 variant can increase expression of N-terminal Cys-deleted non-lipidated P2086 variants.

Further analysis of the non-lipidated variant sequences suggested additional codon optimizations in the Gly/Ser stalk to improve expression. Accordingly, additional non-lipidated variants were constructed by the method of Example 2 using forward primers comprising such codon optimized sequences. The forward primers used to generate optimized Gly/Ser stalks include any of the following sequences:

```
ATGAGCTCTGGAGGTGGAGGAAGCGGGGGCGGTGGA  (SEQ ID NO: 28)
 M   S   S   G   G   G   S   G   G   G   G    (SEQ ID NO: 29)

ATGAGCTCTGGAAGCGGAAGCGGGGGCGGTGGA  (SEQ ID NO: 30)
 M   S   S   G   S   G   S   G   G   G   G    (SEQ ID NO: 31)

ATGAGCTCTGGAGGTGGAGGA  (SEQ ID NO: 32)
 M   S   S   G   G   G                         (SEQ ID NO: 33)

ATGAGCAGCGGGGGCGGTGGA  (SEQ ID NO: 34)
 M   S   S   G   G   G                         (SEQ ID NO: 33)
```

Example 5: Immunogenic Composition Formulation Optimization

ISCOMATRIX formulated vaccines generate a rapid immune response resulting in a reduction in the number of dosages required to achieve a greater than 4 fold response rate as measured in a serum bactericidal assay. Groups of five rhesus macaques were immunized with different formulations of a bivalent non-lipidated rP2086 vaccine. The vaccine included a non-pyruvylated non-lipidated A05 variant (SEQ ID NO: 13 wherein the N-terminal Cys at position 1 is deleted or SEQ ID NO: 55 encoded by SEQ ID NO: 54) and a non-pyruvylated non-lipidated B44 variant (SEQ ID NO: 21 wherein the N-terminal Cys at position 1 is deleted or SEQ ID NO: 44 encoded by SEQ ID NO: 51). The adjuvant units are as follows: $AlPO_4$ is 250 mcg, ISCOMATRIX is between 10 and 100 mcg. The adjuvant units for $AlPO_4$ shown in Tables 2-5 are shown as milligram units, and are therefore shown as 0.25 (milligram) as opposed to 250 mcg.

The immunization schedule was 0, 4 and 24 wks with bleeds at 0, 4, 6 and 26 weeks. There were no increases in SBA titers at post dose one for any of the groups. At post dose two, an increase in SBA titers and the number of responders as defined by a 4 fold increase in SBA titer above baseline was observed for formulations containing the ISCOMATRIX adjuvant. Tables 2 and 3 provide the SBA GMTs observed for a fHBP Subfamily A and B strain respectively. SBA GMTs for the ISCOMATRIX formulations were 3-19 and 4-2 4 fold higher than those observed for the AlPO4 formulation for the A and B subfamily strains respectively. Enhanced titers were also observed at post dose three for the ISCOMATRIX formulations at 13-95 and 2-10 for a fHBP Subfamily A and B strain respectively compared to the AlPO4 formulation. Analysis of the responder rates, as defined by a four fold or greater increase in SBA titer over baseline revealed a similar trend (Tables 4 and 5).

TABLE 2

SBA titers (GMTs) obtained for against a MnB LP2086 Subfamily A strain immune serum from rhesus macaques immunized with different formulations of a bivalent rP2086 vaccine

| Vaccine | lipidation | Adjuvant | | Geometric Mean titer (GMT) | | | |
| --- | --- | --- | --- | --- | --- | --- | --- |
| | | AlPO4 | ISCOMATRIX ® | wk0 | wk4 | wk6 | wk26 |
| A05/B44 | – | 0.25 | — | – | – | – | + |
| | | — | 10 | – | – | + | +++ |
| | | 0.25 | 10 | – | – | + | ++ |
| | | — | 100 | – | – | ++ | ++++ |
| | | 0.25 | 100 | – | – | + | +++ |

Five monkeys per group;
Immunization schedule: 0, 4, 24 weeks;
bleed schedule 0, 4, 6 and 26 wks.
SBA test strain MnB M98 250771.
"–" <8;
"+" 8-32;
"++" 33-128;
"+++" 129-512;
"++++" >512

TABLE 3

SBA titers (GMTs) obtained for against a MnB LP2086 Subfamily B strain immune serum from rhesus macaques immunized with different formulations of a bivalent rP2086 vaccine

| Vaccine | lipidation | Adjuvant | | Geometric Mean titer (GMT) | | | |
|---|---|---|---|---|---|---|---|
| | | AlPO4 | ISCOMATRIX® | wk0 | wk4 | wk6 | wk26 |
| A05/B44 | – | 0.25 | — | – | – | + | +++ |
| | | — | 10 | – | – | +++ | ++++ |
| | | 0.25 | 10 | – | – | +++ | ++++ |
| | | — | 100 | – | – | +++ | ++++ |
| | | 0.25 | 100 | – | – | ++ | ++++ |

Five monkeys per group;
Immunization schedule: 0, 4, 24 weeks;
bleed schedule 0, 4, 6 and 26 wks.
SBA test strain MnB CDC1127.
"–" <8;
"+" 8-32;
"++" 33-128;
"+++" 129-512;
"++++" >512

TABLE 4

Number of rhesus macaques with a ≥4 fold rise in SBA Titer using a MnB LP2086 Subfamily A strain

| Vaccine | lipidation | Adjuvant | | No. of responders[b] | | | |
|---|---|---|---|---|---|---|---|
| | | AlPO4 | ISCOMATRIX® | wk0 | wk4 | wk6 | wk26 |
| A05/B44 | – | 0.25 | — | 0 | 0 | 0 | 2 |
| | | — | 10 | 0 | 0 | 3 | 5 |
| | | 0.25 | 10 | 0 | 0 | 2 | 5 |
| | | — | 100 | 0 | 0 | 4 | 5 |
| | | 0.25 | 100 | 0 | 0 | 2 | 5 |

TABLE 5

Number of rhesus macaques with a ≥4 fold rise in SBA Titer using a MnB LP2086 Subfamily B strain

| Vaccine | lipidation | Adjuvant | | No. of responders[b] | | | |
|---|---|---|---|---|---|---|---|
| | | AlPO4 | ISCOMATRIX® | wk0 | wk4 | wk6 | wk26 |
| A05/B44 | – | 0.25 | — | 0 | 0 | 3 | 5 |
| | | — | 10 | 0 | 0 | 5 | 5 |
| | | 0.25 | 10 | 0 | 0 | 5 | 5 |
| | | — | 100 | 0 | 0 | 4 | 4 |
| | | 0.25 | 100 | 0 | 0 | 3 | 5 |

Example 6: Immunoprotection Conferred by Lipidated and Non-Lipidated Variants A recombinantly expressed non-lipidated P2086 variant (B44) induces broad protection as measured by SBA against strains that represent diverse fHBP variants (from about 85% to about <92% ID) LP2086 sequences. These response rates were obtained for a non lipidated vaccine formulated with AlPO4. See Table 6, which shows SBA response rates to a subfamily B fHBP MnB strain generated by a bivalent fHBP vaccine. The non-lipidated vaccine (represented by a "–" under the "lipidation" column) included 1 mcg per protein of a non-pyruvylated non-lipidated A05 variant (SEQ ID NO: 13 wherein the N-terminal Cys at position 1 is deleted) and a non-pyruvylated non-lipidated B44 variant (SEQ ID NO: 21 wherein the N-terminal Cys at position 1 is deleted).

Alternatively, a recombinantly expressed non-lipidated P2086 variant (B44) induces greater immune responses as measured by SBA titer than a lipidated variant (B01) against strains bearing similar (>92% ID) and diverse (<92% ID) LP2086 sequences. Higher response rates (as defined by a four fold increase or greater in SBA titers over baseline) was observed for the vaccine containing the non-lipidated rP2086 B44 compared to the lipidated rLP2086 B01 vaccine (Table 6).

According to Table 6, non-lipidated B44 is a preferred subfamily B component of fHBP in a composition for providing broad coverage against (e.g., eliciting bactericidal antibodies against) multiple LP2086 variant strains.

Surprisingly, the inventors noted that LP2086 B09 variant strains are particularly unlikely to have positive SBA response rates with regard to heterologous (non-B09) ORF2086 polypeptides. In particular, the inventors found that LP2086 B09 is an exception in terms of an assay strain against which the A05/B44 immunogenic composition described in Table 6 elicited bactericidal antibodies. Therefore, in a preferred embodiment an immunogenic composition of the invention includes a B09 polypeptide, in particular in the context of a composition including more than one ORF2086 subfamily B polypeptide. In a preferred embodiment an immunogenic composition that includes a non lipidated B44 may also include a non-lipidated B09 polypeptide.

the DNA sequence of the B09 allele (SEQ ID NO: 48). The entire non-lipidated coding sequence of the B09 allele (SEQ ID NO: 48) was optimized to reflect the codon changes seen in the B44 optimized allele (SEQ ID NO: 43) wherever the amino acids between B44 (SEQ ID NO: 44) and B09 (SEQ ID NO: 49) were identical. Codon sequences in the B09 allele corresponding to the identical amino acids between the B09 allele and the B44 allele were changed to reflect the codon used in the B44 optimized sequence (SEQ ID NO: 43). Codon sequences for amino acids that differ between B09 (SEQ ID NO: 49) and B44 (SEQ ID NO: 44) were not changed in the B09 DNA sequence.

Additionally, the non-lipidated B44 amino acid sequence (SEQ ID NO: 44) contains two sequential serine-glycine

TABLE 6

SBA response rates to a Subfamily B fHBP MnB strains generated by bivalent fHBP vaccines Immune serum from rhesus macaques.

| Adjuvant | LP2086 Variant of Assay Strain | Vaccine | lipidation | % ID to Matched Subfamily for non-lipidated Vaccine Component | % responders PD3 Wk 26 |
|---|---|---|---|---|---|
| | B02 | A05/B01 | + | 99.6 | 80 |
| | | A05/B44 | − | | 100 |
| AIPO4 0.25 mg | B03 | A05/B01 | + | 86.7 | 50 |
| | | A05/B44 | − | | 80 |
| | B09 | A05/B01 | + | 86.3 | 0 |
| | | A05/B44 | − | | 0 |
| | B15 | A05/B01 | + | 86.7 | 25 |
| | | A05/B44 | − | | 80 |
| | B16 | A05/B01 | + | 87.1 | 0 |
| | | A05/B44 | − | | 50 |
| | B16 | A05/B01 | + | 87.1 | 0 |
| | | A05/B44 | − | | 60 |
| | B24 | A05/B01 | + | 85.9 | 0 |
| | | A05/B44 | − | | 60 |
| | B44 | A05/B01 | + | 100 | 100 |
| | | A05/B44 | − | | 100 |
| ISCOMATRIX ® (10 mcg) | A05 | A05/B44 | − | 100 | 100 |
| ISCOMATRIX ® (100 mcg) | A05 | A05/B44 | − | 100 | 100 |
| ISCOMATRIX ® (10 mcg) | A22 | A05/B44 | − | 88.9 | 80 |
| ISCOMATRIX ® (100 mcg) | A22 | A05/B44 | − | 88.9 | 100 |

Five monkeys per group;
Immunization schedule: 0, 4, 24 weeks;
bleed schedule 0, 4, 6, and 26 wks.

Example 7: Codon Optimization of the B44 and B09 Variants

Although the expression levels achieved in the preceding examples were adequate for many applications, further optimization was desirable, and *E. coli* expression constructs containing additional codon optimization over the full length of the protein were prepared and tested. One such improved sequence for expression of a non-Cys B44 protein was found to be the nucleic acid sequence set forth in SEQ ID NO: 43. As shown in Example 9, the expression construct containing SEQ ID NO: 43 showed enhanced expression compared to that of the non-optimized wild type sequence.

Expression of the N-terminal Cys deleted B09 protein was improved by applying codon changes from the above optimized B44 (SEQ ID NO: 43) construct to B09 (SEQ ID NO: 48). To generate optimized B09 sequences, the B44 optimized DNA sequence (SEQ ID NO: 43) was first aligned to repeat sequences (S-G-G-G-G)(SEQ ID NO: 56)(see also amino acids 2 to 6 of SEQ ID NO: 44) at its N-terminus, whereas the B09 allele contains only one serine-glycine repeat at the N-terminus (see amino acids 2 to 6 and amino acids 7 to 11 of SEQ ID NO: 49). The two serine-glycine repeats at the N-terminus of B44 (amino acids 2 to 6 and amino acids 7 to 11 of SEQ ID NO: 44) also have different codon usage (see nucleotides 4 to 18 and nucleotides 19 to 33 of SEQ ID NO: 43), and different combinations of the optimized B44 serine-glycine repeat (e.g., either nucleotides 4 to 18 of SEQ ID NO: 43, or nucleotides 19 to 33 of SEQ ID NO: 43, or a combination thereof) were applied to the B09 DNA sequence (SEQ ID NO: 48, e.g., applied to nucleotides 4 to 18 of SEQ ID NO: 48) in order to examine the effect on recombinant protein expression.

Three different versions of optimized B09 were constructed: SEQ ID NO: 45 contains both serine-glycine repeats (GS1 and GS2) (nucleic acids 4 to 33 of SEQ ID NO:

43) from the optimized B44, SEQ ID NO: 46 contains GS1 (nucleic acids 4 to 18 of SEQ ID NO: 43), and SEQ ID NO: 47 contains GS2 (nucleic acids 19 to 33 of SEQ ID NO: 43). The DNA for all of the above codon optimized sequences were chemically synthesized using standard in the art chemistry. The resulting DNA was cloned into appropriate plasmid expression vectors and tested for expression in E. coli host cells as described in Examples 8 and 9.

Example 8: Method for Expressing ORF2086, B09 Variant

Cells of E. coli K-12 strain (derivatives of wild-type W3110 (CGSC4474) having deletions in recA, fhuA and araA) were transformed with plasmid pEB063, which includes SEQ ID NO: 45, pEB064, which includes SEQ ID NO: 46, plasmid pEB065, which includes SEQ ID NO: 47, or plasmid pLA134, which includes SEQ ID NO: 48. The preferred modifications to the K-12 strain are helpful for fermentation purposes but are not required for expression of the proteins.

Cells were inoculated to a glucose-salts defined medium. After 8 hours of incubation at 37° C. a linear glucose feed was applied and incubation was continued for an additional 3 hours. Isopropyl β-D-1-thiogalactopyranoside (IPTG) was added to the culture to a final concentration of 0.1 mM followed by 12 hours of incubation at 37° C. Cells were collected by centrifugation at 16,000×g for 10 minutes and lysed by addition of Easy-Lyse™ Cell Lysing Kit" from Lienco Technologies (St. Louis, Mo.) and loading buffer. The cleared lysates were analyzed for expression of B09 by Coomassie staining of SDS-PAGE gels and/or Western blot analysis with quantitation by a scanning densitometer. The results from scanning densitometry are below in Table 7:

TABLE 7

Expression data in E. coli

| Protein | Host cell | Plasmid | Percentage of total cell protein at 12 hours post IPTG induction, as measured by SDS-PAGE, scanning desitometry |
|---|---|---|---|
| B09 | E. coli K-12 | pEB063 SEQ ID NO: 45 | 24% |
| B09 | E. coli K-12 | pEB065 SEQ ID NO: 47 | 12% |
| B09 | E. coli K-12 | pEB064 SEQ ID NO: 46 | 38% |
| B09 | E. coli K-12 | pLA134 SEQ ID NO: 48 | 13% |

Example 9: Method for Expressing ORF2086, B44 Variant

Cells of E. coli B strain (BLR(DE3), Novagen) were transformed with plasmid pLN056, which includes SEQ ID NO: 51. Cells of E. coli K-12 strain (derivative of wild-type W3110) were transformed with plasmid pDK087, which includes SEQ ID NO: 43. Cells were inoculated to a glucose-salts defined medium. After 8 hours of incubation at 37° C. a linear glucose feed was applied and incubation was continued for an additional 3 hours. Isopropyl β-D-1-thiogalactopyranoside (IPTG) was added to the culture to a final concentration of 0.1 mM followed by 12 hours of incubation at 37° C. Cells were collected by centrifugation at 16,000×g for 10 minutes and lysed by addition of Easy-Lyse™ Cell Lysing Kit" from Lienco Technologies (St. Louis, Mo.) and loading buffer. The supermatants were analyzed for expression of B09 by COOMASSIE staining of SDS-PAGE gels and/or Western blot analysis, with quantitation by a scanning densitometer. The results from scanning densitometry are below in Table 8:

TABLE 8

Expression data in E. coli

| Protein | Host cell | Plasmid | Percentage of total cell protein at 12 hours post IPTG induction, as measured by SDS-PAGE, scanning desitometry. |
|---|---|---|---|
| B44 | E. coli B | pLN056 SEQ ID NO: 51 | 1% |
| B44 | E. coli K-12 | pDK087 SEQ ID NO: 43 | 17% |

Example 10: Pyruvylation

The present example demonstrates that the N-terminal Cys residue of non-lipidated ORF2086 proteins can become pyruvylated when expressed in, for example, E. coli.

Heterologous protein accumulation during production of variants A05 (SEQ ID NO: 13) and B44 (SEQ ID NO: 21) were monitored using reverse-phase high performance liquid chromatography (RP-HPLC). This separation was interfaced with a quadrupole time-of-flight mass spectrometer (QTOF-MS) to provide a means of monitoring formation of product related variants.

After being expressed in the E. coli B and/or K-12 host cells, products derived from these fermentations underwent a purification procedure during which a product modification was observed. Deconvolution of the mass spectra characterized the variants as exhibiting mass shifts of +70 Da, as compared to native products of 27640 and 27572 Da for A05 and B44, respectively.

Published literature indicated that a +70 Da mass shift had previously been observed in proteins and has been attributed to pyruvylation of the amino-terminal residue.

The presence and location of the pyruvate group was confirmed using the mass spectral fragmentation data (MS/MS). The data indicated that the modification was on an amino-terminal cysteine residue, i.e., amino acid at position 1, according to A05 and B44. For A05, the percentage of pyruvylated polypeptides was about 30%, as compared to the total number of A05 polypeptides (SEQ ID NO: 13). For B44 the percentage of pyruvylated polypeptides was about 25%, as compared to the total number of B44 polypeptides (SEQ ID NO: 21).

When A05 (SEQ ID NO: 13 wherein the N-terminal Cys at position 1 is deleted or SEQ ID NO: 55) and B44 variants (SEQ ID NO: 21 wherein the N-terminal Cys at position 1 is deleted or SEQ ID NO: 44), which do not contain an amino-terminal cysteine, were purified, there was no detectable pyruvylation (+70 Da).

Example 11: Immunogenicity of B09 and B44, Individually and in Combination 5-10 groups of rhesus maccaques monkeys were immunized with B09 variant (SEQ ID NO: 49 encoded by SEQ ID NO: 48) or B44 variant (SEQ ID NO: 44 encoded by SEQ ID NO: 43), or the A05, B09 and B44 (SEQ ID NO: 55, SEQ ID NO: 49 encoded by SEQ ID NO: 48, and SEQ ID NO: 44 encoded by SEQ ID NO: 43, respectively) formulated with 250 mcg of AlPO$_4$ per dose. The monkeys were vaccinated via the intramuscular route at weeks 0, 4 and 8 with 10 mcg each of non-lipidated fHBP alone or in combination as listed in Table 9 and 10. Both weeks 0 and 12 serum samples were analyzed in SBAs against MnB strains with either subfamily A or subfamily B fHBP variants. Responders were recorded as animals with a 4× rise in titer. The B44 variant tested was the optimized construct (SEQ ID NO: 43) and the broad response rates that were observed in previous studies (table above) were maintained for the optimized construct (Table 9) the B44 vaccine alone or in combination with B09. The B09 vaccine alone (Table 10) could also generate broadly cross reactive immune responses (Table 10).

TABLE 9

Response rates obtained for non lipidated fHBP vaccines in rhesus macaques

| Vaccine (10 mcg per protein; | % ≥ 4 X Rise Against Test Variant (PD3; 10 rhesus macaques per group) | | | | |
|---|---|---|---|---|---|
| | A05 (SEQ ID NO: 13) | B44 (SEQ ID NO: 21) | B16 (SEQ ID NO: 60) | B24 (SEQ ID NO: 20) | B09 (SEQ ID NO: 18) |
| B44 | 0 | 80 | 30 | 40 | 30 |
| B44 + B09 + A05 | 60 | 80 | 40 | 50 | 30 |

Rhesus macaques (n=10) were immunized i.m. at weeks 0, 4 and 8 with 10 mcg each of non-lipidated fHBP alone or in combination as listed in the Vaccine column in formulation with 250 mcg of AlPO$_4$. Both weeks 0 and 10 serum samples were analyzed in SBAs against the MnB strains listed in the table. Responders are recorded as animals with a 4× rise in titer.

Table 9 indicates, for example, that a composition including a combination of non-pyruvylated non-lipidated B44, B09, and A05 showed higher cross-coverage against the test variants as compared to the cross-coverage from a composition including B44 alone. In view of results shown in the present application, including in particular Table 6 and Table 9 together, compositions including B44, B09 and A05 alone or in combination are preferred embodiments of the present invention. In particular, compositions including both B44 and B09 are disclosed. Such composition preferably further includes a subfamily A polypeptide, such as in particular A05.

TABLE 10

Response rates obtained for non lipidated fHBP B09 vaccine in rhesus macaques

| Vaccine (10 mcg per protein) | % ≥ 4 X Rise Against Test Variant (PD3; 5 rhesus macaques per group) | | | | |
|---|---|---|---|---|---|
| | A05 | B44 | B16 | B24 | B09 |
| B09 | 40 | 60 | 40 | 60 | 60 |

Rhesus macaques (n=5) were immunized i.m. at weeks 0, 4 and 8 with 10 mcg each of non-lipidated fHBP alone or in combination as listed in the Vaccine column in formulation with 250 mcg of AlPO$_4$. Both weeks 0 and 10 serum samples were analyzed in SBAs against the MnB strains listed in the table. Responders are recorded as animals with a 4× rise in titer.

Example 12: Immunoprotection Conferred by Lipidated and Non-Lipidated Variants Construct Twenty female New Zealand white rabbits, 2.5-3.5 kg, obtained from Charles River Canada, were pre-screened by whole cell ELISA and 10 animals were selected for this study based on their low background titers against the test strains representing fHBP variants B02 (SEQ ID NO: 16) and B44 (SEQ ID NO: 21) (Table 11). Group of three animals were i.m. immunized with 100 µg of each protein formulated with 50 µg ISCOMATRIX per 0.5 ml dose at weeks 0, 4 and 9 (Table 12). Group 1 was vaccinated with non-lipidated B44 (SEQ ID NO: 44). A control group was included that was vaccinated with lipidated B01 formulated with AlPO4 (250 mcg) Rabbits were bled at weeks 0, 4, 9 and 10. Individual sera from week 10 were prepared and analyzed by serum bactericidal assay against multiple serogroup B meningococcal strains from the fHBP B subfamily.

TABLE 11

Rabbits Used in The Study

| | |
|---|---|
| Species: | Rabbit |
| Strain: | New Zealand white |
| Source:[a] | Charles River Laboratory |
| No. of Animals Per Group: | 3 |
| Total No. of Animals: | 9 |
| Age and Sex: | Female |
| Weight: | 2.5-3.5 kg |

TABLE 12

| Group | # of animals | Variant | lipidated | rfHBP (µg/0.5 ml dose) | ISCOMATRIX (µg/0.5 ml dose) | Aluminium Phosphate (µg/0.5 ml dose) |
|---|---|---|---|---|---|---|
| 1 | 3 | B44 | – | 100 | 50 | |
| 2 | 3 | B01 | – | 100 | 50 | |
| 3 | 3 | B01 | + | 100 | — | 100 |

Immunization schedule Weeks 0, 4, 9; Bleed schedule Weeks 0, 4, 9, 10

Serum Bactericidal Assay (SBA): A microcolony-based serum bactericidal assay (SBA) against multiple serogroup B meningococcal strains (Table 13) was performed on individual serum samples. Human sera from donors were qualified as the complement source for the strain tested in the assay. Complement-mediated antibody-dependent bactericidal titers were interpolated and expressed as the reciprocal of the dilution of the test serum that killed 50% of the meningococcal cells in the assay. The limit of detection of the assay was an SBA titer of 4. An SBA titer of <4 was assigned number of 2. A 4-fold rise of SBA titers in the week 10 sera in comparison to the titers in the pre-bleed was calculated and compared.

Serum bactericidal antibody activity as measured in the SBA is the immunologic surrogate of protection against meningococcal disease. The ability of immunization with non-lipidated rfHBP to elicit bactericidal antibodies in rabbits was determined by SBA. SBA measures the level of antibodies in a serum sample by mimicking the complement-mediated bacterial lysis that occurs naturally. Rabbit serum samples collected from week 10 were analyzed by SBA against strains with a B44 fHBP or a B02 fHBP. As shown in Table 13, one week after the third immunization (week 10), all serum samples displayed bactericidal activity against both test strains. (Table 13). The non-lipidated B44 (SEQ ID NO: 44) was more immunogenic than non-lipidated B01 in New Zealand Rabbits against these strains. The non lipidated B44 (SEQ ID NO: 44) formulated with the iscomatrix adjuvant gave comparable titers to the lipidated B01 formulated with aluminium phosphate against these strains. Rabbit pre-bleed sera showed generally no pre-existing bactericidal activity against the tested strains.

TABLE 13

Serum Bactericidal Activity against fHBP Subfamily B Strains in New Zealand White Rabbits Vaccinated with Recombinant Non-lipidated fHBP

| Subfamily B variant (formulation) | GMT SBA Titer against test variant | |
|---|---|---|
| | B44 (SEQ ID NO: 21) | B02 (SEQ ID NO: 16) |
| Non lipidated B44 (SEQ ID NO: 44) (ISCOMATRIX) | 6675 | 7140 |
| Non lipidated B01 (ISCOMATRIX) | 625 | 1052 |
| Lipidated B01 (AlPO$_4$) | 10099 | 10558 |

Example 13: Immunogenicity of Six Non-Lipidated Factor H Binding Proteins in New Zealand White Rabbits Groups of 5 rabbits were immunized with non-lipidated fHBP variants as described in Table 14. Vaccines were administered at 0, 4 and 9 weeks. Rabbit serum samples collected from weeks 0 and 10 were analyzed by SBA against the strains with homologous and heterologous fHBP sequences. Table 14 shows the percent responders post the third immunization. One week after the third immunization (week 10), all serum samples displayed bactericidal activity against the homologous strains as well as other test strains from the same fHBP subfamily. Rabbits pre-bleed sera showed generally no pre-existing bactericidal activity against the tested strains.

TABLE 14

Post Dose Three Percent of Responders in New Zealand White Rabbits Vaccinated with Recombinant Non-lipidated fHBPs

| MnB fHBP | Dose/0.5 mL | AlPO$_4$/0.5 mL | n | B09 | B16 | B24 | B44 | A05 | A12 | A22 |
|---|---|---|---|---|---|---|---|---|---|---|
| A05 | 100 mcg | 0.25 mg | 5 | | | | | 100 | 80 | 100 |
| A12 | 100 mcg | 0.25 mg | 5 | | | | | 100 | 100 | 100 |
| A22 | 100 mcg | 0.25 mg | 5 | | | | | 80 | 80 | 80 |
| B09 | 100 mcg | 0.25 mg | 5 | 100 | 80 | 60 | 80 | | | |
| B22 | 100 mcg | 0.25 mg | 5 | 40 | 100 | 60 | 100 | | | |
| B44 | 100 mcg | 0.25 mg | 5 | 0 | 60 | 40 | 100 | | | |
| A05, A12, B22, B44 | 100 mcg each/400 mcg total | 0.25 mg | 5 | 100 | 100 | 60 | 100 | 100 | 100 | 100 |

| MnB fHBP Proteins Used | |
|---|---|
| A05 | SEQ ID NO: 13, wherein the Cys at position 1 is deleted, or SEQ ID NO: 55 encoded by SEQ ID NO: 54 |
| A12 | SEQ ID NO: 14, wherein the Cys at position 1 is deleted |
| A22 | SEQ ID NO: 15, wherein the Cys at position 1 is deleted |
| B09 | SEQ ID NO: 18, wherein the Cys at position 1 is deleted, or SEQ ID NO: 49 encoded by SEQ ID NO: 48. |
| B22 | SEQ ID NO: 19, wherein the Cys at position 1 is deleted |
| B44 | SEQ ID NO: 21, wherein the Cys at position 1 is deleted, or SEQ ID NO: 44 encoded by SEQ ID NO: 51 |

TABLE 14-continued

Post Dose Three Percent of Responders in New Zealand White Rabbits
Vaccinated with Recombinant Non-lipidated fHBPs Test variants in Table 14:

| B09 (SEQ ID NO: 18) | B16 (SEQ ID NO: 60) | B24 (SEQ ID NO: 20) | B44 (SEQ ID NO: 21) | A05 (SEQ ID NO: 13) | A12 (SEQ ID NO: 14) | A22 (SEQ ID NO: 15) |
|---|---|---|---|---|---|---|

Example 14

>non-lipidated A05
(SEQ ID NO: 55)
SSGSGSGGGGVAADIGTGLADALTAPLDHKDKGLKSLTLEDSISQNGTL
TLSAQGAEKTFKVGDKDNSLNTGKLKNDKISRFDFVQKIEVDGQTITLA
SGEFQIYKQDHSAVVALQIEKINNPDKIDSLINQRSFLVSGLGGEHTAF
NQLPSGKAEYHGKAFSSDDAGGKLTYTIDFAAKQGHGKIEHLKTPEQNV
ELASAELKADEKSHAVILGDTRYGSEEKGTYHLALFGDRAQEIAGSATV
KIREKVHEIGIAGKQ >pEB042
(SEQ ID NO: 65)
ATGAGCTCTGGAAGCGGAAGCGGGGGCGGTGGAGTTGCAGCAGACATTG
GAACAGGATTAGCAGATGCACTGACGGCACCGTTGGATCATAAAGACAA
AGGCTTGAAATCGCTTACCTTAGAAGATTCTATTTCACAAAATGGCACC
CTTACCTTGTCCGCGCAAGGCGCTGAAAAAACTTTTAAAGTCGGTGACA
AAGATAATAGCTTAAATACAGGTAAACTCAAAAATGATAAAATCTCGCG
TTTTGATTTCGTGCAAAAAATCGAAGTAGATGGCCAAACCATTACATTA
GCAAGCGGTGAATTCCAAATATATAAACAAGACCATTCAGCAGTCGTTG
CATTGCAAATTGAAAAAATCAACAACCCCGACAAAATCGACAGCCTGAT
AAACCAACGTTCCTTCCTTGTCAGCGGTTTGGGCGGTGAACATACAGCC
TTCAACCAATTACCAAGCGGCAAAGCGGAGTATCACGGTAAAGCATTTA
GCTCAGATGATGCAGGCGGTAAATTAACTTATACAATTGACTTTGCAGC
AAAACAAGGACATGGCAAAATTGAACATTTAAAAACACCCGAACAGAAC
GTAGAGCTCGCATCCGCAGAACTCAAAGCAGATGAAAAATCACACGCAG
TCATTTTGGGTGACACGCGCTACGGCAGCGAAGAAAAAGGTACTTACCA
CTTAGCTCTTTTTGGCGACCGAGCTCAAGAAATCGCAGGTAGCGCAACC
GTAAAGATAAGGGAAAAGGTTCACGAAATTGGGATCGCGGGCAAACAAT
AA >non-lipidated A12
(SEQ ID NO: 66)
SSGGGGSGGGGVAADIGAGLADALTAPLDHKDKSLQSLTLDQSVRKNEK
LKLAAQGAEKTYGNGDSLNTGKLKNDKVSRFDFIRQIEVDGQTITLASG
EFQIYKQNHSAVVALQIEKINNPDKIDSLINQRSFLVSGLGGEHTAFNQ
LPDGKAEYHGKAFSSDDPNGRLHYSIDFTKKQGYGRIEHLKTPEQNVEL
ASAELKADEKSHAVILGDTRYGGEEKGTYHLALFGDRAQEIAGSATVKI
REKVHEIGIAGKQ >pEB043
(SEQ ID NO: 67)
ATGAGCTCTGGAGGTGGAGGAAGCGGGGGCGGTGGAGTTGCAGCAGACA
TTGGAGCAGGATTAGCAGATGCACTGACGGCACCGTTGGATCATAAAGA
CAAAAGTTTGCAGTCGCTTACCTTAGATCAGTCTGTCAGGAAAAATGAG
AAACTTAAGTTGGCGGCGCAAGGCGCTGAAAAAACTTATGGAAACGGTG
ACAGCTTAAATACAGGTAAACTCAAAAATGATAAAGTCTCGCGTTTTGA
TTTCATTCGTCAAATCGAAGTAGATGGCCAAACCATTACATTAGCAAGC
GGTGAATTCCAAATATATAAACAAAACCATTCAGCAGTCGTTGCATTGC
AAATTGAAAAAATCAACAACCCCGACAAAATCGACGCCTGATAAACCA
ACGTTCCTTCCTTGTCAGCGGTTTGGGCGGTGAACATACAGCCTTCAAC
CAATTACCAGACGGCAAAGCGGAGTATCACGGTAAAGCATTTAGCTCAG
ATGATCCGAACGGTAGGTTACACTATTCCATTGACTTTACCAAAAAACA
AGGATACGGCAGAATTGAACATTTAAAAACGCCCGAACAGAACGTAGAG
CTCGCATCCGCAGAACTCAAAGCAGATGAAAAATCACACGCAGTCATTT
TGGGTGACACGCGCTACGGCGGCGAAGAAAAAGGTACTTACCACTTAGC
CCTTTTTGGCGACCGCGCTCAAGAAATCGCAGGTAGCGCAACCGTAAAG
ATAAGGGAAAAGGTTCACGAAATTGGGATCGCGGGCAAACAATAA >non-lipidated A22
(SEQ ID NO: 68)
SSGGGGVAADIGAGLADALTAPLDHKDKSLQSLTLDQSVRKNEKLKLAA
QGAEKTYGNGDSLNTGKLKNDKVSRFDFIRQIEVDGQLITLESGEFQIY
KQDHSAVVALQIEKINNPDKIDSLINQRSFLVSGLGGEHTAFNQLPSGK
AEYHGKAFSSDDAGGKLTYTIDFAAKQGHGKIEHLKTPEQNVELASAEL
KADEKSHAVILGDTRYGGEEKGTYHLALFGDRAQEIAGSATVKIREKVH
EIGIAGKQ >pEB058
(SEQ ID NO: 69)
ATGAGCTCTGGAGGTGGAGGAGTTGCAGCAGACATTGGAGCAGGATTAG
CAGATGCACTGACGGCACCGTTGGATCATAAAGACAAAAGTTTGCAGTC
GCTTACCTTAGATCAGTCTGTCAGGAAAAATGAGAAACTTAAGTTGGCG
GCGCAAGGCGCTGAAAAAACTTATGGAAACGGTGACAGCTTAAATACAG
GTAAACTCAAAAATGATAAAGTCTCGCGTTTTGATTTCATTCGTCAAAT
CGAAGTAGATGGCCAACTTATTACATTAGAAAGCGGTGAATTCCAAATA
TATAAACAAGACCATTCAGCAGTCGTTGCATTGCAAATTGAAAAAATCA

```
ACAACCCCGACAAAATCGACAGCCTGATAAACCAACGTTCCTTCCTTGT
CAGCGGTTTGGGCGGTGAACATACAGCCTTCAACCAATTACCAAGCGGC
AAAGCGGAGTATCACGGTAAAGCATTTAGCTCAGATGATGCAGGCGGTA
AATTAACTTATACAATTGACTTTGCAGCAAAACAAGGACATGGCAAAAT
TGAACATTTAAAAACACCCGAACAGAACGTAGAGCTCGCATCCGCAGAA
CTCAAAGCAGATGAAAATCACACGCAGTCATTTTGGGTGACACGCGCT
ACGGCGGCAAGAAAAAGGTACTTACCACTTAGCTCTTTTTGGCGACCG
AGCTCAAGAAATCGCAGGTAGCGCAACCGTAAAGATAAGGGAAAAGGTT
CACGAAATTGGGATCGCGGGCAAACAATAA
```

>A62. GenBank: ACI46789.1
(SEQ ID NO: 70)
CSSGGGGVAADIGAGLADALTAPLDHKDKGLQSLTLDQSVRKNEKLKLA
AQGAEKTYGNGDSLNTGKLKNDKVSRFDFIRQIEVDGKLITLESGEFQV
YKQSHSALTALQTEQVQDSEDSGKMVAKRQFRIGDIAGEHTSFDKLPKG
GSATYRGTAFGSDDAGGKLTYTIDFAAKQGHGKIEHLKTPEQNVELASA
ELKADEKSHAVILGDTRYGGEEKGTYHLALFGDRAQEIAGSATVKIREK
VHEIGIAGKQ >non-lipidated A62
(SEQ ID NO: 71)
SSGGGGVAADIGAGLADALTAPLDHKDKGLQSLTLDQSVRKNEKLKLAA
QGAEKTYGNGDSLNTGKLKNDKVSRFDFIRQIEVDGKLITLESGEFQVY
KQSHSALTALQTEQVQDSEDSGKMVAKRQFRIGDIAGEHTSFDKLPKGG
SATYRGTAFGSDDAGGKLTYTIDFAAKQGHGKIEHLKTPEQNVELASAE
LKADEKSHAVILGDTRYGGEEKGTYHLALFGDRAQEIAGSATVKIREKV
HEIGIAGKQ >pLA164
(SEQ ID NO: 72)
ATGAGCAGCGGAGGGGCGGTGTCGCCGCCGACATCGGTGCGGGCTTG
CCGATGCACTAACCGCACCGCTCGACCATAAAGACAAAGGTTTGCAGTC
TTTAACGCTGGATCAGTCCGTCAGGAAAAACGAGAAACTGAAGCTGGCG
GCACAAGGTGCGGAAAAAACTTATGGAAACGGCGACAGCCTTAATACGG
GCAAATTGAAGAACGACAAGGTCAGCCGCTTCGACTTTATCCGTCAAAT
CGAAGTGGACGGGAAGCTCATTACCTTGGAGAGCGGAGAGTTCCAAGTG
TACAAACAAAGCCATTCCGCCTTAACCGCCCTTCAGACCGAGCAAGTAC
AAGACTCGGAGGATTCCGGGAAGATGGTTGCAAACGCCAGTTCAGAAT
CGGCGACATAGCGGGCAACATACATCTTTTGACAAGCTTCCCAAAGGC
GGCAGTGCGACATATCGCGGGACGGCGTTCGGTTCAGACGATGCTGGCG
GAAAACTGACCTATACTATAGATTTCGCCGCCAAACAGGGACACGGCAA
AATCGAACACTTGAAAACACCCGAGCAAATGTCGAGCTTGCCTCCGCC
GAACTCAAAGCAGATGAAAATCACACGCCGTCATTTTGGGCGACACGC
GCTACGGCGGCGAAGAAAAAGGCACTTACCACCTCGCCCTTTTCGGCGA
CCGCGCCCAAGAAATCGCCGGCTCGGCAACCGTGAAGATAAGGGAAAAG
GTTCACGAAATCGGCATCGCCGGCAAACAGTAA >pDK086
(SEQ ID NO: 73)
ATGTCCAGCGGTTCAGGCAGCGGCGGTGGAGGCGTGGCAGCAGATATCG
GAACAGGTTTAGCAGATGCTCTGACAGCACCCTTAGATCACAAAGACAA
AGGACTTAAATCACTGACATTGGAAGATTCTATCTCGCAAAATGGTACT
CTCACTCTTTCAGCCCAAGGCGCAGAAAAAACATTTAAAGTAGGCGATA
AAGATAACTCCTTAAATACAGGTAAATTAAAAAATGACAAAATCTCACG
GTTTGATTTCGTTCAGAAAATTGAAGTAGATGGACAAACGATTACATTA
GCAAGCGGCGAATTCCAAATTTATAAACAAGACCATTCAGCAGTAGTAG
CATTACAAATCGAAAAAATTAACAACCCGGACAAAATTGATTCTCTTAT
TAACCAACGCTCTTTTCTCGTATCAGGACTTGGTGGTGAACATACAGCG
TTTAATCAACTGCCGTCAGGAAAAGCAGAATATCATGGTAAAGCATTTT
CATCAGACGACGCAGGTGGCAAACTGACCTATACTATTGACTTTGCAGC
AAAACAGGGACATGGAAAAATTGAACATTTAAAAACACCCGAACAGAAC
GTAGAACTGGCCTCAGCAGAATTGAAAGCTGATGAAAATCCCATGCAG
TAATTTTAGGCGATACACGTTACGGTAGCGAAGAAAAAGGTACATATCA
CTTAGCTCTTTTTGGCGATCGTGCTCAAGAAATTGCTGGTTCCGCAACA
GTTAAAATCCGTGAAAAGTACATGAAATCGGCATTGCAGGTAAACAAT
AA >A29
(SEQ ID NO: 74)
CSSGGGGSGGGGVAADIGTGLADALTAPLDHKDKGLKSLTLEDSIPQNG
TLTLSAQGAEKTFKAGDKDNSLNTGKLKNDKISRFDFVQKIEVDGQTIT
LASGEFQIYKQNHSAVVALQIEKINNPDKIDSLINQRSFLVSGLGGEHT
AFNQLPGDKAEYHGKAFSSDDPNGRLHYTIDFTNKQGYGRIEHLKTPEL
NVDLASAELKADEKSHAVILGDTRYGSEEKGTYHLALFGDRAQEIAGSA
TVKIGEKVHEIGIAGKQ >non-lipidated B22
(SEQ ID NO: 75)
SSGGGGVAADIGAVLADALTAPLDHKDKSLQSLTLDQSVRKNEKLKLAA
QGAEKTYGNGDSLNTGKLKNDKVSRFDFIRQIEVDGQLITLESGEFQVY
KQSHSALTALQTEQVQDSEHSGKMVAKRQFRIGDIAGEHTSFDKLPEGG
RATYRGTAFGSDDASGKLTYTIDFAAKQGHGKIEHLKSPELNVDLAASD
IKPDKKRHAVISGSVLYNQAEKGSYSLGIFGGQAQEVAGSAEVETANGI
RHIGLAAKQ >non-lipidated A05 (pPW102)
(SEQ ID NO: 76)
CGSSGGGGVAADIGTGLADALTAPLDHKDKGLKSLTLEDSISQNGTLTL
SAQGAEKTFKVGDKDNSLNTGKLKNDKISRFDFVQKIEVDGQTITLASG
EFQIYKQDHSAVVALQIEKINNPDKIDSLINQRSFLVSGLGGEHTAFNQ -continued
LPSGKAEYHGKAFSSDDAGGKLTYTIDFAAKQGHGKIEHLKTPEQNVEL

ASAELKADEKSHAVILGDTRYGSEEKGTYHLALFGDRAQEIAGSATVKI

REKVHEIGIAGKQ

>non-lipidated A05
(SEQ ID NO: 77)
GSSGGGGVAADIGTGLADALTAPLDHKDKGLKSLTLEDSISQNGTLTLS

AQGAEKTFKVGDKDNSLNTGKLKNDKISRFDFVQKIEVDGQTITLASGE

FQIYKQDHSAVVALQIEKINNPDKIDSLINQRSFLVSGLGGEHTAFNQL

PSGKAEYHGKAFSSDDAGGKLTYTIDFAAKQGHGKIEHLKTPEQNVELA

SAELKADEKSHAVILGDTRYGSEEKGTYHLALFGDRAQEIAGSATVKIR

EKVHEIGIAGKQ

>Consensus
(SEQ ID NO: 78)
CSSGGGGVAADIGAGLADALTAPLDHKDKGLQSLTLDQSVRKNEKLKLA

AQGAEKTYGNGDSLNTGKLKNDKVSRFDFIRQIEVDGQLITLESGEFQI

YKQSHSALVALQTEQINNSDKSGSLINQRSFRISGIAGEHTAFNQLPKG

GKATYRGTAFSSDDAGGKLTYTIDFAAKQGHGKIEHLKTPEQNVELASA

ELKADEKSHAVILGDTRYGGEEKGTYHLALFGDRAQEIAGSATVKIREK

VHEIGIAGKQ

>Consensus
(SEQ ID NO: 79)
SSGGGGVAADIGAGLADALTAPLDHKDKGLQSLTLDQSVRKNEKLKLAA

QGAEKTYGNGDSLNTGKLKNDKVSRFDFIRQIEVDGQLITLESGEFQIY

KQSHSALVALQTEQINNSDKSGSLINQRSFRISGIAGEHTAFNQLPKGG

KATYRGTAFSSDDAGGKLTYTIDFAAKQGHGKIEHLKTPEQNVELASAE

LKADEKSHAVILGDTRYGGEEKGTYHLALFGDRAQEIAGSATVKIREKV

HEIGIAGKQ

Example 15: Generation of Non-Lipidated Variants of Subfamily A rP2086-Cloning of Non Lipidated fHBP Genes The coding sequence of non lipidated A05 fHBP protein (SEQ ID NO: 55) was aligned to an expression-optimized B44 sequence (SEQ ID NO: 43). Wherever the amino acids between the two were identical, the codon from the B44 (SEQ ID NO: 43) was used to substitute in the A05 gene. The optimized sequence was synthesized de novo at Celtek Genes, adding restriction endonuclease sites NdeI and BamHI at the N- and C-termini, respectively. The resulting gene (SEQ ID NO: 65) was subcloned into pET30a at those sites.

Recombinant non lipidated A12 fHBP (SEQ ID NO: 66) was expressed from pEB043 (SEQ ID NO: 67). The A12 allele was expression-optimized by Blue Heron Technologies. This gene was optimized by the same process as for A05 (pEB042). In addition, the Blue Heron optimized B44 SGGGGSGGGG (amino acid residues 2 to 11 of SEQ ID NO: 44) amino terminal codons replaced the native A12 SSGGGG (amino acid residues 1 to 6 of SEQ ID NO: 66) codons. The optimized sequence was synthesized de novo at Celtek Genes, adding restriction endonuclease sites NdeI and BamHI at the N- and C-termini, respectively. The resulting gene (SEQ ID NO: 67) was subcloned into pET30a at those sites.

Recombinant non lipidated A22 fHBP (SEQ ID NO: 68) was expressed from pEB058 (SEQ ID NO: 69). This gene was optimized by the same process as for pEB042. In addition, the Blue Heron optimized B44 SGGGG (amino acid residues 2 to 6 of SEQ ID NO: 44) amino terminal codons replaced the native A22 SSGGGG (amino acid residues 1 to 6 of SEQ ID NO: 68) codons. The optimized sequence was synthesized de novo at Celtek Genes, adding restriction endonuclease sites NdeI and BamHI at the N- and C-termini, respectively. The resulting gene (SEQ ID NO: 69) was subcloned into pET30a at those sites.

Recombinant A62 fHBP (SEQ ID NO: 71) was expressed from pLA164 (SEQ ID NO: 72). The A62_002 allele from strain 0167/03 was PCR amplified with primers containing restriction endonuclease sites NdeI and BamHI at the N- and C-termini, respectively. The resulting gene (SEQ ID NO: 72) was subcloned into pET30a at those sites.

Example 16: Expression, Fermentation, and Purification of Subfamily A rP2086 Proteins *E. coli* Expression Strains BLR(DE3) *E. coli* B recA-transformed with pLA164 (SEQ ID NO: 72) was used for expression of A62 (SEQ ID NO: 71). Plasmid pEB042 (SEQ ID NO: 65) was transformed to *E. coli* host BD643 (W3110:DE3 ΔrecA ΔfhuA ΔaraA) to give strain BD660 for expression of A05 (SEQ ID NO: 55). Expression of A22 (SEQ ID NO: 68) was from strain BD592 which consists of plasmid pEB058 (SEQ ID NO: 69) residing in host BD559 (which is also W3110:DE3 ΔrecA ΔfhuA ΔaraA). Lastly, plasmid pEB043 (SEQ ID NO: 67) was transformed to host BD483 (W3110:DE3 ΔrecA) to give strain BD540 for expression of A12 (SEQ ID NO: 66).

Fermentation

Expression strains were fermented in a glucose-based minimal medium. An overnight starter culture was inoculated to ten liter fermentors operated at 37° C., 1 wm aeration with cascade dO control at 20%. When batched glucose was exhausted from the medium (at ~$OD_{600}$=15) a limiting linear glucose feed at 3.8 g/L/hr was initiated. The feed was continued up to induction with 0.1 mM IPTG and through the subsequent protein expression period. For expression of A05 (SEQ ID NO: 55), strain BD660 was induced at $OD_{600}$=25 and fermentation was continued through 7 hours post-induction (HPI). Expression of A22 (SEQ ID NO: 68) and A12 (SEQ ID NO: 66) from strains BD592 and BD540, respectively, was achieved by inducing at $OD_{600}$=40 and fermenting for 24 HPI. At the end of the fermentation, cell pastes were collected by centrifugation.

A62 (SEQ ID NO: 71)

rP2086 proteins are produced as soluble proteins in the cytoplasm of *E. coli* strains. The soluble cytoplasmic extract is typically obtained by thawing frozen cells expressing a particular variant of the subfamily A of rP2086 in hypotonic buffer (10 mM Hepes-NaOH pH 7.4 containing protease inhibitors) and disrupting the cells in a Microfluidizer under ~20,000 psi. RNase and DNAse are added to digest nucleic acids and the cytoplasmic extract is collected as the supernatant following centrifugation at low speed to remove any unbroken cells and then high speed (>100,000×g) to remove membranes, cell walls and other larger subcellular components. The cytoplasmic extract is further clarified by sequential adjustments to 25% then 50% saturated ammonium sulfate and removal of precipitated material after each adjustment by low speed centrifugation. Low molecular weight ionic cell components are then removed by adsorbing the rP2086 in 50% ammonium saturated sulfate in a buffer of 10 mM Hepes-NaOH pH7.4, 1 mM $Na_2EDTA$ to a hydrophobic interaction column (phenyl sepharose purchased from GE Healthcare) then eluting the rP2086 by linearly decreasing the ammonium sulfate concentration to 0% with a buffer of 10 mM Hepes-NaOH pH7.4, 1 mM $Na_2EDTA$. The majority of the negatively charged proteins are then removed by adjusting the rP2086 containing fractions to a buffer of 10 mM Tris-HCl, pH 8.6, 1 mM Na2EDTA passage of the pooled fractions over an anion exchange column (TMAE purchased from EMD) equilibrated with the same buffer. The rP2086 is then further purified by chromatography on ceramic hydroxyapatite (obtained from BioRad) by exchanging the buffer containing the rP2086 to 10 mM Hepes-NaOH, pH7.4 containing 1 mM sodium phosphate adsorbing the protein to the ceramic hydroxyapatite then eluting with a linear gradient of sodium phosphate to 250 mM at pH 7.4. The unit operations listed above are often sufficient to yield purified rP2086 subfamily A members. However, since the expression level can vary over 10-fold, when the rP2086 is expressed at the lower end of the range or when ultra pure rP2086 is need (at high concentrations for NMR structural determinations) the following additional unit operations are added: chromatofocusing followed by ceramic hydroxyapatite chromatography. The buffer containing rP2086 protein from the earlier hydroxyapatite step is exchanged to 25 mM Tris-acetate, pH8.3 and the protein is adsorbed to a chromatofocusing PBE94 column (obtained from GE Healthcare) equilibrated with the same buffer and then eluted with a buffer of polybuffer 94-acetate, pH 6. The rP2086 proteins will elute at their ~pl and the fractions containing the protein are pooled. The buffer of the rP2086 containing fractions is then exchanged to 10 mM Hepes-NaOH pH7.4 containing 1 mM sodium phosphate and adsorbed and eluted as above. The rP2086 subfamily A members prepared by this process are typically >95% homogeneous by SDS-PAGE analysis and most often >99% homogeneous.

A05, A12 and A22 (SEQ ID NOs: 55, 66, and 68, Respectively)

At the end of fermentation, the cell slurry is recovered by continuous centrifugation and re-suspended to ~¼ the original fermentation volume in 20 mM Tris, 5 mM EDTA, pH 6.0. Lysis of the cell suspension is achieved by high-pressure homogenization (2 passes, 4000-9000 psi). To the homogenate is added DADMAC to a final concentration of 0.5%. The solution is stirred at 15-25° C. for 60 minutes during which time a heavy precipitate forms. The solution is clarified by continuous centrifugation. The proteins (A05, A12 and A22) are purified using two chromatographic steps followed by a final buffer exchange. The pH of the centrate is adjusted to 5.5 and loaded onto a GigaCap-S column (CEX). The protein binds to the resin and is subsequently eluted using a sodium chloride gradient. To the pool from the CEX column is added sodium citrate to a final concentration of 1.5 M, and the solution is loaded onto a Phenyl-650M column (HIC). The protein binds to the resin and is subsequently eluted using a sodium citrate step gradient. The HIC pool containing purified protein is exchanged into the final drug substance buffer by diafiltration. A 5 kD regenerated cellulose acetate ultrafiltration cassette is utilized. The protein concentration is targeted to 1.5-2.0 mg/mL. The diafiltered retentate is filtered through a 0.2 micron filter prior to filling into the storage bottles. Drug substance is stored at −70° C.

Example 17: Serum Bactericidal Assay

Functional antibody titers were examined by serum bactericidal assay (SBA) against wildtype or engineered *Neisseria meningitidis* serogroup B strains expressing fHBP either with sequences homologous or heterologous to those contained in the vaccine. Serum bactericidal antibodies in rabbits immunized with rP2086 vaccines were determined using SBAs with human complement. Rabbit immune sera was heat-inactivated to remove intrinsic complement activity and subsequently serially diluted two-fold in Dulbecco's PBS with Ca2+ and Mg2+(D-PBS) in a 96-well microtiter plate to test for serum bactericidal activity against *N. meningitidis* strains. For combination studies with engineered strains, sera of interest was mixed in a 1:1 ratio before the serial dilution described above, so the effective concentration of each component was half that when each was tested individually. Bacteria used in the assay were grown in GC media supplemented with Kellogg's supplement (GCK) and monitored by optical density at 650 nm. Bacteria were harvested for use in the assay at a final $OD_{650}$ of 0.50-0.55, diluted in D-PBS and 1000-3000 CFU were added to the assay mixture. Human serum with no detectable bactericidal activity was used as the exogenous complement source. Complement sources were tested for suitability against each individual test strain. For the isogenic strains, a single human serum was identified and qualified for SBAs against all isogenic strains. A complement source was used only if the number of bacteria surviving in controls without added immune sera was >75%. After a 30 minute incubation at 37° C. with 5% $CO_2$ and an agitation of 700 rpm on a shaker, D-PBS was added to the reaction mixture and aliquots transferred to microfilter plates prefilled with 50% GCK media for the wild type strains and 100% GCK media for the engineered strains. The microfilter plates were filtered, incubated overnight at 37° C. with 5% $CO_2$ and microcolonies were stained and quantified. The serum bactericidal titers were defined as the interpolated reciprocal serum dilution that yielded a 50% reduction in CFU compared to the CFU in control wells without immune sera. Susceptibility to killing by anti-rP2086 immune sera was established if there was a 4-fold or greater rise in SBA titer for anti-rP2086 immune sera compared to the corresponding pre-immune sera. Sera that were negative against the assay strain at the starting dilution were assigned a titer of one half the limit of detection for the assay.

Example 18: Immunogenicity of Non-Lipidated Variants of rP2086 Sub Family A Proteins White New Zealand female rabbits (2.5-3.5 kg) obtained from Charles River (Canada) were used in two studies. For the first study, groups of 3 rabbits were immunized with either 30 mcg or 3 mcg each of either a lipidated A05 or a non-lipidated A05 fHBP formulation. For the second study, five rabbits/group were immunized intramuscularly at the right hind leg with rP2086A variants at 20 μg/mL adjuvanted with 500 μg/mL of AlPO4 (0.5 ml/dose/two sites). Animals were vaccinated at weeks 0, 4 and 9, bled at weeks 0 and 6 and exsanguinated at week 10. LP2086 specific bactericidal antibody titers were determined at weeks 0, 6 and 10.

The goal of these studies was to mimic the reduced responses that are observed for immunologically naïve populations such as infants. First we compared a low and high dosage (30 vs 3 mcg per antigen per dose) of vaccines containing either lipidated A05 (SEQ ID NO: 13) or non-lipidated A05 (SEQ ID NO: 55) (Tables 15 A and 15B). Low dosages were used so that differences in the response rate could be discerned between each vaccine. SBA analysis was conducted using two strain sets. The first set consisted of wildtype strains that had caused invasive disease. The second was a genetically engineered strain set that had the same strain background and differed only by the sequence of the fHBP being expressed as follows: the *N. menigitidis* strain PMB3556, which expresses a B24 variant of fHBP, was engineered such that its endogenous fhbp gene was replaced with genes encoding for other fHBP variants. The constructs were designed such that only the region encoding the ORF was "switched" and the surrounding genetic background was left intact. SBA analysis using this strain set therefore allowed for evaluation of reactivity against different subfamily A fHBP proteins expressed at the same level and in the same genetic background using one source of human complement. All strains had fHBP expression levels that were above the threshold identified by Jiang et al (2010). As shown in Tables 15A and 15B, both the high and low dose levels of the lipidated A05-containing vaccine elicited broad protection across the genetically diverse subfamily A variants, whereas reduced responses were observed at both doses for the vaccine containing the non-lipidated A05 variant. This side-by-side comparison therefore revealed that, although the non-lipidated A05 variant is cross protective across subfamily A expressing strains, it is not as immunogenic as the lipidated variant which is more likely to form a native configuration (Tables 15A and 15B).

For the subsequent study, the dose level was raised to 10 mcg per non-lipidated subfamily A variant to assess each for its potential to provide broad coverage against subfamily A strains. SBA analysis reveal that at this raised dose level sera from rabbits immunized with non-lipidated A05 (SEQ ID NO: 55), A62 (SEQ ID NO: 71), A12 (SEQ ID NO: 66) and A22 (SEQ ID NO: 68) fHBP variants all induced titers to wildtype strains expressing both homologous and heterologous subfamily A variants, indicating that all were cross-protective at this low dose within subfamily A. Therefore we observed that the N2C1 vaccine (A05) could generate antibodies that could kill the N1C2 (A22) and N2C2 (A12) variant strains and likewise vaccines from these other groups could kill strains with opposing variants. Under these conditions, it was observed that the A05 and A62 variants induced the highest SBA responder rates across strains (Table 16). Accordingly, this shows a protective effect across these variants.

TABLE 15A

Lipidated A05 formulation

Geometric Mean SBA Titers
Lipidated A05 formulation

|  |  |  | 30 mcg dose | | | 3 mcg dose | | |
| --- | --- | --- | --- | --- | --- | --- | --- | --- |
|  | fHBP variant | strain name | pre | PD3 | ≥4xrise | pre | PD3 | ≥4xrise |
| Wildtype | A05 | PMB1745 | 2 | 697 | 3 | 2 | 382 | 3 |
| strains | A12 | PMB258 | 5 | 406 | 3 | 2 | 99 | 3 |
|  | A22 | PMB3570 | 2 | 956 | 3 | 3 | 185 | 3 |
|  | A62 | PMB3037 | 2 | 959 | 3 | 2 | 50 | 3 |
| Isogenic | A05 | RD3040-A05 | 102 | 3424 | 3 | 38 | 583 | 3 |
| strains | A12 | RD3044-A12 | 15 | 1233 | 3 | 8 | 183 | 3 |
|  | A22 | RD3042-A22 | 24 | 3289 | 3 | 6 | 582 | 3 |
|  | A29 | RD3043-A29 | 63 | 4086 | 3 | 19 | 1359 | 3 |

TABLE 15B

Non-lipidated A05 formulation

Geometric Mean SBA Titers
Non-lipidated A05 formulation

|  |  |  | 30 mcg dose | | | 3 mcg dose | | |
| --- | --- | --- | --- | --- | --- | --- | --- | --- |
|  | fHBP variant | strain name | pre | PD3 | ≥4xrise | pre | PD3 | ≥4xrise |
| Wildtype | A05 | PMB1745 | 2 | 1182 | 3 | 2 | 281 | 3 |
| strains | A12 | PMB258 | 5 | 31 | 2 | 6 | 23 | 1 |
|  | A22 | PMB3570 | 2 | 76 | 3 | 2 | 11 | 2 |
|  | A62 | PMB3037 | 2 | 35 | 2 | 2 | 2 | 0 |
| Isogenic | A05 | RD3040-A05 | 95 | 258 | 0 | 78 | 134 | 1 |
| strains | A12 | RD3044-A12 | 34 | 228 | 2 | 50 | 105 | 1 |
|  | A22 | RD3042-A22 | 24 | 221 | 2 | 23 | 85 | 1 |
|  | A29 | RD3043-A29 | 36 | 326 | 3 | 52 | 267 | 2 |

Tables 15A and 15B.

Geometric Mean SBA Titers against *N. meningitidis* group B strains of sera taken pre and post (PD3=10 weeks) cross-reactivity activity extends to subfamily B proteins. A62 appears to be composed of both subfamily A (A22) and subfamily B (B09) domains (FIG. 9).

TABLE 17

Isogenic "switched" strains were engineered from the parental *N. meningitidis* strain (PMB3556) such that the entire ORF of its endogenous fHBP (a B24 variant) was replaced with either A05 (SEQ ID NO: 13), A22 (SEQ ID NO: 15), A29 (SEQ ID NO: 74) or A12 (SEQ ID NO: 14) variants. KA3011 is a negative control strain (i.e. the parental PMB3556 whose fhbp gene has been deleted). The Geometric Mean SBA Titers (n = 5) of sera (taken before or 10 weeks after immunization of rabbits with three doses of 10 mcg non-lipidated A subfamily fHBP variants) against these strains is shown in the upper panel. The percentage of responders demonstrating at least a 4-fold rise in response over background is shown in the lower panel.

| | Geometric Mean SBA Titers vs. Isogenic Strain Set | | | | | | | | | | |
|---|---|---|---|---|---|---|---|---|---|---|---|
| | RD3040-A05 | | RD3042-A22 | | RD3043-A29 | | RD3044-A12 | | PMB3556 (B24 parent) | | KA3011 |
| Vaccine | pre | PD3 | pre | PD3 | pre | PD3 | pre | PD3 | pre | PD3 | pre | PD3 |
| A62 | 17 | 36 | 31 | 69 | 4 | 95 | 23 | 45 | 44 | 109 | 4 | 2 |
| A05 | 7 | 67 | 5 | 64 | 20 | 132 | 16 | 58 | 34 | 40 | 3 | 2 |
| A12 | 12 | 40 | 8 | 34 | 3 | 40 | 25 | 149 | 27 | 46 | 3 | 2 |
| A22 | 9 | 46 | 13 | 36 | 5 | 30 | 13 | 38 | 28 | 34 | 4 | 2 |

| | Percent of Responders (≥4-fold rise) | | | | | |
|---|---|---|---|---|---|---|
| Vaccine | RD3040-A05 | RD3042-A22 | RD3043-A29 | RD3044-A12 | PMB3556 | KA3011 |
| A62 | 40 | 80 | 100 | 40 | 40 | 0 |
| A05 | 80 | 80 | 60 | 40 | 0 | 0 |
| A12 | 40 | 40 | 60 | 60 | 20 | 0 |
| A22 | 80 | 40 | 60 | 60 | 20 | 0 | immunization of rabbits (n=3) with either 30 or 3 mcg vaccines containing lipidated or non-lipidated A05. The upper panels (labeled "wildtype strains") of Tables 15A and 15B summarizes activity against clinical isolates. The lower panels (labeled "isogenic strains") of Tables 15 A and 15B summarizes activity against a set of isogenic strains which were engineered from the parental *N. meningitidis* strain (PMB3556) such that the entire ORF of its endogenous fHBP was replaced with either A05 (SEQ ID NO: 13), A22 (SEQ ID NO: 15), A29 (SEQ ID NO: 74) or A12 (SEQ ID NO: 14) variants.

TABLE 16

The percentage of responders demonstrating at least 4-fold rise in SBA GMT levels over background from 10 week sera taken from rabbits immunized with 10 mcg of non-lipidated A subfamily fHBP variants against strains expressing A05, A62, A12 or A22 fHBP variants.

| | Percent of Responders with > 4 fold rise | | | | |
|---|---|---|---|---|---|
| vaccine | A05 | A62 | A12 | A22 | average |
| A62 | 100 | 100 | 60 | 60 | 80 |
| A05 | 80 | 80 | 60 | 80 | 75 |
| A12 | 60 | 80 | 60 | 60 | 65 |
| A22 | 60 | 60 | 40 | 40 | 50 |

Cross-protection was also observed for all variants using the isogenic strain set described above at the increased dose of 10 mcg, with sera from rabbits immunized with the A62 variant (SEQ ID NO: 71) demonstrating the most cross-reactivity, followed by A05 anti-sera (Table 17). In addition, sera from rabbits immunized with the A62 variant (SEQ ID NO: 71) showed reactivity to both the parental PMB3556 strain and the B09 switched strain (Table 18), indicating that

TABLE 18

The Geometric Mean SBA Titers of sera (taken before or 10 weeks after immunization of rabbits (n = 5) with 10 mcg non-lipidated subfamily A proteins (A62 (SEQ ID NO: 71); A05 (SEQ ID NO: 55); A12 (SEQ ID NO: 66); A22 (SEQ ID NO: 68)) against two subfamily B isogenic strains.

| | Geometric mean SBA titers against isogenic subfamily B strains | | | | | |
|---|---|---|---|---|---|---|
| | PMB3556 (parent) | | | RD30337-B09 | | |
| Vaccine | pre | PD3 | % responders (>4-fold rise) | pre | PD3 | % responders (>4-fold rise) |
| A62 | 44 | 109 | 60 | 31 | 163 | 60 |
| A05 | 34 | 40 | 0 | 32 | 28 | 0 |
| A12 | 27 | 46 | 20 | 19 | 23 | 20 |
| A22 | 28 | 34 | 0 | 29 | 30 | 0 |

Example 19: Evaluation of the Effect of Combining Sera Raised Against Non-Lipidated Subfamily A Proteins on SBA Combinations of serum were assessed to evaluate the effect on the breath of coverage. Paired pre vs post vaccination serum were tested to confirm that there was no non-specific killing induced as a result of combining the serum. The GM fold rise was calculated for the individual sera and for the combinations of serum across the 4 isogenic strains that represented diversity within subfamily A. Fold rise increases were detected for some of the combinations tested providing evidence that the breadth of coverage can be increased by including more subfamily A variants (Table 19). Optimal combinations appear to be A05 (SEQ ID NO: 55) with A62 (SEQ ID NO: 71) or A62 (SEQ ID NO: 71) with A12 (SEQ ID NO: 66) (Table 20).

TABLE 19

SBA Titers of sera from the highest responders of each vaccine group were retested against the isogenic strain set as shown in Table 17. Sera was tested in one to one mixtures to determine the extent of synergistic activity.

| | BC50 titer | | | | | | | | |
|---|---|---|---|---|---|---|---|---|---|
| | A05 AQ508-5 | | | A12 AQ509-4 | | | A62 AQ507-5 | | |
| Strain | Wk0 | Wk10 | Fold rise | Wk0 | Wk10 | Fold rise | Wk0 | Wk10 | Fold rise |
| RD3040-A05 | 2 | 98 | 49 | 2 | 65 | 33 | 3 | 14 | 5 |
| RD3042-A22 | 2 | 116 | 58 | 2 | 94 | 47 | 2 | 81 | 40 |
| RD3043-A29 | 3 | 368 | 123 | 2 | 198 | 99 | 5 | 54 | 11 |
| RD3044-A12 | 2 | 37 | 19 | 3 | 486 | 162 | 3 | 45 | 15 |
| GM fold rise | | | 50 | | | 70 | | | 13 |
| KA3011 | 2 | 2 | 1 | 2 | 2 | 1 | 9 | 5 | 1 |

| | BC50 titer | | | | | | | | |
|---|---|---|---|---|---|---|---|---|---|
| | A05 + A12 AQ508-5 + AQ509-4 | | | A05 + A62 AQ508-5 + AQ507-5 | | | A12 + A62 AQ509-4 + AQ507-5 | | |
| Strain | Wk0 | Wk10 | Fold rise | Wk0 | Wk10 | Fold rise | Wk0 | Wk10 | Fold rise |
| RD3040-A05 | 7 | 170 | 24 | 8 | 107 | 13 | 2 | 97 | 49 |
| RD3042-A22 | 6 | 3418 | 570 | 6 | 160 | 27 | 2 | 181 | 91 |
| RD3043-A29 | 2 | 509 | 255 | 7 | 1181 | 169 | 6 | 478 | 80 |
| RD3044-A12 | 8 | 335 | 42 | 5 | 1302 | 260 | 7 | 3707 | 530 |
| GM fold rise | | | 110 | | | 63 | | | 117 |
| KA3011 | 13 | 2 | 0 | 2 | 5 | 3 | 7 | 5 | 1 |

TABLE 20

The fold rise increase for sera tested in combination as compared to each tested alone (calculated from Table 19).

| | Fold Rise Increase for Combination Vaccine vs Monovalent | | |
|---|---|---|---|
| Combination | A05 | A12 | A62 |
| A05 (SEQ ID NO: 55) + A12 (SEQ ID NO: 66) | 2.2 | 1.6 | |
| A05 (SEQ ID NO: 55) + A62 (SEQ ID NO: 71) | 1.3 | | 4.8 |
| A12 (SEQ ID NO: 66) + A62 (SEQ ID NO: 71) | | 1.7 | 8.9 |

The results presented above in Examples 18-19 show that non-lipidated subfamily A proteins are immunogenic and may provide protection against infection with *N. meningitidis* strains bearing either homologous or heterologous variants. The data presented here illustrates that selected non-lipidated subfamily A variants retain immunogenicity and provide cross-protection against heterologous strains, though these responses are lower than the lipidated variants. We also demonstrate that the A62 (SEQ ID NO: 71) rP2086 antigen, having sequence similarity to subfamily B (see, for example, FIG. 9), may protect across the subfamilies because the A62 (SEQ ID NO: 71) vaccine may kill strains expressing subfamily B variants B09 or B24).

The data presented above shows that not only are non-lipidated subfamily A variants capable of the type of synergy observed with combinations of lipidated fHBP, but also that they may provide coverage against B subfamily variants.

Example 20: Evaluation of Immunogenicity of the Combination of Factor H Binding Proteins and Tetravalent Meningococcal Conjugate Vaccine in New Zealand White Rabbits The study was carried out in New Zealand White rabbits in the 2.5-3.5 kg range obtained from Charles River, Canada (Table 21). Prior to entering the study, 55 rabbits were pre-screened for existing antibodies using whole cell ELISAs against strains A05 and B02. After the screening, the rabbits with relatively low antibody titers (specific IgG titers <350) were vaccinated intramuscularly at the hind legs, 0.5 mL per site (1.0 mL per dose, see Table 22) at weeks 0, 4, and 9. There were three rabbits per group. Rabbits were bled at weeks 0, 4, 6, 9, and exsanguinated at week 10. Serum samples were prepared and week 0 and 10 serum samples were analyzed by SBA. The meningococcal conjugate vaccine (MENVEO®, meningococcal (Groups A, C, Y and W-135) oligosaccharide diphtheria $CRM_{197}$ conjugate vaccine, Novartis), bivalent rLP2086 and tetravalent non-lipidated variants and their combinations were prepared according to Tables 23-26.

TABLE 21

| Rabbits Used in This Study | |
|---|---|
| Species: | Rabbit |
| Strain: | New Zealand white |
| Source:[a] | Charles River Laboratory |
| No. of Animals Per Group: | 3 |
| Total No. of Animals: | 30 |
| Age and Sex: | Male |
| Weight: | 2.5-3.5 kg |

[a]Rabbits were maintained in accordance with the established Institutional Animal Care and Use Committee guidelines.

The design of the study is shown in Table 22.

TABLE 22

Experimental Design

| Group | # of Rabbit | Immunogen | Adjuvant | Vax (wk) | Serum Prep |
|---|---|---|---|---|---|
| 1 | 3 | 1 Human Dosage MENVEO/dose 1.0 mL/2 sites | None | 0, 4, 9 | Wk 0, 4, 6, 9 Exsang: Wk 10 |
| 2 | 3 | 1:10 Human Dosage MENVEO/dose 1.0 mL/2 sites | None | 0, 4, 9 | Wk 0, 4, 6, 9 Exsang: Wk 10 |
| 3 | 3 | 1 Human Dosage MENVEO + 30 µg rLP2086-A (A05 (SEQ ID NO: 13)) + 30 µg rLP2086-B (B01 (SEQ ID NO: 58))/dose 1.0 mL/2 sites | AlPO$_4$ 250 µg/dose/1.0 mL | 0, 4, 9 | Wk 0, 4, 6, 9 Exsang: Wk 10 |
| 4 | 3 | 1:10 Human Dosage MENVEO + 3 µg rLP2086-A (A05 (SEQ ID NO: 13)) + 3 µg rLP2086-B (B01 (SEQ ID NO: 58))/dose 1.0 mL/2 sites | AlPO$_4$ 250 µg/dose/1.0 mL | 0, 4, 9 | Wk 0, 4, 6, 9 Exsang: Wk 10 |
| 5 | 3 | 30 µg rLP2086-A (A05 (SEQ ID NO: 13)) + 30 µg rLP2086-B (B01 (SEQ ID NO: 58)/dose 1.0 mL/2 sites | AlPO$_4$ 250 µg/dose/1.0 mL | 0, 4, 9 | Wk 0, 4, 6, 9 Exsang: Wk 10 |
| 6 | 3 | 3 µg rLP2086-A (A05 (SEQ ID NO: 13)) + 3 µg rLP2086-B (B01 (SEQ ID NO: 58)/dose 1.0 mL/2 sites | AlPO$_4$ 250 µg/dose/1.0 mL | 0, 4, 9 | Wk 0, 4, 6, 9 Exsang: Wk 10 |
| 7 | 3 | Non-Lipidated rP2086-A05 (SEQ ID NO: 55), B09 (SEQ ID NO: 49), B22 (SEQ ID NO: 75), and B44 (SEQ ID NO: 44), 30 µg each/dose 1.0 mL/2 sites | AlPO$_4$ 250 µg/dose/1.0 mL | 0, 4, 9 | Wk 0, 4, 6, 9 Exsang: Wk 10 |
| 8 | 3 | Non-Lipidated rP2086-A05, B09, B22, and B44, 3 µg each/dose 1.0 mL/2 sites | AlPO$_4$ 250 µg/dose/1.0 mL | 0, 4, 9 | Wk 0, 4, 6, 9 Exsang: Wk 10 |
| 9 | 3 | 1 Human Dosage MENVEO + Non-Lipidated rP2086-A05, B09, B22, and B44, 30 µg each/dose 1.0 mL/2 sites | AlPO$_4$ 250 µg/dose/1.0 mL | 0, 4, 9 | Wk 0, 4, 6, 9 Exsang: Wk 10 |
| 10 | 3 | 1:10 Human Dosage of MENVEO + Non-Lipidated rP2086-A05, B09, B22, and B44, 3 µg each/dose 1.0 mL/2 sites | AlPO$_4$ 250 µg/dose/1.0 mL | 0, 4, 9 | Wk 0, 4, 6, 9 Exsang: Wk 10 |

Summary of Formulations

TABLE 23

Formulations for Immunization

| Material | Function | Formulation | Presentation/ Appearance | Amount Provided for 3 doses |
|---|---|---|---|---|
| MENVEO ® meningococcal (Groups A, C, Y and W-135) | Active | Novartis product contains Meningococccal groups A, C, Y and | Lyo A: White, fluffy cake Liquid C, Y, W-135: Clear, | 3 × 15 doses |

TABLE 23-continued

Formulations for Immunization

| Material | Function | Formulation | Presentation/ Appearance | Amount Provided for 3 doses |
|---|---|---|---|---|
| oligosaccharide diphtheria $CRM_{197}$ conjugate vaccine, Novartis | | W-135 | colorless solution | |
| rLP2086-A (A05 (SEQ ID NO: 13)), rLP2086-B (B01 (SEQ ID NO: 58)) | Active | rLP2086 subfamily A and B at 120 µg/mL per protein in Histidine pH 6.0, appox 0.005% PS80 with 0.5 mg/mL Al of $AlPO_4$ | White to off white homogeneous cloudy suspension | 3 × 15 syringes (0.57 mL fill volume) |
| L44857-50 MnB tetravalent non-lipidated | Active | A05 (SEQ ID NO: 55), B44 (SEQ ID NO: 44), B22 (SEQ ID NO: 75), and B09 (SEQ ID NO: 49) at 0.6 mg/mL formulated in 10 mM Histidine buffer, pH 6.5 with 0.01% PS80, 4.5% Trehalose, and WFI | Lyophilized; white fluffy cake | 3 × 15 vials (0.7 mL recon volume) |
| $AlPO_4$ | Adjuvant | $AlPO_4$, 60 mM NaCl, WFI | White to off white homogeneous cloudy suspension | 30 mL 0.5 mg/mL in 3 glass vials 30 mL 0.25 mg/mL in 3 glass vials |
| 60 mM Saline | Diluent | NA | Clear, colorless solution | 3 × 20 vials (1.0 mL fill volume) |

35

TABLE 24

Excipients and Container/Closure Information

| Formulation | Lot # | Source | Excipients |
|---|---|---|---|
| MENVEO ® | MenCYW-135 Liquid Conjugate Component (091101) MenA Lyophilized Conjugate Component (029011) | Novartis | The vaccine contains no preservative or adjuvant. Each dose of vaccine contains 10 µg MenA oligosaccharide, 5 µg of each of MenC, MenY and MenW135 oligosaccharides and 32.7 to 64.1 µg $CRM_{197}$ protein. Residual formaldehyde per dose is estimated to be not more than 0.30 µg. (Unknown previously). |
| rLP2086-A (A05 (SEQ ID NO: 13)), rLP2086-B (B01 (SEQ ID NO: 58)) | 962-UPD-09-007 v1.0 | CSMD, Pfizer Pearl River, NY | Histidine pH 6.0, appox 0.005% PS80, 0.5 mg/mL Al of $AlPO_4$ |
| MnB non-lipidated tetravalent L44857-50 | rPA05 (SEQ ID NO: 55) (L35408-140), rPB44 (SEQ ID NO: 44) (L37024-36A), rPB22 (SEQ ID NO: 75) (L37024-61), rPB09 (SEQ ID NO: 49)(L43930-80) | Formulation Development, Pearl River, NY | Histidine buffer, pH 6.5 (L44130-129), Polysorbate 80 (L44130-127), Trehalose (L44863-68), WFI (B\|Braun J0A012) |
| $AlPO_4$ | 0.5 mg/mL: L44863-86A 0.25 mg/mL: L44863-86B | Pfizer Pearl River, NY | $AlPO_4$ bulk H000000606-D86864M 0.9% saline (B/Broun |

TABLE 24-continued

Excipients and Container/Closure Information

| Formulation | Lot # | Source | Excipients |
|---|---|---|---|
| | | | J0A017), WFI (B/Broun J0A012) |
| 60 mM Saline | 962-UPD-10-004 | CSMD, Pfizer Pearl River, NY | N/A |

Contain/Closure for MnB Tetravalent:
Vials: 2 mL type-1 glass, West Pharmaceuticals
Stoppers: 13 mm vial stoppers for lyophilization, gray butyl, coated with Flurotec (WPS V2-F451W 4432/50 Gray B2-TR Westar ® RU Verisure Ready-Pack), West Pharmaceuticals
Contain/Closure for 60 mM Saline:
Vials: 2 mL type-1 glass, Schott (Vendor Part #: 8M002PD-CS)
Stoppers: 13 mm Daikyo D777-1, S2-F451, B2-40 Westar RS West, (Vendor Part #: 19560180)
Container/Closure for AlPO$_4$ Solutions:
Vials: Sterile Empty Vials, Size 30 mL-20 mm, Stoppers included, Allergy Laboratories, Lot # SEV070708A

TABLE 25

DATA ANALYSIS
Table 25: Analytical Tests of MnB non-lipidated Tetra-Antigen Lot L44857-50

| Test | Target B22, B09, A05, B44 (µg/mL) | B22 Concentration (µg/mL) | B09 Concentration (µg/mL) | A05 Concentration (µg/mL) | B44 Concentration (µg/mL) |
|---|---|---|---|---|---|
| IEX-HPLC | 60/60/60/60 | 59.7 | 61.9 | 64.1 | 63.0 |
| pH | 6.5 | | 6.52 | | |
| Appearance | Clear, colorless solution | Lyo: White, fluffy cake. Reconstitution (w/ 60 mM NaCl): Clear, colorless solution | | | |
| Moisture | <3% | | 0.60% | | |

Lyophilized formulation was reconstitituted with Mobile Phase A during quantitation of B22, B09, A05, and B44 by IEX-HPLC, and with 60 mM NaCl diluent for pH and appearance.
Karl-Fischer (ICH) method was used to measure moisture (using methanol to reconstitute lyophilized formulations).

TABLE 26 pH and Appearance of AlPO$_4$ Solutions

| Sample | Lot # | pH | Appearance |
|---|---|---|---|
| AlPO$_4$ @ 0.5 mg/mL | L44863-86A | 5.95 | Cloudy, white to off white suspension |
| AlPO$_4$ @ 0.25 mg/mL | L44863-86B | 5.91 | Cloudy, white to off white suspension |

The non-lipidated tetravalent protein (B22, B09, A05 and B44) were monitored for stability for 6 hours at 2-8° C. upon combination with MENVEO®.

Example 21: Serum Bactericidal Assay (SBA)

A microcolony-based serum bactericidal assay (SBA) against multiple serogroup B, C and Y meningococcal strains (Table 27) was performed on individual serum samples. Human sera from donors were qualified as the complement source for the strain tested in the assay. Complement-mediated antibody-dependent bactericidal titers were interpolated and expressed as the reciprocal of the dilution of the test serum that killed 50% of the meningococcal cells in the assay. The limit of detection of the assay was an SBA titer of 4. An SBA titer of <4 was assigned number of 2. A 4-fold rise of SBA titers in the week 10 sera in comparison to the titers in the pre-bleed was calculated and compared.

TABLE 27

SBA Strains

| Serogroup | fHBP Variant | Strain name |
|---|---|---|
| B | A05 | PMB1745 |
| B | B02 | PMB17 |
| B | B09 | PMB1489 |
| B | B16 | PMB2882 |
| B | B44 | PMB147 |
| C | A68 | PMB2432 |
| C | B24 | PMB2240 |
| Y | A121 | PMB3386 |
| Y | B09 | PMB3210 |

Example 22: Immunogenicity of the Combination of Lipidated or Non-Lipidated Factor H Binding Proteins and the Conjugated Vaccine in New Zealand White Rabbits Serum bactericidal antibody is the immunologic surrogate of protection against meningococcal disease. Whether immunization with lipidated, non-lipidated rfHBP, tetravalent conjugate vaccines alone or in combination elicited bactericidal antibodies in rabbits was determined by SBA. SBA measures the level of antibodies in a serum sample by mimicking the complement-mediated bacterial lysis that occurs naturally. In humans a SBA titer of 1:4 is considered the protective; a four fold rise in titer, pre vs post immunization also considered to be an immunologically relevant immune response. Rabbit serum samples collected from weeks 0 and 10 were analyzed by SBA against strains of several meningococcal serogroups. As shown in Table 28 (higher dose) and 29 (lower dose), one week after the third immunization (week 10), the tetravalent conjugate vaccines only elicited SBA responses against MnC and MnY strains tested. All other serum samples displayed bactericidal activity against the homologous strains as well as other test strains from the same fHBP subfamily as in the vaccine formulations. It is noted that immunization with lipidated A05/B01 (SEQ ID NOs: 13 and 58, respectively) alone at 30 mcg dose each elicited the highest bactericidal antibodies against the homologous strains as well as against other tested strains from both fHBP subfamilies (Table 28). Similarly, immunization with non-lipidated A05/B09/B22/B44 (SEQ ID NOs: 55, 49, 75, and 44, respectively) alone also elicited bactericidal antibodies against strains of several meningococcal serogroups, even though the SBA titers were 3 to 15-folder lower than the lipidated bivalent vaccine (Table 30). A 100% responder rate (≥4-folder rise in an SBA titer) was achieved against all strains of various sergroups for lipidated fHBP, high dose of non-lipidated fHBP and all the combinations.

TABLE 28

Fold rise increase in SBA titers against meningococcus serogroup B, C and Y strains using sera from rabbits immunized with a higher dose combination of fHBPs and conjugate vaccine

| | | Fold Rise in PD3 SBA Titers | | | | | | | | |
|---|---|---|---|---|---|---|---|---|---|---|
| | | MnB strains | | | | | MnC strains | | MnY strains | |
| VACCINE | Dose | A05 | B02 | B09 | B16 | B44 | A68 | B24 | A121 | B09 |
| MENVEO | 1 hu dose | 1 | 2 | 1 | 1 | 1 | 244 | 53 | 708 | 226 |
| MENVEO/ lipidated A05/B01 | 1 hu dose, proteins: 30 mcg each | 349 | 871 | 279 | 806 | 2048 | 1592 | 401 | 1037 | 894 |
| Lipidated A05/B01 | 30 mcg each | 591 | 624 | 745 | 842 | 1955 | 1926 | 344 | 595 | 905 |
| Non-lipidated A05/B09/B22/B44 | 30 mcg each | 39 | 105 | 192 | 300 | 391 | 61 | 137 | 52 | 148 |
| MENVEO/non-lipidated A05/B09/B22/B44 | 1 hu dose, proteins: 30 mcg each | 34 | 98 | 108 | 113 | 178 | 219 | 125 | 299 | 135 |

Rabbits pre-bleed sera showed no pre-existing bactericidal activity against the tested strains. NZW rabbits (n=3) were vaccinated at weeks 0, 4 and 8 with 0.5 mL vaccine, im; data Wk 10

TABLE 29

Fold rise increase in SBA titers against meningococcus serogroup B, C and Y strains using sera from rabbits immunized with a lower dose combination of fHBPs and conjugate vaccine

| | | Fold Rise in PD3 SBA Titers | | | | | | | | |
|---|---|---|---|---|---|---|---|---|---|---|
| | | MnB strains | | | | | MnC strains | | MnY strains | |
| VACCINE | Dose | A05 | B02 | B09 | B16 | B44 | A68 | B24 | A121 | B09 |
| MENVEO | 1:10 hu dose | 1 | 1 | 2 | 1 | 1 | 49 | 24 | 81 | 143 |
| MENVEO/lipidated A05/B01 | 1:10 hu dose, proteins: 3 mcg each | 191 | 140 | 124 | 336 | 926 | 940 | 172 | 560 | 366 |
| Lipidated A05/B01 | 3 mcg each | 142 | 164 | 440 | 246 | 834 | 476 | 162 | 515 | 294 |
| Non-lipidated A05/B09/B22/B44 | 3 mcg each | 6 | 22 | 29 | 22 | 40 | 34 | 39 | 16 | 25 |

TABLE 29-continued

Fold rise increase in SBA titers against meningococcus serogroup B, C and Y strains using sera from rabbits immunized with a lower dose combination of fHBPs and conjugate vaccine

| | | Fold Rise in PD3 SBA Titers | | | | | | | |
|---|---|---|---|---|---|---|---|---|---|
| | | MnB strains | | | | | MnC strains | | MnY strains |
| VACCINE | Dose | A05 | B02 | B09 | B16 | B44 | A68 | B24 | A121 | B09 |
| MENVEO/non-lipidated A05/B09/B22/B44 | 1:10 hu dose, proteins: 3 mcg each | 10 | 52 | 76 | 60 | 158 | 102 | 100 | 122 | |

Rabbits pre-bleed sera showed no pre-existing bactericidal activity against the tested strains. NZW rabbits (n=3) were vaccinated at weeks 0, 4 and 8 with 0.5 mL vaccine, im; data Wk 10

TABLE 30

SBA responder rates against meningococcus serogroup B, C and Y strains using sera from rabbits immunized with a combination of fHBPs and conjugate vaccine

| | | PD3 Responders (≥4 fold rise) | | | | | | | |
|---|---|---|---|---|---|---|---|---|---|
| | | MnB strains | | | | | MnC strains | | MnY strains |
| VACCINE | Dose | A05 | B02 | B09 | B16 | B44 | A68 | B24 | A121 | B09 |
| MENVEO | 1 hu dose | 0 | 0 | 0 | 0 | 0 | 100 | 100 | 100 | 100 |
| MENVEO | 1:10 hu dose | 0 | 0 | 0 | 0 | 0 | 100 | 100 | 100 | 100 |
| MENVEO/lipidated A05/B01 | 1 hu dose, proteins: 30 μg each | 100 | 100 | 100 | 100 | 100 | 100 | 100 | 100 | 100 |
| MENVEO/lipidated A05/B01 | 1:10 hu dose, proteins: 3 μg each | 100 | 100 | 100 | 100 | 100 | 100 | 100 | 100 | 100 |
| Lipidated A05/B01 | 30 μg each | 100 | 100 | 100 | 100 | 100 | 100 | 100 | 100 | 100 |
| Lipidated A05/B01 | 3 μg each | 100 | 100 | 100 | 100 | 100 | 100 | 100 | 100 | 100 |
| Non-lipidated A05/B09/B22/B44 | 30 μg each | 100 | 100 | 100 | 100 | 100 | 100 | 100 | 100 | 100 |
| Non-lipidated A05/B09/B22/B44 | 3 μg each | 67 | 67 | 67 | 67 | 100 | 67 | 100 | 67 | 100 |
| MENVEO/non-lipidated A05/B09/B22/B44 | 1 hu dose, proteins: 30 μg each | 100 | 100 | 100 | 100 | 100 | 100 | 100 | 100 | 100 |
| MENVEO/non-lipidated A05/B09/B22/B44 | 1:10 hu dose, proteins: 3 μg each | 67 | 100 | 100 | 100 | 100 | 100 | 100 | 100 | 100 |

NZQ rabbits (n=3) were vaccinated at weeks 0, 4 and 8 with 0.5 mL vaccine, im; data Wk 10

Lipidated fHBP Elicited Higher SBA Titers than the Non-Lipidated fHBP.

The lipidated fHBP at 30 mcg each per dose elicited 3-15-folder higher SBA titers to all the meningococcal B, C and Y strains tested. The non-lipidated fHBP at 30 mcg each per dose elicited 4-23-folder higher SBA titers to all the meningococcal B, C and Y strains tested (Tables 28-29).

Dose Titration was Achieved with the fHBPs, the Conjugate Vaccine or the Combinations With a higher dose of conjugate vaccine, fHBPs or their combinations increased the SBA responses than with a lower dose (Tables 28-30). The one human dose of the conjugate vaccine elicited 2-8-folder high SBA titers against meningococcal C and Y strains than the one tenth dose of the conjugate vaccine. The lipidated fHBP at 30 mcg each per dose elicited 2-4 folder high SBA titers against all the strains tested than the 3 mcg each per dose. The non-lipidated fHBP at 30 mcg each per dose elicited 4-15-folder high SBA titers against all the meningococcal serogroups B, C and Y strains than the 3 mcg each per dose.

Synergistic SBA Responses by Combination of fHBP and Conjugate Vaccines

There is a trend that the SBA responses are higher against meningococcal serogroups C and Y strains when the combination of conjugate vaccine and fHBP was used than by using either component alone, especially with the addition of a lower dose of lipidated or non-lipidated fHBP (Table 29). In the present study, the functional activity was evaluated against strains of several meningococcal serogroups using sera from New Zealand white rabbits immunized with recombinant lipidated or non-lipidated fHBP in formulation with $AlPO_4$ and the conjugate vaccine alone or in combination. Rabbits receiving the conjugate vaccine elicited SBA responses only against meningococcal serogroup C and Y strains, but not to the serogroup B strains. The lipidated or non-lipidated fHBP in formulation with $AlPO_4$ elicited serum antibodies which were bactericidal against strains of all the meningococcal serogroups tested.

New Zealand white rabbits receiving three doses of the lipidated or non-lipidated fHBP in formulation with $AlPO_4$ elicited serum antibodies which were bactericidal against meningococcal serogroups B, C and Y strains tested. A 100% of responder rate (≥4-folder rise in an SBA titer) was achieved against all the strains tested except the lower dose non-lipidated group.

The lipidated fHBP elicited greater bactericidal antibody titers than the non-lipidated forms. A clear dose response was observed with the lipidated or non-lipidated fHBP and the conjugate vaccine alone or in combinations.

There is a trend of synergistic SBA responses against meningococcal serogroup C and Y strains between the conjugate vaccine and fHBP especially at the addition of lower dose proteins.

Example 23: Evaluation of the Immunogenicity of Combinations of Non-Lipidated Factor H Binding Proteins in New Zealand White Rabbits Studies were carried out in New Zealand White rabbits in the 2.5-3.5 kg range obtained from Charles River, Canada (Table 31). Rabbits were vaccinated intramuscularly at the hind leg, 0.5 mL per site (1.0 mL per dose, see Table 32) at weeks 0, 4 and 9. The Sequence ID Numbers for each of the antigens tested are listed in Table 33. There were 10 rabbits per group. Rabbits were bled at weeks 0, 6 and exsanguinated at week 10. Serum samples were prepared and week 0 and 10 serum samples were analyzed in the SBA against a panel of *N. meningitidis* isolates.

TABLE 31

Rabbits Used in these Studies[a]

| | |
|---|---|
| Species | Rabbit |
| Strain | New Zealand White |
| Source | Charles River Laboratory |
| Number Animals per group | 10 |
| Sex | Female |
| Weight | 2.5-3.5 kg |

[a]Rabbits were maintained in accordance with established Institutional Animal Care and Use Committee guidelines

TABLE 32

Study Design[a]

| # of rabbits | Antigenic composition fHBP Variants | Lipidated | Dose | $AlPO_4$ (0.25 mg/dose) |
|---|---|---|---|---|
| 10 | A62 + B44 | No | 10 mcg each | Yes |
| 10 | A05 + A62 + B44 | No | 10 mcg each | Yes |
| 10 | A05 + A62 + B09 + B44 | No | 10 mcg each | Yes |
| 10 | A05 + A62 + B09 + B44 | No | 5 mcg each | Yes |
| 10 | A05 + A12 + B09 + B44 | No | 5 mcg each | Yes |
| 10 | A12 + A62 + B09 + B44 | No | 5 mcg each | Yes |
| 10 | A05 + A12 + A62 + B09 + B44 | No | 5 mcg each | Yes |
| 10 | A05 + B01 | Yes | 10 mcg each | Yes |

[a]Rabbits were vaccinated intramuscularly (weeks 0, 4 and 9) and bled (weeks 0, 6 and 10) to prepare serum samples for SBA analysis

TABLE 33

*N. meningitidis* Serogroup B fHBP Protein Variants Used

| | |
|---|---|
| rP2086-A05 | SEQ ID NO: 13, wherein the Cys at position 1 is deleted, or SEQ ID NO: 55, e.g., encoded by SEQ ID NO: 54 |
| rP2086-A12 | SEQ ID NO: 14, wherein the Cys at position 1 is deleted, or SEQ ID NO: 66, e.g., encoded by SEQ ID NO: 67 |
| rP2086-A62 | SEQ ID NO: 70, wherein the Cys at position 1 is deleted, or SEQ ID NO: 71, e.g., encoded by SEQ ID NO: 72 |
| rP2086-B09 | SEQ ID NO: 18, wherein the Cys at position 1 is deleted, or SEQ ID NO: 49 |
| rLP2086-B44 | SEQ ID NO: 21, wherein the Cys at position 1 is deleted, or SEQ ID NO: 44, e.g., encoded by SEQ ID NO: 43 |
| rLP2086-A05 | SEQ ID NO: 76 |
| rLP2086-B01 | SEQ ID NO: 58 |

Table 34 summarizes the immune response in rabbits to mixtures of non-lipidated fHBP proteins compared to the immune response to the rLP2086-A05 and rLP2086-601 pair of lipidated antigens. Rabbit pre-bleed sera generally showed no pre-existing bactericidal activity against the tested strains. The immune response is presented as the percent of animals in each treatment group that respond to the respective combinations of fHBP antigens following the third immunization with an increase in SBA titer of ≥4 fold. The SBA assay was performed using target *N. meningitidis* strains that either express fHBP variants identical to the vaccine immunogen (A05, A12), or strains that express heterologous fHBP variants (A22, B16, B24). The comparative amino acid sequence identity of the A22 fHBP variant diverges up to 15% from the subfamily A variants tested. Similarly, the comparative amino acid sequence identity of the B16 and B24 fHBP variants diverges up to 12% from the subfamily B variants included as antigens.

TABLE 34

Percent of New Zealand White Rabbits Vaccinated with Recombinant Non-lipidated fHBPs that Respond With a ≥4 Fold Rise in SBA Titers Post-Dose Three

| Immunogen[a] | Lipidated | Dose per antigen (mcg/0.5 mL) | % Responders at PD3 with ≥4X rise SBA Titers | | | | |
|---|---|---|---|---|---|---|---|
| | | | A05 | A12 | A22 | B16 | B24 |
| A62 + B44 | No | 10 | nd | 50 | 100 | 100 | 50 |
| A05 + A62 + B44 | No | 10 | nd | 40 | 80 | 80 | 60 |
| A05 + A62 + B09 + B44 | No | 10 | nd | 60 | 100 | 100 | 100 |
| A05 + A62 + B09 + B44 | No | 5 | nd | 40 | 40 | 100 | 70 |
| A05 + A12 + B09 + B44 | No | 5 | 60 | 40 | 60 | 60 | 60 |
| A12 + A62 + B09 + B44 | No | 5 | 100 | 70 | 100 | 100 | 70 |
| A05 + A12 + A62 + B09 + B44 | No | 5 | 100 | 100 | 100 | 100 | 60 |
| A05 + B01 | Yes | 10 | nd | 80 | 90 | 100 | 90 |

[a]10 animals per treatment group; all treatments formulated with AlPO$_4$ adjuvant (250 mcg/dose)

In those groups of rabbits immunized with 10 mcg of each test rP2086 variant, serum samples from animals treated with the combination of A05+A62+B09+B44 had the highest bactericidal response rate. The SBA response was somewhat reduced in animals treated with only 5 mcg each of the same mixture of four non-lipidated fHBP variants. Other 4-valent groups of fHBP antigens dosed at 5 mcg did as well as the combination of non-lipidated A05+A62+B09+B44. Of the 4-valent combinations tested, serum samples from the treatment group that included 5 mcg each of non-lipidated fHBP variants A12+A62+B09+B44 had the best SBA response rates for the selected assay strains. The response rate to the pentavalent non-lipidated combination of A05+A12+A62+B09+B44 is somewhat better than the response to any of the 4-valent combinations tested.

---

What is claimed is:

1. A method of eliciting an immune response against Neisseria meningitidis comprising administering to a mammal an effective amount of a composition comprising at least two polypeptides selected from the group consisting of: (a) a non-lipidated non-pyruvylated polypeptide comprising the amino acid sequence SEQ ID NO: 71; (b) a non-lipidated non-pyruvylated polypeptide comprising the amino acid sequence SEQ ID NO: 77; (c) a non-lipidated non-pyruvylated polypeptide comprising the amino acid sequence SEQ ID NO: 55; (d) a non-lipidated non-pyruvylated polypeptide comprising the amino acid sequence SEQ ID NO: 68; and (e) a non-lipidated non-pyruvylated polypeptide comprising the amino acid sequence SEQ ID NO: 66, wherein the composition comprises aluminum.

2. The method according to claim 1, wherein the composition comprises (a) a non-lipidated non-pyruvylated polypeptide comprising the amino acid sequence SEQ ID NO: 71 and (b) a non-lipidated non-pyruvylated polypeptide comprising the amino acid sequence SEQ ID NO: 77.

3. The method according to claim 1, wherein the composition comprises (a) a non-lipidated non-pyruvylated polypeptide comprising the amino acid sequence SEQ ID NO: 71 and (b) a non-lipidated non-pyruvylated polypeptide comprising the amino acid sequence SEQ ID NO: 55.

4. The method according to claim 1, wherein the composition comprises a non-lipidated non-pyruvylated polypeptide comprising the amino acid sequence SEQ ID NO: 71 and a non-lipidated non-pyruvylated polypeptide comprising the amino acid sequence SEQ ID NO: 68.

5. The method according to claim 1, wherein the composition comprises a non-lipidated non-pyruvylated polypeptide comprising the amino acid sequence SEQ ID NO: 71 and a non-lipidated non-pyruvylated polypeptide comprising the amino acid sequence SEQ ID NO: 66.

6. The method according to claim 1, wherein the composition comprises a non-lipidated non-pyruvylated polypeptide comprising the amino acid sequence SEQ ID NO: 55 and a non-lipidated non-pyruvylated polypeptide comprising the amino acid sequence SEQ ID NO: 66.

7. The method according to claim 1, wherein the composition comprises a non-lipidated non-pyruvylated polypeptide comprising the amino acid sequence SEQ ID NO: 66 and a non-lipidated non-pyruvylated polypeptide comprising the amino acid sequence SEQ ID NO: 68.

8. The method according to claim 1, wherein the composition comprises a non-lipidated non-pyruvylated polypeptide comprising the amino acid sequence SEQ ID NO: 55; a non-lipidated non-pyruvylated polypeptide comprising the amino acid sequence SEQ ID NO: 66; and a non-lipidated non-pyruvylated polypeptide comprising the amino acid sequence SEQ ID NO: 68.

9. The method according to claim 1, further comprising administering to the mammal an immunogenic conjugate of a capsular saccharide of Neisseria meningitidis serogroup A.

10. The method according to claim 1, further comprising administering to the mammal an immunogenic conjugate of a capsular saccharide of Neisseria meningitidis serogroup C.

11. The method according to claim 1, further comprising administering to the mammal an immunogenic conjugate of a capsular saccharide of Neisseria meningitidis serogroup W135.

12. The method according to claim 1, further comprising administering to the mammal an immunogenic conjugate of a capsular saccharide of Neisseria meningitidis serogroup Y.

13. The method according to claim 1, further comprising administering to the mammal at least two immunogenic conjugates selected from:
   a) a conjugate of a capsular saccharide of Neisseria meningitidis serogroup A
   b) a conjugate of a capsular saccharide of Neisseria meningitidis serogroup C
   c) a conjugate of a capsular saccharide of Neisseria meningitidis serogroup W135; and
   a) a conjugate of a capsular saccharide of Neisseria meningitidis serogroup Y.

14. The method according to claim 1, further comprising administering to the mammal at least three conjugates selected from:
   a) a conjugate of a capsular saccharide of Neisseria meningitidis serogroup A
   b) a conjugate of a capsular saccharide of Neisseria meningitidis serogroup C
   c) a conjugate of a capsular saccharide of Neisseria meningitidis serogroup W135; and
   d) a conjugate of a capsular saccharide of Neisseria meningitidis serogroup Y.

15. The method according to claim 1, further comprising administering to the mammal an immunogenic conjugate of a capsular saccharide of Neisseria meningitidis serogroup A; an immunogenic conjugate of a capsular saccharide of Neisseria meningitidis serogroup C; an immunogenic conjugate of a capsular saccharide of Neisseria meningitidis serogroup W135; and an immunogenic conjugate of a capsular saccharide of Neisseria meningitidis serogroup Y.

* * * * *

SEQUENCE LISTING

<160> NUMBER OF SEQ ID NOS: 81

<210> SEQ ID NO 1
<211> LENGTH: 780
<212> TYPE: DNA
<213> ORGANISM: Neisseria meningitidis (group B)

<400> SEQUENCE: 1

```
tgcagcagcg gaggcggagg cggcggtgtc gccgccgaca tcggcacggg gcttgccgat      60
gcactaactg cgccgctcga ccataaagac aaaggtttga atccctgac attggaagac     120 tccattcccc aaaacggaac actgaccctg tcggcacaag gtgcggaaaa aactttcaaa     180
gccggcgaca aagacaacag cctcaacacg ggcaaactga agaacgacaa aatcagccgc     240
ttcgacttcg tgcaaaaaat cgaagtggac ggacaaacca tcacactggc aagcggcgaa     300
tttcaaatat acaaacagga ccactccgcc gtcgttgccc tacagattga aaaaatcaac     360
aaccccgaca aaatcgacag cctgataaac caacgctcct tccttgtcag cggtttgggc     420
ggagaacata ccgccttcaa ccaactgccc ggcgacaaag ccgagtatca cggcaaagca     480
ttcagctccg acgatgccgg cggaaaactg acctatacca tagattttgc cgccaaacag     540
ggacacggca aaatcgaaca cctgaaaaca cccgagcaaa atgtcgagct tgccgccgcc     600
gaactcaaag cagatgaaaa atcacacgcc gtcattttgg gcgacacgcg ctacggcagc     660
gaagaaaaag gcacttacca cctcgccctt ttcggcgacc gcgcccaaga aatcgccggc     720
tcggcaaccg tgaagatagg ggaaaaggtt cacgaaatcg gcatcgccgg caaacagtag     780
```

<210> SEQ ID NO 2
<211> LENGTH: 786
<212> TYPE: DNA
<213> ORGANISM: Neisseria meningitidis (group B)

<400> SEQUENCE: 2

| | |
|---|---|
| tgcagcagcg gaagcggaag cggaggcggc ggtgtcgccg ccgacatcgg cacagggctt | 60 |
| gccgatgcac taactgcgcc gctcgaccat aaagacaaag gtttgaaatc cctgacattg | 120 |
| gaagactcca tttcccaaaa cggaacactg accctgtcgg cacaaggtgc ggaaaaaact | 180 |
| ttcaaagtcg gcgacaaaga caacagtctc aatacaggca aattgaagaa cgacaaaatc | 240 |
| agccgcttcg actttgtgca aaaaatcgaa gtggacggac aaaccatcac gctggcaagc | 300 |
| ggcgaatttc aaatatacaa acaggaccac tccgccgtcg ttgccctaca gattgaaaaa | 360 |
| atcaacaacc ccgacaaaat cgacagcctg ataaaccaac gctccttcct tgtcagcggt | 420 |
| ttgggcggag aacataccgc cttcaaccaa ctgcccagcg gcaaagccga gtatcacggc | 480 |
| aaagcattca gctccgacga tgccggcgga aaactgacct ataccataga ttttgccgcc | 540 |
| aaacagggac acggcaaaat cgaacacctg aaaacacccg agcagaatgt cgagcttgcc | 600 |
| tccgccgaac tcaaagcaga tgaaaaatca cacgccgtca ttttgggcga cacgcgctac | 660 |
| ggcagcgaag aaaaaggcac ttaccacctc gctcttttcg gcgaccgagc caagaaatc | 720 |
| gccggctcgg caaccgtgaa gataagggaa aaggttcacg aaatcggcat cgccggcaaa | 780 |
| cagtag | 786 |

<210> SEQ ID NO 3
<211> LENGTH: 765
<212> TYPE: DNA
<213> ORGANISM: Neisseria meningitidis (group B)

<400> SEQUENCE: 3

| | |
|---|---|
| tgcagcagcg gaggcggcgg tgtcgccgcc gacatcggcg cggggcttgc cgatgcacta | 60 |
| accgcaccgc tcgaccataa agacaaaagt ttgcagtctt tgacgctgga tcagtccgtc | 120 |
| aggaaaaacg agaaactgaa gctggcggca caaggtgcgg aaaaaactta tggaaacggc | 180 |
| gacagcctca atacgggcaa attgaagaac gacaaggtca gccgcttcga ctttatccgt | 240 |
| caaatcgaag tggacggaca aaccatcacg ctggcaagcg gcgaatttca aatatacaaa | 300 |
| cagaaccact ccgccgtcgt tgccctacag attgaaaaaa tcaacaaccc cgacaaaatc | 360 |
| gacagcctga taaaccaacg ctccttcctt gtcagcggtt tgggcggaga acataccgcc | 420 |
| ttcaaccaac tgcctgacgg caaagccgag tatcacggca aagcattcag ctccgacgac | 480 |
| ccgaacggca ggctgcacta ctccattgat tttaccaaaa aacagggtta cggcagaatc | 540 |
| gaacacctga aaacgcccga gcagaatgtc gagcttgcct ccgccgaact caaagcagat | 600 |
| gaaaaatcac acgccgtcat tttgggcgac acgcgctacg gcggcgaaga aaaaggcact | 660 |
| taccacctcg cccttttcgg cgaccgcgcc caagaaatcg ccggctcggc aaccgtgaag | 720 |
| ataagggaaa aggttcacga aatcggcatc gccggcaaac agtag | 765 |

<210> SEQ ID NO 4
<211> LENGTH: 765
<212> TYPE: DNA
<213> ORGANISM: Neisseria meningitidis (group B)

<400> SEQUENCE: 4

| | |
|---|---|
| tgcagcagcg gaggggcgg tgtcgccgcc gacattggtg cggggcttgc cgatgcacta | 60 |
| accgcaccgc tcgaccataa agacaaaagt ttgcagtctt tgacgctgga tcagtccgtc | 120 |
| aggaaaaacg agaaactgaa gctggcggca caaggtgcgg aaaaaactta tggaaacggc | 180 |
| gacagcctca atacgggcaa attgaagaac gacaaggtca gccgcttcga ctttatccgt | 240 |
| caaatcgaag tggacggaca aaccatcacg ctggcaagcg gcgaatttca aatatacaaa | 300 |

```
cagaaccact ccgccgtcgt tgccctacag attgaaaaaa tcaacaaccc cgacaaaatc    360
gacagcctga taaaccaacg ctccttcctt gtcagcggtt tgggcggaga acataccgcc    420
ttcaaccaac tgcctgacgg caaagccgag tatcacggca agcattcag ctccgacgac     480 ccgaacggca ggctgcacta ctccattgat tttaccaaaa aacagggtta cggcagaatc    540
gaacacctga aaacgcccga gcagaatgtc gagcttgcct ccgccgaact caaagcagat    600
gaaaaatcac acgccgtcat tttgggcgac acgcgctacg gcggcgaaga aaaaggcact    660
taccacctcg cccttttcgg cgaccgcgcc aagaaatcg ccggctcggc aaccgtgaag     720
ataagggaaa aggttcacga aatcggcatc gccggcaaac agtag                    765
```

<210> SEQ ID NO 5
<211> LENGTH: 765
<212> TYPE: DNA
<213> ORGANISM: Neisseria meningitidis (group B)

<400> SEQUENCE: 5

```
tgcagcagcg gaggcggcgg tgtcgccgcc gacatcggcg cggggcttgc cgatgcacta     60
accgcaccgc tcgaccataa agacaaaagt ttgcagtctt tgacgctgga tcagtccgtc    120
aggaaaaacg agaaactgaa gctggcggca caaggtgcgg aaaaaactta tggaaacggc    180
gacagcctca atacgggcaa attgaagaac gacaaggtca gccgcttcga ctttatccgt    240
caaatcgaag tggacgggca gctcattacc ttggagagcg gagagttcca aatatacaaa    300
caggaccact ccgccgtcgt tgccctacag attgaaaaaa tcaacaaccc cgacaaaatc    360
gacagcctga taaaccaacg ctccttcctt gtcagcggtt tgggtggaga acataccgcc    420
ttcaaccaac tgcccagcgg caaagccgag tatcacggca agcattcag ctccgacgat     480 gctggcggaa aactgaccta taccatagat ttcgccgcca acagggaca cggcaaaatc     540 gaacacttga aaacacccga gcaaaatgtc gagcttgcct ccgccgaact caaagcagat    600
gaaaaatcac acgccgtcat tttgggcgac acgcgctacg gcggcgaaga aaaaggcact    660
taccacctcg cccttttcgg cgaccgcgcc aagaaatcg ccggctcggc aaccgtgaag     720
ataagggaaa aggttcacga aatcggcatc gccggcaaac agtag                    765
```

<210> SEQ ID NO 6
<211> LENGTH: 792
<212> TYPE: DNA
<213> ORGANISM: Neisseria meningitidis (group B)

<400> SEQUENCE: 6

```
tgcagcagcg gaggcggcgg aagcggaggc ggcggtgtcg ccgccgacat cggcgcgggg     60
cttgccgatg cactaaccgc accgctcgac cataaagaca aaggtttgaa atccctgaca    120
ttggaagact ccatttccca aaacggaaca ctgaccctgt cggcacaagg tgcggaaaga    180
actttcaaag ccggcgacaa agacaacagt ctcaacacag caaactgaa gaacgacaaa     240 atcagccgct tcgactttat ccgtcaaatc gaagtggacg ggcagctcat taccttggag    300
agcggagagt tccaagtgta caaacaaagc cattccgcct taaccgccct tcagaccgag    360
caagtacaag actcggagca ttccgggaag atggttgcga acgccagtt cagaatcggc     420 gacatagtgg gcgaacatac atcttttgac aagcttccca agacgtcat ggcgacatat      480 cgcgggacgc cgttcggttc agacgatgcc ggcggaaaac tgacctacac catagatttc    540
gccgccaagc agggacacgg caaaatcgaa catttgaaat cgcctgaact caatgttgac    600
```

```
ctggccgccg ccgatatcaa gccggatgaa aaacaccatg ccgtcatcag cggttccgtc      660
ctttacaacc aagccgagaa aggcagttac tctctaggca tctttggcgg gcaagcccag      720
gaagttgccg gcagcgcgga agtggaaacc gcaaacggca tacgccatat cggtcttgcc      780
gccaagcaat aa                                                          792

<210> SEQ ID NO 7
<211> LENGTH: 768
<212> TYPE: DNA
<213> ORGANISM: Neisseria meningitidis (group B)

<400> SEQUENCE: 7
tgcagcagcg gaggcggcgg tgtcgccgcc gacatcggcg cggggcttgc cgatgcacta       60
accgcaccgc tcgaccataa agacaaaagt ttgcagtctt tgacgctgga tcagtccgtc      120
aggaaaaacg agaaactgaa gctggcggca caaggtgcgg aaaaaactta tggaaacggc      180
gacagcctta atacgggcaa attgaagaac gacaaggtca gccgtttcga ctttatccgt      240
caaatcgaag tggacgggca gctcattacc ttggagagcg gagagttcca agtgtacaaa      300
caaagccatt ccgccttaac cgcccttcag accgagcaag aacaagatcc agagcattcc      360
gggaagatgg ttgcgaaacg ccggttcaaa atcggcgaca tagcgggcga acatacatct      420
tttgacaagc ttcccaaaga cgtcatggcg acatatcgcg ggacggcgtt cggttcagac      480
gatgccggcg aaaactgac ctatactata gattttgctg ccaaacaggg acacggcaaa      540
atcgaacatt tgaaatcgcc cgaactcaat gtcgagcttg ccaccgccta tcaagccg       600 gatgaaaaac accatgccgt catcagcggt tccgtccttt acaatcaaga cgagaaaggc      660
agttactccc tcggtatctt tggcgggcaa gcccaggaag ttgccggcag cgcggaagtg      720
gaaaccgcaa acggcataca ccatatcggt cttgccgcca gcaataa                    768

<210> SEQ ID NO 8
<211> LENGTH: 768
<212> TYPE: DNA
<213> ORGANISM: Neisseria meningitidis (group B)

<400> SEQUENCE: 8
tgcagcagcg gaggggcgg tgtcgccgcc gacatcggtg cggggcttgc cgatgcacta       60
accgcaccgc tcgaccataa agacaaaggt ttgcagtctt taacgctgga tcagtccgtc      120
aggaaaaacg agaaactgaa gctggcggca caaggtgcgg aaaaaactta tggaaacggc      180
gacagcctta atacgggcaa attgaagaac gacaaggtca gccgcttcga ctttatccgt      240
caaatcgaag tggacgggaa gctcattacc ttggagagcg gagagttcca agtgtacaaa      300
caaagccatt ccgccttaac cgcccttcag accgagcaag tacaagactc ggaggattcc      360
gggaagatgg ttgcgaaacg ccagttcaga atcggcgaca tagcgggcga acatacatct      420
tttgacaagc ttcccaaagg cggcagtgcg acatatcgcg ggacggcgtt cggttcagac      480
gatgctggcg aaaactgac ctatactata gatttcgccg ccaagcaggg acacggcaaa      540
atcgaacatt tgaaatcgcc cgaactcaat gtcgagcttg ccaccgccta tcaagccg       600 gatgaaaaac gccatgccgt tatcagcggt tccgtccttt acaaccaaga cgagaaaggc      660
agttactccc tcggtatctt tggcgggcaa gcccaggaag ttgccggcag cgcggaagtg      720
gaaaccgcaa acggcataca ccatatcggt cttgccgcca gcagtaa                    768

<210> SEQ ID NO 9
<211> LENGTH: 768
```

<212> TYPE: DNA
<213> ORGANISM: Neisseria meningitidis (group B)

<400> SEQUENCE: 9

```
tgcagcagcg gaggcggcgg tgtcgccgcc gacatcggcg cggtgcttgc cgatgcacta    60
accgcaccgc tcgaccataa agacaaaagt ttgcagtctt tgacgctgga tcagtccgtc   120
aggaaaaacg agaaactgaa gctggcggca caaggtgcgg aaaaaactta tggaaacggc   180
gacagcctca atacgggcaa attgaagaac gacaaggtca gccgcttcga ctttatccgt   240
caaatcgaag tggacgggca gctcattacc ttggagagcg agagttccaa agtgtacaaa   300
caaagccatt ccgccttaac cgcccttcag accgagcaag tacaagattc ggagcattca   360
gggaagatgg ttgcgaaacg ccagttcaga atcggcgata tagcgggtga acatacatct   420
tttgacaagc ttcccgaagg cggcagggcg acatatcgcg ggacggcatt cggttcagac   480
gatgccagtg gaaaactgac ctacaccata gatttcgccg ccaagcaggg acacggcaaa   540
atcgaacatt tgaaatcgcc agaactcaat gttgacctgg ccgcctccga tatcaagccg   600
gataaaaaac gccatgccgt catcagcggt tccgtccttt acaaccaagc cgagaaaggc   660
agttactctc taggcatctt tggcgggcaa gcccaggaag ttgccggcag cgcagaagtg   720
gaaaccgcaa acggcatacg ccatatcggt cttgccgcca agcagtaa                768
```

<210> SEQ ID NO 10
<211> LENGTH: 768
<212> TYPE: DNA
<213> ORGANISM: Neisseria meningitidis (group B)

<400> SEQUENCE: 10

```
tgcagcagcg gagggggtgg tgtcgccgcc gacatcggtg cggggcttgc cgatgcacta    60
accgcaccgc tcgaccataa agacaaaggt ttgcagtctt tgacgctgga tcagtccgtc   120
aggaaaaacg agaaactgaa gctggcggca caaggtgcgg aaaaaactta tggaaacggt   180
gacagcctca atacgggcaa attgaagaac gacaaggtca gccgtttcga ctttatccgc   240
caaatcgaag tggacgggca gctcattacc ttggagagtg agagttccaa agtatacaaa   300
caaagccatt ccgccttaac cgcctttcag accgagcaaa tacaagattc ggagcattcc   360
gggaagatgg ttgcgaaacg ccagttcaga atcggcgaca tagcgggcga acatacatct   420
tttgacaagc ttcccgaagg cggcagggcg acatatcgcg ggacggcgtt cggttcagac   480
gatgccggcg gaaaactgac ctacaccata gatttcgccg ccaagcaggg aaacggcaaa   540
atcgaacatt tgaaatcgcc agaactcaat gtcgacctgg ccgccgccga tatcaagccg   600
gatggaaaac gccatgccgt catcagcggt tccgtccttt acaaccaagc cgagaaaggc   660
agttactccc tcggtatctt tggcggaaaa gcccaggaag ttgccggcag cgcggaagtg   720
aaaaccgtaa acggcatacg ccatatcggc cttgccgcca agcaataa                768
```

<210> SEQ ID NO 11
<211> LENGTH: 792
<212> TYPE: DNA
<213> ORGANISM: Neisseria meningitidis (group B)

<400> SEQUENCE: 11

```
tgcagcagcg gaggcggcgg aagcggaggc ggcggtgtcg ccgccgacat cggcgcgggg    60
cttgccgatg cactaaccgc accgctcgac cataaagaca aaggtttgaa atccctgaca   120
ttggaagact ccatttccca aaacggaaca ctgaccctgt cggcacaagg tgcggaaaga   180
```

```
actttcaaag ccggcgacaa agacaacagt ctcaacacag gcaaactgaa gaacgacaaa    240
atcagccgct tcgactttat ccgtcaaatc gaagtggacg ggcagctcat taccttggag    300
agcggagagt tccaagtgta caaacaaagc cattccgcct taaccgccct tcagaccgag    360
caagtacaag actcggagca ttccgggaag atggttgcga acgccagtt cagaatcggc     420
gacatagtgg gcgaacatac atcttttggc aagcttccca aagacgtcat ggcgacatat    480
cgcgggacgg cgttcggttc agacgatgcc ggcggaaaac tgacctacac catagatttc    540
gccgccaagc agggacacgg caaaatcgaa catttgaaat cgccagaact caatgttgac    600
ctggccgccg ccgatatcaa gccggatgaa aacaccatg ccgtcatcag cggttccgtc      660
ctttacaacc aagccgagaa aggcagttac tctctaggca tctttggcgg gcaagcccag    720
gaagttgccg gcagcgcgga agtggaaacc gcaaacggca tacgccatat cggtcttgcc    780
gccaagcaat aa                                                         792
```

<210> SEQ ID NO 12
<211> LENGTH: 259
<212> TYPE: PRT
<213> ORGANISM: Neisseria meningitidis (group B)

<400> SEQUENCE: 12

```
Cys Ser Ser Gly Gly Gly Gly Gly Val Ala Ala Asp Ile Gly Thr
1               5                   10                  15

Gly Leu Ala Asp Ala Leu Thr Ala Pro Leu Asp His Lys Asp Lys Gly
            20                  25                  30

Leu Lys Ser Leu Thr Leu Glu Asp Ser Ile Pro Gln Asn Gly Thr Leu
        35                  40                  45

Thr Leu Ser Ala Gln Gly Ala Glu Lys Thr Phe Lys Ala Gly Asp Lys
    50                  55                  60

Asp Asn Ser Leu Asn Thr Gly Lys Leu Lys Asn Asp Lys Ile Ser Arg
65                  70                  75                  80

Phe Asp Phe Val Gln Lys Ile Glu Val Asp Gly Gln Thr Ile Thr Leu
                85                  90                  95

Ala Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr
    130                 135                 140

Ala Phe Asn Gln Leu Pro Gly Asp Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln
```

<210> SEQ ID NO 13
<211> LENGTH: 261
<212> TYPE: PRT
<213> ORGANISM: Neisseria meningitidis (group B)

<400> SEQUENCE: 13

```
Cys Ser Ser Gly Ser Gly Ser Gly Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
        35                  40                  45

Thr Leu Thr Leu Ser Ala Gln Gly Ala Glu Lys Thr Phe Lys Val Gly
    50                  55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
    130                 135                 140

His Thr Ala Phe Asn Gln Leu Pro Ser Gly Lys Ala Glu Tyr His Gly
145                 150                 155                 160

Lys Ala Phe Ser Ser Asp Asp Ala Gly Gly Lys Leu Thr Tyr Thr Ile
                165                 170                 175

Asp Phe Ala Ala Lys Gln Gly His Gly Lys Ile Glu His Leu Lys Thr
            180                 185                 190

Pro Glu Gln Asn Val Glu Leu Ala Ser Ala Glu Leu Lys Ala Asp Glu
        195                 200                 205

Lys Ser His Ala Val Ile Leu Gly Asp Thr Arg Tyr Gly Ser Glu Glu
    210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
                245                 250                 255

Ile Ala Gly Lys Gln
            260
```

<210> SEQ ID NO 14
<211> LENGTH: 254
<212> TYPE: PRT
<213> ORGANISM: Neisseria meningitidis (group B)

<400> SEQUENCE: 14

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60
```

```
Thr Gly Lys Leu Lys Asn Asp Lys Val Ser Arg Phe Asp Phe Ile Arg
 65                  70                  75                  80

Gln Ile Glu Val Asp Gly Gln Thr Ile Thr Leu Ala Ser Gly Glu Phe
                 85                  90                  95

Gln Ile Tyr Lys Gln Asn His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 15
<211> LENGTH: 254
<212> TYPE: PRT
<213> ORGANISM: Neisseria meningitidis (group B)

<400> SEQUENCE: 15

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
```

```
                    180                 185                 190
Ala Ser Ala Glu Leu Lys Ala Asp Glu Lys Ser His Ala Val Ile Leu
            195                 200                 205

Gly Asp Thr Arg Tyr Gly Gly Glu Lys Gly Thr Tyr His Leu Ala
210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
            245                 250

<210> SEQ ID NO 16
<211> LENGTH: 263
<212> TYPE: PRT
<213> ORGANISM: Neisseria meningitidis (group B)

<400> SEQUENCE: 16

Cys Ser Ser Gly Gly Gly Gly Ser Gly Gly Gly Gly Val Ala Ala Asp
1               5                   10                  15

Ile Gly Ala Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Arg Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Ile Arg Gln Ile Glu Val Asp Gly Gln Leu
                85                  90                  95

Ile Thr Leu Glu Ser Gly Glu Phe Gln Val Tyr Lys Gln Ser His Ser
            100                 105                 110

Ala Leu Thr Ala Leu Gln Thr Glu Gln Val Gln Asp Ser Glu His Ser
        115                 120                 125

Gly Lys Met Val Ala Lys Arg Gln Phe Arg Ile Gly Asp Ile Val Gly
    130                 135                 140

Glu His Thr Ser Phe Asp Lys Leu Pro Lys Asp Val Met Ala Thr Tyr
145                 150                 155                 160

Arg Gly Thr Ala Phe Gly Ser Asp Asp Ala Gly Gly Lys Leu Thr Tyr
                165                 170                 175

Thr Ile Asp Phe Ala Ala Lys Gln Gly His Gly Lys Ile Glu His Leu
            180                 185                 190

Lys Ser Pro Glu Leu Asn Val Asp Leu Ala Ala Ala Asp Ile Lys Pro
        195                 200                 205

Asp Glu Lys His His Ala Val Ile Ser Gly Ser Val Leu Tyr Asn Gln
    210                 215                 220

Ala Glu Lys Gly Ser Tyr Ser Leu Gly Ile Phe Gly Gly Gln Ala Gln
225                 230                 235                 240

Glu Val Ala Gly Ser Ala Glu Val Glu Thr Ala Asn Gly Ile Arg His
                245                 250                 255

Ile Gly Leu Ala Ala Lys Gln
            260

<210> SEQ ID NO 17
<211> LENGTH: 255
<212> TYPE: PRT
<213> ORGANISM: Neisseria meningitidis (group B)
```

<400> SEQUENCE: 17

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Glu Gln Asp Pro Glu His Ser Gly Lys Met Val Ala Lys Arg Arg
        115                 120                 125

Phe Lys Ile Gly Asp Ile Ala Gly Glu His Thr Ser Phe Asp Lys Leu
    130                 135                 140

Pro Lys Asp Val Met Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys His His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255

<210> SEQ ID NO 18
<211> LENGTH: 255
<212> TYPE: PRT
<213> ORGANISM: Neisseria meningitidis (group B)

<400> SEQUENCE: 18

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Lys Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

```
Gln Val Gln Asp Ser Glu Asp Ser Gly Lys Met Val Ala Lys Arg Gln
            115                 120                 125

Phe Arg Ile Gly Asp Ile Ala Gly Glu His Thr Ser Phe Asp Lys Leu
        130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys Arg His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255

<210> SEQ ID NO 19
<211> LENGTH: 255
<212> TYPE: PRT
<213> ORGANISM: Neisseria meningitidis (group B)

<400> SEQUENCE: 19

Cys Ser Ser Gly Gly Gly Gly Val Ala Ala Asp Ile Gly Ala Val Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Gln Ala Gln Glu Val Ala Gly Ser Ala Glu Val
225                 230                 235                 240
```

Glu Thr Ala Asn Gly Ile Arg His Ile Gly Leu Ala Ala Lys Gln
            245                 250                 255

<210> SEQ ID NO 20
<211> LENGTH: 255
<212> TYPE: PRT
<213> ORGANISM: Neisseria meningitidis (group B)

<400> SEQUENCE: 20

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
        130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
            195                 200                 205

Ser Gly Ser Val Leu Tyr Asn Gln Ala Glu Lys Gly Ser Tyr Ser Leu
        210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 21
<211> LENGTH: 263
<212> TYPE: PRT
<213> ORGANISM: Neisseria meningitidis (group B)

<400> SEQUENCE: 21

Cys Ser Ser Gly Gly Gly Ser Gly Gly Gly Val Ala Ala Asp
1               5                   10                  15

Ile Gly Ala Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
            35                  40                  45

Gly Thr Leu Thr Leu Ser Ala Gln Gly Ala Glu Arg Thr Phe Lys Ala
        50                  55                  60

-continued

Gly Asp Lys Asp Asn Ser Leu Asn Thr Gly Lys Leu Lys Asn Asp Lys
65                  70                  75                  80

Ile Ser Arg Phe Asp Phe Ile Arg Gln Ile Glu Val Asp Gly Gln Leu
                85                  90                  95

Ile Thr Leu Glu Ser Gly Glu Phe Gln Val Tyr Lys Gln Ser His Ser
            100                 105                 110

Ala Leu Thr Ala Leu Gln Thr Glu Gln Val Gln Asp Ser Glu His Ser
        115                 120                 125

Gly Lys Met Val Ala Lys Arg Gln Phe Arg Ile Gly Asp Ile Val Gly
    130                 135                 140

Glu His Thr Ser Phe Gly Lys Leu Pro Lys Asp Val Met Ala Thr Tyr
145                 150                 155                 160

Arg Gly Thr Ala Phe Gly Ser Asp Asp Ala Gly Gly Lys Leu Thr Tyr
                165                 170                 175

Thr Ile Asp Phe Ala Ala Lys Gln Gly His Gly Lys Ile Glu His Leu
            180                 185                 190

Lys Ser Pro Glu Leu Asn Val Asp Leu Ala Ala Ala Asp Ile Lys Pro
        195                 200                 205

Asp Glu Lys His His Ala Val Ile Ser Gly Ser Val Leu Tyr Asn Gln
210                 215                 220

Ala Glu Lys Gly Ser Tyr Ser Leu Gly Ile Phe Gly Gly Gln Ala Gln
225                 230                 235                 240

Glu Val Ala Gly Ser Ala Glu Val Glu Thr Ala Asn Gly Ile Arg His
                245                 250                 255

Ile Gly Leu Ala Ala Lys Gln
            260

<210> SEQ ID NO 22
<211> LENGTH: 26
<212> TYPE: DNA
<213> ORGANISM: Artificial
<220> FEATURE:
<223> OTHER INFORMATION: Synthetic nucleotide sequence: Forward primer

<400> SEQUENCE: 22
tgccatatga gcagcggaag cggaag                                    26

<210> SEQ ID NO 23
<211> LENGTH: 27
<212> TYPE: DNA
<213> ORGANISM: Artificial
<220> FEATURE:
<223> OTHER INFORMATION: Synthetic nucleotide sequence: Reverse primer

<400> SEQUENCE: 23
cggatccctA ctgtttgccg gcgatgc                                   27

<210> SEQ ID NO 24
<211> LENGTH: 49
<212> TYPE: DNA
<213> ORGANISM: Artificial
<220> FEATURE:
<223> OTHER INFORMATION: Synthetic nucleotide sequence: Forward primer

<400> SEQUENCE: 24
tttcttcccg ggaaggagat atacatatgt gcagcagcgg aggcggcgg           49

<210> SEQ ID NO 25
<211> LENGTH: 38

```
<212> TYPE: DNA
<213> ORGANISM: Artificial
<220> FEATURE:
<223> OTHER INFORMATION: Synthetic nucleotide sequence: Reverse primer

<400> SEQUENCE: 25
tttcttgctc agcattattg cttggcggca agaccgat                           38

<210> SEQ ID NO 26
<211> LENGTH: 46
<212> TYPE: DNA
<213> ORGANISM: Artificial
<220> FEATURE:
<223> OTHER INFORMATION: Synthetic nucleotide sequence: Forward primer

<400> SEQUENCE: 26
tttcttcccg ggaaggagat atacatatga gcagcggagg cggcgg                  46

<210> SEQ ID NO 27
<211> LENGTH: 38
<212> TYPE: DNA
<213> ORGANISM: Artificial
<220> FEATURE:
<223> OTHER INFORMATION: Synthetic nucleotide sequence: Reverse primer

<400> SEQUENCE: 27
tttcttgctc agcattattg cttggcggca agaccgat                           38

<210> SEQ ID NO 28
<211> LENGTH: 36
<212> TYPE: DNA
<213> ORGANISM: Artificial
<220> FEATURE:
<223> OTHER INFORMATION: Synthetic nucleotide sequence

<400> SEQUENCE: 28
atgagctctg gaggtggagg aagcgggggc ggtgga                             36

<210> SEQ ID NO 29
<211> LENGTH: 12
<212> TYPE: PRT
<213> ORGANISM: Artificial
<220> FEATURE:
<223> OTHER INFORMATION: Synthetic amino acid sequence

<400> SEQUENCE: 29

Met Ser Ser Gly Gly Gly Gly Ser Gly Gly Gly Gly
1               5                   10

<210> SEQ ID NO 30
<211> LENGTH: 33
<212> TYPE: DNA
<213> ORGANISM: Artificial
<220> FEATURE:
<223> OTHER INFORMATION: Synthetic nucleotide sequence

<400> SEQUENCE: 30
atgagctctg gaagcggaag cggggcggt gga                                 33

<210> SEQ ID NO 31
<211> LENGTH: 11
<212> TYPE: PRT
<213> ORGANISM: Artificial
<220> FEATURE:
<223> OTHER INFORMATION: Synthetic amino acid sequence

<400> SEQUENCE: 31
```

```
Met Ser Ser Gly Ser Gly Ser Gly Gly Gly Gly
1               5                   10
```

<210> SEQ ID NO 32
<211> LENGTH: 21
<212> TYPE: DNA
<213> ORGANISM: Artificial
<220> FEATURE:
<223> OTHER INFORMATION: Synthetic nucleotide sequence

<400> SEQUENCE: 32
atgagctctg gaggtggagg a                                              21

<210> SEQ ID NO 33
<211> LENGTH: 7
<212> TYPE: PRT
<213> ORGANISM: Artificial
<220> FEATURE:
<223> OTHER INFORMATION: Synthetic amino acid sequence

<400> SEQUENCE: 33

```
Met Ser Ser Gly Gly Gly Gly
1               5
```

<210> SEQ ID NO 34
<211> LENGTH: 21
<212> TYPE: DNA
<213> ORGANISM: Artificial
<220> FEATURE:
<223> OTHER INFORMATION: Synthetic nucleotide sequence

<400> SEQUENCE: 34
atgagcagcg ggggcggtgg a                                              21

<210> SEQ ID NO 35
<211> LENGTH: 28
<212> TYPE: PRT
<213> ORGANISM: Neisseria meningitidis (group B)

<400> SEQUENCE: 35

```
Cys Ser Ser Gly Gly Gly Gly Ser Gly Gly Gly Val Thr Ala Asp
1               5                   10                  15

Ile Gly Thr Gly Leu Ala Asp Ala Leu Thr Ala Pro
            20                  25
```

<210> SEQ ID NO 36
<211> LENGTH: 28
<212> TYPE: PRT
<213> ORGANISM: Neisseria meningitidis (group B)

<400> SEQUENCE: 36

```
Cys Ser Ser Gly Gly Gly Gly Ser Gly Gly Gly Val Ala Ala Asp
1               5                   10                  15

Ile Gly Ala Gly Leu Ala Asp Ala Leu Thr Ala Pro
            20                  25
```

<210> SEQ ID NO 37
<211> LENGTH: 27
<212> TYPE: PRT
<213> ORGANISM: Neisseria meningitidis (group B)

<400> SEQUENCE: 37

```
Cys Ser Ser Gly Ser Gly Ser Gly Gly Gly Val Ala Ala Asp Ile
1               5                   10                  15
```

Gly Thr Gly Leu Ala Asp Ala Leu Thr Ala Pro
            20                  25

<210> SEQ ID NO 38
<211> LENGTH: 23
<212> TYPE: PRT
<213> ORGANISM: Neisseria meningitidis (group B)

<400> SEQUENCE: 38

Cys Ser Ser Gly Gly Gly Gly Val Ala Ala Asp Ile Gly Ala Gly Leu
1               5                   10                  15

Ala Asp Ala Leu Thr Ala Pro
            20

<210> SEQ ID NO 39
<211> LENGTH: 23
<212> TYPE: PRT
<213> ORGANISM: Neisseria meningitidis (group B)

<400> SEQUENCE: 39

Cys Ser Ser Gly Gly Gly Gly Val Ala Ala Asp Ile Gly Ala Val Leu
1               5                   10                  15

Ala Asp Ala Leu Thr Ala Pro
            20

<210> SEQ ID NO 40
<211> LENGTH: 23
<212> TYPE: PRT
<213> ORGANISM: Neisseria meningitidis (group B)

<400> SEQUENCE: 40

Cys Ser Ser Gly Gly Gly Gly Val Ala Ala Asp Ile Gly Ala Gly Leu
1               5                   10                  15

Ala Asp Ala Leu Thr Ala Pro
            20

<210> SEQ ID NO 41
<211> LENGTH: 15
<212> TYPE: PRT
<213> ORGANISM: Artificial
<220> FEATURE:
<223> OTHER INFORMATION: Synthetic amino acid sequence
<220> FEATURE:
<221> NAME/KEY: MISC_FEATURE
<222> LOCATION: (15)..(15)
<223> OTHER INFORMATION: X is G or V

<400> SEQUENCE: 41

Met Ser Ser Gly Gly Gly Gly Val Ala Ala Asp Ile Gly Ala Xaa
1               5                   10                  15

<210> SEQ ID NO 42
<211> LENGTH: 45
<212> TYPE: DNA
<213> ORGANISM: Artificial
<220> FEATURE:
<223> OTHER INFORMATION: Synthetic nucleotide sequence

<400> SEQUENCE: 42
atgagcagcg gaggcggcgg tgtcgccgcc gacatcggcg cgggg           45

<210> SEQ ID NO 43
<211> LENGTH: 789
<212> TYPE: DNA

<213> ORGANISM: Artificial
<220> FEATURE:
<223> OTHER INFORMATION: Synthetic nucleotide sequence

<400> SEQUENCE: 43

```
agctctggag gtggaggaag cgggggcggt ggagttgcag cagacattgg agcaggatta      60
gcagatgcac tgacggcacc gttggatcat aaagacaaag gcttgaaatc gcttacctta     120
gaagattcta tttcacaaaa tggcaccctt accttgtccg cgcaaggcgc tgaacgtact     180
tttaaagccg gtgacaaaga taatagctta aatacaggta aactcaaaaa tgataaaatc     240
tcgcgttttg atttcattcg tcaaatcgaa gtagatggcc aacttattac attagaaagc     300
ggtgaattcc aagtatataa acaatcccat tcagcactta cagcattgca aaccgaacag     360
gtccaagact cagaacattc cggcaaaatg gtagctaaac gtcaattccg catcggtgac     420
attgtcggtg aacatacaag cttcggaaaa ttaccaaaag atgtgatggc gacctatcgc     480
ggtacggcat ttggatcaga tgatgcaggc ggtaaattaa cttatacaat tgactttgca     540
gcaaaacaag gacatggcaa aattgaacat ttaaaatctc ccgaacttaa cgtagatctc     600
gcagcagcag atattaaacc agatgaaaaa caccacgcag tcatttcagg ttcagtttta     660
tacaatcagg cagaaaaagg ttcgtactct ttaggtattt ttggcgggca agctcaagaa     720
gttgcaggta gcgcagaagt agaaacggca aatggcattc gtcacattgg gttagcggcg     780
aaacaataa                                                             789
```

<210> SEQ ID NO 44
<211> LENGTH: 262
<212> TYPE: PRT
<213> ORGANISM: Artificial
<220> FEATURE:
<223> OTHER INFORMATION: Synthetic amino acid sequence

<400> SEQUENCE: 44

```
Ser Ser Gly Gly Gly Gly Ser Gly Gly Gly Gly Val Ala Ala Asp Ile
1               5                   10                  15

Gly Ala Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
        35                  40                  45

Thr Leu Thr Leu Ser Ala Gln Gly Ala Glu Arg Thr Phe Lys Ala Gly
    50                  55                  60

Asp Lys Asp Asn Ser Leu Asn Thr Gly Lys Leu Lys Asn Asp Lys Ile
65                  70                  75                  80

Ser Arg Phe Asp Phe Ile Arg Gln Ile Glu Val Asp Gly Gln Leu Ile
                85                  90                  95

Thr Leu Glu Ser Gly Glu Phe Gln Val Tyr Lys Gln Ser His Ser Ala
            100                 105                 110

Leu Thr Ala Leu Gln Thr Glu Gln Val Gln Asp Ser Glu His Ser Gly
        115                 120                 125

Lys Met Val Ala Lys Arg Gln Phe Arg Ile Gly Asp Ile Val Gly Glu
    130                 135                 140

His Thr Ser Phe Gly Lys Leu Pro Lys Asp Val Met Ala Thr Tyr Arg
145                 150                 155                 160

Gly Thr Ala Phe Gly Ser Asp Asp Ala Gly Gly Lys Leu Thr Tyr Thr
                165                 170                 175

Ile Asp Phe Ala Ala Lys Gln Gly His Gly Lys Ile Glu His Leu Lys
            180                 185                 190
```

```
Ser Pro Glu Leu Asn Val Asp Leu Ala Ala Ala Asp Ile Lys Pro Asp
        195                 200                 205

Glu Lys His His Ala Val Ile Ser Gly Ser Val Leu Tyr Asn Gln Ala
    210                 215                 220

Glu Lys Gly Ser Tyr Ser Leu Gly Ile Phe Gly Gly Gln Ala Gln Glu
225                 230                 235                 240

Val Ala Gly Ser Ala Glu Val Glu Thr Ala Asn Gly Ile Arg His Ile
                245                 250                 255

Gly Leu Ala Ala Lys Gln
        260

<210> SEQ ID NO 45
<211> LENGTH: 780
<212> TYPE: DNA
<213> ORGANISM: Artificial
<220> FEATURE:
<223> OTHER INFORMATION: Synthetic nucleotide sequence

<400> SEQUENCE: 45
agctctggag gtggaggaag cgggggcggt ggagttgcag cagacattgg agcaggatta      60
gcagatgcac tgacggcacc gttggatcat aaagacaaag gcttgcagtc gcttaccttg     120
gatcagtctg tcaggaaaaa tgagaaactt aagttggcgg cgcaaggcgc tgaaaaaact     180
tatggaaacg gtgacagctt aaatacaggt aaactcaaaa atgataaagt ctcgcgtttt     240
gatttcattc gtcaaatcga agtagatggc aagcttatta cattagaaag cggtgaattc     300
caagtatata acaatccca ttcagcactt acagcattgc aaaccgaaca ggtccaagac     360
tcagaagatt ccggcaaaat ggtagctaaa cgtcaattcc gcatcggtga cattgcgggt     420
gaacatacaa gcttcgacaa attaccaaaa ggcggcagtg cgacctatcg cggtacggca     480
tttggatcag atgatgcagg cggtaaatta acttatacaa ttgactttgc agcaaaacaa     540
ggacatggca aaattgaaca tttaaaatct cccgaactta cgtagagct cgcaaccgca     600 tatattaaac cagatgaaaa acgccacgca gtcatttcag gttcagtttt atacaatcag     660
gacgaaaaag gttcgtactc tttaggtatt tttggcgggc aagctcaaga agttgcaggt     720
agcgcagaag tagaaacggc aaatggcatt caccacattg ggttagcggc gaaacaataa     780

<210> SEQ ID NO 46
<211> LENGTH: 765
<212> TYPE: DNA
<213> ORGANISM: Artificial
<220> FEATURE:
<223> OTHER INFORMATION: Synthetic nucleotide sequence

<400> SEQUENCE: 46
agctctggag gtggaggagt tgcagcagac attggagcag gattagcaga tgcactgacg      60
gcaccgttgg atcataaaga caaaggcttg cagtcgctta ccttagatca gtctgtcagg     120
aaaaatgaga aacttaagtt ggcggcgcaa ggcgctgaaa aaacttatgg aaacggtgac     180
agcttaaata caggtaaact caaaaatgat aaagtctcgc gttttgattt cattcgtcaa     240
atcgaagtag atggcaagct tattacatta gaaagcggtg aattccaagt atataaacaa     300
tcccattcag cacttacagc attgcaaacc gaacaggtcc aagactcaga agattccggc     360
aaaatggtag ctaaacgtca attccgcatc ggtgacattg cgggtgaaca tacaagcttc     420
gacaaattac caaaaggcgg cagtgcgacc tatcgcggta cggcatttgg atcagatgat     480
gcaggcggta aattaactta tacaattgac tttgcagcaa acaaggaca tggcaaaatt     540
```

```
gaacatttaa aatctcccga acttaacgta gagctcgcaa ccgcatatat taaaccagat    600
gaaaaacgcc acgcagtcat ttcaggttca gttttataca atcaggacga aaaaggttcg    660 tactctcttag gtattttttgg cgggcaagct caagaagttg caggtagcgc agaagtagaa    720
acggcaaatg gcattcacca cattgggtta gcggcgaaac aataa                   765

<210> SEQ ID NO 47
<211> LENGTH: 765
<212> TYPE: DNA
<213> ORGANISM: Artificial
<220> FEATURE:
<223> OTHER INFORMATION: Synthetic nucleotide sequence

<400> SEQUENCE: 47
agcagcgggg gcggtggagt tgcagcagac attggagcag gattagcaga tgcactgacg     60
gcaccgttgg atcataaaga caaaggcttg cagtcgctta ccttagatca gtctgtcagg    120
aaaaatgaga aacttaagtt ggcggcgcaa ggcgctgaaa aaacttatgg aaacggtgac    180
agcttaaata caggtaaact caaaaatgat aaagtctcgc gttttgattt cattcgtcaa    240
atcgaagtag atggcaagct tattacatta gaaagcggtg aattccaagt atataaacaa    300
tcccattcag cacttacagc attgcaaacc gaacaggtcc aagactcaga agattccggc    360
aaaatggtag ctaaacgtca attccgcatc ggtgacattg cgggtgaaca tacaagcttc    420
gacaaattac caaaaggcgg cagtgcgacc tatcgcggta cggcatttgg atcagatgat    480
gcaggcggta aattaactta tacaattgac tttgcagcaa acaaggaca tggcaaaatt    540 gaacatttaa aatctcccga acttaacgta gagctcgcaa ccgcatatat taaaccagat    600
gaaaaacgcc acgcagtcat ttcaggttca gttttataca atcaggacga aaaaggttcg    660 tactctcttag gtattttttgg cgggcaagct caagaagttg caggtagcgc agaagtagaa    720
acggcaaatg gcattcacca cattgggtta gcggcgaaac aataa                   765

<210> SEQ ID NO 48
<211> LENGTH: 765
<212> TYPE: DNA
<213> ORGANISM: Artificial
<220> FEATURE:
<223> OTHER INFORMATION: Synthetic nucleotide sequence

<400> SEQUENCE: 48
agcagcggag ggggcggtgt cgccgccgac atcggtgcgg ggcttgccga tgcactaacc     60
gcaccgctcg accataaaga caaaggtttg cagtctttaa cactggatca gtccgtcagg    120
aaaaacgaga aactgaagct ggcggcacaa ggtgcggaaa aaacttatgg aaacggcgac    180
agccttaata cgggcaaatt gaagaacgac aaggtcagcc gcttcgactt tatccgtcaa    240
atcgaagtgg acgggaagct cattaccttg gagagcggag agttccaagt gtacaaacaa    300
agccattccg ccttaaccgc ccttcagacc gagcaagtac aagactcgga ggattccggg    360
aagatggttg cgaaacgcca gttcagaatc ggcgacatag cgggcgaaca tacatctttt    420
gacaagcttc ccaaaggcgg cagtgcgaca tatcgcggga cggcgttcgg ttcagacgat    480
gctggcggaa aactgaccta tactatagat ttcgccgcca agcagggaca cggcaaaatc    540
gaacatttga aatcgcccga actcaatgtc gagcttgcca ccgcctatat caagccggat    600
gaaaaacgcc atgccgttat cagcggttcc gtccttttaca accaagacga gaaggcagt    660 tactccctcg gtatctttgg cgggcaagcc caggaagttg ccggcagcgc ggaagtggaa    720
```
accgcaaacg gcatacacca tatcggtctt gccgccaagc agtaa     765

<210> SEQ ID NO 49
<211> LENGTH: 254
<212> TYPE: PRT
<213> ORGANISM: Artificial
<220> FEATURE:
<223> OTHER INFORMATION: Synthetic amino acid sequence

<400> SEQUENCE: 49

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
            20                  25                  30

Leu Thr Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr
    50                  55                  60

Gly Lys Leu Lys Asn Asp Lys Val Ser Arg Phe Asp Phe Ile Arg Gln
65                  70                  75                  80

Ile Glu Val Asp Gly Lys Leu Ile Thr Leu Glu Ser Gly Glu Phe Gln
                85                  90                  95

Val Tyr Lys Gln Ser His Ser Ala Leu Thr Ala Leu Gln Thr Glu Gln
            100                 105                 110

Val Gln Asp Ser Glu Asp Ser Gly Lys Met Val Ala Lys Arg Gln Phe
        115                 120                 125

Arg Ile Gly Asp Ile Ala Gly Glu His Thr Ser Phe Asp Lys Leu Pro
    130                 135                 140

Lys Gly Gly Ser Ala Thr Tyr Arg Gly Thr Ala Phe Gly Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Ser Pro Glu Leu Asn Val Glu Leu
            180                 185                 190

Ala Thr Ala Tyr Ile Lys Pro Asp Glu Lys Arg His Ala Val Ile Ser
        195                 200                 205

Gly Ser Val Leu Tyr Asn Gln Asp Glu Lys Gly Ser Tyr Ser Leu Gly
    210                 215                 220

Ile Phe Gly Gly Gln Ala Gln Glu Val Ala Gly Ser Ala Glu Val Glu
225                 230                 235                 240

Thr Ala Asn Gly Ile His His Ile Gly Leu Ala Ala Lys Gln
                245                 250

<210> SEQ ID NO 50
<211> LENGTH: 259
<212> TYPE: PRT
<213> ORGANISM: Artificial
<220> FEATURE:
<223> OTHER INFORMATION: Synthetic amino acid sequence

<400> SEQUENCE: 50

Ser Ser Gly Gly Gly Gly Ser Gly Gly Gly Gly Val Ala Ala Asp Ile
1               5                   10                  15

Gly Ala Gly Leu Ala Asp Ala Leu Thr Ala Pro Leu Asp His Lys Asp
            20                  25                  30

Lys Gly Leu Gln Ser Leu Thr Leu Asp Gln Ser Val Arg Lys Asn Glu
        35                  40                  45

```
Lys Leu Lys Leu Ala Ala Gln Gly Ala Glu Lys Thr Tyr Gly Asn Gly
 50                  55                  60

Asp Ser Leu Asn Thr Gly Lys Leu Lys Asn Asp Lys Val Ser Arg Phe
 65                  70                  75                  80

Asp Phe Ile Arg Gln Ile Glu Val Asp Gly Lys Leu Ile Thr Leu Glu
                 85                  90                  95

Ser Gly Glu Phe Gln Val Tyr Lys Gln Ser His Ser Ala Leu Thr Ala
                100                 105                 110

Leu Gln Thr Glu Gln Val Gln Asp Ser Glu Asp Ser Gly Lys Met Val
            115                 120                 125

Ala Lys Arg Gln Phe Arg Ile Gly Asp Ile Ala Gly Glu His Thr Ser
    130                 135                 140

Phe Asp Lys Leu Pro Lys Gly Ser Ala Thr Tyr Arg Gly Thr Ala
145                 150                 155                 160

Phe Gly Ser Asp Asp Ala Gly Gly Lys Leu Thr Tyr Thr Ile Asp Phe
                165                 170                 175

Ala Ala Lys Gln Gly His Gly Lys Ile Glu His Leu Lys Ser Pro Glu
            180                 185                 190

Leu Asn Val Glu Leu Ala Thr Ala Tyr Ile Lys Pro Asp Glu Lys Arg
        195                 200                 205

His Ala Val Ile Ser Gly Ser Val Leu Tyr Asn Gln Asp Glu Lys Gly
    210                 215                 220

Ser Tyr Ser Leu Gly Ile Phe Gly Gly Gln Ala Gln Glu Val Ala Gly
225                 230                 235                 240

Ser Ala Glu Val Glu Thr Ala Asn Gly Ile His His Ile Gly Leu Ala
                245                 250                 255

Ala Lys Gln

<210> SEQ ID NO 51
<211> LENGTH: 789
<212> TYPE: DNA
<213> ORGANISM: Artificial
<220> FEATURE:
<223> OTHER INFORMATION: Synthetic nucleotide sequence

<400> SEQUENCE: 51
agcagcggag gcggcggaag cggaggcggc ggtgtcgccg ccgacatcgg cgcggggctt      60
gccgatgcac taaccgcacc gctcgaccat aaagacaaag gtttgaaatc cctgacattg     120
gaagactcca tttcccaaaa cggaacactg accctgtcgg cacaaggtgc ggaaagaact     180
ttcaaagccg cgacaaaga caacagtctc aacacaggca aactgaagaa cgacaaaatc     240
agccgcttcg actttatccg tcaaatcgaa gtggacgggc agctcattac cttggagagc     300
ggagagttcc aagtgtacaa acaaagccat tccgccttaa ccgcccttca gaccgagcaa     360
gtacaagact cggagcattc cgggaagatg gttgcgaaac gccagttcag aatcggcgac     420
atagtgggcg aacatacatc ttttggcaag cttcccaaag acgtcatggc gacatatcgc     480
gggacggcgt tcggttcaga cgatgccggc ggaaaactga cctacaccat agatttcgcc     540
gccaagcagg gacacggcaa aatcgaacat ttgaaatcgc cagaactcaa tgttgacctg     600
gccgccgccg atatcaagcc ggatgaaaaa caccatgccg tcatcagcgg ttccgtcctt     660
tacaaccaag ccgagaaagg cagttactct ctaggcatct ttggcgggca agcccaggaa     720
gttgccggca gcgcggaagt ggaaaccgca acggcatac gccatatcgg tcttgccgcc     780
aagcaataa                                                            789
```

<210> SEQ ID NO 52
<211> LENGTH: 45
<212> TYPE: DNA
<213> ORGANISM: Artificial
<220> FEATURE:
<223> OTHER INFORMATION: Synthetic nucleotide sequence

<400> SEQUENCE: 52
atgagcagcg gaggcggcgg tgtcgccgcc gacatcggcg cggtg         45

<210> SEQ ID NO 53
<211> LENGTH: 45
<212> TYPE: DNA
<213> ORGANISM: Artificial
<220> FEATURE:
<223> OTHER INFORMATION: Synthetic nucleotide sequence

<400> SEQUENCE: 53
atgagcagcg gaggggggcgg tgtcgccgcc gacatcggtg cgggg         45

<210> SEQ ID NO 54
<211> LENGTH: 783
<212> TYPE: DNA
<213> ORGANISM: Artificial
<220> FEATURE:
<223> OTHER INFORMATION: Synthetic nucleotide sequence

<400> SEQUENCE: 54

```
agcagcggaa gcggaagcgg aggcggcggt gtcgccgccg acatcggcac agggcttgcc    60
gatgcactaa ctgcgccgct cgaccataaa gacaaaggtt tgaaatccct gacattggaa   120
gactccattt cccaaaacgg aacactgacc ctgtcggcac aaggtgcgga aaaaactttc   180
aaagtcggcg acaaagacaa cagtctcaat acaggcaaat tgaagaacga caaaatcagc   240
cgcttcgact ttgtgcaaaa aatcgaagtg gacggacaaa ccatcacgct ggcaagcggc   300
gaatttcaaa tatacaaaca ggaccactcc gccgtcgttg ccctacagat tgaaaaaatc   360
aacaaccccg acaaaatcga cagcctgata aaccaacgct ccttccttgt cagcggtttg   420
ggcggagaac ataccgcctt caaccaactg cccagcggca agccgagta tcacggcaaa   480
gcattcagct ccgacgatgc cggcggaaaa ctgacctata ccatagattt tgccgccaaa   540
cagggacacg gcaaaatcga cacctgaaa cacccgagc agaatgtcga gcttgcctcc   600
gccgaactca agcagatga aaaatcacac gccgtcattt tgggcgacac gcgctacggc   660
agcgaagaaa aaggcactta ccacctcgct cttttcggcg accgagccca agaaatcgcc   720
ggctcggcaa ccgtgaagat aagggaaaag gttcacgaaa tcggcatcgc cggcaaacag   780
tag                                                                 783
```

<210> SEQ ID NO 55
<211> LENGTH: 260
<212> TYPE: PRT
<213> ORGANISM: Artificial
<220> FEATURE:
<223> OTHER INFORMATION: Synthetic amino acid sequence

<400> SEQUENCE: 55

Ser Ser Gly Ser Gly Ser Gly Gly Gly Gly Val Ala Ala Asp Ile Gly
1               5                   10                  15

Thr Gly Leu Ala Asp Ala Leu Thr Ala Pro Leu Asp His Lys Asp Lys
            20                  25                  30

Gly Leu Lys Ser Leu Thr Leu Glu Asp Ser Ile Ser Gln Asn Gly Thr

```
                35                  40                  45
Leu Thr Leu Ser Ala Gln Gly Ala Glu Lys Thr Phe Lys Val Gly Asp
 50                  55                  60

Lys Asp Asn Ser Leu Asn Thr Gly Lys Leu Lys Asn Asp Lys Ile Ser
 65                  70                  75                  80

Arg Phe Asp Phe Val Gln Lys Ile Glu Val Asp Gly Gln Thr Ile Thr
                 85                  90                  95

Leu Ala Ser Gly Glu Phe Gln Ile Tyr Lys Gln Asp His Ser Ala Val
                100                 105                 110

Val Ala Leu Gln Ile Glu Lys Ile Asn Asn Pro Asp Lys Ile Asp Ser
                115                 120                 125

Leu Ile Asn Gln Arg Ser Phe Leu Val Ser Gly Leu Gly Gly Glu His
                130                 135                 140

Thr Ala Phe Asn Gln Leu Pro Ser Gly Lys Ala Glu Tyr His Gly Lys
145                 150                 155                 160

Ala Phe Ser Ser Asp Asp Ala Gly Gly Lys Leu Thr Tyr Thr Ile Asp
                165                 170                 175

Phe Ala Ala Lys Gln Gly His Gly Lys Ile Glu His Leu Lys Thr Pro
                180                 185                 190

Glu Gln Asn Val Glu Leu Ala Ser Ala Glu Leu Lys Ala Asp Glu Lys
                195                 200                 205

Ser His Ala Val Ile Leu Gly Asp Thr Arg Tyr Gly Ser Glu Glu Lys
210                 215                 220

Gly Thr Tyr His Leu Ala Leu Phe Gly Asp Arg Ala Gln Glu Ile Ala
225                 230                 235                 240

Gly Ser Ala Thr Val Lys Ile Arg Glu Lys Val His Glu Ile Gly Ile
                245                 250                 255

Ala Gly Lys Gln
            260

<210> SEQ ID NO 56
<211> LENGTH: 5
<212> TYPE: PRT
<213> ORGANISM: Artificial
<220> FEATURE:
<223> OTHER INFORMATION: Synthetic amino acid sequence

<400> SEQUENCE: 56

Ser Gly Gly Gly Gly
1               5

<210> SEQ ID NO 57
<211> LENGTH: 259
<212> TYPE: PRT
<213> ORGANISM: Artificial
<220> FEATURE:
<223> OTHER INFORMATION: Synthetic amino acid sequence

<400> SEQUENCE: 57

Ser Ser Gly Gly Gly Gly Ser Gly Gly Gly Val Thr Ala Asp Ile
1               5                  10                  15

Gly Thr Gly Leu Ala Asp Ala Leu Thr Ala Pro Leu Asp His Lys Asp
                20                  25                  30

Lys Gly Leu Lys Ser Leu Thr Leu Glu Asp Ser Ile Ser Gln Asn Gly
                35                  40                  45

Thr Leu Thr Leu Ser Ala Gln Gly Ala Glu Lys Thr Tyr Gly Asn Gly
 50                  55                  60
```

```
Asp Ser Leu Asn Thr Gly Lys Leu Lys Asn Asp Lys Val Ser Arg Phe
 65                  70                  75                  80

Asp Phe Ile Arg Gln Ile Glu Val Asp Gly Gln Leu Ile Thr Leu Glu
                 85                  90                  95

Ser Gly Glu Phe Gln Val Tyr Lys Gln Ser His Ser Ala Leu Thr Ala
            100                 105                 110

Leu Gln Thr Glu Gln Glu Gln Asp Pro Glu His Ser Glu Lys Met Val
        115                 120                 125

Ala Lys Arg Arg Phe Arg Ile Gly Asp Ile Ala Gly Glu His Thr Ser
130                 135                 140

Phe Asp Lys Leu Pro Lys Asp Val Met Ala Thr Tyr Arg Gly Thr Ala
145                 150                 155                 160

Phe Gly Ser Asp Asp Ala Gly Gly Lys Leu Thr Tyr Thr Ile Asp Phe
                165                 170                 175

Ala Ala Lys Gln Gly His Gly Lys Ile Glu His Leu Lys Ser Pro Glu
            180                 185                 190

Leu Asn Val Asp Leu Ala Val Ala Tyr Ile Lys Pro Asp Glu Lys His
        195                 200                 205

His Ala Val Ile Ser Gly Ser Val Leu Tyr Asn Gln Asp Glu Lys Gly
210                 215                 220

Ser Tyr Ser Leu Gly Ile Phe Gly Glu Lys Ala Gln Glu Val Ala Gly
225                 230                 235                 240

Ser Ala Glu Val Glu Thr Ala Asn Gly Ile His His Ile Gly Leu Ala
                245                 250                 255

Ala Lys Gln

<210> SEQ ID NO 58
<211> LENGTH: 260
<212> TYPE: PRT
<213> ORGANISM: Neisseria meningitidis (group B)

<400> SEQUENCE: 58

Cys Ser Ser Gly Gly Gly Gly Ser Gly Gly Gly Gly Val Thr Ala Asp
 1               5                  10                  15

Ile Gly Thr Gly Leu Ala Asp Ala Leu Thr Ala Pro Leu Asp His Lys
                 20                  25                  30

Asp Lys Gly Leu Lys Ser Leu Thr Leu Glu Asp Ser Ile Ser Gln Asn
            35                  40                  45

Gly Thr Leu Thr Leu Ser Ala Gln Gly Ala Glu Lys Thr Tyr Gly Asn
        50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                 85                  90                  95

Glu Ser Gly Glu Phe Gln Val Tyr Lys Gln Ser His Ser Ala Leu Thr
            100                 105                 110

Ala Leu Gln Thr Glu Gln Glu Gln Asp Pro Glu His Ser Glu Lys Met
        115                 120                 125

Val Ala Lys Arg Arg Phe Arg Ile Gly Asp Ile Ala Gly Glu His Thr
130                 135                 140

Ser Phe Asp Lys Leu Pro Lys Asp Val Met Ala Thr Tyr Arg Gly Thr
145                 150                 155                 160

Ala Phe Gly Ser Asp Asp Ala Gly Gly Lys Leu Thr Tyr Thr Ile Asp
                165                 170                 175
```

```
Phe Ala Ala Lys Gln Gly His Gly Lys Ile Glu His Leu Lys Ser Pro
                180                 185                 190

Glu Leu Asn Val Asp Leu Ala Val Ala Tyr Ile Lys Pro Asp Glu Lys
            195                 200                 205

His His Ala Val Ile Ser Gly Ser Val Leu Tyr Asn Gln Asp Glu Lys
        210                 215                 220

Gly Ser Tyr Ser Leu Gly Ile Phe Gly Glu Lys Ala Gln Glu Val Ala
225                 230                 235                 240

Gly Ser Ala Glu Val Glu Thr Ala Asn Gly Ile His His Ile Gly Leu
                245                 250                 255

Ala Ala Lys Gln
            260

<210> SEQ ID NO 59
<211> LENGTH: 255
<212> TYPE: PRT
<213> ORGANISM: Neisseria meningitidis (group B)

<400> SEQUENCE: 59

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Ile Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Ser Ser Asp
145                 150                 155                 160

Asp Ala Gly Gly Lys Leu Ile Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ala Asp Ile Lys Pro Asp Glu Lys His His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 60
<211> LENGTH: 255
<212> TYPE: PRT
<213> ORGANISM: Neisseria meningitidis (group B)
```

<400> SEQUENCE: 60

```
Cys Ser Ser Gly Gly Gly Val Ala Ala Asp Ile Gly Ala Gly Leu
1               5                   10                  15
Ala Asp Ala Leu Thr Ala Pro Leu Asp His Lys Asp Lys Ser Leu Gln
            20                  25                  30
Ser Leu Thr Leu Asp Gln Ser Val Arg Lys Asn Glu Lys Leu Lys Leu
        35                  40                  45
Ala Ala Gln Gly Ala Glu Lys Thr Tyr Gly Asn Gly Asp Ser Leu Asn
    50                  55                  60
Thr Gly Lys Leu Lys Asn Asp Lys Val Ser Arg Phe Asp Phe Ile Arg
65                  70                  75                  80
Gln Ile Glu Val Asp Gly Gln Leu Ile Thr Leu Glu Ser Gly Glu Phe
                85                  90                  95
Gln Val Tyr Lys Gln Ser His Ser Ala Leu Thr Ala Leu Gln Thr Glu
            100                 105                 110
Gln Val Gln Asp Ser Glu His Ser Gly Lys Met Val Ala Lys Arg Gln
        115                 120                 125
Phe Arg Ile Gly Asp Ile Ala Gly Glu His Thr Ser Phe Asp Lys Leu
    130                 135                 140
Pro Glu Gly Gly Arg Ala Thr Tyr Arg Gly Thr Ala Phe Gly Ser Asp
145                 150                 155                 160
Asp Ala Ser Gly Lys Leu Thr Tyr Thr Ile Asp Phe Ala Ala Lys Gln
                165                 170                 175
Gly His Gly Lys Ile Glu His Leu Lys Ser Pro Glu Leu Asn Val Asp
            180                 185                 190
Leu Ala Ala Ser Asp Ile Lys Pro Asp Lys Lys Arg His Ala Val Ile
        195                 200                 205
Ser Gly Ser Val Leu Tyr Asn Gln Ala Glu Lys Gly Ser Tyr Ser Leu
    210                 215                 220
Gly Ile Phe Gly Gly Gln Ala Gln Glu Val Ala Gly Ser Ala Glu Val
225                 230                 235                 240
Glu Thr Ala Asn Gly Ile Arg His Ile Gly Leu Ala Ala Lys Gln
                245                 250                 255
```

<210> SEQ ID NO 61
<211> LENGTH: 768
<212> TYPE: DNA
<213> ORGANISM: Artificial
<220> FEATURE:
<223> OTHER INFORMATION: Synthetic nucleic acid sequence

<400> SEQUENCE: 61

```
ggcagcagcg gaggcggcgg tgtcgccgcc gacatcggcg cggtgcttgc cgatgcacta      60
accgcaccgc tcgaccataa agacaaaagt ttgcagtctt tgacgctgga tcagtccgtc     120
aggaaaaacg agaaactgaa gctggcggca caaggtgcgg aaaaaactta tggaaacggc     180
gacagcctca atacgggcaa attgaagaac gacaaggtca gccgcttcga ctttatccgt     240
caaatcgaag tggacgggca gctcattacc ttggagagcg gagagttcca agtgtacaaa     300
caaagccatt ccgccttaac cgcccttcag accgagcaag tacaagattc ggagcattca     360
gggaagatgg ttgcgaaacg ccagttcaga atcggcgata tagcgggtga acatacatct     420
tttgacaagc ttcccgaagg cggcagggcg acatatcgcg ggacggcatt cggttcagac     480
gatgccagtg gaaaactgac ctacaccata gatttcgccg ccaagcaggg gacacggcaaa    540
```

```
atcgaacatt tgaaatcgcc agaactcaat gttgacctgg ccgcctccga tatcaagccg    600
gataaaaaac gccatgccgt catcagcggt tccgtccttt acaaccaagc cgagaaaggc    660
agttactctc taggcatctt tggcgggcaa gcccaggaag ttgccggcag cgcagaagtg    720
gaaaccgcaa acggcatacg ccatatcggt cttgccgcca agcagtaa                 768
```

<210> SEQ ID NO 62
<211> LENGTH: 255
<212> TYPE: PRT
<213> ORGANISM: Artificial
<220> FEATURE:
<223> OTHER INFORMATION: Synthetic amino acid sequence

<400> SEQUENCE: 62

```
Gly Ser Ser Gly Gly Gly Gly Val Ala Ala Asp Ile Gly Ala Val Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255
```

<210> SEQ ID NO 63
<211> LENGTH: 765
<212> TYPE: DNA
<213> ORGANISM: Artificial
<220> FEATURE:
<223> OTHER INFORMATION: Synthetic nucleic acid sequence

<400> SEQUENCE: 63

```
ggcagcagcg gaggcggcgg tgtcgccgcc gacatcggcg cggggcttgc cgatgcacta    60
accgcaccgc tcgaccataa agacaaaagt ttgcagtctt tgacgctgga tcagtccgtc   120
```

```
aggaaaaacg agaaactgaa gctggcggca caaggtgcgg aaaaaactta tggaaacggc      180
gacagcctca atacgggcaa attgaagaac gacaaggtca gccgcttcga ctttatccgt      240
caaatcgaag tggacgggca gctcattacc ttggagagcg gagagttcca aatatacaaa      300
caggaccact ccgccgtcgt tgccctacag attgaaaaaa tcaacaaccc cgacaaaatc      360
gacagcctga taaccaacg ctccttcctt gtcagcggtt tgggtggaga acataccgcc       420
ttcaaccaac tgcccagcgg caaagccgag tatcacggca agcattcag ctccgacgat       480 gctggcggaa aactgaccta taccatagat tcgccgcca acagggaca cggcaaaatc        540 gaacacttga aaacacccga gcaaaatgtc gagcttgcct ccgccgaact caaagcagat      600
gaaaaatcac acgccgtcat tttgggcgac acgcgctacg gcggcgaaga aaaaggcact      660
taccacctcg ccctttttcgg cgaccgcgcc aagaaaatcg ccggctcggc aaccgtgaag    720
ataagggaaa aggttcacga aatcggcatc gccggcaaac agtaa                      765
```

<210> SEQ ID NO 64
<211> LENGTH: 254
<212> TYPE: PRT
<213> ORGANISM: Artificial
<220> FEATURE:
<223> OTHER INFORMATION: Synthetic amino acid sequence

<400> SEQUENCE: 64

```
Gly Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 65
<211> LENGTH: 786
<212> TYPE: DNA
<213> ORGANISM: Artificial Sequence
<220> FEATURE:
<223> OTHER INFORMATION: Synthetic nucleic acid sequence

<400> SEQUENCE: 65

```
atgagctctg gaagcggaag cgggggcggt ggagttgcag cagacattgg aacaggatta      60
gcagatgcac tgacggcacc gttggatcat aaagacaaag cttgaaatc gcttaccta      120
gaagattcta tttcacaaaa tggcacccct accttgtccg cgcaaggcgc tgaaaaaact      180
tttaaagtcg gtgacaaaga taatagctta aatacaggta aactcaaaaa tgataaaatc      240
tcgcgttttg atttcgtgca aaaaatcgaa gtagatggcc aaaccattac attagcaagc      300
ggtgaattcc aaatatataa acaagaccat tcagcagtcg ttgcattgca aattgaaaaa      360
atcaacaacc ccgacaaaat cgacagcctg ataaaccaac gttccttcct tgtcagcggt      420
ttgggcggtg aacatacagc cttcaaccaa ttaccaagcg gcaaagcgga gtatcacggt      480
aaagcattta gctcagatga tgcaggcggt aaattaactt atacaattga ctttgcagca      540
aaacaaggac atggcaaaat tgaacattta aaaacacccg aacagaacgt agagctcgca      600
tccgcagaac tcaaagcaga tgaaaaatca cacgcagtca ttttgggtga cacgcgctac      660
ggcagcgaag aaaaaggtac ttaccactta gctcttttg gcgaccgagc tcaagaaatc      720
gcaggtagcg caaccgtaaa gataagggaa aaggttcacg aaattgggat cgcgggcaaa      780
caataa                                                                786
```

<210> SEQ ID NO 66
<211> LENGTH: 258
<212> TYPE: PRT
<213> ORGANISM: Artificial Sequence
<220> FEATURE:
<223> OTHER INFORMATION: Synthetic amino acid sequence

<400> SEQUENCE: 66

```
Ser Ser Gly Gly Gly Ser Gly Gly Gly Val Ala Ala Asp Ile
1               5                   10                  15

Gly Ala Gly Leu Ala Asp Ala Leu Thr Ala Pro Leu Asp His Lys Asp
            20                  25                  30

Lys Ser Leu Gln Ser Leu Thr Leu Asp Gln Ser Val Arg Lys Asn Glu
        35                  40                  45

Lys Leu Lys Leu Ala Ala Gln Gly Ala Glu Lys Thr Tyr Gly Asn Gly
    50                  55                  60

Asp Ser Leu Asn Thr Gly Lys Leu Lys Asn Asp Lys Val Ser Arg Phe
65                  70                  75                  80

Asp Phe Ile Arg Gln Ile Glu Val Asp Gly Gln Thr Ile Thr Leu Ala
                85                  90                  95

Ser Gly Glu Phe Gln Ile Tyr Lys Gln Asn His Ser Ala Val Val Ala
            100                 105                 110

Leu Gln Ile Glu Lys Ile Asn Asn Pro Asp Lys Ile Asp Ser Leu Ile
        115                 120                 125

Asn Gln Arg Ser Phe Leu Val Ser Gly Leu Gly Gly Glu His Thr Ala
    130                 135                 140

Phe Asn Gln Leu Pro Asp Gly Lys Ala Glu Tyr His Gly Lys Ala Phe
145                 150                 155                 160
```

Ser Ser Asp Asp Pro Asn Gly Arg Leu His Tyr Ser Ile Asp Phe Thr
            165                 170                 175

Lys Lys Gln Gly Tyr Gly Arg Ile Glu His Leu Lys Thr Pro Glu Gln
        180                 185                 190

Asn Val Glu Leu Ala Ser Ala Glu Leu Lys Ala Asp Glu Lys Ser His
        195                 200                 205

Ala Val Ile Leu Gly Asp Thr Arg Tyr Gly Gly Glu Glu Lys Gly Thr
    210                 215                 220

Tyr His Leu Ala Leu Phe Gly Asp Arg Ala Gln Glu Ile Ala Gly Ser
225                 230                 235                 240

Ala Thr Val Lys Ile Arg Glu Lys Val His Glu Ile Gly Ile Ala Gly
                245                 250                 255

Lys Gln

<210> SEQ ID NO 67
<211> LENGTH: 780
<212> TYPE: DNA
<213> ORGANISM: Artificial Sequence
<220> FEATURE:
<223> OTHER INFORMATION: Synthetic nucleic acid sequence

<400> SEQUENCE: 67
atgagctctg gaggtggagg aagcgggggc ggtggagttg cagcagacat tggagcagga      60
ttagcagatg cactgacggc accgttggat cataaagaca aaagtttgca gtcgcttacc     120
ttagatcagt ctgtcaggaa aaatgagaaa cttaagttgg cggcgcaagg cgctgaaaaa     180
acttatggaa acggtgacag cttaaataca ggtaaactca aaaatgataa agtctcgcgt     240
tttgatttca ttcgtcaaat cgaagtagat ggccaaacca ttacattagc aagcggtgaa     300
ttccaaatat ataaacaaaa ccattcagca gtcgttgcat tgcaaattga aaaaatcaac     360
aaccccgaca aaatcgacag cctgataaac caacgttcct tccttgtcag cggtttgggc     420
ggtgaacata cagccttcaa ccaattacca gacggcaaag cggagtatca cggtaaagca     480
tttagctcag atgatccgaa cggtaggtta cactattcca ttgactttac caaaaaacaa     540
ggatacggca gaattgaaca tttaaaaacg cccgaacaga acgtagagct cgcatccgca     600
gaactcaaag cagatgaaaa atcacacgca gtcattttgg gtgacacgcg ctacggcggc     660
gaagaaaaag gtacttacca cttagccctt tttggcgacc gcgctcaaga aatcgcaggt     720
agcgcaaccg taaagataag ggaaaaggtt cacgaaattg ggatcgcggg caaacaataa     780

<210> SEQ ID NO 68
<211> LENGTH: 253
<212> TYPE: PRT
<213> ORGANISM: Artificial Sequence
<220> FEATURE:
<223> OTHER INFORMATION: Synthetic amino acid sequence

<400> SEQUENCE: 68

Ser Ser Gly Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
            20                  25                  30

Leu Thr Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr
    50                  55                  60

```
Gly Lys Leu Lys Asn Asp Lys Val Ser Arg Phe Asp Phe Ile Arg Gln
 65                  70                  75                  80

Ile Glu Val Asp Gly Gln Leu Ile Thr Leu Glu Ser Gly Glu Phe Gln
                 85                  90                  95

Ile Tyr Lys Gln Asp His Ser Ala Val Val Ala Leu Gln Ile Glu Lys
            100                 105                 110

Ile Asn Asn Pro Asp Lys Ile Asp Ser Leu Ile Asn Gln Arg Ser Phe
        115                 120                 125

Leu Val Ser Gly Leu Gly Gly Glu His Thr Ala Phe Asn Gln Leu Pro
130                 135                 140

Ser Gly Lys Ala Glu Tyr His Gly Lys Ala Phe Ser Ser Asp Asp Ala
145                 150                 155                 160

Gly Gly Lys Leu Thr Tyr Thr Ile Asp Phe Ala Ala Lys Gln Gly His
                165                 170                 175

Gly Lys Ile Glu His Leu Lys Thr Pro Glu Gln Asn Val Glu Leu Ala
            180                 185                 190

Ser Ala Glu Leu Lys Ala Asp Glu Lys Ser His Ala Val Ile Leu Gly
        195                 200                 205

Asp Thr Arg Tyr Gly Gly Glu Glu Lys Gly Thr Tyr His Leu Ala Leu
210                 215                 220

Phe Gly Asp Arg Ala Gln Glu Ile Ala Gly Ser Ala Thr Val Lys Ile
225                 230                 235                 240

Arg Glu Lys Val His Glu Ile Gly Ile Ala Gly Lys Gln
                245                 250
```

<210> SEQ ID NO 69
<211> LENGTH: 765
<212> TYPE: DNA
<213> ORGANISM: Artificial Sequence
<220> FEATURE:
<223> OTHER INFORMATION: Synthetic nucleic acid sequence

<400> SEQUENCE: 69

```
atgagctctg gaggtggagg agttgcagca gacattggag caggattagc agatgcactg      60
acggcaccgt tggatcataa agacaaaagt ttgcagtcgc ttaccttaga tcagtctgtc    120
aggaaaaatg agaaacttaa gttggcggcg caaggcgctg aaaaaactta tggaacggtt    180
gacagcttaa atacaggtaa actcaaaaat gataaagtct cgcgttttga tttcattcgt    240
caaatcgaag tagatggcca acttattaca ttagaaagcg gtgaattcca aatatataaa    300
caagaccatt cagcagtcgt tgcattgcaa attgaaaaaa tcaacaaccc cgacaaaatc    360
gacagcctga taaccaacg ttccttcctt gtcagcggtt tgggcggtga acatacagcc    420
ttcaaccaat taccaagcgg caaagcggag tatcacggta agcatttagc tcagatgat    480
gcaggcggta aattaactta caattgac tttgcagcaa acaaggaca tggcaaaatt     540
gaacatttaa aaacacccga acagaacgta gagctcgcat ccgcagaact caaagcagat    600
gaaaaatcac acgcagtcat tttgggtgac acgcgctacg gcggcgaaga aaaaggtact    660
taccacttag ctcttttttgg cgaccgagct caagaaatcg caggtagcgc aaccgtaaag    720
ataagggaaa aggttcacga aattgggatc gcgggcaaac aataa                    765
```

<210> SEQ ID NO 70
<211> LENGTH: 255
<212> TYPE: PRT
<213> ORGANISM: Neisseria meningitidis (group B)

<400> SEQUENCE: 70

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
50                  55                  60

Thr Gly Lys Leu Lys Asn Asp Lys Val Ser Arg Phe Asp Phe Ile Arg
65                  70                  75                  80

Gln Ile Glu Val Asp Gly Lys Leu Ile Thr Leu Glu Ser Gly Glu Phe
                85                  90                  95

Gln Val Tyr Lys Gln Ser His Ser Ala Leu Thr Ala Leu Gln Thr Glu
                100                 105                 110

Gln Val Gln Asp Ser Glu Asp Ser Gly Lys Met Val Ala Lys Arg Gln
            115                 120                 125

Phe Arg Ile Gly Asp Ile Ala Gly Glu His Thr Ser Phe Asp Lys Leu
130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Thr Pro Glu Gln Asn Val Glu
            180                 185                 190

Leu Ala Ser Ala Glu Leu Lys Ala Asp Glu Lys Ser His Ala Val Ile
                195                 200                 205

Leu Gly Asp Thr Arg Tyr Gly Gly Glu Lys Gly Thr Tyr His Leu
            210                 215                 220

Ala Leu Phe Gly Asp Arg Ala Gln Glu Ile Ala Gly Ser Ala Thr Val
225                 230                 235                 240

Lys Ile Arg Glu Lys Val His Glu Ile Gly Ile Ala Gly Lys Gln
                245                 250                 255

<210> SEQ ID NO 71
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 71

Ser Ser Gly Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
50                  55                  60

Gly Lys Leu Lys Asn Asp Lys Val Ser Arg Phe Asp Phe Ile Arg Gln
65                  70                  75                  80

Ile Glu Val Asp Gly Lys Leu Ile Thr Leu Glu Ser Gly Glu Phe Gln
                85                  90                  95

Val Tyr Lys Gln Ser His Ser Ala Leu Thr Ala Leu Gln Thr Glu Gln
                100                 105                 110

Val Gln Asp Ser Glu Asp Ser Gly Lys Met Val Ala Lys Arg Gln Phe
            115                 120                 125

Arg Ile Gly Asp Ile Ala Gly Glu His Thr Ser Phe Asp Lys Leu Pro
        130                 135                 140

Lys Gly Gly Ser Ala Thr Tyr Arg Gly Thr Ala Phe Gly Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 72
<211> LENGTH: 768
<212> TYPE: DNA
<213> ORGANISM: Artificial Sequence
<220> FEATURE:
<223> OTHER INFORMATION: Synthetic nucleic acid sequence

<400> SEQUENCE: 72
atgagcagcg gagggggcgg tgtcgccgcc gacatcggtg cggggcttgc cgatgcacta      60
accgcaccgc tcgaccataa agacaaaggt ttgcagtctt taacgctgga tcagtccgtc     120
aggaaaaacg agaaactgaa gctggcggca aaggtgcgg aaaaaactta tggaaacggc      180
gacagcctta tacgggcaa attgaagaac gacaaggtca gccgcttcga ctttatccgt      240
caaatcgaag tggacgggaa gctcattacc ttggagagcg gagagttcca agtgtacaaa     300
caaagccatt ccgccttaac cgcccttcag accgagcaag tacaagactc ggaggattcc     360
gggaagatgg ttgcgaaacg ccagttcaga atcggcgaca tagcgggcga acatacatct     420
tttgacaagc ttcccaaagg cggcagtgcg acatatcgcg ggacggcgtt cggttcagac     480
gatgctggcg gaaaactgac ctatactata gatttcgccg ccaaacaggg cacggcaaa     540 atcgaacact tgaaaacacc cgagcaaaat gtcgagcttg cctccgccga actcaaagca     600
gatgaaaaat cacacgccgt cattttgggc gacacgcgct acggcggcga agaaaaggc      660 acttaccacc tcgcccttt cggcgaccgc gcccagaaa tcgccggctc ggcaaccgtg      720
aagataaggg aaaaggttca cgaaatcggc atcgccggca acagtaa                   768

<210> SEQ ID NO 73
<211> LENGTH: 786
<212> TYPE: DNA
<213> ORGANISM: Artificial Sequence
<220> FEATURE:
<223> OTHER INFORMATION: Synthetic nucleic acid sequence

<400> SEQUENCE: 73
atgtccagcg gttcaggcag cggcggtgga ggcgtggcag cagatatcgg aacaggttta      60
gcagatgctc tgacagcacc cttagatcac aaagacaaag gacttaaatc actgacattg     120
gaagattcta tctcgcaaaa tggtactctc actctttcag cccaaggcgc agaaaaaaca     180

-continued

```
tttaaagtag gcgataaaga taactcctta aatacaggta aattaaaaaa tgacaaaatc      240
tcacggtttg atttcgttca gaaaattgaa gtagatggac aaacgattac attagcaagc      300
ggcgaattcc aaatttataa acaagaccat tcagcagtag tagcattaca aatcgaaaaa      360
attaacaacc cggacaaaat tgattctctt attaaccaac gctctttcct cgtatcagga      420
cttggtggtg aacatacagc gtttaatcaa ctgccgtcag gaaaagcaga atatcatggt      480
aaagcatttt catcagacga cgcaggtggc aaactgacct atactattga ctttgcagca      540
aaacagggac atggaaaaat tgaacattta aaaacacccg aacagaacgt agaactggcc      600
tcagcagaat tgaaagctga tgaaaaatcc catgcagtaa ttttaggcga tacacgttac      660
ggtagcgaag aaaaaggtac atatcactta gctcttttg gcgatcgtgc tcaagaaatt      720
gctggttccg caacagttaa aatccgtgaa aagtacatg aaatcggcat tgcaggtaaa      780
caataa                                                                 786
```

<210> SEQ ID NO 74
<211> LENGTH: 262
<212> TYPE: PRT
<213> ORGANISM: Neisseria meningitidis (group B)

<400> SEQUENCE: 74

```
Cys Ser Ser Gly Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Asp Lys Ala Glu Tyr His
145                 150                 155                 160

Gly Lys Ala Phe Ser Ser Asp Asp Pro Asn Gly Arg Leu His Tyr Thr
                165                 170                 175

Ile Asp Phe Thr Asn Lys Gln Gly Tyr Gly Arg Ile Glu His Leu Lys
            180                 185                 190

Thr Pro Glu Leu Asn Val Asp Leu Ala Ser Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255
```

```
Gly Ile Ala Gly Lys Gln
            260

<210> SEQ ID NO 75
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 75

Ser Ser Gly Gly Gly Val Ala Ala Asp Ile Gly Ala Val Leu Ala
1               5                   10                  15

Asp Ala Leu Thr Ala Pro Leu Asp His Lys Asp Lys Ser Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Val Tyr Lys Gln Ser His Ser Ala Leu Thr Ala Leu Gln Thr Glu Gln
            100                 105                 110

Val Gln Asp Ser Glu His Ser Gly Lys Met Val Ala Lys Arg Gln Phe
        115                 120                 125

Arg Ile Gly Asp Ile Ala Gly Glu His Thr Ser Phe Asp Lys Leu Pro
130                 135                 140

Glu Gly Gly Arg Ala Thr Tyr Arg Gly Thr Ala Phe Gly Ser Asp Asp
145                 150                 155                 160

Ala Ser Gly Lys Leu Thr Tyr Thr Ile Asp Phe Ala Ala Lys Gln Gly
                165                 170                 175

His Gly Lys Ile Glu His Leu Lys Ser Pro Glu Leu Asn Val Asp Leu
            180                 185                 190

Ala Ala Ser Asp Ile Lys Pro Asp Lys Arg His Ala Val Ile Ser
        195                 200                 205

Gly Ser Val Leu Tyr Asn Gln Ala Glu Lys Gly Ser Tyr Ser Leu Gly
    210                 215                 220

Ile Phe Gly Gly Gln Ala Gln Glu Val Ala Gly Ser Ala Glu Val Glu
225                 230                 235                 240

Thr Ala Asn Gly Ile Arg His Ile Gly Leu Ala Ala Lys Gln
                245                 250

<210> SEQ ID NO 76
<211> LENGTH: 258
<212> TYPE: PRT
<213> ORGANISM: Artificial Sequence
<220> FEATURE:
<223> OTHER INFORMATION: Synthetic amino acid sequence

<400> SEQUENCE: 76

Cys Gly Ser Ser Gly Gly Gly Val Ala Ala Asp Ile Gly Thr Gly
1               5                   10                  15

Leu Ala Asp Ala Leu Thr Ala Pro Leu Asp His Lys Asp Lys Gly Leu
                20                  25                  30

Lys Ser Leu Thr Leu Glu Asp Ser Ile Ser Gln Asn Gly Thr Leu Thr
            35                  40                  45
```

Leu Ser Ala Gln Gly Ala Glu Lys Thr Phe Lys Val Gly Asp Lys Asp
    50                  55                  60

Asn Ser Leu Asn Thr Gly Lys Leu Lys Asn Asp Lys Ile Ser Arg Phe
65                  70                  75                  80

Asp Phe Val Gln Lys Ile Glu Val Asp Gly Gln Thr Ile Thr Leu Ala
                85                  90                  95

Ser Gly Glu Phe Gln Ile Tyr Lys Gln Asp His Ser Ala Val Val Ala
                100                 105                 110

Leu Gln Ile Glu Lys Ile Asn Asn Pro Asp Lys Ile Asp Ser Leu Ile
            115                 120                 125

Asn Gln Arg Ser Phe Leu Val Ser Gly Leu Gly Gly Glu His Thr Ala
    130                 135                 140

Phe Asn Gln Leu Pro Ser Gly Lys Ala Glu Tyr His Gly Lys Ala Phe
145                 150                 155                 160

Ser Ser Asp Asp Ala Gly Gly Lys Leu Thr Tyr Thr Ile Asp Phe Ala
                165                 170                 175

Ala Lys Gln Gly His Gly Lys Ile Glu His Leu Lys Thr Pro Glu Gln
                180                 185                 190

Asn Val Glu Leu Ala Ser Ala Glu Leu Lys Ala Asp Gly Lys Ser His
            195                 200                 205

Ala Val Ile Leu Gly Asp Thr Arg Tyr Gly Ser Glu Glu Lys Gly Thr
    210                 215                 220

Tyr His Leu Ala Leu Phe Gly Asp Arg Ala Gln Glu Ile Ala Gly Ser
225                 230                 235                 240

Ala Thr Val Lys Ile Arg Glu Lys Val His Glu Ile Gly Ile Ala Gly
                245                 250                 255

Lys Gln

<210> SEQ ID NO 77
<211> LENGTH: 257
<212> TYPE: PRT
<213> ORGANISM: Artificial Sequence
<220> FEATURE:
<223> OTHER INFORMATION: Synthetic amino acid sequence

<400> SEQUENCE: 77

Gly Ser Ser Gly Gly Gly Val Ala Ala Asp Ile Gly Thr Gly Leu
1               5                   10                  15

Ala Asp Ala Leu Thr Ala Pro Leu Asp His Lys Asp Lys Gly Leu Lys
            20                  25                  30

Ser Leu Thr Leu Glu Asp Ser Ile Ser Gln Asn Gly Thr Leu Thr Leu
        35                  40                  45

Ser Ala Gln Gly Ala Glu Lys Thr Phe Lys Val Gly Asp Lys Asp Asn
    50                  55                  60

Ser Leu Asn Thr Gly Lys Leu Lys Asn Asp Lys Ile Ser Arg Phe Asp
65                  70                  75                  80

Phe Val Gln Lys Ile Glu Val Asp Gly Gln Thr Ile Thr Leu Ala Ser
                85                  90                  95

Gly Glu Phe Gln Ile Tyr Lys Gln Asp His Ser Ala Val Val Ala Leu
                100                 105                 110

Gln Ile Glu Lys Ile Asn Asn Pro Asp Lys Ile Asp Ser Leu Ile Asn
            115                 120                 125

Gln Arg Ser Phe Leu Val Ser Gly Leu Gly Gly Glu His Thr Ala Phe
    130                 135                 140

Asn Gln Leu Pro Ser Gly Lys Ala Glu Tyr His Gly Lys Ala Phe Ser
145                 150                 155                 160

Ser Asp Asp Ala Gly Gly Lys Leu Thr Tyr Thr Ile Asp Phe Ala Ala
                165                 170                 175

Lys Gln Gly His Gly Lys Ile Glu His Leu Lys Thr Pro Glu Gln Asn
            180                 185                 190

Val Glu Leu Ala Ser Ala Glu Leu Lys Ala Asp Glu Lys Ser His Ala
        195                 200                 205

Val Ile Leu Gly Asp Thr Arg Tyr Gly Ser Glu Lys Gly Thr Tyr
    210                 215                 220

His Leu Ala Leu Phe Gly Asp Arg Ala Gln Glu Ile Ala Gly Ser Ala
225                 230                 235                 240

Thr Val Lys Ile Arg Glu Lys Val His Glu Ile Gly Ile Ala Gly Lys
                245                 250                 255

Gln

<210> SEQ ID NO 78
<211> LENGTH: 255
<212> TYPE: PRT
<213> ORGANISM: Artificial Sequence
<220> FEATURE:
<223> OTHER INFORMATION: Synthetic amino acid sequence

<400> SEQUENCE: 78

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Ser His Ser Ala Leu Val Ala Leu Gln Thr Glu
            100                 105                 110

Gln Ile Asn Asn Ser Asp Lys Ser Gly Ser Leu Ile Asn Gln Arg Ser
        115                 120                 125

Phe Arg Ile Ser Gly Ile Ala Gly Glu His Thr Ala Phe Asn Gln Leu
    130                 135                 140

Pro Lys Gly Gly Lys Ala Thr Tyr Arg Gly Thr Ala Phe Ser Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Thr Pro Glu Gln Asn Val Glu
            180                 185                 190

Leu Ala Ser Ala Glu Leu Lys Ala Asp Glu Lys Ser His Ala Val Ile
        195                 200                 205

Leu Gly Asp Thr Arg Tyr Gly Gly Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Arg Glu Lys Val His Glu Ile Gly Ile Ala Gly Lys Gln

-continued

```
                245                 250                 255

<210> SEQ ID NO 79
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 79

Ser Ser Gly Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
            20                  25                  30

Leu Thr Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr
    50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Ile Tyr Lys Gln Ser His Ser Ala Leu Val Ala Leu Gln Thr Glu Gln
            100                 105                 110

Ile Asn Asn Ser Asp Lys Ser Gly Ser Leu Ile Asn Gln Arg Ser Phe
        115                 120                 125

Arg Ile Ser Gly Ile Ala Gly Glu His Thr Ala Phe Asn Gln Leu Pro
    130                 135                 140

Lys Gly Gly Lys Ala Thr Tyr Arg Gly Thr Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 80
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 80

Ser Ser Gly Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
            20                  25                  30

Leu Thr Leu Asp Gln Ser Val Arg Lys Asn Glu Lys Leu Lys Leu Ala
        35                  40                  45
```

-continued

```
Ala Gln Gly Ala Glu Lys Thr Tyr Gly Asn Gly Asp Ser Leu Asn Thr
 50                  55                  60

Gly Lys Leu Lys Asn Asp Lys Val Ser Arg Phe Asp Phe Ile Arg Gln
 65                  70                  75                  80

Ile Glu Val Asp Gly Gln Leu Ile Thr Leu Glu Ser Gly Glu Phe Gln
                 85                  90                  95

Val Tyr Lys Gln Ser His Ser Ala Leu Thr Ala Phe Gln Thr Glu Gln
            100                 105                 110

Ile Gln Asp Ser Glu His Ser Gly Lys Met Val Ala Lys Arg Gln Phe
        115                 120                 125

Arg Ile Gly Asp Ile Ala Gly Glu His Thr Ser Phe Asp Lys Leu Pro
130                 135                 140

Glu Gly Gly Arg Ala Thr Tyr Arg Gly Thr Ala Phe Gly Ser Asp Asp
145                 150                 155                 160

Ala Gly Gly Lys Leu Thr Tyr Thr Ile Asp Phe Ala Ala Lys Gln Gly
                165                 170                 175

Asn Gly Lys Ile Glu His Leu Lys Ser Pro Glu Leu Asn Val Asp Leu
            180                 185                 190

Ala Ala Ala Asp Ile Lys Pro Asp Gly Lys Arg His Ala Val Ile Ser
        195                 200                 205

Gly Ser Val Leu Tyr Asn Gln Ala Glu Lys Gly Ser Tyr Ser Leu Gly
210                 215                 220

Ile Phe Gly Gly Lys Ala Gln Glu Val Ala Gly Ser Ala Glu Val Lys
225                 230                 235                 240

Thr Val Asn Gly Ile Arg His Ile Gly Leu Ala Ala Lys Gln
                245                 250
```

<210> SEQ ID NO 81
<211> LENGTH: 252
<212> TYPE: PRT
<213> ORGANISM: Artificial Sequence
<220> FEATURE:
<223> OTHER INFORMATION: Synthetic amino acid sequence

<400> SEQUENCE: 81

```
Gly Gly Gly Gly Val Ala Ala Asp Ile Gly Ala Gly Leu Ala Asp Ala
 1               5                  10                  15

Leu Thr Ala Pro Leu Asp His Lys Asp Lys Gly Leu Gln Ser Leu Thr
                 20                  25                  30

Leu Asp Gln Ser Val Arg Lys Asn Glu Lys Leu Lys Leu Ala Ala Gln
             35                  40                  45

Gly Ala Glu Lys Thr Tyr Gly Asn Gly Asp Ser Leu Asn Thr Gly Lys
 50                  55                  60

Leu Lys Asn Asp Lys Val Ser Arg Phe Asp Phe Ile Arg Gln Ile Glu
 65                  70                  75                  80

Val Asp Gly Gln Leu Ile Thr Leu Glu Ser Gly Glu Phe Gln Val Tyr
                 85                  90                  95

Lys Gln Ser His Ser Ala Leu Thr Ala Phe Gln Thr Glu Gln Ile Gln
            100                 105                 110

Asp Ser Glu His Ser Gly Lys Met Val Ala Lys Arg Gln Phe Arg Ile
        115                 120                 125

Gly Asp Ile Ala Gly Glu His Thr Ser Phe Asp Lys Leu Pro Glu Gly
130                 135                 140

Gly Arg Ala Thr Tyr Arg Gly Thr Ala Phe Gly Ser Asp Asp Ala Gly
145                 150                 155                 160
```

-continued

```
Gly Lys Leu Thr Tyr Thr Ile Asp Phe Ala Ala Lys Gln Gly Asn Gly
                165             170             175

Lys Ile Glu His Leu Lys Ser Pro Glu Leu Asn Val Asp Leu Ala Ala
            180             185             190

Ala Asp Ile Lys Pro Asp Gly Lys Arg His Ala Val Ile Ser Gly Ser
        195             200             205

Val Leu Tyr Asn Gln Ala Glu Lys Gly Ser Tyr Ser Leu Gly Ile Phe
    210             215             220

Gly Gly Lys Ala Gln Glu Val Ala Gly Ser Ala Glu Val Lys Thr Val
225             230             235             240

Asn Gly Ile Arg His Ile Gly Leu Ala Ala Lys Gln
                245             250
```